United States Patent [19]
Dawson et al.

[11] Patent Number: 5,652,397
[45] Date of Patent: Jul. 29, 1997

[54] COMPOSITE WASTEWATER SAMPLER

[75] Inventors: Brian D. Dawson; Richard D. Hartz, both of Lincoln, Nebr.

[73] Assignee: Isco, Inc., Lincoln, Nebr.

[21] Appl. No.: 424,226

[22] Filed: Apr. 19, 1995

Related U.S. Application Data

[60] Continuation of Ser. No. 142,688, Oct. 25, 1993, abandoned, which is a division of Ser. No. 421,559, Oct. 13, 1989, Pat. No. 5,341,690.

[51] Int. Cl.⁶ ................................................. G01N 1/20
[52] U.S. Cl. ................................. 73/863.61; 73/863.58
[58] Field of Search .................... 73/864.74, 863.43, 73/863.58, 863.61, 864.34, 863.83, 863.84, 863.02, 863.03, 864.35, 864.73, 763.52, 863.51, 863.81

[56] References Cited

U.S. PATENT DOCUMENTS

| | | | |
|---|---|---|---|
| 2,363,625 | 11/1944 | Swearingen | 73/863.43 |
| 2,447,595 | 8/1948 | Pigott et al. | 73/863.43 |
| 2,650,497 | 9/1953 | Renwanz | 73/863.58 X |
| 3,595,087 | 7/1971 | Starks | 73/863.58 X |
| 4,091,835 | 5/1978 | Frampton | 73/863.58 X |
| 4,150,574 | 4/1979 | Wolf | 73/863.58 |
| 4,461,185 | 7/1984 | Schoffel | 73/864.74 X |
| 4,899,601 | 2/1990 | Lee | 73/864.74 X |
| 4,939,940 | 7/1990 | Tsukida | 73/864.74 |

FOREIGN PATENT DOCUMENTS

| | | | |
|---|---|---|---|
| 161961 | 4/1964 | U.S.S.R. | 73/863.58 |
| 1142750 | 2/1985 | U.S.S.R. | 73/863.58 |

*Primary Examiner*—Thomas P. Noland
*Attorney, Agent, or Firm*—Vincent L. Carney

[57] ABSTRACT

A composite wastewater sampler includes a flow-through-chamber having an inlet port and an outlet port with a path between them that gradually increases in depth and width and then decreases in width. It is shaped to cause fluid to: (1) flow from the inlet port; (2) drop to a lower level of flow within the flow-through-chamber; (3) gradually adjust in cross-sectional shape to the outlet port; and (4) flow back into a wastewater pipe. A sampling nozzle extends into the flow-through-chamber adjacent to the inlet port and within the path of the downwardly flowing wastewater so that wastewater exiting the port contacts the nozzle and flows downwardly across it.

4 Claims, 8 Drawing Sheets

COMPOSITE WASTEWATER SAMPLER

REFERENCES TO RELATED APPLICATIONS

This application is a continuation of Ser. No. 08/142,688, filed Oct. 25, 1993, abandoned, which is a division of application Ser. No. 07/421,559, filed Oct. 13, 1989 now U.S. Pat. No. 5,341,690.

BACKGROUND OF THE INVENTION

This invention relates to composite wastewater samplers.

In one type of composite wastewater sampler, samples are automatically periodically drawn from a wastewater pipe under the control of a computer and the samples are permitted to flow into a large container which accumulates the samples. The waste-water in the container is used to determine the content of flow over a period of time to learn of the amount of different solids and liquids in a wastewater system.

In one prior art wastewater sampler of this type, a peristaltic pump periodically draws samples directly from the pipe and flows it to a single container. A composite wastewater sampler of this type is sold under the designation model 2710FR Fiberglass Refridgerated Composite Wastewater Sampler by Isco, Inc., P.O. Box 82531, Lincoln, Nebr. 68501-2531, U.S.A. This type of composite wastewater sampler has some disadvantages in that: (1) the nozzle which draws fluid from the pipe is easily clogged; and (2) if not carefully monitored by a human operator, the container may overflow.

Another prior art type of composite wastewater sampler includes a wastewater pipe which extends into a cabinet and has an outlet port opening into a flow-through-chamber which is larger than the waste-water pipe. Wastewater flows into the flow-through-chamber of a larger flow-bed area from which samples of wastewater are scooped up and permitted to flow into a container. After the wastewater flows through the flow-through-chamber, it is forced back into a return section of the pipe. A composite wastewater sampler of this type is sold under the designation model TC-2 Sampler by Sonford Samplers, a Divison of Comelex Corporation, 905 North 5th Street, Minneapolis, Minn. 55401, U.S.A.

This type of composite wastewater sampler has several disadvantages, such as: (1) it does not draw an accurate sample of the solids in the waste-water because the solids settle to a lower level before the scoop receives them; (2) it is relatively complicated; and (3) it requires careful monitoring by human operators to be sure that containers gathering the composite sample do not overflow and are replaced timely.

SUMMARY OF THE INVENTION

Accordingly, it is an object of the invention to provide a novel composite wastewater sampler.

It is a further object of the invention to provide a novel method for drawing wastewater and storing it in a container.

It is a further object of the invention to provide a composite wastewater sampler that provides a better and more accurate indication of the content of wastewater.

It is a still further object of the invention to provide a wastewater sampler that automatically ends the sampling for one container and applies sampling to another container at a predetermined amount of fluid to prevent overflowing of a container even though the sampler is not attended by a human operator.

It is a still further object of the invention to provide a novel wastewater sampler which is not subject to clogging as prior art samplers.

According to the above and further objects of the invention, a composite wastewater sampler includes a flow-through-chamber having an inlet port and an outlet port with a path between them that gradually increases in depth and width and then decreases in width. It is shaped to cause fluid to: (1) flow from the inlet port; (2) drop to a lower level of flow within the flow-through-chamber; (3) gradually adjust in cross-sectional shape to the outlet port; and (4) flow back into a wastewater pipe. A sampling nozzle extends into the flow-through-chamber adjacent to the inlet port and within the path of the downwardly flowing wastewater so that wastewater exiting the port contacts the nozzle and flows downwardly across it.

Advantageously, the intake nozzle is located from between just outside the surface of the inlet port of the flow-through-chamber such as one-quarter inch to four inches from the inlet port in the direction of the flow-through-chamber depending on the expected velocity of the fluid. In the preferred embodiment, it is approximately three-quarters inch from the opening. The nozzle is tapered and smooth except for an aligning keyway. The taper is between 1½ to 3 degrees in slope with respect to a longitudinal axis inwardly toward the longitudinal axis opposite in direction to the flow of fluid and in the direction of the inlet port.

The intake nozzel: (1) is positioned at an angle to the vertical of between 5 and 40 degrees and preferably at an angle of 25 degrees from the vertical pointing in the direction of flow and normally at an angle that is at the same angle as the surface of the inlet port into the flow-through-chamber; (2) extends approximately to the middle of the flow stream from the inlet port but in its location is selected to provide substantial flow of fluid downwardly and to permit the tip to be in contact with the fluid for drawing fluid instead of air; and (3) has a bottom open end cut to provide an intake port facing the flow of the wastewater at an angle of 10 degrees with respect to the center line of the inlet port of the flow-through-chamber but may be at differing angles which are selected together with the angle with respect to the longitudinal axis of the nozzle and center axis of the inlet port to cancel venturi effect and permit drawing of fluid instead of air by a peristaltic pump at sampling intervals. The angle of the nozzel intake port may be between 5 and 40 degrees with respect to the longitudinal axis of the inlet port to the flow-through-chamber but in the preferred embodiment is 10 degrees.

A computer controlled peristaltic pump draws fluid at the same velocity as the fluid flowing through the wastewater pipe at preprogrammed intervals and deposits them into the sampling container. A computer counts revolutions of the peristalic pump and the number of samples drawn and deposited into a container and from these measurements, it calculates the volume of samples in the container. Before the container is full, at a pre-programmed amount of liquid, the computer activates a motor which moves the outlet end of the peristaltic pump tubing over a second container to begin drawing samples and transferring them into the second container. With this arrangement, continuous human monitoring is not needed and yet overflowing of containers is avoided.

From the above description, it can be understood that the composite wastewater sampler of this invention has several advantages such as: (1) it is not easily clogged and is self-cleaning; (2) it takes a more representative and accurate sample of the amount of solids in the wastewater than the prior art wastewater samples; (3) it is relatively uncomplicated; (4) it is readily adaptable to scooping samples manually; (5) it permits automatic direct pumping for higher accuracy; and (6) it does not require continuous attendance and may fill sequentially composite containers automatically.

SUMMARY OF THE DRAWINGS

The above noted and other features of the invention will be better understood from the following detailed description when considered with reference to the accompanying drawings, in which.

DETAILED DESCRIPTION

Figure 1:
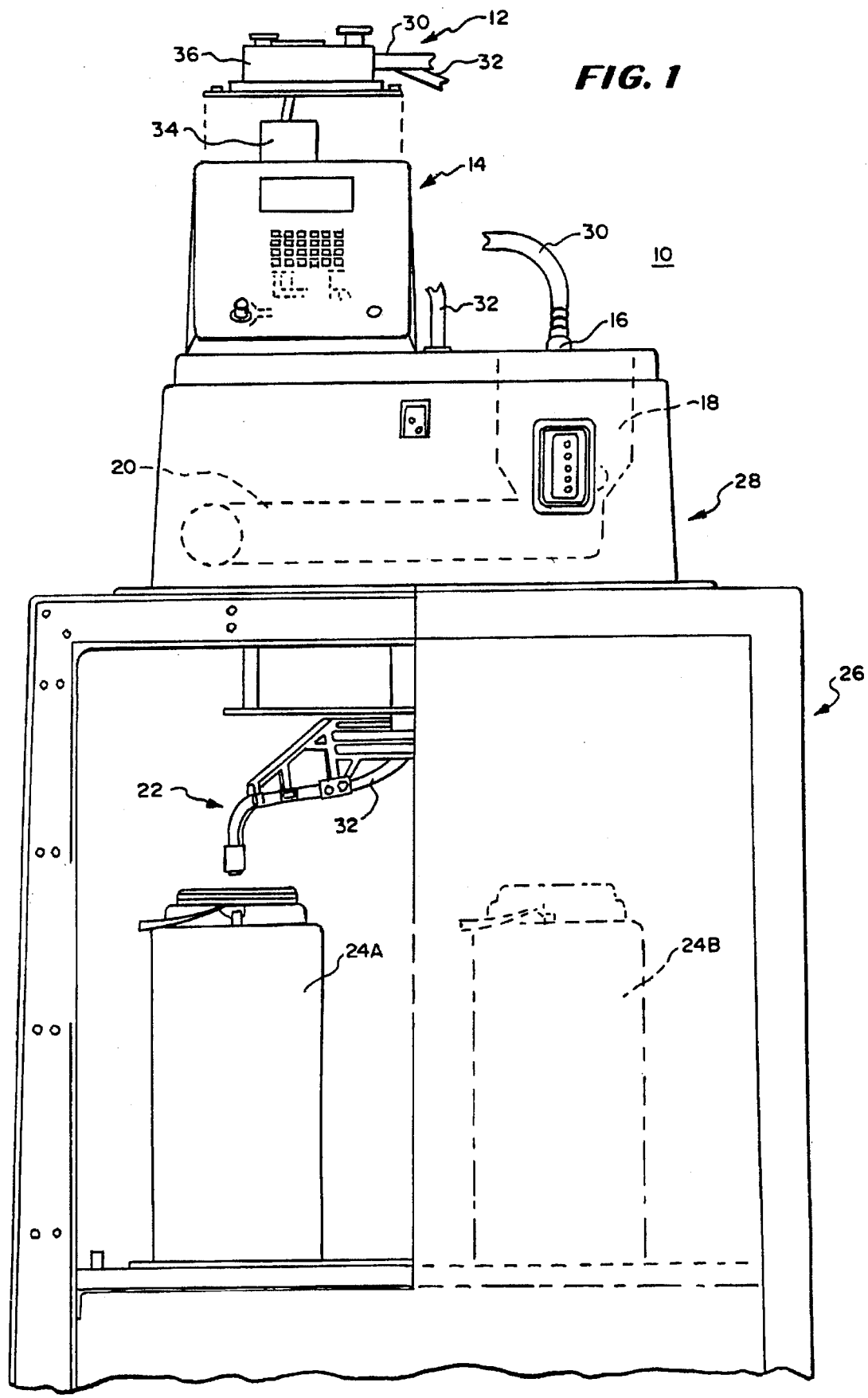
FIG. 1 is a fragmentary elevational view partly exploded of the composite wastewater sampler which is an embodiment of the invention.

In FIG. 1, there is shown a fragmentary elevational view, partly exploded, of a composite wastewater sampler 10 having a pump assembly 12, a computer 14, an intake nozzle 16, a flow-through-channel 18, a front horizontal portion 20 of the wastewater pipe and a distributor assembly 22. Wastewater flows through the wastewater pipe and through the flow-through-channel 18 in a continuous flow. During that flow, the computer 14 measures periods of time and activates the pump assembly 12 at preset intervals of time or wastewater flow to draw samples of predetermined amounts of wastewater.

During the drawing of a sample, the pump pumps at a predetermined rate set to be approximately the rate of flow of the wastewater through the front horizontal portion 20. During this pumping action, the pump pumps wastewater: (1) from the flow-through-channel 18; (2) through the intake nozzle 16 which is inserted into the flow-through-chamber 18; (3) through the hose sectors 30 and 32; and (4) to the distributor assembly 22 which deposits it in one of two sample composite containers 24A or 24B.

To provide pumping, the pump assembly 12 includes a peristaltic portion 36 having rollers which receive tubing, an inlet portion of which is indicated at 30 and an outlet portion of which is indicated at 32. The rollers are driven against a section of hose in a conventional manner by a motor 34 which is energized under the control of the computer 14 to cause power to be applied. The computer 14 counts revolutions of the peristaltic pump to monitor the purging of liquid from the tubing, and then pumping a fixed amount of sample into the composite container 24A through the hose sectors 30 and 32. This cycle is repeated to form a composite sample.

Figure 2:
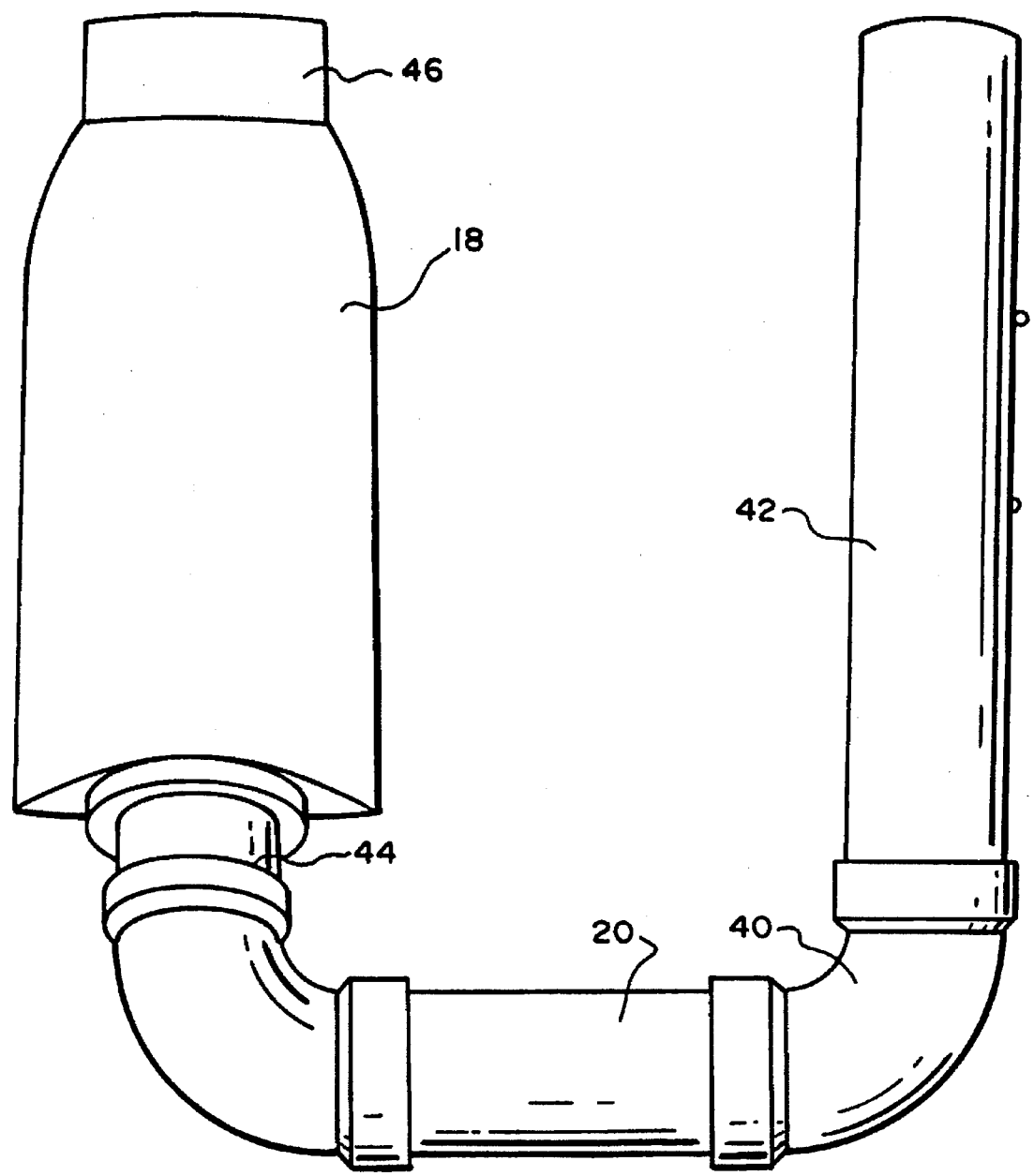
FIG. 2 is a bottom view of a portion of the wastewater sampler showing some pipes and a flow-through-chamber.

In FIG. 2, there is shown a bottom view of the flow-through-chamber 18 and front horizontal portion of the pipe 20 with the connecting pipe sections 40, 42, 44 and 46. As shown in this view, wastewater flows through the composite wastewater sampler 10 (FIG. 1) from a pipe 42, a connecting elbow 40, the front horizontal portion 20, a connecting upwardly angled pipe 44, the flow-through-chamber 18 and the connecting pipe section 46 in the named order. The water flows through these pipes at a linear velocity of between 1 foot per second and 12 feet per second and preferably at 1.8 feet per second. The rate of flow together with the angled curves maintains solid waste portions in suspension through the pipe sections and at least the entrance port of the flow-through-chamber 18.

Figure 3:
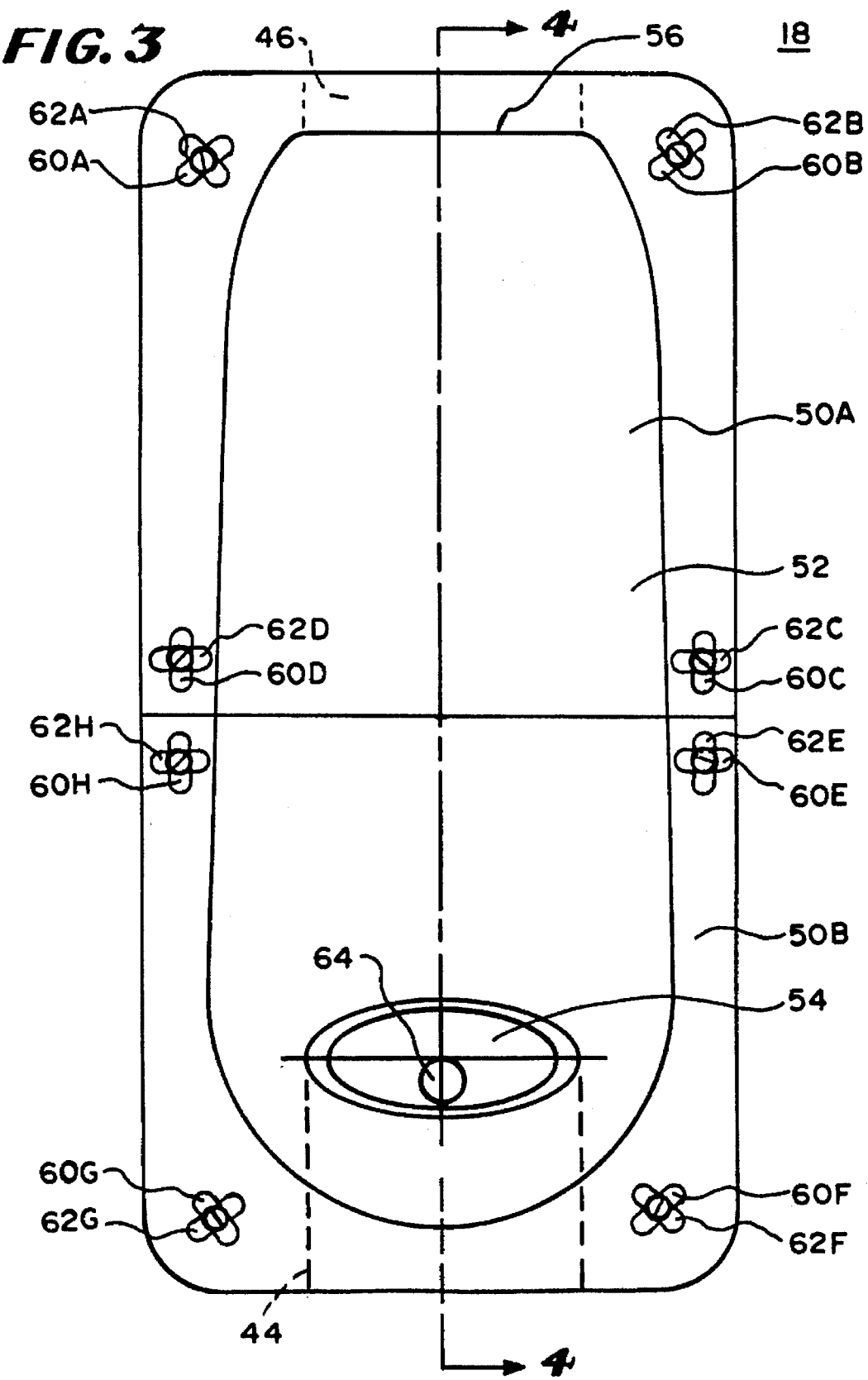
FIG. 3 is a plan view of the flow-through-chamber of FIG. 2.

In FIG. 3, there is shown a plan view of the flow-through-chamber 18 having a two-part cover 50A and 50B, shaped flow-bed walls 52 of the flow-through-chamber 18, an inlet port 54 and outlet port 56 as its principal parts. The cover parts 50A and 50B are transparent and removable to permit manual scooping of samples from the flow-through-chamber 18 and include a circular opening 64 through which the intake nozzle 16 (not shown in FIG. 3) may extend adjacent to the inlet port 54 for drawing samples of wastewater as it flows into the flow-through-chamber 18.

The flow-bed walls 52 of the flow-through-chamber 18 are shaped so that wastewater exiting the inlet port 54 drops to a lower wider level. The level of wastewater gradually changes to avoid turbulence between the inlet port 54 and outlet port 56. It drops as explained above and gradually reaches the level of the oulet port 56, at which time the cross section of the wastewater has a shape that channels the water smoothly without backup through the outlet port 56. For this purpose, the walls 52 drop steeply down from the inlet port 54 which extends into an inwardly slanted wall. Gradually the depth decreases and the width increases and then decreases as the distance from the inlet port increases up to the exit port to provide a smooth transition.

In the preferred embodiment, the inlet port 54 and outlet port 56 are spaced approximately 10 inches from each other and the inlet port 54 is circular on a slanted surface to appear elliptical in the view of FIG. 3, being at approximately a 65 degree angle with a horizontal and slanting inwardly toward the flow-through-chamber 18. It has a diameter of approximately 2.5 inches. However, these dimensions may vary with the principal criteria being to permit a flow over the intake nozzle 16 that is inserted through the aperture 64 in the cover.

To provide a transparent removable cover, the first section of the cover includes four elongated openings 60A, 60B, 60C and 60D through it and the second section includes a corresponding four openings, 60E, 60F, 60G and 60H. Eight elongated members 62A–62H extend into the walls of the flow-through-chamber 18 and are rotatably held spaced from the walls a distance equal to the thickness of the cover by screws. These elongated members may be rotated so they fit through the corresponding elongated openings 60A–60H or moved at an angle to them to hold the covers in place. Thus, by aligning the holding members with the slots, either side of the cover 50A and 50B can be removed.

Figure 4:
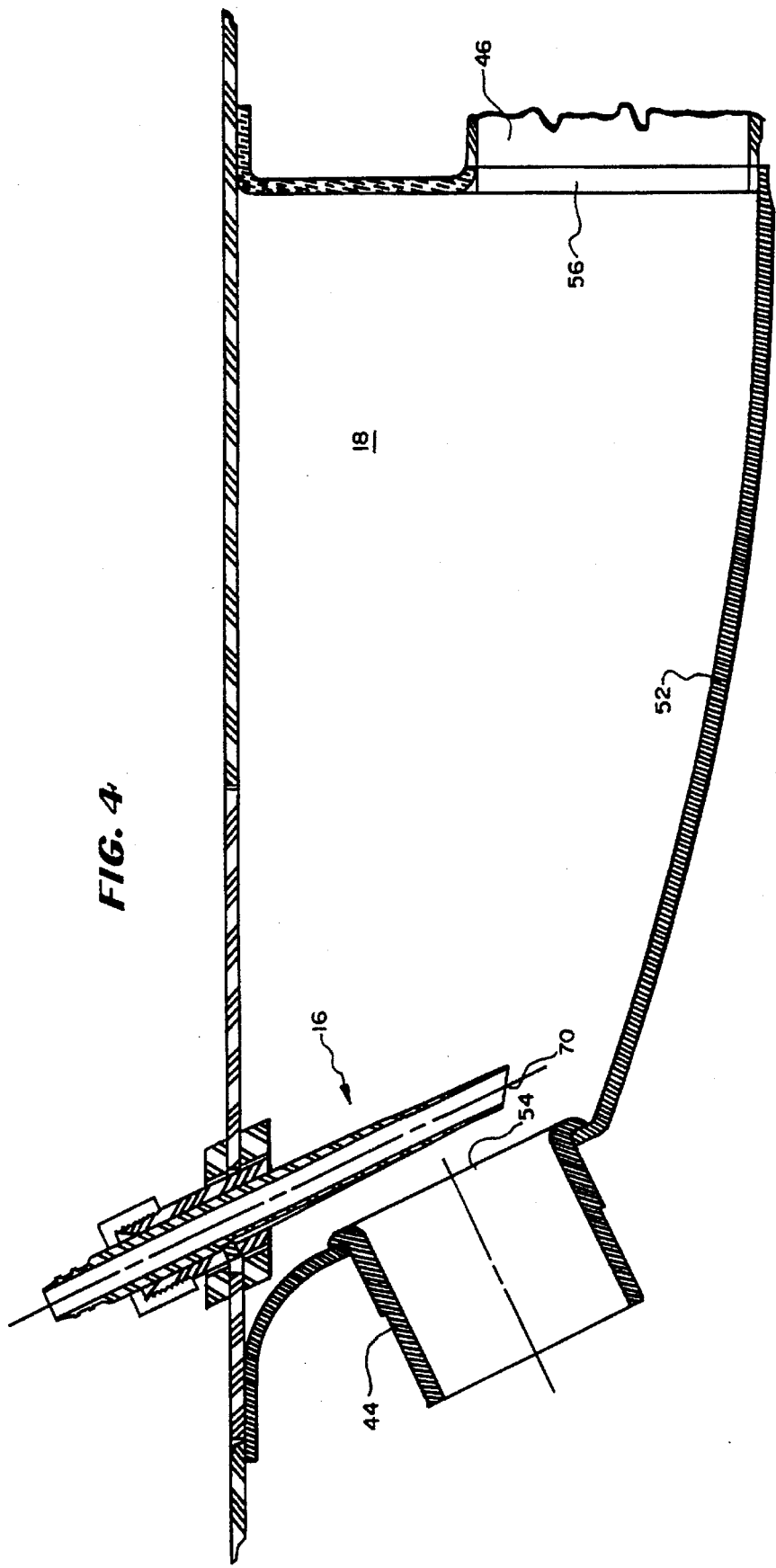
FIG. 4 is a sectional view taken through lines 4—4 of FIG. 3 illustrating the flow-through-chamber.

In FIG. 4, there is shown a sectional view of the flow-through-chamber 18 taken through lines 4—4 of FIG. 3 having a portion of the intake nozzle 16, the inlet port 54, the upwardly extending pipe member 44, the outlet port 56, and outlet pipe 46. As best shown in this view, the intake nozzle 16 tapers inwardly at angles of between 1½ and 3 degrees and preferably at an angle of approximately 2 degrees.

When mounted in place, the intake nozzle 16 is at an angle of approximately 25 degrees with the vertical but may be between 5 and 40 degrees. It is positioned sufficiently close to the inlet port 54 so that water flows across its tip. Depending on the velocity of the water, the tip of the intake nozzel 16 is anywhere from one-quarter inch away from the surface of the inlet port 54 to four inches from the surface of the inlet port 54 but is generally approximately three-quarters inch from the inlet port 54. The tip is cut upwardly to provide an intake port 70 having a portion facing into flow of the water flowing through the inlet port 54. The angle of the intake port 70 is selected so that the pressure of the flowing wastewater cancels venturi forces and permits smooth uptake of liquid without air. Generally, the tip is some distance from the center line of the flow-through-chamber inlet port 54 but may be lower just so that the wastewater continually covers the inlet port 54 of the intake nozzle 16 during sample drawing. The angle of the inlet port.54 of the intake nozzle with the longitudinal axis of the intake nozzle 16 is approximately 30 degrees so that it is approximately 60 degrees from the perpendicular to the longitudinal axis of the intake nozzle 16.

Figure 5:
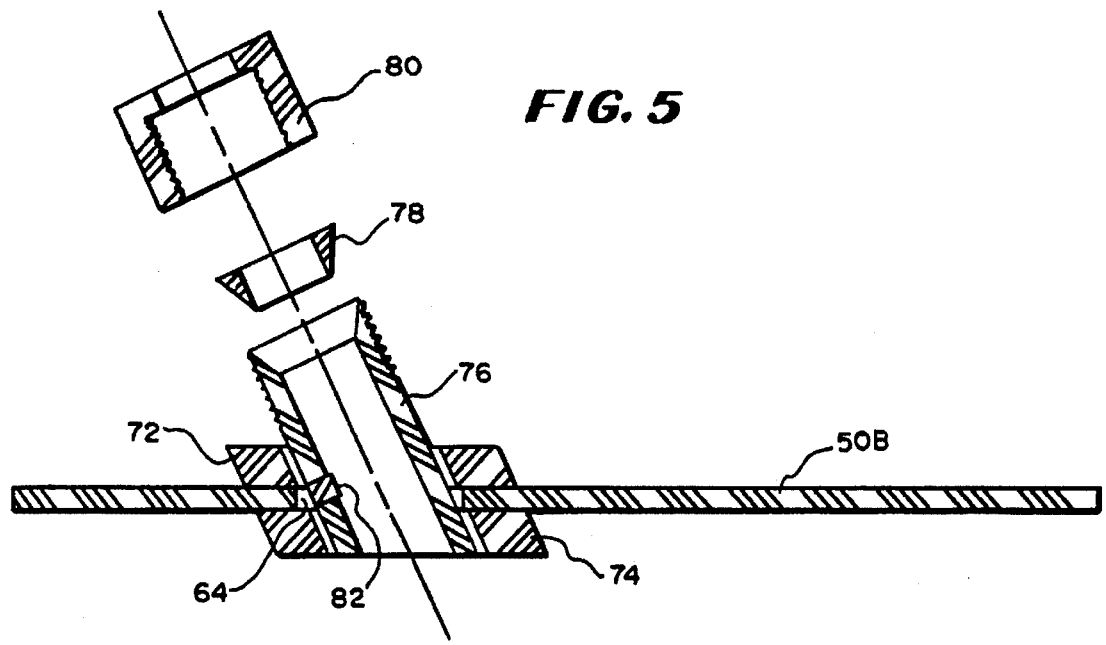
FIG. 5 is a fragmentary sectional view of a nozzle holder used in the embodiment of FIG. 1.

In FIG. 5, there is shown a holder for the intake nozzle 16 mounted in the plate 50B about the aperture 64 and includes first and second collars 72 and 74, a housing 76, a ferrule member 78 and an end member 80. The collars 72 and 74 are generally annular and shaped to receive a portion of the housing 76, with the collar 72 fitting above the plate 50B and the collar 74 below to form a seal about the housing 76.

The outer surface of the housing 76 has external threads to engage with internal threads on the inner surface of the end member 80 to receive the ferrule member 78 between them and compress it to hold the intake nozzle 16 in place and form a liquid tight seal thereabout. The housing 76 and upper and lower collars 72 and 74 are fastened in place about the aperture 64 with the end member 80 extending above the plate 50B. The housing 76 includes a key member 82 adapted to align the intake nozzle 16 in a manner to be described in connection with FIG. 6. With this arrangement, an installer can position the transparent covers over the flow-through-chamber with the collars 72 and 74 and housing 76 in place, slide the intake nozzle 16 into the housing 76 and position it with its inlet port 54 near the center of flowing wastewater, insert the ferrule member 78 and tighten the end member 80 to hold the intake nozzle 16 in place.

Figure 6:
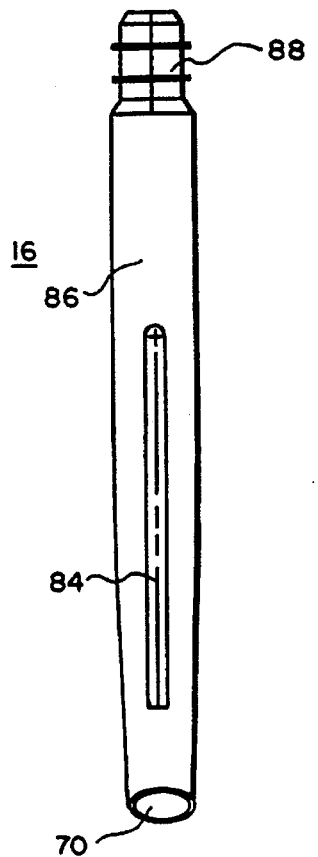
FIG. 6 is a rear elevational view of a nozzle used in the embodiment of FIG. 1.

In FIG. 6, there is shown an elevational view of an intake nozzle 16 having a tubular generally tapered cylindrical body 86, a keyway 84 sized to engage the key 82 (FIG. 5) for aligning the body 86 of the nozzle and a nipple 88. The nipple 88 receives the hose 30 (FIG. 1) of the peristaltic pump 12 (FIG. 1) to permit the drawing of fluid. The keyway 84 aligns the intake nozzle 16 so that the tip 70 faces the inlet port 54 (FIG. 4) to receive wastewater.

With this arrangement, wastewater continually flows downwardly over the tapered portion of the intake nozzle 16 in the direction of the taper, keeping it clear and free of clogging. When the pump assembly 12 draws a sample, the flow of fluid is pulled upwardly without air and turbulence partly because the flow of wastewater is at the same velocity as the pump is drawing and the intake part of the nozzle 16 is at an angle to receive the fluid in a manner that equalizes any venturi effect that might disrupt the intake. The intake linear velocity of the water in the tube 30 should be within 20 percent of the linear velocity of the wastewater in the wastewater pipes.

Figure 7:
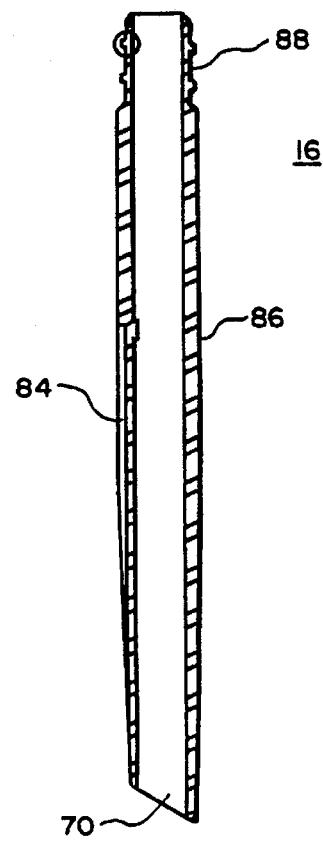
FIG. 7 is a sectional view of the nozzle of FIG. 6.

In FIG. 7, there is shown a sectional view of the intake nozzle 16 illustrating the taper on the wall 86 that prevents clogging of the tube by waste flowing in the wastewater stream and the keyway 84 that makes proper alignment convenient. The nozzel has an inside diameter of a size that provides a smooth transition between the intake hose of the pump assembly 12 and the intake nozzle 16.

In mounting the intake nozzle 16, the installer inserts the intake nozzle 16 and observes the flow of wastewater in the flow-through-chamber 18. The intake nozzle is manually adjusted by sliding it in its holder and the cover of the holder threades to lock the nozzle in place.

Figure 8:
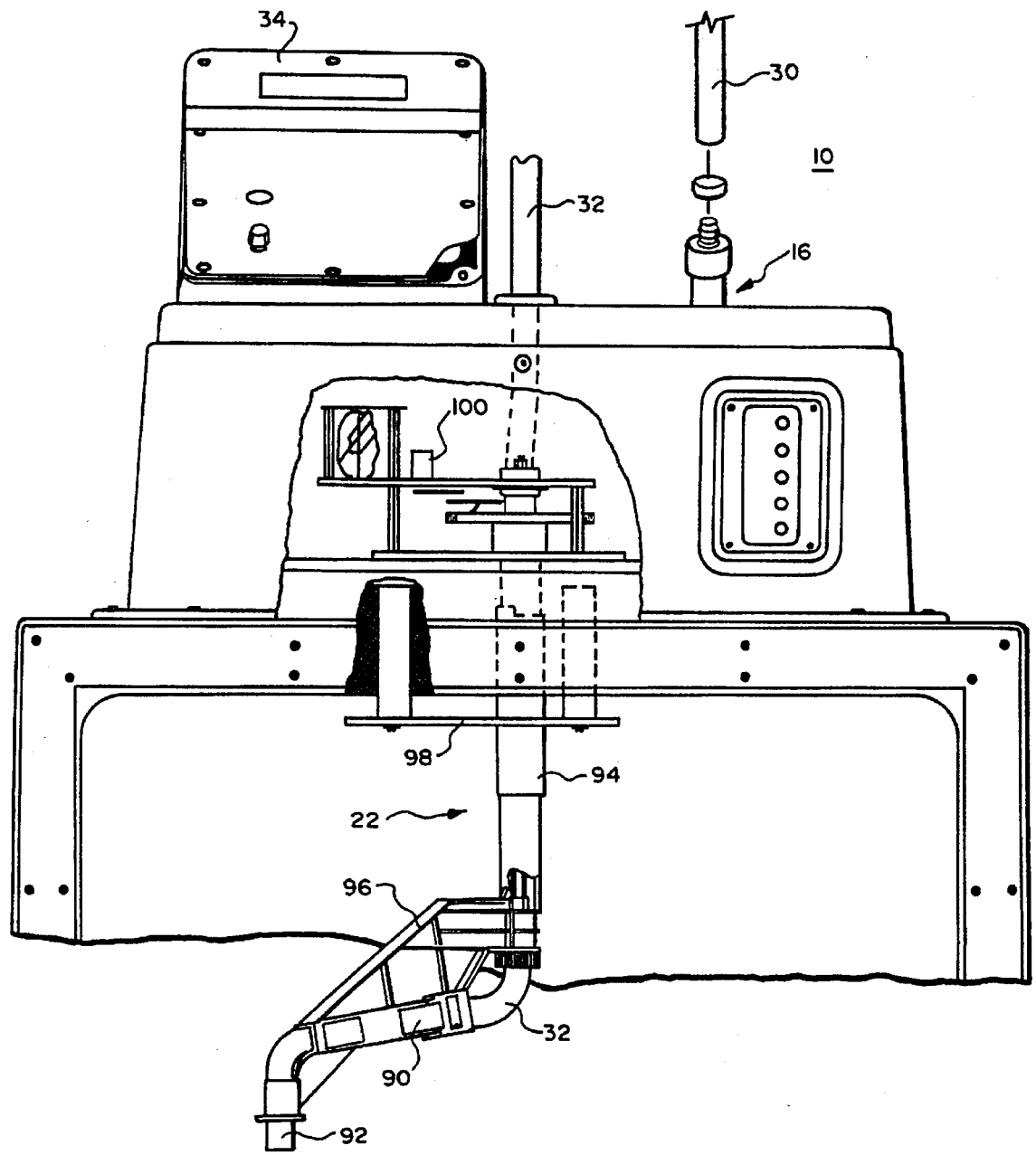
FIG. 8 is a fractional view partly broken away of an embodiment of a distributor of samples useful in the embodiment of FIG. 1.

In FIG. 8, there is shown a broken away, fragmentary elevational view of the composite flow through sampler 10 showing the manner in which the hose 32 from the pump assembly 12 extends downwardly from the pump assembly 12 (FIG. 1) to a distributor arm 96 of the distributor assembly 22. The distributor assembly arm 96 receives the hose 32 and supports it through an offset portion 90 and a downwardly extending portion 92 so that it extends outwardly from a central axis of rotation 94. The hose 32 is held in this position by the distributor arm 96 which rotates within a support section 98 under the control of a motor 100.

With this arrangement, the motor 100 when activated rotates the distributor arm 96 to move the downwardly extending portion 92 through 120 degrees from a position where it is over the container 24A to a position where it is over the container 24B. This is done under the control of the computer 14 so that, when a predetermined number of samples have been drawn, the arm is rotated to avoid overflowing of one of the containers 24A and 24B and to collect samples in the next container.

Figure 9:
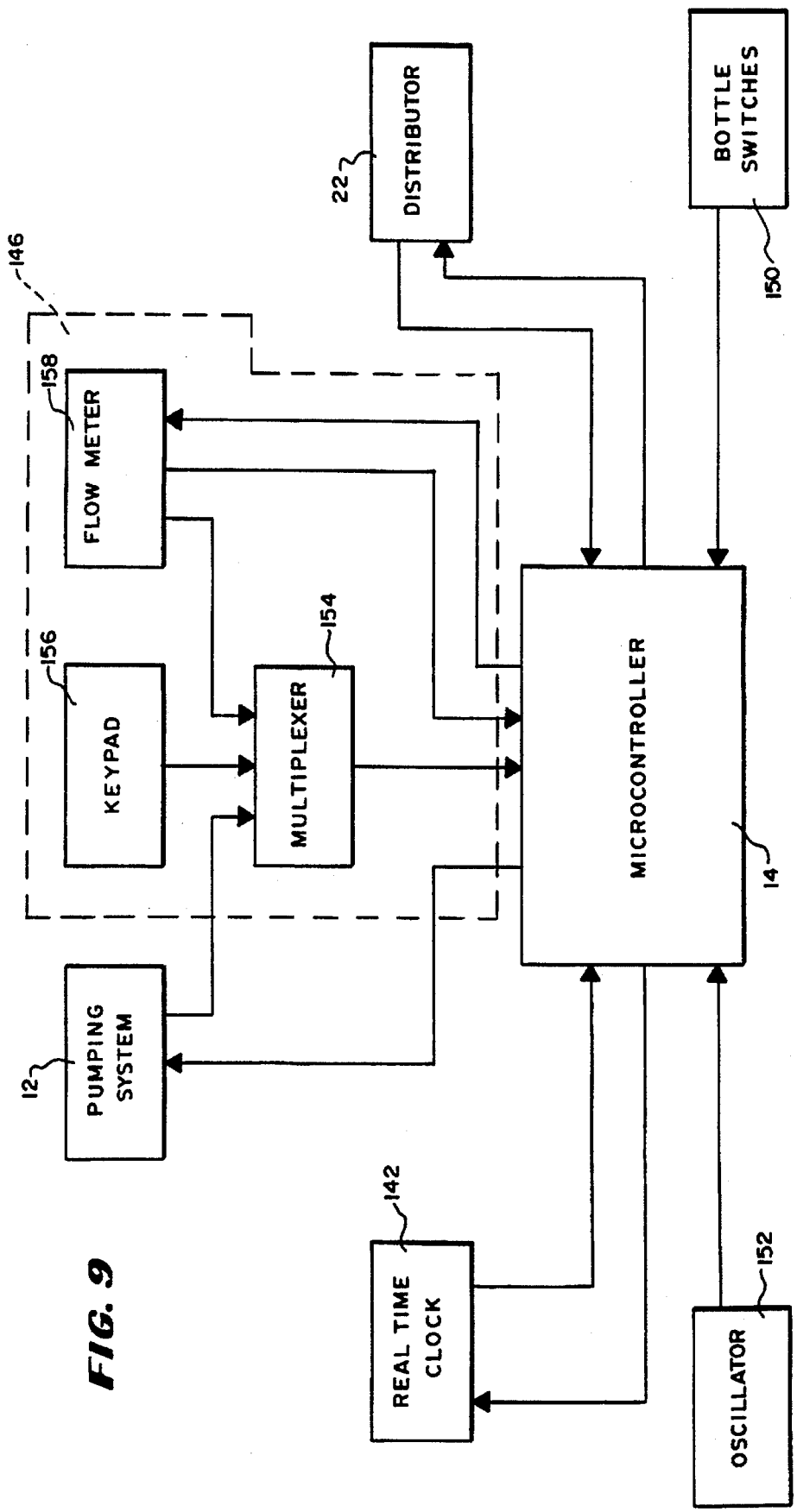
FIG. 9 is a block diagram of a control system for the sampler.

In FIG. 9, there is shown a block diagram of the microprocessor control system used in the preferred embodiment having the microcontroller 14, the pumping system 12, a real time clock 142, an input interface 146, a distributor 22 and a set of bottle switches 150. The microcontroller 14 is a Motorola MC68HC705C8P microcontroller sold by Motorola, Inc., Microprocessor Products Group, Microcontroller Division, Oak Hill, Tex. programmed in accordance with the software listing of attachment A to this specification.

To control the wastewater sampler, an external oscillator 152 is connected to the microcontroller 14 in a conventional manner to establish a basic clock rate. The microcontroller receives signals from the real time clock 142 and from the input interface 146 to which it is electrally connected. The real time clock 142 provides presetable periodic signals to the microcontroller 14. Their signals are used to time events such as the drawing of samples or the like. The real time clock 142 periodically applies signals to the microcontroller 14 and is powered by a separate source of power such as a lithium battery which enables it to continue sending coded pulses that indicate the real time. It receives a signal from the microcontroller 14 upon initialization which sets the real time into the real time clock 142 so that it may provide accurate indications of time to the microcontroller.

The microcontroller 14, if it loses power, inquires of the real time clock 142 about the actual time upon receiving power to reset its registers. The real time clock also receives signals from the microcontroller 14 as to the duration of periodic intervals between signals to be sent by the real time clock 142 to the microprocessor 14 for timing events such as the drawing of samples or the like as preprogrammed into the microcontroller 14 through the user interface.

For programming and timing some events, the input interface 146 includes: (1) a flow-meter connector 158; and (2) a keypad 156 and a display that permits an operator to set the parameters such as the amount of flow between samples or the like. The flow meter connector may be electrically connected to a flow meter that provides a measure of wastewater flowing through the wastewater pipe that is being sampled. The signals from the flow meter may be utilized to cause a sample to be drawn at periodic intervals.

To prevent overflow of sample, the distributer 22 moves the outlet hose 32 between the first container 24A (FIG. 1) and 24B (FIG. 2) under the control of the microcontroller 14 when the microcontroller 14 determines that the container into which it is depositing samples is full from a calculation based on the number of samples and the volume of each sample. It may then cause the distributor to begin depositing samples into the other container. The microcontroller 14 may be programmed to make this change at any selected volume of sample.

The bottle switches 150 are lever actuated push button switches which sense the presence of a container 24A or 24B and apply the signal to the microcontroller 14 indicating the presence or absence of the container. With this arrangement, the microcontroller 14 senses the presence of at least one of the containers 24A and 24B before it begins actuating the pump to draw samples.

To control the pumping intervals, the microcontroller 14 may be programmed through the user interface to initiate pumping action from the pumping system 12 at intervals which occur after a predetermined amount of time or after a predetermined amount of flow as set through the user interface. The microcontroller 14 also has programmed into it the number of pumping cycles from the pumping system 12 for a continuous sample and the volume of the wastewater that is to be applied to the containers 24A or 24B (FIG. 1) before signaling the distributor 22 to move to a new container, provided the bottle switches 150 indicate that an empty container is in place.

The pumping system 12 is also connected to the user interface which contains a multiplexor and transmitts signals thereto indicating the number of pump cycles. These signals are applied to the microcontroller 14 to count the wastewater which has been drawn either as a sample or to be pumped upwardly to a fixed location and downwardly to clear the line.

To control the positioning of the outlet hose 32 by the distributor 22, the distributor 22 includes a right and left position switch, which in the preferred embodiement are optical switches. These switches are electrically connected to the microcontroller 14 to indicate the initial position of the outlet of the hose 32.

When the microcontroller senses that one of the containers 24A and 24B is full and the other container is empty and in place, it applies a signal to the distributor 22 which is driven into position over the empty container. At that position, the optical switch on that side is interrupted and sends a signal back to the microcontroller and the microcontroller stops movement of the distributor 22 in place. This cycle may be repeated an indefinate number of time assuming that the full containers 24A and 24B are removed and replaced by empty containers.

The user interface 146 includes a multiplex unit 154 which is electrally connected to a keypad 156, the flow meter connector 158 and an output conductor from the pumping system 12. It periodically scans these units and sends signals to the microprocessor indicating the amount of sample drawn by the pumping system 12 or input programming from the keypad or control signals from the keypad 156 or flow volume values from a flow meter connected to the flow meter connector 158. The flow meter connector 158 also receives: (1) event signals from the microcontroller 14 for marking a strip chart or the like connected to the flow meter or internal to the flow meter; and (2) signals from a seperate detector of wastewater in the pipe to signal the microcontroller 14 to indicate the presense of absence of flow through the wastewater pipe.

Figure 10:
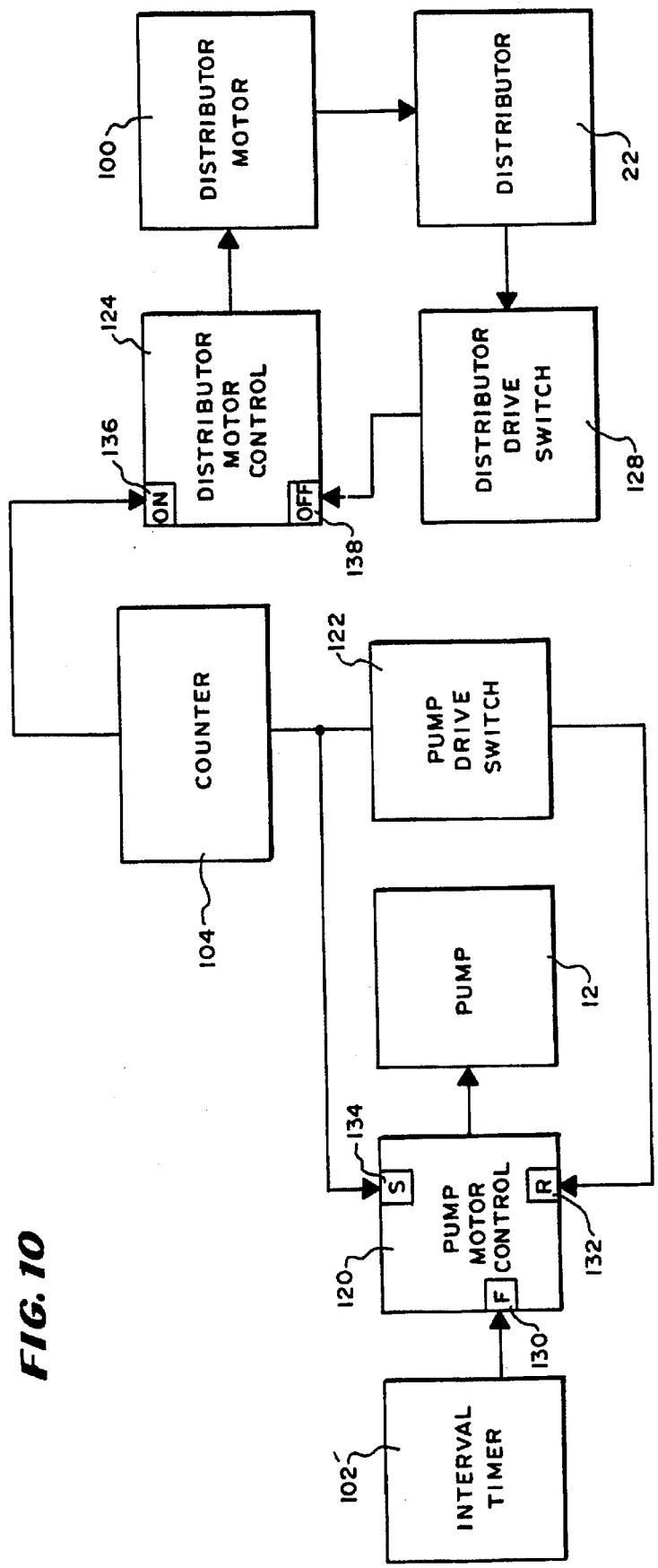
FIG. 10 is a schematic illustrative diagram of a hard wired version of the wastewater sampler.

In FIG. 10, there is shown a block diagram of a hardware control system which performs the functions which in the preferred embodiment are performed by the Motorola microcontroller model MC68HC705C8P used in the preferred embodiment and available from Motorola, Inc. Microproccessor Products Group, Microcontroller Division, Oak Hill, Tex. utilizing the software list of attachment A connected as shown by the block diagram of FIG. 9. The control system shown in FIG. 10 includes an interval timer 102, a ring counter 104, a pump motor control 120, the pump assembly 12, a pump drive switch 122, a distributor motor control 124, a distributor motor 100 and the distributor drive switch 128.

To start, stop and control the direction of rotation of the pump assembly 12, the pump motor control 120 includes a switching arrangement having: (1) a first position into which it is switched by a signal from the interval timer 102 to the forward drive terminal 130 of the pump motor control 120 and in which position it applies power to the pump assembly 12 in a direction that causes the pump assembly 12 to draw fluid into the intake hose 30 (FIG. 1); (2) a second position into which it is switched by a signal from the pump drive switch 122 to the reverse drive terminal 132 and in which position it stops the pump assembly 12 and applies power to the pump assembly 12 in a direction that causes the pump assembly 12 to force fluid out of the inlet of the intake hose 32 to clear the hose of fluid before another sample is taken; and (3) a third position into which it is switched by a signal from the pump drive switch 122 to the stop terminal 134 and in which position it stops the pump assembly 12. This signal is also applied to the adjustable ring counter 104 which has its selectable output terminal connected: (1) to the terminal 136 of the distributor motor control 124 for a purpose to be described hereinafter; and to its own reset terminal to permit another count cycle.

To generate the signals that are applied to the reverse input terminal 132, the stop terminal 134 and the counter 104 input terminal, the pump drive switch 122 includes a cam-operated revolution-sensing switch that is controlled by the rotation of the pump motor and a stepping switch that counts operations of the cam-operated revolution-sensing switch. The stepping switch produces a contact closure to provide a signal to the reverse input terminal 132 of the pump motor control 120 when the pump assembly 12 has rotated a predetermined number of revolutions in the forward direction to draw a certain volume of fluid into the intake hose 16 and then produces another contact closure which provides a signal to the stop input terminal 134 of the pump motor control 120 and to the on terminal 136 of the distributor motor control 124 when the pump has rotated a predetermined number of revolutions in the reverse direction to clear the intake hose 30.

The distributor motor control 124 includes a switching arrangement having an on position in which it applies power to the distributor motor 126 to rotate the distributor 22 into a position in which it is switched by a signal to its on terminal 136 from the counter 104. This counter 104 counts signals from the pump drive switch 122 indicating a predetermined number of samples have been drawn and applied to a container. The distributor motor control 124 is switched to its off position by a signal applied to its input terminal 138 in which position it stops the rotation of the distributor motor 126 to stop the distributor 22 with an outlet of the peristaltic pump hose 32 over the other container. To generate the signal that is applied to the off terminal 136 of the distributor motor control 124 the distributor drive switch 128, which may be a cam-operated switch, is positioned to be depressed each time the distributor 22 is rotated the distance between two successive containers.

With this arrangement, the interval timer 102 in the computer energizes the pump motor control 120 which energizes the pump assembly 12 to draw a sample as measured by the pump drive switch 122. At the end of drawing the sample, the pump drive switch 122 applies the signal to the counter 104 which resets the pump motor control 120 for the next interval and stops the pump motor by applying a signal to the control 134. This signal is also applied to the counter 104 which counts a predetermined number of counts and then applies a signal to the distributor motor control 124 indicating the container is full and initiating motion of the distributor motor to a predetermined position of the distributor 22 where it hits a switch and turns off the distributor motor applying a signal to the off switch 138. The counter 104 is a setable ring counter which may be set to take a predetermined number of samples.

From the above description, it can be understood that the wastewater sampler of this invention has several advantages such as: (1) it is not easily clogged; (2) it provides a more accurate measure of the amount of solids in the wastewater; (3) it is relatively uncomplicated; (4) it is readily adaptable to scooping samples manually while at the same time permitting direct pumping for higher accuracy; and (5) it does not require continuous attendance and may fill sequentially composite containers automatically.

Although a specific embodiment has been described with some particularity, many modifications and variations may be made in this specific embodiment without deviating from the invention. Therefore, it is to be understood that, within the scope of the appended claims, the invention may be practiced other than as specifically described.

ATTACHMENT A

```
0001            *
0002            *   program ram
0003            *
0004 0050           ORG  $0050
0005 0050       FIRST_TIME_FLAG    RMB  1
0006            *
0007 0051       SAMPLER_STATE      RMB  1
0008 0052       PROGRAM_CHOICE     RMB  1
0009            *
0010 0053       SAMPLER_PACE       RMB  1
0011 0054       SAMPLER_MODE       RMB  1
0012 0055       SWITCH_MODE        RMB  1
0013 0056       NOMINAL_VOLUME0    RMB  1
0014 0057       NOMINAL_VOLUME     RMB  2
0015 0059       NUM_OF_SAMPLES0    RMB  1
0016 005a       NUM_OF_SAMPLES     RMB  2
0017            *
0018 005c       NOMINAL_COUNT      RMB  3
0019 005f       CALIBRATE_COUNT    RMB  2
0020 0061       LIMIT_SAMPLES0     RMB  1
0021 0062       LIMIT_SAMPLES      RMB  2
0022            ***** could be temp
0023            ***** cannot interfere with divide or add?
0024            *
0025 0064       YEAR_OF_FIRST      RMB  1
0026 0065       MONTH_OF_FIRST     RMB  1
0027 0066       DAY_OF_FIRST       RMB  1
0028 0067       HOUR_OF_FIRST      RMB  1
0029 0068       MINUTE_OF_FIRST    RMB  1
0030 0069       INTERVAL_HOURS     RMB  1
0031 006a       INTERVAL_MINUTE    RMB  1
0032 006b       INTERVAL_FLOW      RMB  2
0033            *
0034 006d       BOTTLE_VOLUME      RMB  3
0035 0070       YES_NO_QUESTION    RMB  1
0036 0071       WARN_COUNT         RMB  4
0037 0075       FLOW_SAMPLE        RMB  1
0038 0076       INHIBIT_SAMPLE     RMB  1
0039 0077       INHIBIT_LOAD_T     RMB  1
0040 0078       INHIBIT_COUNT      RMB  1
0041 0079       CALIBRATE          RMB  1
0042 007a       PROGRAM_LOCK       RMB  1
0043 007b       PUMP_LIGHT_MODE    RMB  1
0044 007c       ENTER_MODE         RMB  1
0045 007d       RESTORE_SAMPLE     RMB  1
0046 007e       MANUAL_GRAB        RMB  1
0047            *
0048 007f       TAKE_A_SAMPLE      RMB  2
0049 0081       SAMPLE_NUMBER      RMB  2
0050 0083       PUMP_CYCLE         RMB  1
0051            *   indicates what stage of sampling is occurring
0052            *   = 0 when not sampling
0053            *   = 1 during prepurge
0054            *   = 2 during fill cycle
```

```
0055                  *      = 3 during postpurge
0056 0084             PUMP_COUNT      RMB 2
0057 0086             SAMPLE_PAUSE    RMB 1
0058 0087             FLOW_PULSES     RMB 3
0059 008a             FLOW_TO_NEXT    RMB 2
0060 008c             BOTTLE_NUMBER   RMB 1
0061 008d             SAMPLE_BOTTLE   RMB 1
0062 008e             SAMPLES_TAKEN   RMB 2
0063                  *
0064 0090             FAULT_BYTE      RMB 1
0065                  *
0066 0091             RTC_YEAR        RMB 1
0067 0092             RTC_MONTH       RMB 1
0068 0093             RTC_DAY         RMB 1
0069 0094             RTC_HOUR        RMB 1
0070 0095             RTC_MINUTE      RMB 1
0071 0096             RTC_SECOND      RMB 1
0072 0097             RTC_MILLISECOND RMB 1
0073                  *
0074 0098             TUBING_WEAR     RMB 4
0075                  *
0076 009c             PASS_NUMBER     RMB 2
0077                  ***** could be temp
0078 009e             VOLUME_DELIVER  RMB 2
0079                  ***** could be temp
0080                  *
0081 00a0             KEY_MASK        RMB 1
0082 00a1             PGM_BRANCH      RMB 1
0083 00a2             PGM_CHOICE      RMB 1
0084 00a3             PGM_VALUE       RMB 9
0085 00ac             PGM_STORAGE     RMB 1
0086 00ad             PGM_SELECTIONS  RMB 1
0087 00ae             PGM_LENGTH      RMB 1
0088 00af             PGM_DIGIT       RMB 1
0089 00b0             PGM_LCD         RMB 1
0090 00b1             FLASH           RMB 1
0091 00b2             PGM_LIMIT       RMB 1
0092                  *
0093 00b3             KEY_CODE        RMB 1
0094 00b4             KEY_COUNT       RMB 1
0095 00b5             IRQ_INTERRUPT   RMB 1
0096                  *
0097 00b6             TEMP            RMB 1
0098 00b7             TEMP2           RMB 1
0099 00b8             TEMP3           RMB 1
0100 00b9             TEMP4           RMB 1
0101 00ba             TEMP5           RMB 1
0102                  TEMP_YEAR
0103 00bb             TEMP6           RMB 1
0104                  TEMP_MONTH
0105 00bc             TEMP7           RMB 1
0106                  TEMP_DAY
0107                  TEMP_BOTTLE
0108 00bd             TEMP8           RMB 1
```

```
0109              TEMP_HOUR
0110              TEMP_VOLUME
0111              TEMP_SAMPLES
0112 00be         TEMP9           RMB  1
0113 00bf         TEMP_MINUTE     RMB  1
0114              *
0115 00c0         BIT_DATA        RMB  3
0116 00c3         DIST_TIMER      RMB  1
0117              *   indicates when distributor is moving
0118              *    = 0 when distributor is not moving
0119              *    = seconds to timeout when distributor is moving
0120 00c4         DISPLAY_TIMEOUT RMB  1
0121 00c5         DELAY_TIMER     RMB  1
0122 00c6         REVIEW_BRANCH   RMB  1
0123 00c7         PUMP_JAM        RMB  1
0124 00c8         EVENT_MARK_TIME RMB  1
0125 00c9         MINUTE_PASSED   RMB  1
0126              ***** could be temp
0127 00ca         PURGE_TIMER     RMB  1
0128 00cb         MATH_COUNTER    RMB  1
0129 00cc         CHECKSUM        RMB  1
0130 00cd         RTC_SAVE        RMB  1
0131              *
0132              *    ORG  $00E6
0133 00ce         EXTENDED        RMB  4
0134              *
0135 00d2         RUN_PARAMETERS  RMB  9
0136              ***** does nominal count need to be in run parameters?
0137 00db         PGM_SAVE        RMB  3
0138              *
0139              *   program equ
0140              *
0141 0000         PORT_A          EQU  $00
0142 0001         PORT_B          EQU  $01
0143 0002         PORT_C          EQU  $02
0144 0003         PORT_D          EQU  $03
0145 0004         PORT_A_DIR      EQU  $04
0146 0005         PORT_B_DIR      EQU  $05
0147 0006         PORT_C_DIR      EQU  $06
0148 0007         PORT_D_DIR      EQU  $07
0149
0150 0012         TIMER_CONTROL   EQU  $12
0151 0007         INT_CAPTURE     EQU  7
0152 0006         INT_COMPARE     EQU  6
0153 0005         INT_OVERFLOW    EQU  5
0154 0001         INPUT_EDGE      EQU  1
0155 0000         OUTPUT_LEVEL    EQU  0
0156 0013         TIMER_STATUS    EQU  $13
0157 0007         INPUT_CAPTURE   EQU  7
0158 0006         OUTPUT_COMPARE  EQU  6
0159 0005         TIMER_OVERFLOW  EQU  5
0160
0161 0014         CAPTURE_HIGH    EQU  $14
0162 0015         CAPTURE_LOW     EQU  $15
```

```
0163 0016           COMPARE_HIGH        EQU  $16
0164 0017           COMPARE_LOW         EQU  $17
0165 0018           COUNTER_HIGH        EQU  $18
0166 0019           COUNTER_LOW         EQU  $19
0167 001a           A_COUNTER_HIGH      EQU  $1A
0168 001b           A_COUNTER_LOW       EQU  $1B
0169
0170 00a5           FIRST_TIME_SET      EQU  $A5
0171
0172 0003           PUMP_REVERSE        EQU  3
0173 0001           PUMP_REVERSE_P      EQU  PORT_B
0174 0004           PUMP_FORWARD        EQU  4
0175 0001           PUMP_FORWARD_P      EQU  PORT_B
0176 0005           DIST_RIGHT          EQU  5          *motor
0177 0001           DIST_RIGHT_P        EQU  PORT_B
0178 0006           DIST_LEFT           EQU  6          *motor
0179 0001           DIST_LEFT_P         EQU  PORT_B
0180 0007           RIGHT_LIGHT         EQU  7
0181 0001           RIGHT_LIGHT_P       EQU  PORT_B
0182
0183 0000           LEFT_LIGHT          EQU  0
0184 0002           LEFT_LIGHT_P        EQU  PORT_C
0185 0001           FAULT_LIGHT         EQU  1
0186 0002           FAULT_LIGHT_P       EQU  PORT_C
0187 0002           BUZZER              EQU  2
0188 0002           BUZZER_P            EQU  PORT_C
0189 0003           PUMP_LIGHT          EQU  3
0190 0002           PUMP_LIGHT_P        EQU  PORT_C
0191
0192 0001           MUX                 EQU  1
0193 0003           MUX_P               EQU  PORT_D
0194 0002           DIVERT_BOTTLE       EQU  2          *distributor position
0195 0003           DIVERT_BOTTLE_P     EQU  PORT_D
0196 0003           DIVERT_QUAD         EQU  3          *distributor position
0197 0003           DIVERT_QUAD_P       EQU  PORT_D
0198 0004           INHIBIT             EQU  4
0199 0003           INHIBIT_P           EQU  PORT_D
0200 0005           BOTTLE_RIGHT        EQU  5
0201 0003           BOTTLE_RIGHT_P      EQU  PORT_D
0202 0007           BOTTLE_LEFT         EQU  7
0203 0003           BOTTLE_LEFT_P       EQU  PORT_D
0204
0205 00f6           FLOW_PULSE          EQU  $F6
0206 00f7           PUMP_VOLUME         EQU  $F7
0207
0208 0006           TEST                EQU  6
0209
0210 0006           LCD_RS              EQU  6
0211 0002           LCD_RS_P            EQU  PORT_C
0212 0005           LCD_RW              EQU  5
0213 0002           LCD_RW_P            EQU  PORT_C
0214 0004           LCD_E               EQU  4
0215 0002           LCD_E_P             EQU  PORT_C
0216 0000           LCD_BUS_P           EQU  PORT_A
```

```
0217 0004              LCD_BUS_PD        EQU   PORT_A_DIR
0218 0001              LCD_CLEAR         EQU   $01
0219 0007              LCD_BUSY_FLAG     EQU   7
0220 0040              LCD_LINE_2        EQU   $40
0221 0080              LCD_ADDRESS       EQU   $80
0222 002f              SLASH             EQU   $2F
0223 003a              COLON             EQU   $3A
0224 0020              SPACE             EQU   $20
0225
0226 0006              RTC_RD            EQU   6
0227 0002              RTC_RD_P          EQU   PORT_C
0228 0005              RTC_WR            EQU   5
0229 0002              RTC_WR_P          EQU   PORT_C
0230 0007              RTC_CS            EQU   7
0231 0002              RTC_CS_P          EQU   PORT_C
0232 0000              RTC_BUS_P         EQU   PORT_A
0233 0004              RTC_BUS_PD        EQU   PORT_A_DIR
0234
0235 0000              RTC_SEC_1         EQU   $00
0236 0010              RTC_SEC_10        EQU   $10
0237 0020              RTC_MIN_1         EQU   $20
0238 0030              RTC_MIN_10        EQU   $30
0239 0040              RTC_HOUR_1        EQU   $40
0240 0050              RTC_HOUR_10       EQU   $50
0241 0060              RTC_DAY_1         EQU   $60
0242 0070              RTC_DAY_10        EQU   $70
0243 0080              RTC_MON_1         EQU   $80
0244 0090              RTC_MON_10        EQU   $90
0245 00a0              RTC_YEAR_1        EQU   $A0
0246 00b0              RTC_YEAR_10       EQU   $B0
0247 00c0              RTC_WEEK          EQU   $C0
0248 00d0              RTC_REG_D         EQU   $D0
0249 00e0              RTC_REG_E         EQU   $E0
0250 00f0              RTC_REG_F         EQU   $F0
0251
0252 0000              DATA_BUS_P        EQU   PORT_A
0253 0004              DATA_BUS_PD       EQU   PORT_A_DIR
0254 0000              DATA_BUS_IN       EQU   $00
0255 00ff              DATA_BUS_OUT      EQU   $FF
0256 00f0              DATA_BUS_IN_OUT   EQU   $F0
0257
0258 0000              STATE_OFF         EQU   00
0259 0001              STATE_STANDBY     EQU   01
0260 0002              STATE_PGM         EQU   02
0261 0003              STATE_FULL        EQU   03
0262                   ***** same as standby
0263                   ***** would change sampler states in main
0264 0004              STATE_RUN         EQU   04    ***** run states must be highest numbers
0265 0004              STATE_RUN_FIRST   EQU   04
0266 0005              STATE_RUN_TIME    EQU   05
0267 0006              STATE_RUN_FLOW    EQU   06
0268
0269 0000              PGM_SAMPLER_YES   EQU   $00
0270 0001              PGM_OPTIONS_YES   EQU   $01
```

```
0271 0000            PACE_TIME           EQU  $00
0272 0001            PACE_FLOW           EQU  $01
0273 0000            MODE_CONTINUOUS     EQU  $00
0274 0001            MODE_SPLIT          EQU  $01
0275 0000            TIME_SWITCHED       EQU  $00
0276 0001            FLOW_SWITCHED       EQU  $01
0277
0278 0000            YES_NO_YES          EQU  $00
0279 0001            YES_NO_NO           EQU  $01
0280 0000            INH_SAMPLE_YES      EQU  $00
0281 0001            INH_SAMPLE_NO       EQU  $01
0282 0000            INH_LOAD_T_YES      EQU  $00
0283 0001            INH_LOAD_T_NO       EQU  $01
0284 0000            INH_COUNT_YES       EQU  $00
0285 0001            INH_COUNT_NO        EQU  $01
0286 0000            FLOW_SAMPLE_YES     EQU  $00
0287 0001            FLOW_SAMPLE_NO      EQU  $01
0288 0000            PUMP_LIGHT_BOTH     EQU  $00
0289 0001            PUMP_LIGHT_FWD      EQU  $01
0290 0002            PUMP_LIGHT_REV      EQU  $02
0291 0000            ENTER_SAMPLES       EQU  $00
0292 0001            ENTER_VOLUME        EQU  $01
0293 0002            ENTER_BOTH          EQU  $02
0294 0000            CAL_ENABLE          EQU  $00
0295 0001            CAL_DISABLE         EQU  $01
0296 0000            LOCK_ENABLE         EQU  $00
0297 0001            LOCK_DISABLE        EQU  $01
0298 0000            RESTORE_YES         EQU  $00
0299 0001            RESTORE_NO          EQU  $01
0300 0000            MANUAL_SAMPLE       EQU  $00
0301 0001            GRAB_SAMPLE         EQU  $01
0302
0303 0005            LIMIT_9_BIT         EQU  5
0304 0020            LIMIT_9_YES         EQU  $20
0305 0000            LIMIT_9_NO          EQU  $00
0306 0006            LEADING_0_BIT       EQU  6
0307 0040            LEADING_0_YES       EQU  $40
0308 0000            LEADING_0_NO        EQU  $00
0309 0007            VALID_0_BIT         EQU  7
0310 0080            VALID_0_YES         EQU  $80
0311 0000            VALID_0_NO          EQU  $00
0312
0313 0004            PUMP_CYCLE_MAX      EQU  $04
0314 0002            PUMP_CYCLE_2        EQU  $02
0315 0001            PRE_PURGE_HIGH      EQU  $01
0316 0000            PRE_PURGE_LOW       EQU  $00
0317 0003            POST_PURGE_HIGH     EQU  $03
0318 0000            POST_PURGE_LOW      EQU  $00
0319 0005            RESUME_PURGE        EQU  $5
0320 0008            SAMPLE_PAUSE_1      EQU  8
0321 0008            SAMPLE_PAUSE_2      EQU  8
0322 0008            SAMPLE_PAUSE_3      EQU  8
0323 0004            PUMP_PAUSE_TIME     EQU  $04
0324 0000            NEITHER_BOTTLE      EQU  0
```

```
0325 0001              LEFT_BOTTLE       EQU  1
0326 0002              RIGHT_BOTTLE      EQU  2
0327
0328 0003              KEY_COUNT_MAX     EQU  3
0329 0000              MASK_OFF          EQU  $00
0330 0004              MASK_STANDBY      EQU  $04
0331 0004              MASK_FULL         EQU  $04
0332 0008              MASK_PGM_SELECT   EQU  $08
0333 000c              MASK_PGM_ENTER    EQU  $0C
0334 0010              MASK_RUN          EQU  $10
0335 0014              MASK_PGM_MANUAL   EQU  $14
0336 0018              MASK_PGM_STOP     EQU  $18
0337 001c              MASK_PGM_NONE     EQU  $1C
0338
0339 0002              DELAY_TIME        EQU  2
0340
0341 0018              CODE_STOP         EQU  @30
0342 0019              CODE_BOTTLE       EQU  @31
0343 001a              CODE_LEFT         EQU  @32
0344 001b              CODE_0            EQU  @33
0345 001c              CODE_RIGHT        EQU  @34
0346 001d              CODE_ENTER_PGM    EQU  @35
0347 0010              CODE_JOG_REV      EQU  @20
0348 0011              CODE_MANUAL       EQU  @21
0349 0012              CODE_1            EQU  @22
0350 0013              CODE_2            EQU  @23
0351 0014              CODE_3            EQU  @24
0352 0015              CODE_CLEAR        EQU  @25
0353 000B              CODE_JOG_FWD      EQU  @10
0354 0009              CODE_RESUME       EQU  @11
0355 000a              CODE_4            EQU  @12
0356 000b              CODE_5            EQU  @13
0357 000c              CODE_6            EQU  @14
0358 000d              CODE_EXIT_PGM     EQU  @15
0359 0000              CODE_ON_OFF       EQU  @00
0360 0001              CODE_START_PGM    EQU  @01
0361 0002              CODE_7            EQU  @02
0362 0003              CODE_8            EQU  @03
0363 0004              CODE_9            EQU  @04
0364 0005              CODE_STATUS       EQU  @05
0365
0366 00dc              PGM_NODE          EQU  $DC
0367 00dd              PGM_FOLLOW        EQU  $DD
0368 00de              PGM_YES_NO_NO     EQU  $DE
0369 00df              END_OF_MESSAGE    EQU  $DF
0370 00e0              END_OF_DISPLAY    EQU  $E0
0371 00e1              END_OF_BRANCH     EQU  $E1
0372 00e2              PGM_SPECIAL_1     EQU  $E2
0373 00e3              PGM_SPECIAL_2     EQU  $E3
0374 00e4              PGM_SPECIAL_3     EQU  $E4
0375 00e5              PGM_SPECIAL_4     EQU  $E5
0376 00e6              PGM_SPECIAL_5     EQU  $E6
0377 00e7              PGM_SPECIAL_6     EQU  $E7
0378 00e8              PGM_SPECIAL_7     EQU  $E8
```

```
0379 00e9          PGM_SPECIAL_8      EQU  $E9
0380 00ea          PGM_SPECIAL_9      EQU  $EA
0381 00eb          PGM_SPECIAL_10     EQU  $EB
0382 00ec          PGM_SPECIAL_11     EQU  $EC
0383 00ed          PGM_SPECIAL_12     EQU  $ED
0384 00ee          PGM_SPECIAL_13     EQU  $EE
0385 00ef          PGM_SPECIAL_14     EQU  $EF
0386 00f0          PGM_SPECIAL_15     EQU  $F0
0387 00f1          PGM_SPECIAL_16     EQU  $F1
0388 00f2          PGM_SPECIAL_17     EQU  $F2
0389 00f3          PGM_SPECIAL_18     EQU  $F3
0390 00f4          PGM_SPECIAL_19     EQU  $F4
0391 00f5          PGM_SPECIAL_20     EQU  $F5
0392 00f6          PGM_SPECIAL_21     EQU  $F6
0393 00f7          PGM_SPECIAL_22     EQU  $F7
0394 00f8          PGM_SPECIAL_23     EQU  $F8
0395 00f9          PGM_SPECIAL_24     EQU  $F9
0396 00fa          PGM_SPECIAL_25     EQU  $FA
0397 00fb          PGM_SPECIAL_26     EQU  $FB
0398 00fc          PGM_SPECIAL_27     EQU  $FC
0399 00fd          PGM_SPECIAL_28     EQU  $FD
0400 00fe          PGM_SPECIAL_29     EQU  $FE
0401 00ff          PGM_SPECIAL_30     EQU  $FF
0402
0403 00c6          OPCODE_LDA_EXT     EQU  $C6
0404 00b7          OPCODE_STA_DIR     EQU  $B7
0405 0081          OPCODE_RTS         EQU  $81
0406
0407 0006          DIST_TIMER_MAX     EQU  6
0408 00ff          PUMP_JAM_MAX       EQU  255
0409 0040          EVENT_MARK_MAX     EQU  64
0410 000f          DISPLAY_MAX        EQU  15
0411
0412 0000          READY_LEFT         EQU  0
0413 00c0          READY_LEFT_B       EQU  BIT_DATA
0414 0001          READY_RIGHT        EQU  1
0415 00c0          READY_RIGHT_B      EQU  BIT_DATA
0416 0002          LEFT_FULL          EQU  2
0417 00c0          LEFT_FULL_B        EQU  BIT_DATA
0418 0003          RIGHT_FULL         EQU  3
0419 00c0          RIGHT_FULL_B       EQU  BIT_DATA
0420 0004          SAMPLING_BIT       EQU  4
0421 00c0          SAMPLING_BYTE      EQU  BIT_DATA
0422               *    indicates when programmed or grab sampling is occurring
0423               *    = 0 when not sampling
0424               *    = 1 when sampling
0425 0005          MANUAL_BIT         EQU  5
0426 00c0          MANUAL_BYTE        EQU  BIT_DATA
0427               *    indicates when grab sampling is occurring
0428               *    = 0 when not grab sampling
0429               *    = 1 when grab sampling
0430 0006          DIGIT_DISPLAYED    EQU  6
0431 00c0          DIGIT_DISP_BYTE    EQU  BIT_DATA
0432
```

```
0433 0000              INHIBIT_BIT      EQU  0
0434 00c1              INHIBIT_BYTE     EQU  BIT_DATA+1
0435 0001              FLOW_PIN         EQU  1
0436 00c1              FLOW_BYTE        EQU  BIT_DATA+1
0437 0002              VOLUME_PIN       EQU  2
0438 00c1              VOLUME_BYTE      EQU  BIT_DATA+1
0439 0003              READY_BIT        EQU  3
0440 0008              READY_B          EQU  $08
0441 00c1              READY_BYTE       EQU  BIT_DATA+1
0442 0004              YES_NO_BIT       EQU  4
0443 0010              YES_NO_B         EQU  $10
0444 00c1              YES_NO_BYTE      EQU  BIT_DATA+1
0445 0005              PGM_UNLOCK_BIT   EQU  5
0446 00c1              PGM_UNLOCK_BYTE  EQU  BIT_DATA+1
0447 0006              BOTTLE_BIT       EQU  6
0448 00c1              BOTTLE_BYTE      EQU  BIT_DATA+1
0449
0450 0000              DIVERT_LEFT      EQU  0
0451 00c2              DIVERT_LEFT_P    EQU  BIT_DATA+2
0452 0001              DIVERT_RIGHT     EQU  1
0453 00c2              DIVERT_RIGHT_P   EQU  BIT_DATA+2
0454
0455 0001              F_POWER_FAIL     EQU  $01
0456 0002              F_EPROM_FAIL     EQU  $02
0457 0004              F_PUMP_JAM       EQU  $04
0458 0008              F_DIST_JAM       EQU  $08
0459 0010              F_TUBING         EQU  $10
0460 0000              B_POWER_FAIL     EQU  0
0461 0001              B_EPROM_FAIL     EQU  1
0462 0002              B_PUMP_JAM       EQU  2
0463 0003              B_DIST_JAM       EQU  3
0464 0004              B_TUBING         EQU  4
0465 00f0              FAULTS_W_D_TUBE  EQU  $F0
0466
0467 00a0              VOCABULARY       EQU  $A0   -
0468
0469 00a1              V__BASED         EQU  VOCABULARY+1
0470 00a2              V_BOTTLE         EQU  VOCABULARY+2
0471 00a3              V_CALIBRATE_     EQU  VOCABULARY+3
0472 00a4              V_CONTINUOUS     EQU  VOCABULARY+4
0473 00a5              V_COUNT          EQU  VOCABULARY+5
0474 00a6              V_DISABLE        EQU  VOCABULARY+6
0475 00a7              V_EACH           EQU  VOCABULARY+7
0476 00a8              V_ENABLE         EQU  VOCABULARY+8
0477 00a9              V_ENTER_         EQU  VOCABULARY+9
0478 00aa              V_EVERY          EQU  VOCABULARY+10
0479 00ab              V_FAIL_          EQU  VOCABULARY+11
0480 00ac              V___FAULT___     EQU  VOCABULARY+12
0481 00ad              V__FAULTS        EQU  VOCABULARY+13
0482 00ae              V_FIRST          EQU  VOCABULARY+14
0483 00af              V_FLOW           EQU  VOCABULARY+15
0484 00b0              V_FWD            EQU  VOCABULARY+16
0485 00b1              V_GRAB_          EQU  VOCABULARY+17
0486 00b2              V_HOURS          EQU  VOCABULARY+18
```

```
0487 00b3            V_INHIBIT       EQU   VOCABULARY+19
0488 00b4            V_JAMMED        EQU   VOCABULARY+20
0489 00b5            V_KEY           EQU   VOCABULARY+21
0490 00b6            V_LIGHT         EQU   VOCABULARY+22
0491 00b7            V_LOCK_         EQU   VOCABULARY+23
0492 00b8            V_MANUAL_       EQU   VOCABULARY+24
0493 00b9            V_MINUTES       EQU   VOCABULARY+25
0494 00ba            V_ml_           EQU   VOCABULARY+26
0495 00bb            V_NO            EQU   VOCABULARY+27
0496 00bc            V__OF_          EQU   VOCABULARY+28
0497 00bd            V____OK_        EQU   VOCABULARY+29
0498 00be            V_OPTION        EQU   VOCABULARY+30
0499 00bf            V_PACED         EQU   VOCABULARY+31
0500 00c0            V_POWER_        EQU   VOCABULARY+32
0501 00c1            V_PRESS_        EQU   VOCABULARY+33
0502 00c2            V_PROGRAM_      EQU   VOCABULARY+34
0503 00c3            V_PULSES        EQU   VOCABULARY+35
0504 00c4            V_PUMP_         EQU   VOCABULARY+36
0505 00c5            V_READY____     EQU   VOCABULARY+37
0506 00c6            V_RESET_        EQU   VOCABULARY+38
0507 00c7            V_REV           EQU   VOCABULARY+39
0508 00c8            V_REVISION      EQU   VOCABULARY+40
0509 00c9            V_RUNNING_      EQU   VOCABULARY+41
0510 00ca            V_SAMPLE        EQU   VOCABULARY+42
0511 00cb            V_SAMPLES       EQU   VOCABULARY+43
0512 00cc            V_SAMPLING      EQU   VOCABULARY+44
0513 00cd            V_SOFTWARE_     EQU   VOCABULARY+45
0514 00ce            V_SPLIT         EQU   VOCABULARY+46
0515 00cf            V_START         EQU   VOCABULARY+47
0516 00d0            V_SWITCH        EQU   VOCABULARY+48
0517 00d1            V_TAKE          EQU   VOCABULARY+49
0518 00d2            V_THEN_         EQU   VOCABULARY+50
0519 00d3            V_TIME          EQU   VOCABULARY+51
0520 00d4            V_TUBING        EQU   VOCABULARY+52
0521 00d5            V_VOLUME        EQU   VOCABULARY+53
0522 00d6            V_WARNING       EQU   VOCABULARY+54
0523 00d7            V__WHEN_        EQU   VOCABULARY+55
0524 00d8            V_YES           EQU   VOCABULARY+56
0525 00d9            V__YES__NO_     EQU   VOCABULARY+57
0526                 *
0527                 *    program main
0528                 *
0529 1ff4                ORG    $1FF4
0530 1ff4 01 00          FDB    MAIN              *interrupt vectors
0531 1ff6 01 00          FDB    MAIN              *spi
0532 1ff8 01 65          FDB    TIMER             *sci
0533 1ffa 01 00          FDB    MAIN              *timer
0534 1ffc 01 00          FDB    MAIN              *irq
0535 1ffe 01 00          FDB    MAIN              *svi
0536                                              *reset
0537 1efe                ORG    $1EFE
0538                 VERSION_NUMBER
0539 1efe 02             FCB    $02               *software version number
0540                 CHECKSUM_BYTE
```

```
0541 1eff 1a              FCB   $1A              *eprom checksum byte
0542                  *
0543 0020                 ORG   $0020
0544                  MODEL_NUMBER
0545 0020 37 60           FDB   $3760            *model number for program lock
0546                  MAXIMUM_VOLUME0
0547                  MAXIMUM_NUMBER0
0548 0022 00              FCB   $00              *maximum nominal sample volume in ml
0549                  MAXIMUM_VOLUME
0550                  MAXIMUM_NUMBER
0551 0023 09              FCB   $09              *also maximum number of samples
0552 0024 99              FCB   $99
0553                  MINIMUM_VOLUME0
0554 0025 00              FCB   $00              *minimum nominal sample volume in ml
0555                  MINIMUM_VOLUME
0556 0026 00              FCB   $00
0557 0027 10              FCB   $10
0558                  MAXIMUM_COUNT
0559 0028 02              FCB   $02              *maximum calibration addition
0560 0029 50              FCB   $50
0561                  MINIMUM_COUNT
0562 002a 97              FCB   $97              *maximum calibration subtraction
0563 002b 50              FCB   $50
0564                  *
0565                  *   lda extended indirect using self modifying code
0566                  *   increment double byte address for extended indirect
0567                  *
0568                  LDA_EXTENDED
0569 002c a6 c6           LDA   #OPCODE_LDA_EXT
0570 002e b7 ce           STA   EXTENDED         ***** could locate opcode at last rom byte
0571 0030 a6 81           LDA   #OPCODE_RTS
0572 0032 b7 d1           STA   EXTENDED+3
0573 0034 bd ce           JSR   EXTENDED
0574                  INC_EXTENDED
0575 0036 b7 b6           STA   TEMP
0576 0038 a6 01           LDA   #1
0577 003a bb d0           ADD   EXTENDED+2
0578 003c b7 d0           STA   EXTENDED+2
0579 003e 4f              CLRA
0580 003f b9 cf           ADC   EXTENDED+1
0581 0041 b7 cf           STA   EXTENDED+1
0582 0043 b6 b6           LDA   TEMP
0583 0045 81              RTS
0584                  *
0585 0100                 ORG   $0100
0586                  *
0587                  MAIN
0588                  *
0589 0100 9b              SEI                    *disable interrupts
0590 0101 9c              RSP                    *reset stack pointer
0591                  *
0592 0102 4f              CLRA                   *clear option register
0593 0103 c7 1f df        STA   $1FDF            *irq edge sensitive only
0594                  *
```

```
0595 0106 1e b3          BSET 7,KEY_CODE         *set key code to invalid key
0596                 *
0597 0108 3f b5          CLR  IRQ_INTERRUPT
0598 010a 3f c3          CLR  DIST_TIMER
0599 010c 3f c6          CLR  REVIEW_BRANCH
0600 010e 3f c8          CLR  EVENT_MARK_TIME
0601 0110 3f b1          CLR  FLASH
0602 0112 3f ca          CLR  PURGE_TIMER
0603 0114 3f cb          CLR  MATH_COUNTER
0604                 *
0605                 *   initialize bit flags
0606                 *
0607                 *   bottle = 0
0608                 *   pgm unlock = 0
0609                 *   yes no bit = 0
0610                 *   ready bit = 0
0611                 *   volume pin = 0
0612                 *   flow pin = 0
0613                 *   inhibit bit = 1
0614 0116 a6 01          LDA  #%00000001
0615 0118 b7 c1          STA  BIT_DATA+1
0616                 *
0617                 *   divert right = 0
0618                 *   divert left = 0
0619 011a a6 00          LDA  #%00
0620 011c b7 c2          STA  BIT_DATA+2
0621                 *
0622                 *   initialize port pins, inputs, and outputs
0623                 *
0624                 *   port a
0625                 *   bidirectional data bus
0626                 *
0627                 *   port b
0628                 *   7 = output, right bottle full light off
0629                 *   6 = output, distributor reverse off
0630                 *   5 = output, distributor forward off
0631                 *   4 = output, pump reverse off
0632                 *   3 = output, pump forward off
0633                 *   2 = input, spare
0634                 *   1 = input, spare
0635                 *   0 = input, spare
0636 011e a6 00          LDA  #%00000000
0637 0120 b7 01          STA  PORT_B
0638 0122 a6 f8          LDA  #%11111000
0639 0124 b7 05          STA  PORT_B_DIR
0640                 *
0641                 *   port c
0642                 *   7 = output, rtc /chip select high
0643                 *   6 = output, lcd register select, rtc read low
0644                 *   5 = output, lcd read/write, rtc write low
0645                 *   4 = output, lcd enable low
0646                 *   3 = output, pump running light off
0647                 *   2 = output, buzzer off
0648                 *   1 = output, fault light off
```

```
0649                  *    0 = output, left bottle full light off
0650 0126 a6 82            LDA   #Z10000010
0651 0128 b7 02            STA   PORT_C
0652 012a a6 ff            LDA   #Z11111111
0653 012c b7 06            STA   PORT_C_DIR
0654                  *
0655                  *    port d
0656                  *    7 = input, left bottle presence
0657                  *    5 = input, right bottle presence
0658                  *    4 = input, inhibit
0659                  *    3 = input, distributor position right
0660                  *    2 = input, distributor position left
0661                  *    1 = input, multiplexer output
0662                  *    0 = input, spare
0663                  *
0664                  *    initialization routines
0665                  *
0666 012e cd 01 f6         JSR   RAM_INIT          *initialize ram
0667 0131 cd 01 6c         JSR   RTC_INIT          *initialize real time clock
0668 0134 a6 a5            LDA   #FIRST_TIME_SET   *set first time flag
0669 0136 b7 50            STA   FIRST_TIME_FLAG
0670 0138 cd 02 5a         JSR   LCD_INIT          *initialize lcd
0671 013b cd 03 a3         JSR   NEW_FIRST_TIME    *update time of first/next sample
0672 013e cd 16 50         JSR   RUN_CLEAR
0673 0141 cd 05 65         JSR   PERIODIC_SCAN
0674                  *
0675 0144 b6 51            LDA   SAMPLER_STATE
0676 0146 ae 03            LDX   #3
0677 0148 42               MUL                     *multiply sampler state by 3
0678 0149 97               TAX
0679 014a dc 01 4d         JMP   SAMPLER_STATES,X  *branch to sampler state
0680                  *
0681                  SAMPLER_STATES
0682 014d cc 06 8e         JMP   OFF_STATE
0683 0150 cc 06 a6         JMP   STANDBY_STATE
0684 0153 cc 09 64         JMP   PGM_STATE
0685 0156 cc 13 e3         JMP   FULL_STATE
0686 0159 cc 13 a1         JMP   RUN_STATE
0687 015c cc 13 a1         JMP   RUN_STATE
0688 015f cc 13 a1         JMP   RUN_STATE
0689 0162 cc 13 a1         JMP   RUN_STATE
0690                  *
0691                  *    increments interrupt flag after input capture
0692                  *
0693                  *
0694                  TIMER
0695                  *
0696 0165 b6 13            LDA   TIMER_STATUS
0697 0167 b6 15            LDA   CAPTURE_LOW       *clear input capture flag
0698 0169 3c b5            INC   IRQ_INTERRUPT     *increment interrupt flag
0699 016b 80               RTI
0700                  *
0701                  *    program init
0702                  *
```

```
0703                  *    initialize real time clock
0704                  *
0705                  RTC_INIT
0706                  ***** should set rtc interrupt to 64 hz before using delay
0707 016c b6 50            LDA  FIRST_TIME_FLAG
0708 016e a1 a5            CMP  #FIRST_TIME_SET
0709 0170 26 6f            BNE  RTC_FIRST_TIME    *branch if first time not set
0710 0172 a6 e0            LDA  #$E0
0711 0174 cd 1a f0         JSR  RTC_READ
0712 0177 a1 e0            CMP  #$E0              ***** is this test necessary?
0713 0179 26 66            BNE  RTC_FIRST_TIME    *branch if rtc not initialized
0714 017b a6 f0            LDA  #$F0
0715 017d cd 1a f0         JSR  RTC_READ
0716 0180 a1 f4            CMP  #$F4              ***** is this test necessary?
0717 0182 26 5d            BNE  RTC_FIRST_TIME    *branch if rtc not initialized
0718                  *
0719                  *    reads upper and lower date/time digits from rtc
0720                  *    and stores in ram
0721                  *
0722 0184 4f               CLRA
0723 0185 b7 b6            STA  TEMP              *temp holds rtc address in upper nibble
0724 0187 ae 05            LDX  #5
0725 0189 bf b7            STX  TEMP2             *temp2 holds rtc ram offset
0726                  NXT_RTC_RESTORE
0727 018b cd 1a f0         JSR  RTC_READ          *read low date/time digit
0728 018e a4 0f            AND  #$0F
0729 0190 b7 b8            STA  TEMP3             *and save
0730 0192 b6 b6            LDA  TEMP              *restore address
0731 0194 ab 10            ADD  #$10              *change to high digit address
0732 0196 b7 b6            STA  TEMP              *and resave
0733 0198 cd 1a f0         JSR  RTC_READ          *read high date/time digit
0734 019b 48               ASLA
0735 019c 48               ASLA                   *shift to upper nibble
0736 019d 48               ASLA
0737 019e 48               ASLA
0738 019f ba b8            ORA  TEMP3             *append low date/time digit
0739 01a1 be b7            LDX  TEMP2             *load rtc ram offset
0740 01a3 e7 91            STA  RTC_YEAR,X        *store date/time in ram
0741 01a5 b6 b6            LDA  TEMP              *restore address
0742 01a7 ab 10            ADD  #$10              *change to high digit address
0743 01a9 b7 b6            STA  TEMP              *and resave
0744                  ***** could be bsr subroutine
0745 01ab 3a b7            DEC  TEMP2             *decrement rtc ram offset
0746 01ad 2a dc            BPL  NXT_RTC_RESTORE   *branch if more date/time to restore
0747                  *
0748 01af 20 3c            BRA  RTC_INIT_EXIT
0749                  *
0750                  *    writes upper and lower date/time digits in ram to rtc
0751                  *
0752                  ***** would be better if this initialized seconds last
0753                  RTC_STORE
0754 01b1 4f               CLRA
0755 01b2 b7 b6            STA  TEMP              *temp holds rtc address in upper nibble
0756 01b4 ae 05            LDX  #5
```

```
0757 01b6 bf b7              STX   TEMP2            *temp2 holds rtc ram offset
0758                   NEXT_RTC_STORE
0759 01b8 e6 91              LDA   RTC_YEAR,X       *date/time digit
0760 01ba a4 0f              AND   #$0F             *clear all but lower nibble
0761 01bc ba b6              ORA   TEMP             *append address
0762 01be cd 1a d4           JSR   RTC_WRITE        *write low date/time digit
0763 01c1 b6 b6              LDA   TEMP             *restore address
0764 01c3 ab 10              ADD   #$10             *change to high digit address
0765 01c5 b7 b6              STA   TEMP             *and resave
0766 01c7 be b7              LDX   TEMP2
0767 01c9 e6 91              LDA   RTC_YEAR,X       *date/time digit
0768 01cb 44                 LSRA
0769 01cc 44                 LSRA                   *shift upper nibble down
0770 01cd 44                 LSRA
0771 01ce 44                 LSRA
0772 01cf ba b6              ORA   TEMP             *append address
0773 01d1 cd 1a d4           JSR   RTC_WRITE        *write high date/time digit
0774 01d4 b6 b6              LDA   TEMP             *restore address
0775 01d6 ab 10              ADD   #$10             *change to high digit address
0776 01d8 b7 b6              STA   TEMP             *and resave
0777 01da 3a b7              DEC   TEMP2            *decrement rtc ram offset
0778 01dc be b7              LDX   TEMP2
0779 01de 2a d8              BPL   NEXT_RTC_STORE   *branch if more date/time to restore
0780 01e0 81                 RTS
0781                   *
0782                   RTC_FIRST_TIME
0783 01e1 ad ce              BSR   RTC_STORE        *initialize date/time in rtc
0784                   ***** shouldn't these be write-rtc's?
0785                   ***** shouldn't these be after rtc init exit?
0786 01e3 a6 e0              LDA   #$E0
0787 01e5 cd 1a db           JSR   WRITE_RTC        *64 Hz interrupt mode, std.p output
0788 01e8 a6 f4              LDA   #$F4
0789 01ea cd 1a db           JSR   WRITE_RTC        *24 hour clock
0790                   *
0791                   RTC_INIT_EXIT
0792 01ed 13 12              BCLR  INPUT_EDGE,TIMER_CONTROL
0793                   *                             *negative edge input capture
0794 01ef 1e 12              BSET  INT_CAPTURE,TIMER_CONTROL
0795                   *                             *enable input capture interrupt
0796 01f1 b6 13              LDA   TIMER_STATUS
0797 01f3 b6 15              LDA   CAPTURE_LOW      *clear input capture flag
0798                   *
0799 01f5 81                 RTS
0800                   *
0801                   *  ram check to determine if first time power up
0802                   *
0803                   RAM_INIT
0804 01f6 b6 50              LDA   FIRST_TIME_FLAG
0805 01f8 a1 a5              CMP   #FIRST_TIME_SET
0806 01fa 26 01              BNE   RAM_FIRST_TIME   *branch if first time not set
0807                   RAM_INIT_EXIT
0808 01fc 81                 RTS
0809                   *
0810                   *   initialize ram using table of values
```

```
0811              *
0812              RAM_FIRST_TIME
0813              *
0814              *   initialize bit flags
0815              *
0816              *   digit displayed = 0
0817              *   manual bit = 0
0818              *   sampling = 0
0819              *   right full = 0
0820              *   left full = 0
0821              *   ready right = 1
0822              *   ready left = 1
0823 01fd a6 03       LDA    #%00000011
0824 01ff b7 c0       STA    BIT_DATA
0825              *
0826 0201 5f          CLRX
0827              RAM_INITIALIZE
0828 0202 d6 02 0e    LDA    INITIAL_VALUES,X
0829 0205 a1 df       CMP    #END_OF_MESSAGE
0830 0207 27 f3       BEQ    RAM_INIT_EXIT
0831 0209 e7 51       STA    SAMPLER_STATE,X
0832 020b 5c          INCX
0833 020c 20 f4       BRA    RAM_INITIALIZE
0834              *
0835              INITIAL_VALUES
0836 020e 00          FCB    STATE_OFF           *sampler state
0837 020f 00          FCB    PGM_SAMPLER_YES     *pgm entrance
0838              *
0839 0210 00          FCB    PACE_TIME           *sampler pace
0840 0211 00          FCB    MODE_CONTINUOUS     *sampler mode
0841 0212 00          FCB    TIME_SWITCHED       *switch mode
0842 0213 00          FCB    $00                 *nominal volume
0843 0214 05          FCB    $05
0844 0215 00          FCB    $00
0845 0216 00          FCB    $00                 *number of samples
0846 0217 00          FCB    $00
0847 0218 10          FCB    $10
0848              *
0849 0219 07          FCB    $07                 *nominal count
0850 021a 08          FCB    $08
0851 021b 00          FCB    $00
0852 021c 00          FCB    $00                 *calibrate count
0853 021d 00          FCB    $00
0854 021e 00          FCB    $00                 *limit samples
0855 021f 09          FCB    $09                 ***** does not require initialization
0856 0220 09          FCB    $09
0857              *
0858 0221 89          FCB    $89                 *year of first
0859 0222 09          FCB    $09                 *month of first
0860 0223 01          FCB    $01                 *day of first
0861 0224 12          FCB    $12                 *hour of first
0862 0225 30          FCB    $30                 *minute of first
0863 0226 00          FCB    $00                 *interval hours
0864 0227 30          FCB    $30                 *interval minute
```

```
0865 0228 01              FCB   $01              #interval flow
0866 0229 00              FCB   $00
0867                  *
0868 022a 00              FCB   $00              #bottle volume
0869 022b 75              FCB   $75
0870 022c 70              FCB   $70
0871 022d 00              FCB   YES_NO_YES       #yes no question
0872 022e 05              FCB   $05              #warn count
0873 022f 00              FCB   $00
0874 0230 00              FCB   $00
0875 0231 00              FCB   $00
0876 0232 01              FCB   FLOW_SAMPLE_NO   #flow sample
0877 0233 01              FCB   INH_SAMPLE_NO    #inhibit sample
0878 0234 01              FCB   INH_LOAD_T_NO    #inhibit load t
0879 0235 01              FCB   INH_COUNT_NO     #inhibit count
0880 0236 01              FCB   CAL_DISABLE      #calibrate
0881 0237 01              FCB   LOCK_DISABLE     #program lock
0882 0238 00              FCB   PUMP_LIGHT_BOTH  #pump light mode
0883 0239 02              FCB   ENTER_BOTH       #enter mode
0884 023a 01              FCB   RESTORE_NO       #restore sample
0885 023b 00              FCB   MANUAL_SAMPLE    #manual grab
0886                  *
0887 023c 00              FCB   $00              #take a sample
0888 023d 00              FCB   $00
0889 023e 00              FCB   $00              #sample number
0890 023f 01              FCB   $01
0891 0240 00              FCB   $00              #pump cycle
0892 0241 00              FCB   $00              #pump count
0893 0242 00              FCB   $00
0894 0243 00              FCB   $00              #sample pause
0895 0244 00              FCB   $00              #flow pulses
0896 0245 00              FCB   $00
0897 0246 00              FCB   $00
0898 0247 00              FCB   $00              #flow to next
0899 0248 00              FCB   $00
0900 0249 00              FCB   NEITHER_BOTTLE   #bottle number
0901 024a 00              FCB   NEITHER_BOTTLE   #sample bottle
0902 024b 00              FCB   $00              #samples taken
0903 024c 00              FCB   $00
0904                  *
0905 024d 00              FCB   $00              #fault byte
0906                  *
0907 024e 89              FCB   $89              * rtc year
0908 024f 09              FCB   $09              * rtc month
0909 0250 01              FCB   $01              * rtc day
0910 0251 12              FCB   $12              * rtc hour
0911 0252 00              FCB   $00              * rtc minute
0912 0253 00              FCB   $00              * rtc second
0913 0254 00              FCB   $00              * rtc millisecond
0914                  *
0915 0255 00              FCB   $00              #tubing wear
0916 0256 00              FCB   $00
0917 0257 00              FCB   $00
0918 0258 00              FCB   $00
```

```
0919              *
0920 0259 df              FCB    END_OF_MESSAGE
0921              *
0922              *   initialize lcd
0923              *
0924          LCD_INIT
0925 025a a6 38          LDA    #$38              *function set
0926 025c cd 02 de       JSR    LCD_WRITE_CMD     *without bus flag
0927 025f cd 18 1d       JSR    DELAY             ***** should be bsr's
0928 0262 a6 38          LDA    #$38
0929 0264 ad 78          BSR    LCD_WRITE_CMD
0930 0266 cd 18 1d       JSR    DELAY
0931 0269 a6 38          LDA    #$38
0932 026b ad 71          BSR    LCD_WRITE_CMD
0933 026d a6 38          LDA    #$38              *function set
0934 026f ad 6b          BSR    LCD_CMD_WRITE     *8 bit data bus, 2 lines, 5x7 dots
0935 0271 a6 0c          LDA    #$0C              *display control
0936 0273 ad 67          BSR    LCD_CMD_WRITE     *display on, cursor off, blink off
0937 0275 ad 5f          BSR    CLEAR_LCD         *clear display
0938 0277 a6 06          LDA    #$06              *entry mode set
0939 0279 ad 61          BSR    LCD_CMD_WRITE     *address increment, shift off
0940 027b 81             RTS
0941              *
0942              *   waits until lcd not busy before returning
0943              *
0944          LCD_BUSY
0945 027c 9a             CLI
0946 027d 9d             NOP                      *allow for interrupts
0947 027e 9b             SEI
0948 027f 3f 04          CLR    LCD_BUS_PD
0949 0281 1d 02          BCLR   LCD_RS,LCD_RS_P
0950 0283 1a 02          BSET   LCD_RW,LCD_RW_P
0951 0285 19 02          BCLR   LCD_E,LCD_E_P
0952 0287 18 02          BSET   LCD_E,LCD_E_P
0953 0289 9d             NOP
0954 028a 0e 00 ef       BRSET  LCD_BUSY_FLAG,LCD_BUS_P,LCD_BUSY
0955 028d 19 02          BCLR   LCD_E,LCD_E_P
0956 028f 81             RTS
0957              *
0958              *   writes acc to lcd data register
0959              *
0960          LCD_DATA_WRITE
0961 0290 a1 a0          CMP    #VOCABULARY
0962 0292 25 31          BLO    LCD_WRITE_DATA    *branch if not vocabulary word
0963 0294 cd 02 ac       JSR    FIND_VOCABULARY
0964          WORD_FOUND
0965 0297 bd 2c          JSR    LDA_EXTENDED
0966 0299 a1 e1          CMP    #END_OF_BRANCH
0967 029b 27 04          BEQ    END_OF_WORD       *branch if end of message
0968 029d ad 26          BSR    LCD_WRITE_DATA    *otherwise, display character
0969 029f 20 f6          BRA    WORD_FOUND        *and go on to next byte
0970          END_OF_WORD
0971 02a1 be b9          LDX    TEMP4
0972 02a3 bf cf          STX    EXTENDED+1        *restore position pointer to branch table
```

```
0973 02a5 be ba              LDX  TEMP5
0974 02a7 bf d0              STX  EXTENDED+2
0975 02a9 be b8              LDX  TEMP3           *restore index register
0976 02ab 81                 RTS
0977                    *
0978                    FIND_VOCABULARY
0979 02ac bf b8              STX  TEMP3           *save index register
0980 02ae be cf              LDX  EXTENDED+1
0981 02b0 bf b9              STX  TEMP4           *save position pointer to branch table
0982 02b2 be d0              LDX  EXTENDED+2
0983 02b4 bf ba              STX  TEMP5
0984 02b6 a0 a0              SUB  #VOCABULARY     *otherwise, subtract off code
0985 02b8 97                 TAX
0986 02b9 c6 03 d6           LDA  DICTIONARY
0987 02bc b7 cf              STA  EXTENDED+1
0988 02be c6 03 d7           LDA  DICTIONARY+1
0989 02c1 cd 0a a0           JSR  FIND_REV_BRANCH *position pointer to dictionary table
0990 02c4 81                 RTS
0991                    *
0992                    LCD_WRITE_DATA
0993 02c5 ad b5              BSR  LCD_BUSY        *should be bsr
0994 02c7 3f 04              CLR  LCD_BUS_PD
0995 02c9 3a 04              DEC  LCD_BUS_PD
0996 02cb 1c 02              BSET LCD_RS,LCD_RS_P
0997 02cd 1b 02              BCLR LCD_RW,LCD_RW_P
0998 02cf 18 02              BSET LCD_E,LCD_E_P
0999 02d1 b7 00              STA  LCD_BUS_P
1000 02d3 19 02              BCLR LCD_E,LCD_E_P
1001 02d5 81                 RTS
1002                    *
1003                    *   writes acc to lcd instruction register
1004                    *   lcd_write_cmd allows writing without checking busy flag
1005                    *
1006                    CLEAR_LCD
1007 02d6 a6 01              LDA  #LCD_CLEAR      *clears lcd
1008 02d8 20 02              BRA  LCD_CMD_WRITE
1009                    LCD_CURSOR
1010 02da aa 80              ORA  #LCD_ADDRESS    *sets lcd cursor
1011                    LCD_CMD_WRITE
1012 02dc ad 9e              BSR  LCD_BUSY
1013                    LCD_WRITE_CMD
1014 02de 3f 04              CLR  LCD_BUS_PD
1015 02e0 3a 04              DEC  LCD_BUS_PD
1016 02e2 1d 02              BCLR LCD_RS,LCD_RS_P
1017 02e4 1b 02              BCLR LCD_RW,LCD_RW_P
1018 02e6 18 02              BSET LCD_E,LCD_E_P
1019 02e8 b7 00              STA  LCD_BUS_P
1020 02ea 19 02              BCLR LCD_E,LCD_E_P
1021 02ec 81                 RTS
1022                    *
1023                    *   displays current date and time
1024                    *
1025                    LCD_DATE_TIME
1026 02ed a6 41              LDA  #LCD_LINE_2+1
```

```
1027 02ef ad e9            BSR   LCD_CURSOR        *position cursor
1028 02f1 ae 92            LDX   #RTC_MONTH
1029 02f3 ad 52            BSR   LCD_BLANK_YES     *month, blank leading zero
1030 02f5 a6 2f            LDA   #SLASH
1031 02f7 ad cc            BSR   LCD_WRITE_DATA    *slash
1032 02f9 ae 93            LDX   #RTC_DAY
1033 02fb ad 4e            BSR   LCD_BLANK_NO      *day
1034 02fd a6 2f            LDA   #SLASH
1035 02ff ad c4            BSR   LCD_WRITE_DATA    *slash
1036 0301 ae 91            LDX   #RTC_YEAR
1037 0303 ad 46            BSR   LCD_BLANK_NO      *year
1038                   LCD_TIME
1039 0305 a6 4b            LDA   #LCD_LINE_2+11
1040 0307 ad d1            BSR   LCD_CURSOR        *position cursor
1041 0309 ae 94            LDX   #RTC_HOUR
1042 030b ad 3e            BSR   LCD_BLANK_NO      *hour
1043 030d a6 3a            LDA   #COLON
1044 030f ad b4            BSR   LCD_WRITE_DATA    *colon
1045 0311 ae 95            LDX   #RTC_MINUTE
1046 0313 ad 36            BSR   LCD_BLANK_NO      *minute
1047 0315 a6 3a            LDA   #COLON
1048 0317 ad ac            BSR   LCD_WRITE_DATA    *colon
1049 0319 ae 96            LDX   #RTC_SECOND
1050 031b ad 2e            BSR   LCD_BLANK_NO      *second
1051 031d 81               RTS
1052                   *
1053                   *   displays date and time of first/next sample
1054                   *
1055                   FIRST_NEXT_TIME
1056 031e a6 43            LDA   #LCD_LINE_2+3
1057 0320 ad bB            BSR   LCD_CURSOR        *position cursor
1058                   NEXT_DATE_TIME
1059 0322 ae 65            LDX   #MONTH_OF_FIRST
1060 0324 ad 21            BSR   LCD_BLANK_YES     *month, blank leading zero
1061 0326 a6 2f            LDA   #SLASH
1062 0328 ad 9b            BSR   LCD_WRITE_DATA    *slash
1063 032a ae 66            LDX   #DAY_OF_FIRST
1064 032c ad 1d            BSR   LCD_BLANK_NO      *day
1065 032e a6 2f            LDA   #SLASH
1066 0330 ad 93            BSR   LCD_WRITE_DATA    *slash
1067 0332 ae 64            LDX   #YEAR_OF_FIRST
1068 0334 ad 15            BSR   LCD_BLANK_NO      *year
1069 0336 a6 20            LDA   #SPACE
1070 0338 ad 8b            BSR   LCD_WRITE_DATA
1071                   NEXT_TIME_HERE
1072 033a ae 67            LDX   #HOUR_OF_FIRST
1073 033c ad 0d            BSR   LCD_BLANK_NO      *hour
1074 033e a6 3a            LDA   #COLON
1075 0340 ad 83            BSR   LCD_WRITE_DATA    *colon
1076 0342 ae 68            LDX   #MINUTE_OF_FIRST
1077 0344 ad 05            BSR   LCD_BLANK_NO      *minute
1078 0346 81               RTS
1079                   *
1080                   *   displays number in whose address is in index register
```

```
1081                      *    option to display or blank leading zero
1082                      *
1083                      LCD_BLANK_YES
1084 0347 a6 02               LDA   #2+LEADING_0_NO
1085 0349 20 02               BRA   LCD_BLANK
1086                      LCD_BLANK_NO
1087 034b a6 42               LDA   #2+LEADING_0_YES
1088                      LCD_BLANK
1089 034d b7 ae               STA   PGM_LENGTH
1090 034f bf ac               STX   PGM_STORAGE
1091 0351 ad 13               BSR   NUMBER_CURRENT
1092 0353 81                  RTS
1093                      *
1094                      *    displays byte in accumulator on lcd until end of message
1095                      *    returns with zero flag set if end of message, else cleared
1096                      *
1097                      DISPLAY
1098 0354 a1 df               CMP   #END_OF_MESSAGE
1099 0356 27 04               BEQ   DISPLAY_RTS        *branch if end of message
1100 0358 cd 02 90            JSR   LCD_DATA_WRITE     *otherwise, display character
1101 035b 5c                  INCX                     *and increment pointer
1102                      DISPLAY_RTS
1103 035c 81                  RTS
1104                      *
1105                      *    displays on lcd, right justified with or without leading zeros,
1106                      *    starting at lcd address pointed to by pgm lcd,
1107                      *    bcd number stored at address held in pgm storage
1108                      *    of digit length held in pgm length
1109                      *    may enter with lcd address in x and bcd number address in acc
1110                      *    may display at current lcd address
1111                      *
1112                      DISPLAY_NUMBER
1113 035d b7 ac               STA   PGM_STORAGE
1114 035f bf b0               STX   PGM_LCD
1115                      NUMBER_DISPLAY
1116 0361 b6 b0               LDA   PGM_LCD
1117 0363 cd 02 da            JSR   LCD_CURSOR         *set dd ram address
1118                      NUMBER_CURRENT
1119 0366 1d c0               BCLR  DIGIT_DISPLAYED,DIGIT_DISP_BYTE
1120                      *                            *set digit displayed to no
1121 0368 be ac               LDX   PGM_STORAGE
1122 036a b6 ae               LDA   PGM_LENGTH
1123 036c a4 0f               AND   #$0F
1124 036e b7 b6               STA   TEMP               *temp holds digit count
1125 0370 44                  LSRA
1126 0371 25 0a               BCS   LOW_NIBBLE         *branch if odd number of digits
1127                      HIGH_NIBBLE
1128 0373 f6                  LDA   ,X
1129 0374 44                  LSRA
1130 0375 44                  LSRA               *rotate to high nibble
1131 0376 44                  LSRA
1132 0377 44                  LSRA
1133 0378 cd 03 89            JSR   DIGIT_DISPLAY      *display digit, zero, or blank
1134 037b 3a b6               DEC   TEMP
```

```
1135             LOW_NIBBLE
1136 037d f6         LDA   ,X
1137 037e a4 0f      AND   #$0F           *clear all but low nibble
1138 0380 cd 03 89   JSR   DIGIT_DISPLAY  *and display digit, zero, or blank
1139 0383 5c         INCX                 *advance pointer to next byte
1140 0384 3a b6      DEC   TEMP
1141 0386 26 eb      BNE   HIGH_NIBBLE    *branch if more bcd bytes
1142 0388 81         RTS
1143             *
1144             DIGIT_DISPLAY
1145 0389 26 0c      BNE   DISPLAY_DIGIT  *branch if nonzero digit
1146 038b b6 b6      LDA   TEMP
1147 038d 4a         DECA
1148 038e 27 07      BEQ   DISPLAY_DIGIT  *display zero if last digit
1149 0390 4f         CLRA
1150 0391 0c c0 03   BRSET    DIGIT_DISPLAYED,DIGIT_DISP_BYTE,DISPLAY_DIGIT
1151             *                         *display zero if previous digits displayed
1152 0394 0d ae 08   BRCLR    LEADING_0_BIT,PGM_LENGTH,DISPLAY_SPACE
1153             *                         *display space if leading zeros not specified
1154             DISPLAY_DIGIT
1155 0397 1c c0      BSET  DIGIT_DISPLAYED,DIGIT_DISP_BYTE
1156             *                         *set digit displayed to yes
1157 0399 aa 30      ORA   #$30
1158             DISPLAY_EITHER
1159 039b cd 02 90   JSR   LCD_DATA_WRITE *display digit, zero, or blank
1160 039e 81         RTS
1161             DISPLAY_SPACE
1162 039f a6 20      LDA   #SPACE
1163 03a1 20 f8      BRA   DISPLAY_EITHER *display space
1164             *
1165             *   on restoration of power, updates time of first/next sample
1166             *
1167             NEW_FIRST_TIME
1168 03a3 ae 91      LDX   #RTC_YEAR      *compare current time
1169 03a5 a6 64      LDA   #YEAR_OF_FIRST *to time of first sample
1170 03a7 cd 19 cc   JSR   COMPARE_5
1171 03aa 25 1d      BLO   NEW_FIRST_EXIT *branch if not yet time of first sample
1172             NEXT_FIRST_TIME
1173 03ac cd 1b e4   JSR   TIME_OF_NEXT   *else, update time of next sample
1174 03af ae 91      LDX   #RTC_YEAR      *compare current time
1175 03b1 a6 64      LDA   #YEAR_OF_FIRST *to time of first sample
1176 03b3 cd 19 cc   JSR   COMPARE_5
1177 03b6 24 f4      BHS   NEXT_FIRST_TIME *branch if not yet time of first sample
1178 03b8 b6 51      LDA   SAMPLER_STATE
1179 03ba a1 04      CMP   #STATE_RUN
1180 03bc 25 0b      BLO   NEW_FIRST_EXIT *branch if not run state
1181 03be 00 53 09   BRSET    0,SAMPLER_PACE,NEW_FIRST_FLOW
1182             *                         *branch if flow paced
1183 03c1 00 7d 05   BRSET    0,RESTORE_SAMPLE,NEW_FIRST_EXIT
1184             *                         *branch if no sample upon power restore
1185             TAKE_RESTORE
1186 03c4 a6 7f      LDA   #TAKE_A_SAMPLE
1187 03c6 cd 1a 87   JSR   BCD_INCREMENT_2 *otherwise, increment samples to be taken
1188             NEW_FIRST_EXIT
```

```
1189 03c9 81                    RTS
1190                         NEW_FIRST_FLOW
1191 03ca a1 04                 CMP     #STATE_RUN_FIRST
1192 03cc 27 f6                 BEQ     TAKE_RESTORE        *branch if run first state
1193 03ce 00 54 f8              BRSET   0,SAMPLER_MODE,NEW_FIRST_EXIT
1194                         *                               *branch if not continuous sampling
1195 03d1 00 55 f5              BRSET   0,SWITCH_MODE,NEW_FIRST_EXIT
1196                         *                               *branch if not time switched
1197 03d4 20 ee                 BRA     TAKE_RESTORE        *otherwise, tsfp timeout when restored
1198                         ***** problem occurs when flow paced and sample at start time
1199                         ***** then, if restored after expiration of delay,
1200                         ***** always takes a sample regardless of restore sample setting
1201                         *
1202                         DICTIONARY
1203 03d6 03 d8                 FDB     FIRST_WORD
1204                         *
1205                         FIRST_WORD
1206 03d8 20 42 41 53 45 44     FCC     ' BASED'
1207 03de e1                    FCB     END_OF_BRANCH
1208                         *
1209 03df 42 4f 54 54 4c 45     FCC     'BOTTLE'
1210 03e5 e1                    FCB     END_OF_BRANCH
1211                         *
1212 03e6 43 41 4c 49 42 52     FCC     'CALIBRATE '
     41 54 45 20
1213 03f0 e1                    FCB     END_OF_BRANCH
1214                         *
1215 03f1 43 4f 4e 54 49 4e     FCC     'CONTINUOUS'
     55 4f 55 53
1216 03fb e1                    FCB     END_OF_BRANCH
1217                         *
1218 03fc 43 4f 55 4e 54        FCC     'COUNT'
1219 0401 e1                    FCB     END_OF_BRANCH
1220                         *
1221 0402 44 49 53 41 42 4c     FCC     'DISABLE'
     45
1222 0409 e1                    FCB     END_OF_BRANCH
1223                         *
1224 040a 45 41 43 48           FCC     'EACH'
1225 040e e1                    FCB     END_OF_BRANCH
1226                         *
1227 040f 45 4e 41 42 4c 45     FCC     'ENABLE'
1228 0415 e1                    FCB     END_OF_BRANCH
1229                         *
1230 0416 45 4e 54 45 52 20     FCC     'ENTER '
1231 041c e1                    FCB     END_OF_BRANCH
1232                         *
1233 041d 45 56 45 52 59        FCC     'EVERY'
1234 0422 e1                    FCB     END_OF_BRANCH
1235                         *
1236 0423 46 41 49 4c 20        FCC     'FAIL '
1237 0428 e1                    FCB     END_OF_BRANCH
1238                         *
1239 0429 2a 2a 2a 46 41 55     FCC     '*FAULT*'
```

```
        4c 54 2a 2a 2a
1240 0434 e1                        FCB   END_OF_BRANCH
1241                        *
1242 0435 20 46 41 55 4c 54         FCC   ' FAULTS'
     53
1243 043c e1                        FCB   END_OF_BRANCH
1244                        *
1245 043d 46 49 52 53 54            FCC   'FIRST'
1246 0442 e1                        FCB   END_OF_BRANCH
1247                        *
1248 0443 46 4c 4f 57               FCC   'FLOW'
1249 0447 e1                        FCB   END_OF_BRANCH
1250                        *
1251 0448 46 57 44                  FCC   'FWD'
1252 044b e1                        FCB   END_OF_BRANCH
1253                        *
1254 044c 47 52 41 42 20            FCC   'GRAB '
1255 0451 e1                        FCB   END_OF_BRANCH
1256                        *
1257 0452 48 4f 55 52 53            FCC   'HOURS'
1258 0457 e1                        FCB   END_OF_BRANCH
1259                        *
1260 0458 49 4e 48 49 42 49         FCC   'INHIBIT'
     54
1261 045f e1                        FCB   END_OF_BRANCH
1262                        *
1263 0460 4a 41 4d 4d 45 44         FCC   'JAMMED'
1264 0466 e1                        FCB   END_OF_BRANCH
1265                        *
1266 0467 4b 45 59                  FCC   'KEY'
1267 046a e1                        FCB   END_OF_BRANCH
1268                        *
1269 046b 4c 49 47 48 54            FCC   'LIGHT'
1270 0470 e1                        FCB   END_OF_BRANCH
1271                        *
1272 0471 4c 4f 43 4b 20            FCC   'LOCK '
1273 0476 e1                        FCB   END_OF_BRANCH
1274                        *
1275 0477 4d 41 4e 55 41 4c         FCC   'MANUAL '
     20
1276 047e e1                        FCB   END_OF_BRANCH
1277                        *
1278 047f 4d 49 4e 55 54 45         FCC   'MINUTES'
     53
1279 0486 e1                        FCB   END_OF_BRANCH
1280                        *
1281 0487 6d 6c 20                  FCC   'ml '
1282 048a e1                        FCB   END_OF_BRANCH
1283                        *
1284 048b 4e 4f                     FCC   'NO'
1285 048d e1                        FCB   END_OF_BRANCH
1286                        *
1287 048e 20 4f 46 20               FCC   ' OF '
1288 0492 e1                        FCB   END_OF_BRANCH
```

```
1289                              *
1290 0493 20 20 20 4f 4b 3f       FCC  ' . OK?'
1291 0499 e1                      FCB  END_OF_BRANCH
1292                              *
1293 049a 4f 50 54 49 4f 4e       FCC  'OPTION'
1294 04a0 e1                      FCB  END_OF_BRANCH
1295                              *
1296 04a1 50 41 43 45 44          FCC  'PACED'
1297 04a6 e1                      FCB  END_OF_BRANCH
1298                              *
1299 04a7 50 4f 57 45 52 20       FCC  'POWER '
1300 04ad e1                      FCB  END_OF_BRANCH
1301                              *
1302 04ae 50 52 45 53 53 20       FCC  'PRESS '
1303 04b4 e1                      FCB  END_OF_BRANCH
1304                              *
1305 04b5 50 52 4f 47 52 41       FCC  'PROGRAM '
     4d 20
1306 04bd e1                      FCB  END_OF_BRANCH
1307                              *
1308 04be 50 55 4c 53 45 53       FCC  'PULSES'
1309 04c4 e1                      FCB  END_OF_BRANCH
1310                              *
1311 04c5 50 55 4d 50 20          FCC  'PUMP '
1312 04ca e1                      FCB  END_OF_BRANCH
1313                              *
1314 04cb 52 45 41 44 59 20       FCC  'READY ...'
     2e 2e 2e
1315 04d4 e1                      FCB  END_OF_BRANCH
1316                              *
1317 04d5 52 45 53 45 54 20       FCC  'RESET '
1318 04db e1                      FCB  END_OF_BRANCH
1319                              *
1320 04dc 52 45 56                FCC  'REV'
1321 04df e1                      FCB  END_OF_BRANCH
1322                              *
1323 04e0 52 45 56 49 53 49       FCC  'REVISION'
     4f 4e
1324 04e8 e1                      FCB  END_OF_BRANCH
1325                              *
1326 04e9 52 55 4e 4e 49 4e       FCC  'RUNNING '
     47 20
1327 04f1 e1                      FCB  END_OF_BRANCH
1328                              *
1329 04f2 53 41 4d 50 4c 45       FCC  'SAMPLE'
1330 04f8 e1                      FCB  END_OF_BRANCH
1331                              *
1332 04f9 53 41 4d 50 4c 45       FCC  'SAMPLES'
     53
1333 0500 e1                      FCB  END_OF_BRANCH
1334                              *
1335 0501 53 41 4d 50 4c 49       FCC  'SAMPLING'
     4e 47
1336 0509 e1                      FCB  END_OF_BRANCH
```

```
1337                             *
1338 050a 53 4f 46 54 57 41      FCC  'SOFTWARE '
     52 45 20
1339 0513 e1                     FCB  END_OF_BRANCH
1340                             *
1341 0514 53 50 4c 49 54         FCC  'SPLIT'
1342 0519 e1                     FCB  END_OF_BRANCH
1343                             *
1344 051a 53 54 41 52 54         FCC  'START'
1345 051f e1                     FCB  END_OF_BRANCH
1346                             *
1347 0520 53 57 49 54 43 48      FCC  'SWITCH'
1348 0526 e1                     FCB  END_OF_BRANCH
1349                             *
1350 0527 54 41 4b 45            FCC  'TAKE'
1351 052b e1                     FCB  END_OF_BRANCH
1352                             *
1353 052c 54 48 45 4e 20         FCC  'THEN '
1354 0531 e1                     FCB  END_OF_BRANCH
1355                             *
1356 0532 54 49 4d 45            FCC  'TIME'
1357 0536 e1                     FCB  END_OF_BRANCH
1358                             *
1359 0537 54 55 42 49 4e 47      FCC  'TUBING'
1360 053d e1                     FCB  END_OF_BRANCH
1361                             *
1362 053e 56 4f 4c 55 4d 45      FCC  'VOLUME'
1363 0544 e1                     FCB  END_OF_BRANCH
1364                             *
1365 0545 57 41 52 4e 49 4e      FCC  'WARNING'
     47
1366 054c e1                     FCB  END_OF_BRANCH
1367                             *
1368 054d 20 57 48 45 4e 20      FCC  ' WHEN '
1369 0553 e1                     FCB  END_OF_BRANCH
1370                             *
1371 0554 59 45 53               FCC  'YES'
1372 0557 e1                     FCB  END_OF_BRANCH
1373                             *
1374 0558 5b 59 45 53 2c 20      FCC  '[YES, NO]'
     4e 4f 5d
1375 0561 e1                     FCB  END_OF_BRANCH
1376                             *
1377                             *  program state
1378                             *
1379                             SCAN_W_ENFORCE
1380 0562 cd 08 40                  JSR  ENFORCE_BOTTLE   *check distributor position
1381                             PERIODIC_SCAN
1382 0565 cd 18 62                  JSR  SCAN_AND_DECODE
1383                             SCAN_NO_KEYPAD
1384 0568 ad 10                     BSR  POWER_FAIL    *ok *check input voltage
1385 056a cd 15 2a                  JSR  FLOW_CHECK       *monitor flow or 4-20 pulses
1386 056d cd 1b 32                  JSR  TIMER_UPDATE
1387 0570 cd 17 bb                  JSR  BOTTLE_MONITOR *ok
```

```
1388 0573 ad 16            BSR  FAULT_CHECK    *ok
1389 0575 ad 1f            BSR  INHIBIT_CHECK  *ok  *check status of inhibit pin f
1390 0577 ad 25            BSR  DECODE_DIST
1391 0579 81               RTS
1392                    *
1393                    *   monitors input voltage detector
1394                    *   goes to sleep mode if interrupt pin goes high
1395                    *
1396                    POWER_FAIL
1397 057a 2f 01            BIH  POWER_FAILED      *branch if power lost
1398 057c 81               RTS                    *otherwise, return
1399                    POWER_FAILED
1400 057d 10 90            BSET B_POWER_FAIL,FAULT_BYTE
1401                    *                          *set power fail bit
1402 057f cd 02 d6         JSR  CLEAR_LCD     *****
1403 0582 3f 04            CLR  PORT_A_DIR
1404 0584 3f 05            CLR  PORT_B_DIR        *set all ports to inputs
1405 0586 3f 06            CLR  PORT_C_DIR
1406                    OPCODE_STOP
1407 0588 8e               STOP                   *stop mode
1408 0589 20 fd            BRA  OPCODE_STOP   *****
1409                    *
1410                    *   controls fault light/relay per fault bits
1411                    *
1412                    FAULT_CHECK
1413 058b 3d 90            TST  FAULT_BYTE
1414 058d 26 04            BNE  SET_FAULT         *branch if fault bit set
1415 058f 12 02            BSET FAULT_LIGHT,FAULT_LIGHT_P  *turn off fault light
1416 0591 20 02            BRA  FAULT_CHECK_RTS
1417                    SET_FAULT
1418 0593 13 02            BCLR FAULT_LIGHT,FAULT_LIGHT_P  *turn on fault light
1419                    FAULT_CHECK_RTS
1420 0595 81               RTS
1421                    *
1422                    *   monitors status of inhibit pin f and sets flag accordingly
1423                    *
1424                    INHIBIT_CHECK
1425 0596 10 c1            BSET INHIBIT_BIT,INHIBIT_BYTE
1426                    *                          *assume not inhibited
1427 0598 08 03 02         BRSET    INHIBIT,INHIBIT_P,INHIBIT_CHK_RTS
1428                    *                          *branch if not inhibited
1429 059b 11 c1            BCLR INHIBIT_BIT,INHIBIT_BYTE
1430                    *                          *otherwise, set inhibit flag
1431                    INHIBIT_CHK_RTS
1432 059d 81               RTS
1433                    *
1434                    *   decodes bottle and quadrant switches
1435                    *   into diverter left and right
1436                    *
1437                    DECODE_DIST
1438 059e 11 c2            BCLR DIVERT_LEFT,DIVERT_LEFT_P
1439 05a0 13 c2            BCLR DIVERT_RIGHT,DIVERT_RIGHT_P
1440                    *                          *assume not on left or right bottle
1441 05a2 05 03 09         BRCLR    DIVERT_BOTTLE,DIVERT_BOTTLE_P,DECODE_DIST_RTS
```

```
1442                        *                               *branch if not on either bottle
1443 05a5 06 03 04              BRSET   DIVERT_QUAD,DIVERT_QUAD_P,DECODE_RIGHT
1444 05a8 10 c2                 BSET DIVERT_LEFT,DIVERT_LEFT_P
1445                        *                               *on left bottle
1446 05aa 20 02                 BRA   DECODE_DIST_RTS
1447                        DECODE_RIGHT
1448 05ac 12 c2                 BSET DIVERT_RIGHT,DIVERT_RIGHT_P
1449                        *                               *on right bottle
1450                        DECODE_DIST_RTS
1451 05ae 81                    RTS
1452                        *
1453                        *
1454                        *   eprom checksum verification
1455                        *
1456                        EPROM_CHECKSUM
1457                        ***** careful that breakpoints do not insert swi's and change checksum
1458 05af 3d c6                 TST   REVIEW_BRANCH
1459 05b1 26 38                 BNE   EPROM_EXIT          *branch if during display status
1460 05b3 b6 51                 LDA   SAMPLER_STATE
1461 05b5 a1 02                 CMP   #STATE_PGM
1462 05b7 27 32                 BEQ   EPROM_EXIT          *branch if during programming
1463 05b9 02 90 2f              BRSET   B_EPROM_FAIL,FAULT_BYTE,EPROM_EXIT
1464                        *                               *branch if eprom fail fault set
1465                        *
1466 05bc 4f                    CLRA                      *acc holds exclusive or of all rom bytes
1467                        *
1468 05bd ae 2f                 LDX   #$2F
1469                        CHECKSUM_0020
1470 05bf e8 20                 EOR   $0020,X             *exclusive or all page 0 rom bytes
1471 05c1 5a                    DECX
1472 05c2 2a fb                 BPL   CHECKSUM_0020
1473                        *
1474 05c4 ae 0b                 LDX   #$0B
1475                        CHECKSUM_1FF4
1476 05c6 d8 1f f4              EOR   $1FF4,X             *exclusive or all interrupt vector bytes
1477 05c9 5a                    DECX
1478 05ca 2a fa                 BPL   CHECKSUM_1FF4
1479                        *
1480 05cc b7 cc                 STA   CHECKSUM            *transfer result to temp4
1481                        *
1482 05ce a6 01                 LDA   #$01
1483 05d0 b7 cf                 STA   EXTENDED+1
1484 05d2 3f d0                 CLR   EXTENDED+2
1485                        CHECKSUM_0100
1486 05d4 9a                    CLI
1487 05d5 9d                    NOP                       *allow for interrupts
1488 05d6 9b                    SEI
1489 05d7 bd 2c                 JSR   LDA_EXTENDED        *load eprom byte
1490 05d9 b8 cc                 EOR   CHECKSUM            *exclusive or with current sum of bits
1491 05db b7 cc                 STA   CHECKSUM
1492 05dd be cf                 LDX   EXTENDED+1
1493 05df a3 1f                 CPX   #$1F
1494 05e1 25 f1                 BLO   CHECKSUM_0100       *branch if not finished
1495                        *
```

```
1496 05e3 a1 a5             CMP     #$A5
1497 05e5 27 04             BEQ     EPROM_EXIT      *branch if correct checksum
1498 05e7 ae 01             LDX     #B_EPROM_FAIL
1499 05e9 ad 30             BSR     NEW_FAULT       *set eprom fail fault
1500                 EPROM_EXIT
1501 05eb 81                RTS
1502                 *
1503                 *   turns event mark output on during run state
1504                 *   if split sampling, only if using left bottle
1505                 *
1506                 EVENT_MARK_ON
1507 05ec 0a c0 0c          BRSET   MANUAL_BIT,MANUAL_BYTE,EVENT_MARK_ON_X
1508                 *                               *branch if separate bottle manual sample
1509 05ef 01 54 03          BRCLR   0,SAMPLER_MODE,ON_EVENT_MARK
1510                 *                               *branch if continuous sampling
1511 05f2 01 8d 06          BRCLR   0,SAMPLE_BOTTLE,EVENT_MARK_ON_X
1512                 *                               *branch if not left bottle in split sampling
1513                 ON_EVENT_MARK
1514 05f5 10 12             BSET    OUTPUT_LEVEL,TIMER_CONTROL
1515                 *                               *turn event mark output on
1516 05f7 a6 40             LDA     #EVENT_MARK_MAX
1517 05f9 b7 c8             STA     EVENT_MARK_TIME *load event mark pulse width
1518                 EVENT_MARK_ON_X
1519 05fb 81                RTS
1520                 *
1521                 *   decrements event mark timer if not zero
1522                 *   if now zero, turns event mark output off
1523                 *
1524                 EVENT_MARK_OFF
1525 05fc b6 c8             LDA     EVENT_MARK_TIME
1526 05fe 27 06             BEQ     EVENT_MARK_X    *branch if event mark timer not set
1527 0600 3a c8             DEC     EVENT_MARK_TIME *otherwise, decrement event mark timer
1528 0602 26 02             BNE     EVENT_MARK_X    *branch if not now zero
1529 0604 11 12             BCLR    OUTPUT_LEVEL,TIMER_CONTROL
1530                 *                               *otherwise, turn event mark output off
1531                 EVENT_MARK_X
1532 0606 81                RTS
1533                 *
1534                 *   if not zero, decrement distributor timer
1535                 *
1536                 DIST_TIMER_CHK
1537 0607 3d c3             TST     DIST_TIMER
1538 0609 27 0f             BEQ     DIST_TIMER_X    *branch if distributor timer already zero
1539 060b 3a c3             DEC     DIST_TIMER      *otherwise, decrement
1540 060d 26 0b             BNE     DIST_TIMER_X    *branch if not now zero
1541 060f ae 03             LDX     #B_DIST_JAM
1542 0611 cd 06 1b          JSR     NEW_FAULT       *set distributor jam fault
1543 0614 cd 16 50          JSR     RUN_CLEAR       *clear run parameters
1544 0617 cc 06 a1          JMP     KEY_ON          *return to standby
1545                 DIST_TIMER_X
1546 061a 81                RTS
1547                 *
1548                 *   sets fault bit in fault byte corresponding to bit in acc
1549                 *
```

```
1550            NEW_FAULT
1551 061b d6 06 42    LDA  FAULT_BYTES,X
1552 061e ba 90       ORA  FAULT_BYTE
1553 0620 b7 90       STA  FAULT_BYTE        *set bit in fault byte
1554 0622 b6 c6       LDA  REVIEW_BRANCH
1555 0624 a1 0c       CMP  #12
1556 0626 25 19       BLO  NEW_FAULT_EXIT    *branch if not displaying faults
1557 0628 27 0b       BEQ  SHOW_NEW_FAULT    *branch if displaying no faults
1558 062a a1 12       CMP  #18
1559 062c 27 07       BEQ  SHOW_NEW_FAULT    *branch if displaying clear all faults
1560 062e 9f          TXA
1561 062f ab 0d       ADD  #13
1562 0631 b1 c6       CMP  REVIEW_BRANCH
1563 0633 24 0c       BHS  NEW_FAULT_EXIT    *branch if not displaying later fault
1564            SHOW_NEW_FAULT
1565 0635 19 c1       BCLR YES_NO_BIT,YES_NO_BYTE
1566            *                              *otherwise, clear yes no flashing flag
1567 0637 3f b1       CLR  FLASH
1568 0639 9f          TXA
1569 063a ab 0d       ADD  #13
1570 063c b7 c6       STA  REVIEW_BRANCH     *calculate new review branch number
1571 063e cd 1c 52    JSR  REVIEW_PGM        *and display new fault
1572            NEW_FAULT_EXIT
1573 0641 81          RTS
1574            *
1575            FAULT_BYTES
1576 0642 01          FCB  $01
1577 0643 02          FCB  $02
1578 0644 04          FCB  $04
1579 0645 08          FCB  $08
1580 0646 10          FCB  $10
1581            *
1582            *   program key
1583            *
1584            *###############
1585            *# pump forward #
1586            *###############
1587            KEY_PUMP_FWD
1588 0647 b6 c3       LDA  DIST_TIMER        *branch if distributor moving
1589 0649 ba 83       ORA  PUMP_CYCLE        *or already sampling
1590 064b 26 0d       BNE  PUMP_FWD_EXIT
1591 064d 08 01 0a    BRSET    PUMP_FORWARD,PUMP_FORWARD_P,PUMP_FWD_EXIT
1592            *                              *branch if already pumping forward
1593 0650 9c          RSP
1594 0651 17 01       BCLR PUMP_REVERSE,PUMP_REVERSE_P
1595            *                              *stop pump reverse
1596 0653 cd 1B 2c    JSR  ERROR_BEEP        *beep before pumping
1597 0656 18 01       BSET PUMP_FORWARD,PUMP_FORWARD_P
1598            *                              *pump forward
1599 0658 20 12       BRA  PUMP_JOGGING      *monitor pump jog
1600            PUMP_FWD_EXIT
1601 065a 81          RTS
1602            *
1603            *###############
```

```
1604                         *# pump reverse #
1605                         *###############
1606                         KEY_PUMP_REV
1607 065b b6 c3                  LDA  DIST_TIMER         *branch if distributor moving
1608 065d ba 83                  ORA  PUMP_CYCLE         *or already sampling
1609 065f 26 17                  BNE  PUMP_REV_EXIT
1610 0661 06 01 14               BRSET   PUMP_REVERSE,PUMP_REVERSE_P,PUMP_REV_EXIT
1611                         *                           *branch if already pumping reverse
1612 0664 9c                      RSP
1613 0665 19 01                  BCLR PUMP_FORWARD,PUMP_FORWARD_P
1614                         *                           *stop pump forward
1615 0667 cd 18 2c               JSR  ERROR_BEEP         *beep before pumping
1616 066a 16 01                  BSET PUMP_REVERSE,PUMP_REVERSE_P
1617                         *                           *pump reverse
1618                         PUMP_JOGGING
1619 066c a6 ff                  LDA  #PUMP_JAM_MAX
1620 066e b7 c7                  STA  PUMP_JAM           *initialize pump jam count
1621                         JOGGING_PUMP
1622 0670 cd 17 48               JSR  NEXT_PUMP          *monitor volume pin, pump tubing wear
1623 0673 cd 05 65               JSR  PERIODIC_SCAN
1624 0676 20 f8                  BRA  JOGGING_PUMP
1625                         PUMP_REV_EXIT
1626 0678 81                      RTS
1627                         *
1628                         *########
1629                         *# stop #
1630                         *########
1631                         KEY_STOP
1632 0679 b6 51                  LDA  SAMPLER_STATE
1633 067b a1 02                  CMP  #STATE_PGM
1634 067d 26 22                  BNE  KEY_ON             *branch if not pgm state
1635 067f cd 16 50               JSR  RUN_CLEAR          *otherwise, clear run parameters
1636 0682 a6 12                  LDA  #18
1637 0684 b7 a1                  STA  PGM_BRANCH         *and go to calibrate sample volume screen
1638 0686 cc 09 64               JMP  NEXT_PROGRAM
1639                         *
1640                         KEY_OFF
1641 0689 9c                      RSP                    *reset stack pointer
1642 068a a6 00                  LDA  #STATE_OFF
1643 068c b7 51                  STA  SAMPLER_STATE      *set sampler state
1644                         OFF_STATE
1645 068e cd 16 50               JSR  RUN_CLEAR          *clear pump run parameters
1646 0691 a6 00                  LDA  #MASK_OFF
1647 0693 b7 a0                  STA  KEY_MASK           *set keypad mask
1648 0695 cd 02 d6               JSR  CLEAR_LCD          *clear display
1649                         OFF_LOOP
1650 0698 cd 05 65               JSR  PERIODIC_SCAN      *continuously scan routines
1651 069b 20 fb                  BRA  OFF_LOOP
1652                         *
1653                         *##########
1654                         *# on/off #
1655                         *##########
1656                         KEY_ON_OFF
1657 069d b6 51                  LDA  SAMPLER_STATE
```

```
1658 069f 26 e8              BNE   KEY_OFF
1659                  KEY_ON
1660 06a1 9c                 RSP                        *reset stack pointer
1661 06a2 a6 01              LDA   #STATE_STANDBY
1662 06a4 b7 51              STA   SAMPLER_STATE        *set sampler state
1663                  STANDBY_STATE
1664 06a6 a6 04              LDA   #MASK_STANDBY
1665 06a8 b7 a0              STA   KEY_MASK             *set keypad mask
1666 06aa cd 16 50           JSR   RUN_CLEAR            *clear pump run parameters
1667 06ad cd 16 49           JSR   NO_RUN_DISPLAY
1668 06b0 26 03              BNE   STANDBY_LOOP         *branch if fault display or pgm review
1669 06b2 cd 06 ba           JSR   STANDBY_DISPLAY      *otherwise, display standby message
1670                  STANDBY_LOOP
1671 06b5 cd 05 65           JSR   PERIODIC_SCAN        *continuously scan routines
1672 06b8 20 fb              BRA   STANDBY_LOOP
1673                  *
1674                  STANDBY_DISPLAY
1675 06ba cd 02 d6           JSR   CLEAR_LCD
1676 06bd 5f                 CLRX
1677                  X_MSG_STANDBY
1678 06be d6 06 cf           LDA   MSG_STANDBY,X
1679 06c1 cd 03 54           JSR   DISPLAY
1680 06c4 26 f8              BNE   X_MSG_STANDBY
1681 06c6 a6 8e              LDA   #SAMPLES_TAKEN
1682 06c8 cd 15 f7           JSR   DISPLAY_SAMPLE       *display samples taken
1683 06cb cd 02 ed           JSR   LCD_DATE_TIME        *display current date/time
1684 06ce 81                 RTS
1685                  *
1686                  MSG_STANDBY
1687 06cf 53 54 41 4e 44 42  FCC   'STANDBY '
     59 20 20 20 20 20
     20
1688 06dc cb                 FCB   V_SAMPLES
1689 06dd df                 FCB   END_OF_MESSAGE
1690                  *
1691                  *******************
1692                  ** manual sample *
1693                  *******************
1694                  KEY_MANUAL
1695                  ***** check inhibit?
1696 06de b6 51              LDA   SAMPLER_STATE
1697 06e0 a1 02              CMP   #STATE_PGM
1698 06e2 26 0c              BNE   MANUAL_NOT_PGM       *branch if not calibrate sample volume in pgm
1699 06e4 a6 18              LDA   #MASK_PGM_STOP
1700 06e6 b7 a0              STA   KEY_MASK             *enable pump stop
1701 06e8 1a c0              BSET  MANUAL_BIT,MANUAL_BYTE
1702                  *                                  *set separate bottle manual sample bit
1703 06ea cd 16 67           JSR   C_OR_S_SAMPLE        *take sample
1704 06ed cc 09 34           JMP   GO_TO_NEXT_STEP      *and go on to next pgm step
1705                  MANUAL_NOT_PGM
1706 06f0 b6 c3              LDA   DIST_TIMER           *branch if distributor moving
1707 06f2 ba 83              ORA   PUMP_CYCLE           *or already sampling
1708 06f4 26 5b              BNE   MANUAL_EXIT_3
1709 06f6 08 01 58           BRSET PUMP_FORWARD,PUMP_FORWARD_P,MANUAL_EXIT_3
```

```
1710                *                       *branch if pumping forward
1711 06f9 06 01 55      BRSET   PUMP_REVERSE,PUMP_REVERSE_P,MANUAL_EXIT_3
1712                *                       *branch if pumping reverse
1713                *
1714 06fc cd 02 d6      JSR     CLEAR_LCD
1715 06ff a6 02         LDA     #2
1716 0701 cd 02 da      JSR     LCD_CURSOR          *position cursor
1717 0704 5f            CLRX
1718                NEXT_MANUAL_1
1719 0705 d6 08 04      LDA     MSG_MANUAL_1,X
1720 0708 cd 03 54      JSR     DISPLAY             *display manual sample message
1721 070b 26 f8         BNE     NEXT_MANUAL_1
1722                *
1723 070d a6 44         LDA     #LCD_LINE_2+4
1724 070f cd 02 da      JSR     LCD_CURSOR          *position cursor
1725 0712 5f            CLRX
1726                NEXT_MANUAL_2
1727 0713 d6 08 09      LDA     MSG_MANUAL_2,X
1728 0716 cd 03 54      JSR     DISPLAY             *display grab sample message
1729 0719 26 f8         BNE     NEXT_MANUAL_2
1730                *
1731 071b a6 28         LDA     #40
1732 071d b7 a1         STA     PGM_BRANCH          *set pgm branch with text to flash
1733 071f b6 7e         LDA     MANUAL_GRAB
1734 0721 b7 a2         STA     PGM_CHOICE          *set initial choice
1735 0723 a6 02         LDA     #2
1736 0725 b7 b1         STA     FLASH               *set code to flash on
1737 0727 18 c1         BSET    YES_NO_BIT,YES_NO_BYTE
1738                *                       *set yes no flashing flag
1739                MANUAL_SCAN_0
1740 0729 a6 0f         LDA     #DISPLAY_MAX
1741 072b b7 c4         STA     DISPLAY_TIMEOUT     *load display timeout timer
1742                MANUAL_SCAN_1
1743 072d cd 05 65      JSR     PERIODIC_SCAN
1744 0730 3d c4         TST     DISPLAY_TIMEOUT
1745 0732 26 f9         BNE     MANUAL_SCAN_1
1746 0734 3f b1         CLR     FLASH
1747 0736 19 c1         BCLR    YES_NO_BIT,YES_NO_BYTE
1748                *                       *clear yes no flashing flag
1749 0738 17 c1         BCLR    READY_BIT,READY_BYTE
1750                *                       *and ready to manual sample bit
1751 073a cd 1d 2b      JSR     RESTORE_DISPLAY
1752 073d b6 51         LDA     SAMPLER_STATE
1753 073f a1 04         CMP     #STATE_RUN
1754 0741 25 39         BLO     MANUAL_EXIT_2       *branch if not run state
1755 0743 cd 08 40      JSR     ENFORCE_BOTTLE      *otherwise, position distributor
1756 0746 20 34         BRA     MANUAL_EXIT_2
1757                *
1758                TAKE_GRAB
1759 0748 1a c0         BSET    MANUAL_BIT,MANUAL_BYTE
1760                *                       *set separate bottle manual sample bit
1761 074a 17 c1         BCLR    READY_BIT,READY_BYTE
1762                *                       *and ready to manual sample bit
1763 074c cd 16 67      JSR     C_OR_S_SAMPLE
```

```
1764 074f 3f c4              CLR   DISPLAY_TIMEOUT
1765                    MANUAL_EXIT_3
1766 0751 20 29              BRA   MANUAL_EXIT_2
1767                    SAMPLE_CHOSEN
1768 0753 b6 a2              LDA   PGM_CHOICE
1769 0755 b7 7e              STA   MANUAL_GRAB      #store selection
1770 0757 27 25              BEQ   TAKE_MANUAL      #branch if manual sample
1771 0759 16 c1              BSET  READY_BIT,READY_BYTE
1772                         #                      #set ready for manual sample bit
1773 075b cd 02 d6           JSR   CLEAR_LCD
1774 075e 5f                 CLRX
1775                    NEXT_MANUAL_3
1776 075f d6 0B 0d           LDA   MSG_MANUAL_3,X
1777 0762 cd 03 54           JSR   DISPLAY          #display press manual sample message
1778 0765 26 f8              BNE   NEXT_MANUAL_3
1779                         #
1780 0767 a6 41              LDA   #LCD_LINE_2+1
1781 0769 cd 02 da           JSR   LCD_CURSOR       #position cursor
1782 076c 5f                 CLRX
1783                    NEXT_MANUAL_4
1784 076d d6 0B 11           LDA   MSG_MANUAL_4,X
1785 0770 cd 03 54           JSR   DISPLAY          #display key when ready message
1786 0773 26 f8              BNE   NEXT_MANUAL_4
1787                         #
1788 0775 cd 08 84           JSR   DIST_CENTER      #center distributor
1789 0778 a6 0f              LDA   #DISPLAY_MAX
1790 077a b7 c4              STA   DISPLAY_TIMEOUT  #reload display timeout timer
1791                    MANUAL_EXIT_2
1792 077c 20 45              BRA   MANUAL_EXIT
1793                         #
1794                    TAKE_MANUAL
1795 077e 00 54 27           BRSET 0,SAMPLER_MODE,SPLIT_MANUAL
1796                         #                      #branch if split sampling
1797 0781 00 c2 08           BRSET DIVERT_LEFT,DIVERT_LEFT_P,LEFT_MANUAL
1798                         #                      #branch if on left bottle
1799 0784 02 c2 12           BRSET DIVERT_RIGHT,DIVERT_RIGHT_P,RIGHT_MANUAL
1800                         #                      #branch if on right bottle
1801                    INVALID_MANUAL
1802 0787 cd 18 2c           JSR   ERROR_BEEP       #error beep
1803 078a 20 35              BRA   TAKE_MANUAL_X
1804                    LEFT_MANUAL
1805 078c 0f 03 f8           BRCLR BOTTLE_LEFT,BOTTLE_LEFT_P,INVALID_MANUAL
1806                         #                      #branch if left bottle missing
1807 078f 04 c0 f5           BRSET LEFT_FULL,LEFT_FULL_B,INVALID_MANUAL
1808                         #                      #branch if left bottle full
1809 0792 02 8d f2           BRSET 1,SAMPLE_BOTTLE,INVALID_MANUAL
1810                         #                      #branch if right sample bottle
1811                    ##### problem occurs when sampling in one bottle which is not full
1812                    ##### and want to begin continuous sampling in other bottle with manual sample
1813 0795 a6 01              LDA   #LEFT_BOTTLE     #set bottle to left
1814 0797 20 0b              BRA   CONT_MANUAL
1815                    RIGHT_MANUAL
1816 0799 0b 03 eb           BRCLR BOTTLE_RIGHT,BOTTLE_RIGHT_P,INVALID_MANUAL
1817                         #                      #branch if right bottle missing
```

```
1818 079c 06 c0 e8              BRSET   RIGHT_FULL,RIGHT_FULL_B,INVALID_MANUAL
1819                        *                                   *branch if right bottle full
1820 079f 00 8d e5              BRSET   0,SAMPLE_BOTTLE,INVALID_MANUAL
1821                        *                                   *branch if left sample bottle
1822 07a2 a6 02                 LDA     #RIGHT_BOTTLE           *set bottle to right
1823                        CONT_MANUAL
1824 07a4 b7 8d                 STA     SAMPLE_BOTTLE           *and sample bottle
1825 07a6 20 0c                 BRA     MANUAL_STATE            *branch if not full
1826                        SPLIT_MANUAL
1827 07a8 0f 03 dc              BRCLR   BOTTLE_LEFT,BOTTLE_LEFT_P,INVALID_MANUAL
1828                        *                                   *branch if left bottle missing
1829 07ab 04 c0 d9              BRSET   LEFT_FULL,LEFT_FULL_B,INVALID_MANUAL
1830                        *                                   *branch if left bottle full
1831 07ae 0b 03 d6              BRCLR   BOTTLE_RIGHT,BOTTLE_RIGHT_P,INVALID_MANUAL
1832                        *                                   *branch if right bottle missing
1833 07b1 06 c0 d3              BRSET   RIGHT_FULL,RIGHT_FULL_B,INVALID_MANUAL
1834                        *                                   *branch if right bottle full
1835                        MANUAL_STATE
1836 07b4 ad 0e                 BSR     MANUAL_CHECK
1837 07b6 26 cf                 BNE     INVALID_MANUAL          *branch if manual sample invalid
1838 07b8 cd 16 67              JSR     C_OR_S_SAMPLE           *set sample flags
1839 07bb cd 1d 2b              JSR     RESTORE_DISPLAY         *display standby
1840 07be cd 14 a4              JSR     NEXT_SAMPLE             *increment sample number
1841                        TAKE_MANUAL_X
1842 07c1 3f c4                 CLR     DISPLAY_TIMEOUT
1843                        MANUAL_EXIT
1844 07c3 81                    RTS
1845                        *
1846                        MANUAL_CHECK
1847 07c4 ae 8e                 LDX     #SAMPLES_TAKEN
1848 07c6 cd 19 bd              JSR     COMPARE_TO_0_2
1849 07c9 27 29                 BEQ     FIRST_MANUAL            *branch if no samples taken
1850 07cb a6 8e                 LDA     #SAMPLES_TAKEN          *compare number of samples taken
1851 07cd ae 5a                 LDX     #NUM_OF_SAMPLES         *to programmed number of samples
1852 07cf cd 19 d2              JSR     COMPARE_2
1853 07d2 27 1d                 BEQ     MANUAL_SAMPLE_1         *branch if already full
1854 07d4 a6 09                 LDA     #9
1855 07d6 b7 cb                 STA     MATH_COUNTER
1856 07d8 ae 53                 LDX     #SAMPLER_PACE           *compare sampling parameters at resume pgm
1857 07da a6 d2                 LDA     #RUN_PARAMETERS         *to compare buffer of start pgm
1858 07dc cd 19 d6              JSR     COMPARE
1859 07df 26 0c                 BNE     MANUAL_CHECK_NO         *branch if unable to resume
1860 07e1 ae 8e                 LDX     #SAMPLES_TAKEN          *otherwise, transfer number of samples taken
1861 07e3 a6 81                 LDA     #SAMPLE_NUMBER          *to current sample number
1862 07e5 cd 19 fc              JSR     TRANSFER_2
1863 07e8 cd 14 a4              JSR     NEXT_SAMPLE             *and increment sample number
1864 07eb 20 15                 BRA     MANUAL_CHECK_OK
1865                        MANUAL_CHECK_NO
1866 07ed ae 01                 LDX     #1                      *set flag to separate bottle
1867 07ef 20 12                 BRA     MANUAL_CHECK_X          *and return
1868                        MANUAL_SAMPLE_1
1869 07f1 cd 15 c2              JSR     TAKEN_0_SAMPLES         *clear samples taken
1870                        FIRST_MANUAL
1871 07f4 cd 15 bb              JSR     SAMPLE_NUMBER_1         *set sample number to one
```

```
1872 07f7 a6 09              LDA    #9
1873 07f9 b7 cb              STA    MATH_COUNTER
1874 07fb ae 53              LDX    #SAMPLER_PACE
1875 07fd a6 d2              LDA    #RUN_PARAMETERS    *transfer sampling parameters at start pgm
1876 07ff cd 1a 00           JSR    TRANSFER          *to resume pgm compare buffer
1877                  MANUAL_CHECK_OK
1878 0802 5f                 CLRX
1879                  MANUAL_CHECK_X
1880 0803 81                 RTS
1881                  *
1882                  MSG_MANUAL_1
1883 0804 5b                 FCC    '['
1884 0805 b8                 FCB    V_MANUAL_
1885 0806 ca                 FCB    V_SAMPLE
1886 0807 2c                 FCC    ','
1887 0808 df                 FCB    END_OF_MESSAGE
1888                  *
1889                  MSG_MANUAL_2
1890 0809 b1                 FCB    V_GRAB_
1891 080a ca                 FCB    V_SAMPLE
1892 080b 5d                 FCC    ']'
1893 080c df                 FCB    END_OF_MESSAGE
1894                  *
1895                  MSG_MANUAL_3
1896 080d c1                 FCB    V_PRESS_
1897 080e b8                 FCB    V_MANUAL_
1898 080f ca                 FCB    V_SAMPLE
1899 0810 df                 FCB    END_OF_MESSAGE
1900                  *
1901                  MSG_MANUAL_4
1902 0811 b5                 FCB    V_KEY
1903 0812 d7                 FCB    V__WHEN_
1904 0813 c5                 FCB    V_READY____
1905 0814 df                 FCB    END_OF_MESSAGE
1906                  *
1907                  *######################
1908                  *# next bottle #
1909                  *######################
1910                  KEY_NEXT_BOTTLE
1911 0815 b6 83              LDA    PUMP_CYCLE
1912 0817 26 1f              BNE    BOTTLE_EXIT        *branch if already sampling
1913 0819 08 01 1c           BRSET  PUMP_FORWARD,PUMP_FORWARD_P,BOTTLE_EXIT
1914                  *                                *branch if pumping forward
1915 081c 06 01 19           BRSET  PUMP_REVERSE,PUMP_REVERSE_P,BOTTLE_EXIT
1916                  *                                *branch if pumping reverse
1917 081f 9c                 RSP
1918 0820 00 c2 0c           BRSET  DIVERT_LEFT,DIVERT_LEFT_P,CHANGE_TO_RIGHT
1919                  *                                *branch if on left bottle
1920 0823 02 c2 03           BRSET  DIVERT_RIGHT,DIVERT_RIGHT_P,CHANGE_TO_LEFT
1921                  *                                *branch if on right bottle
1922 0826 0c 01 06           BRSET  DIST_LEFT,DIST_LEFT_P,CHANGE_TO_RIGHT
1923                  *                                *branch if moving to left sample bottle
1924                  CHANGE_TO_LEFT
1925 0829 1b 01              BCLR   DIST_RIGHT,DIST_RIGHT_P
```

```
1926 082b 1c 01            BSET  DIST_LEFT,DIST_LEFT_P   *move diverter left
1927 082d 20 04            BRA   CHANGE_TO
1928                 CHANGE_TO_RIGHT
1929 082f 1d 01            BCLR  DIST_LEFT,DIST_LEFT_P
1930 0831 1a 01            BSET  DIST_RIGHT,DIST_RIGHT_P *move diverter right
1931                 CHANGE_TO
1932 0833 ad 21            BSR   NEW_POSITION
1933 0835 cc 06 a1         JMP   KEY_ON
1934                 BOTTLE_EXIT
1935 0838 81               RTS
1936                 *
1937                 *    changes and monitors distributor position
1938                 *
1939                 BOTTLE_CHANGE
1940 0839 b6 8d            LDA   SAMPLE_BOTTLE
1941 083b a8 03            EOR   #$03                    *change sample bottle
1942 083d b7 8d            STA   SAMPLE_BOTTLE
1943 083f 81               RTS
1944                 *
1945                 ENFORCE_BOTTLE
1946 0840 0a c0 40         BRSET   MANUAL_BIT,MANUAL_BYTE,NO_ENFORCEMENT
1947                 *                            *branch if grab sampling
1948 0843 02 8d 07         BRSET   1,SAMPLE_BOTTLE,ENFORCE_RIGHT
1949                 *                            *branch if right sample bottle specified
1950 0846 00 c2 3a         BRSET   DIVERT_LEFT,DIVERT_LEFT_P,NO_ENFORCEMENT
1951                 *                            *branch if on left bottle
1952 0849 1c 01            BSET DIST_LEFT,DIST_LEFT_P    *move diverter left
1953 084b 20 05            BRA  ENFORCEMENT
1954                 ENFORCE_RIGHT
1955 084d 02 c2 33         BRSET   DIVERT_RIGHT,DIVERT_RIGHT_P,NO_ENFORCEMENT
1956                 *                            *branch if on right bottle
1957 0850 1a 01            BSET DIST_RIGHT,DIST_RIGHT_P  *move diverter right
1958                 ENFORCEMENT
1959 0852 19 01            BCLR PUMP_FORWARD,PUMP_FORWARD_P
1960 0854 17 01            BCLR PUMP_REVERSE,PUMP_REVERSE_P
1961                 *                            *turn off pump in either direction
1962                 NEW_POSITION
1963 0856 a6 06            LDA  #DIST_TIMER_MAX
1964 0858 b7 c3            STA  DIST_TIMER             *load distributor timeout
1965                 NEXT_ENFORCE
1966 085a cd 05 65         JSR  PERIODIC_SCAN          *periodic scan
1967 085d 0a 01 05         BRSET   DIST_RIGHT,DIST_RIGHT_P,CHECK_RIGHT
1968                 *                            *branch if moving to right sample bottle
1969 0860 00 c2 09         BRSET   DIVERT_LEFT,DIVERT_LEFT_P,ENFORCE_OK
1970                 *                            *branch if on left bottle
1971 0863 20 03            BRA  ENFORCE_ABORT
1972                 CHECK_RIGHT
1973 0865 02 c2 04         BRSET   DIVERT_RIGHT,DIVERT_RIGHT_P,ENFORCE_OK
1974                 *                            *branch if on right bottle
1975                 ENFORCE_ABORT
1976 0868 3d c3            TST  DIST_TIMER
1977 086a 26 ee            BNE  NEXT_ENFORCE           *branch if not timed out
1978                 *
1979                 ENFORCE_OK
```

```
1980 086c 1d 01            BCLR  DIST_LEFT,DIST_LEFT_P
1981                    *                          *turn off diverter left
1982 086e 1b 01            BCLR  DIST_RIGHT,DIST_RIGHT_P
1983                    *                          *turn off diverter right
1984 0870 3f c3            CLR   DIST_TIMER
1985 0872 3d 83            TST   PUMP_CYCLE
1986 0874 27 0d            BEQ   NO_ENFORCEMENT   *branch if not during pump cycle
1987 0876 a6 ff            LDA   #PUMP_JAM_MAX
1988 0878 b7 c7            STA   PUMP_JAM          *reinitialize pump jam count
1989 087a 00 83 04         BRSET 0,PUMP_CYCLE,DIST_PUMP_REV
1990                    *                          *branch if not forward pump cycle
1991 087d 18 01            BSET  PUMP_FORWARD,PUMP_FORWARD_P
1992                    *                          *turn on pump in forward direction
1993 087f 20 02            BRA   NO_ENFORCEMENT
1994                    DIST_PUMP_REV
1995 0881 16 01            BSET  PUMP_REVERSE,PUMP_REVERSE_P
1996                    *                          *turn on pump in reverse direction
1997                    NO_ENFORCEMENT
1998 0883 81               RTS
1999                    *
2000                    *   centers distributor
2001                    *
2002                    DIST_CENTER
2003 0884 07 03 04         BRCLR DIVERT_QUAD,DIVERT_QUAD_P,CENTER_RIGHT
2004                    *                          *branch if in left quadrant
2005 0887 1c 01            BSET  DIST_LEFT,DIST_LEFT_P
2006                    *                          *otherwise, move distributor left
2007 0889 20 02            BRA   NEW_CENTER
2008                    CENTER_RIGHT
2009 088b 1a 01            BSET  DIST_RIGHT,DIST_RIGHT_P
2010                    *                          *move distributor right
2011                    NEW_CENTER
2012 088d a6 06            LDA   #DIST_TIMER_MAX
2013 088f b7 c3            STA   DIST_TIMER        *load distributor timeout
2014                    NEXT_CENTER
2015 0891 cd 05 65         JSR   PERIODIC_SCAN    *periodic scan
2016 0894 0a 01 05         BRSET DIST_RIGHT,DIST_RIGHT_P,RIGHT_CENTER
2017                    *                          *branch if moving right
2018 0897 07 03 09         BRCLR DIVERT_QUAD,DIVERT_QUAD_P,CENTER_OK
2019                    *                          *branch if in left quadrant
2020 089a 20 03            BRA   CENTER_ABORT
2021                    RIGHT_CENTER
2022 089c 06 03 04         BRSET DIVERT_QUAD,DIVERT_QUAD_P,CENTER_OK
2023                    *                          *branch if in right quadrant
2024                    CENTER_ABORT
2025 089f 3d c3            TST   DIST_TIMER
2026 08a1 26 ee            BNE   NEXT_CENTER      *branch if not timed out
2027                    *
2028                    CENTER_OK
2029 08a3 1d 01            BCLR  DIST_LEFT,DIST_LEFT_P
2030                    *                          *turn off diverter left
2031 08a5 1b 01            BCLR  DIST_RIGHT,DIST_RIGHT_P
2032                    *                          *turn off diverter right
2033 08a7 3f c3            CLR   DIST_TIMER
```

```
2034 08a9 81              RTS
2035                 *
2036                 *****************************
2037                 ** 9 8 7 6 5 4 3 2 1 0 *
2038                 *****************************
2039 08aa 4c         KEY_9    INCA
2040 08ab 4c         KEY_8    INCA
2041 08ac 4c         KEY_7    INCA
2042 08ad 4c         KEY_6    INCA
2043 08ae 4c         KEY_5    INCA
2044 08af 4c         KEY_4    INCA
2045 08b0 4c         KEY_3    INCA
2046 08b1 4c         KEY_2    INCA
2047 08b2 4c         KEY_1    INCA
2048                 KEY_0
2049 08b3 b7 b6          STA  TEMP            *save number
2050 08b5 be af          LDX  PGM_DIGIT
2051 08b7 e7 a3          STA  PGM_VALUE,X     *save digit
2052 08b9 b6 af          LDA  PGM_DIGIT
2053 08bb 26 06          BNE  NO_CLEAR_LCD
2054 08bd cd 0a 64       JSR  PGM_UNLOCK      *check if program is unlocked
2055 08c0 cd 0a dc       JSR  POSITION_CLEAR  *clear digit display if first digit
2056                 NO_CLEAR_LCD
2057 08c3 a6 0f          LDA  #$0F            *display control
2058 08c5 cd 02 dc       JSR  LCD_CMD_WRITE   *display on, cursor on, blink on
2059 08c8 b6 ae          LDA  PGM_LENGTH
2060 08ca a4 0f          AND  #$0F
2061 08cc b1 af          CMP  PGM_DIGIT
2062 08ce 27 09          BEQ  NUMBER_RETURN   *branch if digits not finished
2063 08d0 b6 b6          LDA  TEMP
2064 08d2 aa 30          ORA  #$30
2065 08d4 cd 02 90       JSR  LCD_DATA_WRITE  *and display
2066 08d7 3c af          INC  PGM_DIGIT       *increment digit counter
2067                 NUMBER_RETURN
2068 08d9 81             RTS
2069                 *
2070                 *    program pgm
2071                 *
2072                 *****************
2073                 ** clear entry *
2074                 *****************
2075                 KEY_CLEAR_ENTRY
2076 08da 3f af          CLR  PGM_DIGIT       *clear digit number
2077 08dc cd 09 f6       JSR  FLASH_ON        *display current value and set flash to on
2078 08df 81             RTS
2079                 *
2080                 *****************
2081                 ** exit program *
2082                 *****************
2083                 KEY_EXIT_PGM
2084 08e0 cc 06 a1       JMP  KEY_ON          *return to standby state
2085                 *
2086                 **********
2087                 ** ----> *
```

```
2088                    **********
2089                    KEY_RIGHT_ARROW
2090 08e3 b6 a0             LDA  KEY_MASK
2091 08e5 a1 0c             CMP  #MASK_PGM_ENTER
2092 08e7 27 37             BEQ  KEY_ENTER_PGM        *branch if pgm enter screen
2093 08e9 cd 09 f6          JSR  FLASH_ON             *restore flashing selection
2094 08ec 3c a2             INC  PGM_CHOICE           *move selection to the right
2095 08ee b6 a2             LDA  PGM_CHOICE
2096 08f0 b1 ad             CMP  PGM_SELECTIONS
2097 08f2 25 02             BLO  RIGHT_ARROW_RTS      *branch if right selection exists
2098 08f4 3f a2             CLR  PGM_CHOICE           *otherwise, choose leftmost selection
2099                    RIGHT_ARROW_RTS
2100 08f6 cd 0a 64          JSR  PGM_UNLOCK           *check if program is unlocked
2101 08f9 cd 09 f6          JSR  FLASH_ON
2102 08fc 81               RTS
2103                    *
2104                    **********
2105                    *# <----- #
2106                    **********
2107                    KEY_LEFT_ARROW
2108 08fd b6 a0             LDA  KEY_MASK
2109 08ff a1 0c             CMP  #MASK_PGM_ENTER
2110 0901 26 0a             BNE  LEFT_CHOICE          *branch if not pgm enter screen
2111 0903 3d a2             TST  PGM_CHOICE
2112 0905 27 15             BEQ  LEFT_ARROW_EXIT      *branch if on first entry
2113 0907 ad d1             BSR  KEY_CLEAR_ENTRY      *clear entry
2114 0909 3a a2             DEC  PGM_CHOICE           *move entry to the left
2115 090b 20 3e             BRA  NEXT_NUMERIC
2116                    LEFT_CHOICE
2117 090d cd 09 f6          JSR  FLASH_ON             *restore flashing selection
2118 0910 3a a2             DEC  PGM_CHOICE           *move selection to the left
2119 0912 2a 05             BPL  LEFT_ARROW_RTS       *branch if left selection exists
2120 0914 b6 ad             LDA  PGM_SELECTIONS
2121 0916 4a                DECA
2122 0917 b7 a2             STA  PGM_CHOICE           *otherwise, choose rightmost selection
2123                    LEFT_ARROW_RTS
2124 0919 cd 0a 64          JSR  PGM_UNLOCK           *check if program is unlocked
2125                    LEFT_ARROW_EXIT
2126 091c cd 09 f6          JSR  FLASH_ON
2127 091f 81               RTS
2128                    *
2129                    *****************
2130                    *# enter/program #
2131                    *****************
2132                    KEY_ENTER_PGM
2133 0920 9c                RSP
2134 0921 b6 51             LDA  SAMPLER_STATE
2135 0923 a1 02             CMP  #STATE_PGM
2136 0925 26 2c             BNE  PROGRAM              *branch if not already in program state
2137 0927 b6 a0             LDA  KEY_MASK
2138 0929 a1 0c             CMP  #MASK_PGM_ENTER
2139 092b 22 07             BHI  GO_TO_NEXT_STEP      *branch if abnormal pgm screen
2140 092d 27 0e             BEQ  NUMERIC_ENTER        *branch if numeric entry screen
2141 092f be ac             LDX  PGM_STORAGE
```

```
2142 0931 b6 a2              LDA  PGM_CHOICE
2143 0933 f7                 STA  ,X                    *otherwise, store new value in variable
2144                    GO_TO_NEXT_STEP
2145 0934 be a1              LDX  PGM_BRANCH            *current location in pgm sequence
2146 0936 d6 12 ad           LDA  PROGRAM_FLOW-1,X      *load next branch number
2147 0939 b7 a1              STA  PGM_BRANCH
2148 093b 20 27              BRA  NEXT_PROGRAM          *go on to next branch
2149                    NUMERIC_ENTER
2150 093d cd 0a f4           JSR  STORE_PROGRAM         *store entry, if any
2151 0940 cd 03 61           JSR  NUMBER_DISPLAY        *and display value right justified
2152 0943 3c a2              INC  PGM_CHOICE
2153 0945 b6 a2              LDA  PGM_CHOICE
2154 0947 b1 ad              CMP  PGM_SELECTIONS
2155 0949 24 e9              BHS  GO_TO_NEXT_STEP       *branch if no more numeric entries
2156                    NEXT_NUMERIC
2157 094b cd 0a cf           JSR  LOAD_PARAMETERS       *load numeric entry parameters for this entry
2158 094e cd 09 f6           JSR  FLASH_ON
2159 0951 20 14              BRA  BRANCH_CHECK          *wait for further keypad entry
2160                    *
2161                    *    entry to program state
2162                    *
2163                    PROGRAM
2164 0953 a6 01              LDA  #1
2165 0955 b7 a1              STA  PGM_BRANCH            *initialize pgm branch
2166 0957 a6 02              LDA  #STATE_PGM
2167 0959 b7 51              STA  SAMPLER_STATE         *set sampler state
2168 095b 1b c1              BCLR PGM_UNLOCK_BIT,PGM_UNLOCK_BYTE
2169                    *                                *clear program unlocked bit
2170 095d cd 16 50           JSR  RUN_CLEAR
2171 0960 3f c6              CLR  REVIEW_BRANCH         *clear position within review pgm
2172 0962 11 70              BCLR 0,YES_NO_QUESTION     *set response to program sampler
2173                    PGM_STATE
2174                    NEXT_PROGRAM
2175 0964 9c                 RSP
2176 0965 ad 05              BSR  LOAD_DISPLAY
2177                    BRANCH_CHECK
2178 0967 cd 05 65           JSR  PERIODIC_SCAN         *continuously scan routines
2179 096a 20 fb              BRA  BRANCH_CHECK
2180                    *
2181                    LOAD_DISPLAY
2182 096c cd 0a 96           JSR  FIND_PGM_BRANCH       *find position in pgm data for this branch
2183 096f cd 02 d6           JSR  CLEAR_LCD             *clear display
2184 0972 a6 08              LDA  #MASK_PGM_SELECT
2185 0974 b7 a0              STA  KEY_MASK              *assume non numeric branch
2186 0976 bd 2c              JSR  LDA_EXTENDED          *load keypad mask
2187 0978 cd 0c 13           JSR  SPECIALS              *check for special function code
2188 097b a1 1c              CMP  #MASK_PGM_NONE
2189 097d 23 08              BLS  NUMERIC_MASK          *branch if numeric branch
2190 097f b7 ac              STA  PGM_STORAGE           *otherwise, store pgm variable
2191 0981 97                 TAX
2192 0982 f6                 LDA  ,X
2193 0983 b7 a2              STA  PGM_CHOICE            *and current value
2194 0985 20 02              BRA  FIXED_DISPLAY
2195                    NUMERIC_MASK
```

```
2196 0987 b7 a0            STA  KEY_MASK            *store numeric keypad mask
2197                    *
2198                    FIXED_DISPLAY
2199 0989 bd 2c            JSR  LDA_EXTENDED        *load lcd position
2200 098b cd 02 da         JSR  LCD_CURSOR          *position cursor
2201 098e 3c ad            INC  PGM_SELECTIONS      *increment number of cursor selections
2202                    NEXT_CHARACTER
2203 0990 bd 2c            JSR  LDA_EXTENDED
2204 0992 a1 df            CMP  #END_OF_MESSAGE
2205 0994 27 f3            BEQ  FIXED_DISPLAY       *branch if end of message
2206 0996 a1 e0            CMP  #END_OF_DISPLAY
2207 0998 27 09            BEQ  END_OF_FIXED        *branch if end of fixed display
2208 099a a1 e1            CMP  #END_OF_BRANCH
2209 099c 27 15            BEQ  END_OF_PGM_STEP     *branch if end of pgm step
2210 099e cd 02 90         JSR  LCD_DATA_WRITE      *otherwise, display character
2211 09a1 20 ed            BRA  NEXT_CHARACTER      *and go on to next byte
2212                    *
2213                    END_OF_FIXED
2214 09a3 b6 a0            LDA  KEY_MASK
2215 09a5 a1 08            CMP  #MASK_PGM_SELECT
2216 09a7 26 18            BNE  DISPLAY_ENTRIES     *branch if numeric branch
2217 09a9 b6 a1            LDA  PGM_BRANCH
2218 09ab a1 13            CMP  #19
2219 09ad 27 08            BEQ  SELECT_OPTION       *branch if select option screen
2220 09af 3f ad            CLR  PGM_SELECTIONS      *otherwise, clear number of selections
2221 09b1 20 d6            BRA  FIXED_DISPLAY       *and display these selections
2222                    *
2223                    END_OF_PGM_STEP
2224 09b3 cd 09 f6         JSR  FLASH_ON            *flash current choice
2225 09b6 81               RTS
2226                    *
2227                    SELECT_OPTION
2228 09b7 b6 52            LDA  PROGRAM_CHOICE
2229 09b9 b7 a2            STA  PGM_CHOICE          *set current selection number
2230 09bb a6 0c            LDA  #12
2231 09bd b7 ad            STA  PGM_SELECTIONS      *set number of selections
2232 09bf 20 f2            BRA  END_OF_PGM_STEP
2233                    *
2234                    DISPLAY_ENTRIES
2235 09c1 3f a2            CLR  PGM_CHOICE          *clear variable number
2236 09c3 3f ad            CLR  PGM_SELECTIONS      *clear number of variables on this screen
2237 09c5 bd 2c            JSR  LDA_EXTENDED
2238                    NEXT_ENTRY
2239 09c7 ad 12            BSR  PARAMETER_ENTRY     *load parameters for each variable
2240 09c9 cd 03 61         JSR  NUMBER_DISPLAY      *and display
2241 09cc 3c ad            INC  PGM_SELECTIONS      *increment number of entries on this display
2242 09ce bd 2c            JSR  LDA_EXTENDED
2243 09d0 a1 e1            CMP  #END_OF_BRANCH
2244 09d2 26 f3            BNE  NEXT_ENTRY          *branch if not end of this branch
2245 09d4 cd 0a cf         JSR  LOAD_PARAMETERS     *load parameters for first numeric variable
2246 09d7 20 da            BRA  END_OF_PGM_STEP
2247                    *
2248                    *   loads parameters for numeric variables
2249                    *
```

```
2250                     ENTRY_PARAMETER
2251 09d9 bd 2c              JSR  LDA_EXTENDED      *load and store pgm storage
2252                     PARAMETER_ENTRY
2253 09db b7 ac              STA  PGM_STORAGE
2254 09dd bd 2c              JSR  LDA_EXTENDED      *and length, leading 0, valid 0, and limit 9
2255 09df b7 ae              STA  PGM_LENGTH
2256 09e1 bd 2c              JSR  LDA_EXTENDED      *and lcd position
2257 09e3 b7 b0              STA  PGM_LCD
2258 09e5 0a ae 04           BRSET   LIMIT_9_BIT,PGM_LENGTH,PARAMETER_EXIT
2259                     *                          *branch if high limit of all 9s
2260 09e8 bd 2c              JSR  LDA_EXTENDED      *and high limit
2261 09ea b7 b2              STA  PGM_LIMIT
2262                     PARAMETER_EXIT
2263 09ec 3f af              CLR  PGM_DIGIT         *clear digit number
2264 09ee 81                  RTS
2265                     *
2266                     *   flashes current selection or numeric value on and off
2267                     *
2268                     FLASH_CHOICE
2269 09ef b6 b1              LDA  FLASH
2270 09f1 27 2c              BEQ  FLASH_ON_EXIT     *branch if nothing flashing
2271 09f3 4a               DECA
2272 09f4 26 2a              BNE  FLASH_OFF         *branch if currently displayed
2273                     *
2274                     *   displays current selection or numeric value
2275                     *
2276                     FLASH_ON
2277 09f6 a6 02              LDA  #2
2278 09f8 b7 b1              STA  FLASH             *set code to flash on
2279 09fa b6 a0              LDA  KEY_MASK
2280 09fc a1 14              CMP  #MASK_PGM_MANUAL
2281 09fe 24 1f              BHS  FLASH_ON_EXIT     *branch if pgm manual or stop
2282 0a00 a1 0c              CMP  #MASK_PGM_ENTER
2283 0a02 26 05              BNE  FLASH_ON_NON      *blank if cursor selection screen
2284 0a04 cd 03 61           JSR  NUMBER_DISPLAY    *otherwise, display value
2285 0a07 20 16              BRA  FLASH_ON_EXIT
2286                     FLASH_ON_NON
2287 0a09 cd 0a bc           JSR  SKIP_TO_CHOICE    *locate message to flash
2288                     NEXT_ON_FLASH
2289 0a0c bd 2c              JSR  LDA_EXTENDED
2290 0a0e a1 df              CMP  #END_OF_MESSAGE
2291 0a10 24 05              BHS  CLEAR_FLASH       *branch if end of message or end of branch
2292 0a12 cd 02 90           JSR  LCD_DATA_WRITE    *otherwise, display choice
2293 0a15 20 f5              BRA  NEXT_ON_FLASH
2294                     CLEAR_FLASH
2295 0a17 b6 a1              LDA  PGM_BRANCH
2296 0a19 a1 13              CMP  #19
2297 0a1b 26 02              BNE  FLASH_ON_EXIT     *branch if not select option screen
2298 0a1d 3f b1              CLR  FLASH             *otherwise, clear flash
2299                     FLASH_ON_EXIT
2300 0a1f 81                  RTS
2301                     *
2302                     *   blanks display of current selection or numeric value
2303                     *
```

```
2304                       FLASH_OFF
2305 0a20 a6 01               LDA  #1
2306 0a22 b7 b1               STA  FLASH              ;set code to flash off
2307 0a24 b6 a0               LDA  KEY_MASK
2308 0a26 a1 14               CMP  #MASK_PGM_MANUAL
2309 0a28 24 1d               BHS  FLASH_OFF_EXIT     ;branch if pgm manual or stop
2310 0a2a a1 0c               CMP  #MASK_PGM_ENTER
2311 0a2c 26 05               BNE  FLASH_OFF_NON      ;branch if cursor selection screen
2312 0a2e cd 0a dc            JSR  POSITION_CLEAR     ;clear numeric display position
2313 0a31 20 14               BRA  FLASH_OFF_EXIT
2314                       FLASH_OFF_NON
2315 0a33 cd 0a bc            JSR  SKIP_TO_CHOICE     ;locate message to flash
2316                       NEXT_OFF_FLASH
2317 0a36 bd 2c               JSR  LDA_EXTENDED
2318 0a38 a1 df               CMP  #END_OF_MESSAGE
2319 0a3a 24 0b               BHS  FLASH_OFF_EXIT     ;branch if end of message or end of branch
2320 0a3c a1 a0               CMP  #VOCABULARY
2321 0a3e 22 08               BHI  VOCABULARY_OFF
2322 0a40 a6 20               LDA  #SPACE
2323 0a42 cd 02 90            JSR  LCD_DATA_WRITE     ;otherwise, blank display
2324 0a45 20 ef               BRA  NEXT_OFF_FLASH
2325                       FLASH_OFF_EXIT
2326 0a47 81                  RTS
2327                       VOCABULARY_OFF
2328 0a48 cd 02 ac            JSR  FIND_VOCABULARY
2329                       NEXT_VOCABULARY
2330 0a4b bd 2c               JSR  LDA_EXTENDED
2331 0a4d a1 e1               CMP  #END_OF_BRANCH
2332 0a4f 27 07               BEQ  END_VOCABULARY     ;branch if end of message
2333 0a51 a6 20               LDA  #SPACE
2334 0a53 cd 02 c5            JSR  LCD_WRITE_DATA     ;otherwise, blank display
2335 0a56 20 f3               BRA  NEXT_VOCABULARY    ;and go on to next byte
2336                       END_VOCABULARY
2337 0a58 be b9               LDX  TEMP4
2338 0a5a bf cf               STX  EXTENDED+1         ;restore position pointer to branch table
2339 0a5c be ba               LDX  TEMP5
2340 0a5e bf d0               STX  EXTENDED+2
2341 0a60 be b8               LDX  TEMP3              ;restore index register
2342 0a62 20 d2               BRA  NEXT_OFF_FLASH
2343                       *
2344                       *   returns if unlocking the program is unnecessary
2345                       *   otherwise, asks user to enter passnumber
2346                       *
2347                       PGM_UNLOCK
2348 0a64 0a c1 2B            BRSET  PGM_UNLOCK_BIT,PGM_UNLOCK_BYTE,PGM_UNLOCK_EXIT
2349                       *                              ;branch if program already unlocked
2350 0a67 00 7a 25            BRSET  0,PROGRAM_LOCK,PGM_UNLOCK_EXIT
2351                       *                              ;branch if program lock disabled
2352 0a6a b6 a1               LDA  PGM_BRANCH
2353 0a6c 97                  TAX
2354 0a6d 54                  LSRX
2355 0a6e 54                  LSRX
2356 0a6f 54                  LSRX
2357 0a70 de 0a 90            LDX  UNLOCKABILITY,X    ;load unlockability bits for this pgm branch
```

```
2358 0a73 a4 07            AND  #$07
2359               UNLOCK_CHECK
2360 0a75 54               LSRX                    *rotate to mask bit for this branch
2361 0a76 4a               DECA
2362 0a77 2a fc            BPL  UNLOCK_CHECK       *branch if not bit for this branch
2363 0a79 25 14            BCS  PGM_UNLOCK_EXIT    *branch if mask bit set
2364               *
2365 0a7b ae a1            LDX  #PGM_BRANCH        *transfer program parameters
2366 0a7d a6 db            LDA  #PGM_SAVE          *to buffer
2367 0a7f cd 19 fa         JSR  TRANSFER_3
2368 0a82 a6 ff            LDA  #$FF
2369 0a84 b7 9c            STA  PASS_NUMBER        *set pass number to question marks
2370 0a86 b7 9d            STA  PASS_NUMBER+1
2371 0a88 a6 25            LDA  #37
2372 0a8a b7 a1            STA  PGM_BRANCH         *go to select option screen
2373 0a8c cc 09 64         JMP  NEXT_PROGRAM
2374               PGM_UNLOCK_EXIT
2375 0a8f 81               RTS
2376               *
2377               UNLOCKABILITY
2378 0a90 42               FCB  %01000010          *7 ... 0
2379 0a91 02               FCB  %00000010
2380 0a92 0c               FCB  %00001100
2381 0a93 00               FCB  %00000000
2382 0a94 20               FCB  %00100000
2383 0a95 00               FCB  %00000000          *47 ... 40
2384               *
2385               *   positions pointer to program branch data in table
2386               *
2387               FIND_PGM_BRANCH
2388 0a96 be a1             LDX  PGM_BRANCH
2389 0a98 c6 0f 19          LDA  PROGRAM_STEP
2390 0a9b b7 cf             STA  EXTENDED+1         *position pointer to branch table
2391 0a9d c6 0f 1a          LDA  PROGRAM_STEP+1
2392               FIND_REV_BRANCH
2393 0aa0 b7 d0             STA  EXTENDED+2
2394               NEXT_BRANCH
2395 0aa2 5a               DECX                    *index register holds program branch number
2396 0aa3 27 08            BEQ  BRANCH_FOUND       *branch if branch found
2397               NO_BRANCH_FOUND
2398 0aa5 bd 2c             JSR  LDA_EXTENDED
2399 0aa7 a1 e1             CMP  #END_OF_BRANCH
2400 0aa9 26 fa             BNE  NO_BRANCH_FOUND    *branch if not end of this branch
2401 0aab 20 f5             BRA  NEXT_BRANCH
2402               BRANCH_FOUND
2403 0aad 81               RTS
2404               *
2405               *   skips past fixed screen text
2406               *
2407               SKIP_FIXED_TEXT
2408 0aae bd 2c             JSR  LDA_EXTENDED
2409 0ab0 a1 e0             CMP  #END_OF_DISPLAY
2410 0ab2 26 fa             BNE  SKIP_FIXED_TEXT    *branch if not end of fixed screen text
2411 0ab4 81               RTS
```

```
2412            *
2413            *   skips past nonflashing messages
2414            *
2415            SKIP_MESSAGE
2416 0ab5 bd 2c     JSR  LDA_EXTENDED
2417 0ab7 a1 df     CMP  #END_OF_MESSAGE
2418 0ab9 26 fa     BNE  SKIP_MESSAGE        *branch if not end of message
2419 0abb 81        RTS
2420            *
2421            *   positions pointer to program branch data in table
2422            *   skips past fixed screen text
2423            *   skips past nonflashing messages
2424            *   and positions cursor
2425            *
2426            SKIP_TO_CHOICE
2427 0abc ad d8     BSR  FIND_PGM_BRANCH     *position within program table
2428 0abe ad ee     BSR  SKIP_FIXED_TEXT     *skip past fixed text
2429 0ac0 be a2     LDX  PGM_CHOICE
2430 0ac2 27 05     BEQ  ON_OFF_FLASH        *branch if leftmost choice flashing
2431            MESSAGE_SKIP
2432 0ac4 ad ef     BSR  SKIP_MESSAGE        *skip past nonflashing messages
2433 0ac6 5a        DECX
2434 0ac7 26 fb     BNE  MESSAGE_SKIP
2435            ON_OFF_FLASH
2436 0ac9 bd 2c     JSR  LDA_EXTENDED
2437 0acb cd 02 da  JSR  LCD_CURSOR          *position cursor
2438 0ace 81        RTS
2439            *
2440            *   locates position with program table
2441            *   skips past fixed screen text
2442            *   loads parameters for current numeric entry screen
2443            *
2444            LOAD_PARAMETERS
2445 0acf ad c5     BSR  FIND_PGM_BRANCH     *position within program table
2446 0ad1 ad db     BSR  SKIP_FIXED_TEXT     *skip past fixed screen text
2447 0ad3 be a2     LDX  PGM_CHOICE
2448            SKIP_PARAMETER
2449 0ad5 cd 09 d9  JSR  ENTRY_PARAMETER     *load numeric parameters for this variable
2450 0ad8 5a        DECX
2451 0ad9 2a fa     BPL  SKIP_PARAMETER      *jump if this is not the current variable
2452 0adb 81        RTS
2453            *
2454            *   clears lcd locations starting at position pgm_lcd
2455            *   of length pgm_length
2456            *   then resets cursor to position pgm_lcd
2457            *
2458            POSITION_CLEAR
2459 0adc b6 b0     LDA  PGM_LCD
2460 0ade cd 02 da  JSR  LCD_CURSOR          *set lcd address
2461 0ae1 b6 ae     LDA  PGM_LENGTH
2462 0ae3 a4 0f     AND  #$0F
2463 0ae5 97        TAX
2464            NEXT_POSITION
2465 0ae6 a6 20     LDA  #SPACE
```

```
2466 0ae8 cd 02 90        JSR   LCD_DATA_WRITE    *clear display
2467 0aeb 5a              DECX
2468 0aec 26 f8           BNE   NEXT_POSITION
2469 0aee b6 b0           LDA   PGM_LCD
2470 0af0 cd 02 da        JSR   LCD_CURSOR        *reset lcd address
2471 0af3 81              RTS
2472                  *
2473                  *   if digits entered
2474                  *   checks valid 0 and high limit
2475                  *   if different value entered
2476                  *   checks if program lock disabled or already unlocked
2477                  *   if so, clears area at pgm storage location of pgm length rounded up
2478                  *   then stores programmed digits in pgm value
2479                  *   of length pgm digit at pgm storage location decremented
2480                  *
2481                  STORE_PROGRAM
2482 0af4 b6 af           LDA   PGM_DIGIT
2483 0af6 27 5a           BEQ   STORE_PGM_CHECK   *skip if no digits entered
2484 0af8 0e ae 15        BRSET VALID_0_BIT,PGM_LENGTH,CHECK_HIGH
2485                  *                             *branch if zero entry valid
2486 0afb b6 af           LDA   PGM_DIGIT
2487 0afd b7 cb           STA   MATH_COUNTER
2488 0aff ae a3           LDX   #PGM_VALUE
2489 0b01 cd 19 c1        JSR   COMPARE_TO_ZERO
2490 0b04 26 0a           BNE   CHECK_HIGH        *branch if nonzero entry
2491                  BAD_ENTRY_EXIT
2492 0b06 9c              RSP
2493 0b07 cd 18 2c        JSR   ERROR_BEEP        *beep
2494 0b0a cd 08 da        JSR   KEY_CLEAR_ENTRY   *display current value
2495 0b0d cc 09 67        JMP   BRANCH_CHECK
2496                  CHECK_HIGH
2497 0b10 0a ae 02        BRSET LIMIT_9_BIT,PGM_LENGTH,PROGRAM_STORE
2498                  *                             *branch if high limit of all 9s
2499 0b13 ad 43           BSR   VALID_LIMIT       *check high limit
2500                  PROGRAM_STORE
2501 0b15 b6 ae           LDA   PGM_LENGTH
2502 0b17 a4 0f           AND   #$0F
2503 0b19 4c              INCA                    *round up digit length
2504 0b1a 44              LSRA
2505 0b1b be ac           LDX   PGM_STORAGE
2506                  NEXT_STORE_CLR
2507 0b1d 7f              CLR   ,X                *clear pgm storage location
2508 0b1e 5c              INCX
2509 0b1f 4a              DECA
2510 0b20 26 fb           BNE   NEXT_STORE_CLR
2511 0b22 b6 ae           LDA   PGM_LENGTH
2512 0b24 a4 0f           AND   #$0F
2513 0b26 4a              DECA
2514 0b27 44              LSRA                    *round down pgm length
2515 0b28 bb ac           ADD   PGM_STORAGE       *add pgm storage location
2516 0b2a b7 b7           STA   TEMP2             *storage address
2517 0b2c be af           LDX   PGM_DIGIT         *load digit count
2518 0b2e 5a              DECX
2519 0b2f bf b8           STX   TEMP3
```

```
2520                    LOW_DIGIT_STORE
2521 0b31 be b8             LDX   TEMP3
2522 0b33 e6 a3             LDA   PGM_VALUE,X     *low digit to store
2523 0b35 be b7             LDX   TEMP2
2524 0b37 f7                STA   ,X
2525 0b38 3a b8             DEC   TEMP3
2526 0b3a 2b 15             BMI   STORE_PGM_EXIT  *branch if no more digits
2527 0b3c b7 b6             STA   TEMP
2528 0b3e be b8             LDX   TEMP3
2529 0b40 e6 a3             LDA   PGM_VALUE,X     *high digit
2530 0b42 48                ASLA
2531 0b43 48                ASLA                  *rotate to high nibble
2532 0b44 48                ASLA
2533 0b45 48                ASLA
2534 0b46 ba b6             ORA   TEMP            *append low digit
2535 0b48 be b7             LDX   TEMP2
2536 0b4a f7                STA   ,X
2537 0b4b 3a b7             DEC   TEMP2           *decrement storage address
2538 0b4d 3a b8             DEC   TEMP3
2539 0b4f 2a e0             BPL   LOW_DIGIT_STORE *branch if more digits
2540                    STORE_PGM_EXIT
2541 0b51 81                RTS
2542                    STORE_PGM_CHECK
2543 0b52 b6 bd             LDA   TEMP_DAY
2544 0b54 ad 13             BSR   VALID_DAY
2545 0b56 20 f9             BRA   STORE_PGM_EXIT
2546                    *
2547                    *   checks validity of day of month given year and month
2548                    *
2549                    VALID_LIMIT
2550 0b58 b6 af             LDA   PGM_DIGIT
2551 0b5a 4a                DECA
2552 0b5b 27 3a             BEQ   VALID_LIMIT_RTS *branch if only one digit entered
2553 0b5d b6 a3             LDA   PGM_VALUE       *combine first digit entered
2554 0b5f 48                ASLA
2555 0b60 48                ASLA
2556 0b61 48                ASLA
2557 0b62 48                ASLA
2558 0b63 ba a4             ORA   PGM_VALUE+1     *with second digit entered
2559 0b65 b1 b2             CMP   PGM_LIMIT       *compare to high limit
2560 0b67 22 9d             BHI   BAD_ENTRY_EXIT  *branch if value too large
2561                    VALID_DAY
2562 0b69 b7 b8             STA   TEMP3           *save day of month entered or current value
2563 0b6b b6 ac             LDA   PGM_STORAGE
2564 0b6d a1 bd             CMP   #TEMP_DAY
2565 0b6f 26 26             BNE   VALID_LIMIT_RTS *branch if not entering day of month
2566 0b71 b6 a1             LDA   PGM_BRANCH
2567 0b73 a1 16             CMP   #22
2568 0b75 27 12             BEQ   VALID_DAY_PASS  *branch if not entering time of first sample
2569 0b77 b6 91             LDA   RTC_YEAR        *assume current year
2570 0b79 b7 bb             STA   TEMP_YEAR       *is year of first/next sample
2571 0b7b ae bc             LDX   #TEMP_MONTH     *compare date/time of first/next sample
2572 0b7d a6 92             LDA   #RTC_MONTH      *to current date/time
2573 0b7f cd 19 ce          JSR   COMPARE_4
```

```
2574 0b82 22 05            BHI   VALID_DAY_PASS       *branch if first after current
2575 0b84 a6 bb            LDA   #TEMP_YEAR
2576 0b86 cd 1a 89         JSR   BCD_INCREMENT_1      *otherwise, increment year of first
2577                 VALID_DAY_PASS
2578 0b89 b6 bb            LDA   TEMP_YEAR            *year
2579 0b8b be bc            LDX   TEMP_MONTH           *and month of first sample
2580 0b8d cd 18 3d         JSR   DAYS_PER_MONTH       *calculate days per month
2581 0b90 b3 b8            CPX   TEMP3
2582 0b92 24 03            BHS   VALID_LIMIT_RTS
2583 0b94 cc 0b 06         JMP   BAD_ENTRY_EXIT       *branch if invalid day
2584                 VALID_LIMIT_RTS
2585 0b97 81               RTS
2586                 *
2587                 *     calculates nominal pump counts
2588                 *     given nominal sample volume, slope, and y intercept
2589                 *
2590                 CALIBRATION
2591                 ***** test
2592                 *     LDX   #NOMINAL_VOLUME
2593                 *     LDA   #NOMINAL_COUNT
2594                 *     JSR   TRANSFER_2
2595                 *     RTS
2596                 *****
2597                 ***** could this now be done with less code space?
2598 0b98 4f               CLRA
2599 0b99 3d 57            TST   NOMINAL_VOLUME
2600 0b9b 26 0B            BNE   CAL_EQUATION         *branch if nominal volume greater than 99
2601 0b9d be 58            LDX   NOMINAL_VOLUME+1
2602 0b9f a3 26            CPX   #$26
2603 0ba1 22 02            BHI   CAL_EQUATION         *branch if nominal volume greater than 26
2604 0ba3 ab 16            ADD   #22                  *otherwise, use bottom line below knee
2605                 CAL_EQUATION
2606 0ba5 b7 b8            STA   TEMP3                *store choice of line
2607                 *
2608 0ba7 b6 57            LDA   NOMINAL_VOLUME       *convert upper digit of nominal volume
2609 0ba9 48               ASLA                       *multiply by 2 for 2 bytes per step
2610 0baa bb b8            ADD   TEMP3                *add position in volume to count steps table
2611 0bac ab 02            ADD   #2                   *skip past slope entry
2612 0bae 97               TAX                        *transfer nominal count for this step
2613 0baf d6 0b f9         LDA   EQUATION_VALUES,X
2614 0bb2 b7 5c            STA   NOMINAL_COUNT        *to nominal count
2615 0bb4 d6 0b fa         LDA   EQUATION_VALUES+1,X
2616 0bb7 b7 5d            STA   NOMINAL_COUNT+1
2617 0bb9 3f 5e            CLR   NOMINAL_COUNT+2      *clear decimal portion of count
2618 0bbb b6 58            LDA   NOMINAL_VOLUME+1     *transfer lower digit of nominal volume
2619 0bbd 27 23            BEQ   CALIBRATION_X        *branch if zero
2620 0bbf b7 b9            STA   TEMP4                *to temp
2621 0bc1 be b8            LDX   TEMP3
2622 0bc3 3f bb            CLR   TEMP6
2623 0bc5 d6 0b f9         LDA   EQUATION_VALUES,X    *transfer slope
2624 0bc8 b7 bc            STA   TEMP6+1              *to temp
2625 0bca d6 0b fa         LDA   EQUATION_VALUES+1,X
2626 0bcd b7 bd            STA   TEMP6+2
2627                 NEXT_MILLILITER
```

```
2628 0bcf 9a                CLI
2629 0bd0 9d                NOP                     *allow interrupts
2630 0bd1 9b                SEI
2631 0bd2 ae bb             LDX  #TEMP6             *add slope
2632 0bd4 a6 5c             LDA  #NOMINAL_COUNT     *to nominal count
2633 0bd6 cd 1a 46          JSR  ADD_3
2634 0bd9 a6 b9             LDA  #TEMP4
2635 0bdb cd 1a 9f          JSR  BCD_DECREMENT_1    *decrement temp nominal sample volume
2636 0bde 3d b9             TST  TEMP4
2637 0be0 26 ed             BNE  NEXT_MILLILITER    *branch if not zero
2638                        CALIBRATION_X
2639 0be2 ae 5f             LDX  #CALIBRATE_COUNT   *add calibrate count
2640 0be4 a6 5c             LDA  #NOMINAL_COUNT     *to nominal count
2641 0be6 cd 1a 48          JSR  ADD_2
2642 0be9 ae 5c             LDX  #NOMINAL_COUNT
2643 0beb a6 2a             LDA  #MINIMUM_COUNT
2644 0bed cd 19 d2          JSR  COMPARE_2
2645 0bf0 25 06             BLO  CALIBRATION_Y      *branch if no borrow
2646 0bf2 3f 5c             CLR  NOMINAL_COUNT
2647 0bf4 3f 5d             CLR  NOMINAL_COUNT+1
2648 0bf6 3c 5d             INC  NOMINAL_COUNT+1    *otherwise, set nominal count to one
2649                        CALIBRATION_Y
2650 0bf8 81                RTS
2651                        *
2652                        EQUATION_VALUES
2653                        *above 26ml knee
2654                        *nominal count = (1.22 x nominal sample volume) + 98
2655 0bf9 01 22             FDB  $0122             *slope
2656 0bfb 00 98             FDB  $0098
2657 0bfd 02 20             FDB  $0220
2658 0bff 03 42             FDB  $0342
2659 0c01 04 64             FDB  $0464
2660 0c03 05 86             FDB  $0586
2661 0c05 07 08             FDB  $0708
2662 0c07 08 30             FDB  $0830
2663 0c09 09 52             FDB  $0952
2664 0c0b 10 74             FDB  $1074
2665 0c0d 11 96             FDB  $1196
2666                        *at and below 26ml knee
2667                        *nominal count = (3.70 x nominal sample volume) + 29
2668 0c0f 03 70             FDB  $0370             *slope
2669 0c11 00 29             FDB  $0029
2670                        *
2671                        *    program spec
2672                        *
2673                        SPECIALS
2674 0c13 a1 e2             CMP  #PGM_SPECIAL_1
2675 0c15 25 04             BLO  NOT_SPECIAL       *branch if no special effects
2676 0c17 ad 14             BSR  SPECIAL
2677 0c19 bd 2c             JSR  LDA_EXTENDED      *return with next pgm table value in acc
2678                        NOT_SPECIAL
2679 0c1b 81                RTS
2680                        *
2681                        SPECIAL_NEXT_3
```

```
2682 0c1c 3c a1            INC  PGM_BRANCH
2683                  SPECIAL_NEXT_2
2684 0c1e 3c a1            INC  PGM_BRANCH
2685                  SPECIAL_NEXT_1
2686 0c20 3c a1            INC  PGM_BRANCH
2687 0c22 cc 09 64         JMP  NEXT_PROGRAM
2688                  *
2689                  SPECIAL_REPEAT
2690 0c25 cd 18 2c         JSR  ERROR_BEEP
2691 0c28 3a a1            DEC  PGM_BRANCH            *return to previous pgm branch
2692 0c2a cc 09 64         JMP  NEXT_PROGRAM
2693                  *
2694                  SPECIAL
2695 0c2d a0 e2            SUB  #PGM_SPECIAL_1
2696 0c2f ae 03            LDX  #3
2697 0c31 42              MUL
2698 0c32 97              TAX
2699 0c33 dc 0c 36         JMP  SPECIAL_EFFECTS,X     *branch to special effects routine
2700                  *
2701                  SPECIAL_EFFECTS
2702 0c36 cc 0c 87         JMP  SPECIAL_1
2703 0c39 cc 0c 95         JMP  SPECIAL_2
2704 0c3c cc 0c a1         JMP  SPECIAL_3
2705 0c3f cc 0c aa         JMP  SPECIAL_4
2706 0c42 cc 0c ad         JMP  SPECIAL_5
2707 0c45 cc 0c b7         JMP  SPECIAL_6
2708 0c48 cc 0c c1         JMP  SPECIAL_7
2709 0c4b cc 0c d2         JMP  SPECIAL_8
2710 0c4e cc 0c f8         JMP  SPECIAL_9
2711 0c51 cc 0d 39         JMP  SPECIAL_10
2712 0c54 cc 0d 93         JMP  SPECIAL_11
2713 0c57 cc 0d a9         JMP  SPECIAL_12
2714 0c5a cc 0d bc         JMP  SPECIAL_13
2715 0c5d cc 0d f7         JMP  SPECIAL_14
2716 0c60 cc 0e 24         JMP  SPECIAL_15
2717 0c63 cc 0e 2e         JMP  SPECIAL_16
2718 0c66 cc 0e 86         JMP  SPECIAL_17
2719 0c69 cc 0e 8f         JMP  SPECIAL_18
2720 0c6c cc 0e a4         JMP  SPECIAL_19
2721 0c6f cc 0e ae         JMP  SPECIAL_20
2722 0c72 cc 0e bb         JMP  SPECIAL_21
2723 0c75 cc 0e be         JMP  SPECIAL_22
2724 0c78 cc 0e d2         JMP  SPECIAL_23
2725 0c7b cc 0e e5         JMP  SPECIAL_24
2726 0c7e cc 0e f5         JMP  SPECIAL_25
2727 0c81 cc 0f 03         JMP  SPECIAL_26
2728 0c84 cc 0f 11         JMP  SPECIAL_27
2729                  *
2730                  *    in tubing life warning option
2731                  *    if yes to reset pump counter
2732                  *    clears tubing wear and pump tubing worn fault
2733                  *
2734                  SPECIAL_1
2735 0c87 00 70 0a         BRSET    0,YES_NO_QUESTION,SPEC_1_EXIT
```

```
2736                   *                        *branch if no to reset pump counter
2737 0c8a 3f 98            CLR  TUBING_WEAR
2738 0c8c 3f 99            CLR  TUBING_WEAR+1   *clear tubing wear counter
2739 0c8e 3f 9a            CLR  TUBING_WEAR+2
2740 0c90 3f 9b            CLR  TUBING_WEAR+3
2741 0c92 19 90            BCLR B_TUBING,FAULT_BYTE *clear pump tubing worn fault
2742                   SPEC_1_EXIT
2743 0c94 81               RTS
2744                   *
2745                   *   displays tubing wear
2746                   *
2747                   SPECIAL_2
2748 0c95 a6 08            LDA  #8+LEADING_0_NO
2749 0c97 b7 ae            STA  PGM_LENGTH
2750 0c99 ae 00            LDX  #0
2751 0c9b a6 98            LDA  #TUBING_WEAR
2752 0c9d cd 03 5d         JSR  DISPLAY_NUMBER  *display current tubing wear count
2753 0ca0 81               RTS
2754                   *
2755                   *   skips inhibit countdown if reset sample interval
2756                   *
2757                   SPECIAL_3
2758 0ca1 01 77 01         BRCLR  0,INHIBIT_LOAD_T,SPEC_3_ABORT
2759                   *                        *branch if yes to reset sample interval
2760 0ca4 81               RTS
2761                   SPEC_3_ABORT
2762 0ca5 10 78            BSET 0,INHIBIT_COUNT  *set inhibit count to no
2763 0ca7 cc 09 34         JMP  GO_TO_NEXT_STEP *go to select option screen
2764                   *
2765                   *   exits programming after program options
2766                   *
2767                   SPECIAL_4
2768 0caa cc 06 a1         JMP  KEY_ON          *go to standby state
2769                   *
2770                   *   transfers current date/time to temporary date/time
2771                   *   at start of set clock
2772                   *
2773                   SPECIAL_5
2774 0cad ae 91            LDX  #RTC_YEAR       *transfer current date/time
2775 0caf a6 bb            LDA  #TEMP_YEAR      *to temporary date/time
2776 0cb1 cd 19 f6         JSR  TRANSFER_5
2777 0cb4 cc 0c 20         JMP  SPECIAL_NEXT_1  *go on to enter time and date screen
2778                   *
2779                   *   skips bottle switching if not flow paced continuous sampling
2780                   *
2781                   SPECIAL_6
2782 0cb7 01 53 04         BRCLR  0,SAMPLER_PACE,SPEC_6_ABORT
2783                   *                        *branch if not flow paced sampling
2784 0cba 00 54 01         BRSET  0,SAMPLER_MODE,SPEC_6_ABORT
2785                   *                        *branch if not continuous sampling
2786                   SPEC_6_EXIT
2787 0cbd 81               RTS                  *otherwise, check bottle switching
2788                   SPEC_6_ABORT
2789 0cbe cc 0c 20         JMP  SPECIAL_NEXT_1  *skip bottle switching branch
```

```
2790            *
2791            *   skips bottle interval if not time switched continuous
2792            *
2793            SPECIAL_7
2794 0cc1 00 55 0b      BRSET   0,SWITCH_MODE,SPEC_7_ABORT
2795            *                           *branch if not time switched
2796 0cc4 00 54 08      BRSET   0,SAMPLER_MODE,SPEC_7_ABORT
2797            *                           *branch if not continuous sampling
2798 0cc7 ae 69         LDX     #INTERVAL_HOURS   *transfer interval hours and minute
2799 0cc9 a6 be         LDA     #TEMP_HOUR        *to temporary hours and minute
2800 0ccb cd 19 fc      JSR     TRANSFER_2
2801 0cce 81            RTS
2802            SPEC_7_ABORT
2803 0ccf cc 0c 1e      JMP     SPECIAL_NEXT_2    *skip bottle switching branch
2804            *
2805            *   skip sample volume entry if enter mode is samples
2806            *
2807            SPECIAL_8
2808 0cd2 3d 7c         TST     ENTER_MODE
2809 0cd4 27 08         BEQ     SPEC_8_ABORT      *branch if samples only entry
2810 0cd6 ae 57         LDX     #NOMINAL_VOLUME   *otherwise, transfer nominal volume
2811 0cd8 a6 be         LDA     #TEMP_VOLUME      *to temp volume
2812 0cda cd 19 fc      JSR     TRANSFER_2
2813 0cdd 81            RTS                       *and continue as usual
2814            SPEC_8_ABORT
2815            *                           *bottle volume is numerator
2816 0cde ae 25         LDX     #MINIMUM_VOLUME0  *minimum sample volume is denominator
2817 0ce0 a6 61         LDA     #LIMIT_SAMPLES0   *limit number of samples will be result
2818 0ce2 cd 1a 13      JSR     DIVIDE            *calculate limit number of samples
2819 0ce5 ae 61         LDX     #LIMIT_SAMPLES0   *compare limit number of samples
2820 0ce7 a6 22         LDA     #MAXIMUM_NUMBER0  *to maximum number of samples
2821 0ce9 cd 19 d0      JSR     COMPARE_3
2822 0cec 23 07         BLS     SPEC_8_PASS       *branch if less than or same
2823 0cee ae 22         LDX     #MAXIMUM_NUMBER0  *otherwise, transfer maximum number of samples
2824 0cf0 a6 61         LDA     #LIMIT_SAMPLES0   *to limit number of samples
2825 0cf2 cd 19 fa      JSR     TRANSFER_3
2826            SPEC_8_PASS
2827 0cf5 cc 0c 1c      JMP     SPECIAL_NEXT_3    *otherwise, skip volume only branches
2828            *
2829            *   if enter samples only, calculate sample volume
2830            *   if zero, enter number of samples again
2831            *   otherwise, display sample volume
2832            *
2833            SPECIAL_9
2834 0cf8 ae be         LDX     #TEMP_SAMPLES     *compare number of samples entered
2835 0cfa a6 62         LDA     #LIMIT_SAMPLES    *to limit on number of samples
2836 0cfc cd 19 d2      JSR     COMPARE_2
2837 0cff 22 35         BHI     SPEC_9_ABORT      *branch if too high
2838            *
2839 0d01 ae be         LDX     #TEMP_SAMPLES     *transfer temp samples
2840 0d03 a6 5a         LDA     #NUM_OF_SAMPLES   *to number of samples
2841 0d05 cd 19 fc      JSR     TRANSFER_2
2842            *
2843 0d08 3d 7c         TST     ENTER_MODE
```

```
2844 0d0a 26 27              BNE  SPEC_9_PASS          #branch if not samples only entry
2845                     #                              #bottle volume is numerator
2846 0d0c 3f 59              CLR  NUM_OF_SAMPLES0      ##### is this necessary?
2847 0d0e ae 59              LDX  #NUM_OF_SAMPLES0     #number of samples is denominator
2848 0d10 a6 56              LDA  #NOMINAL_VOLUME0     #nominal volume will be result
2849 0d12 cd 1a 13           JSR  DIVIDE               #calculate nominal volume
2850                     #   BEQ  SPEC_9_ABORT         #branch if result is zero
2851 0d15 ae 56              LDX  #NOMINAL_VOLUME0     #compare nominal volume
2852 0d17 a6 22              LDA  #MAXIMUM_VOLUME0     #to maximum nominal volume
2853 0d19 cd 19 d0           JSR  COMPARE_3
2854 0d1c 23 07              BLS  DISPLAY_VOLUME       #branch if less than or equal max
2855 0d1e ae 22              LDX  #MAXIMUM_VOLUME0     #otherwise, transfer max volume
2856 0d20 a6 56              LDA  #NOMINAL_VOLUME0     #to nominal sample volume
2857 0d22 cd 19 fa           JSR  TRANSFER_3
2858                     DISPLAY_VOLUME
2859 0d25 a6 03              LDA  #3+LEADING_0_NO
2860 0d27 b7 ae              STA  PGM_LENGTH
2861 0d29 ae 00              LDX  #0
2862 0d2b a6 57              LDA  #NOMINAL_VOLUME
2863 0d2d cd 03 5d           JSR  DISPLAY_NUMBER       #display calculated nominal volume
2864 0d30 11 70              BCLR 0,YES_NO_QUESTION    #set response to yes
2865 0d32 81                 RTS
2866                     SPEC_9_PASS
2867 0d33 cc 0c 1e           JMP  SPECIAL_NEXT_2       #skip to next branch
2868                     SPEC_9_ABORT
2869 0d36 cc 0c 25           JMP  SPECIAL_REPEAT       #return to number of samples entry screen
2870                     #
2871                     #   if enter volume only, calculate number of samples
2872                     #   if not, calculates pump counts given nominal volume
2873                     #
2874                     SPECIAL_10
2875 0d39 ae be              LDX  #TEMP_VOLUME         #compare nominal sample volume
2876 0d3b a6 26              LDA  #MINIMUM_VOLUME      #to minimum sample volume
2877 0d3d cd 19 d2           JSR  COMPARE_2
2878 0d40 25 4e              BLO  SPEC_10_ABORT        #branch if too small
2879                     #
2880 0d42 ae be              LDX  #TEMP_VOLUME         #transfer temp volume
2881 0d44 a6 57              LDA  #NOMINAL_VOLUME      #to nominal volume
2882 0d46 cd 19 fc           JSR  TRANSFER_2
2883                     #
2884                     #                              #bottle volume is numerator
2885 0d49 3f 56              CLR  NOMINAL_VOLUME0      ##### is this necessary?
2886 0d4b ae 56              LDX  #NOMINAL_VOLUME0     #nominal volume is denominator
2887 0d4d a6 61              LDA  #LIMIT_SAMPLES0      #number of samples will be result
2888 0d4f cd 1a 13           JSR  DIVIDE               #calculate number of samples
2889                     #   BEQ  SPEC_10_ABORT        #branch if result is zero
2890 0d52 ae 61              LDX  #LIMIT_SAMPLES0      #compare limit on number of samples
2891 0d54 a6 22              LDA  #MAXIMUM_NUMBER0     #to maximum number of samples
2892 0d56 cd 19 d0           JSR  COMPARE_3
2893 0d59 23 07              BLS  SPEC_10_XFER         #branch if less than or equal max
2894 0d5b ae 22              LDX  #MAXIMUM_NUMBER0     #otherwise, transfer max number
2895 0d5d a6 61              LDA  #LIMIT_SAMPLES0      #to limit on number of samples
2896 0d5f cd 19 fa           JSR  TRANSFER_3
2897                     SPEC_10_XFER
```

```
2898 0d62 00 7c 16            BRSET   0,ENTER_MODE,SPEC_10_PASS
2899                      *                           *branch if volume only entry
2900 0d65 ae 5a               LDX     #NUM_OF_SAMPLES *compare number of samples
2901 0d67 a6 62               LDA     #LIMIT_SAMPLES  *to maximum number of samples
2902 0d69 cd 19 d2            JSR     COMPARE_2
2903 0d6c 23 07               BLS     SPEC_10_JUMP    *branch if less than or equal max
2904 0d6e ae 62               LDX     #LIMIT_SAMPLES  *otherwise, transfer max number
2905 0d70 a6 5a               LDA     #NUM_OF_SAMPLES *to number of samples
2906 0d72 cd 19 fc            JSR     TRANSFER_2
2907                      SPEC_10_JUMP
2908 0d75 cd 0b 98            JSR     CALIBRATION
2909 0d78 cc 0c 1e            JMP     SPECIAL_NEXT_2  *skip to number of samples branch
2910                      SPEC_10_PASS
2911 0d7b ae 61               LDX     #LIMIT_SAMPLES0 *transfer limit number of samples
2912 0d7d a6 59               LDA     #NUM_OF_SAMPLES0 *to number of samples
2913 0d7f cd 19 fa            JSR     TRANSFER_3
2914 0d82 a6 03               LDA     #3+LEADING_0_NO
2915 0d84 b7 ae               STA     PGM_LENGTH
2916 0d86 ae 00               LDX     #0
2917 0d88 a6 5a               LDA     #NUM_OF_SAMPLES
2918 0d8a cd 03 5d            JSR     DISPLAY_NUMBER  *display calculated number of samples
2919 0d8d 11 70               BCLR    0,YES_NO_QUESTION *set response to yes
2920 0d8f 81                  RTS
2921                      SPEC_10_ABORT
2922 0d90 cc 0c 25            JMP     SPECIAL_REPEAT  *return to sample volume entry screen
2923                      *
2924                      *    compares bottle volume to maximum nominal sample volume
2925                      *    returns if greater than or equal
2926                      *    otherwise, returns to bottle volume screen
2927                      *
2928                      SPECIAL_11
2929 0d93 ae bd               LDX     #TEMP_BOTTLE    *compare bottle volume
2930 0d95 a6 22               LDA     #MAXIMUM_VOLUME0 *to maximum nominal sample volume
2931 0d97 cd 19 d0            JSR     COMPARE_3
2932 0d9a 25 0a               BLO     SPEC_11_ABORT   *branch if entered value too small
2933                      *
2934 0d9c ae bd               LDX     #TEMP_BOTTLE    *transfer temp bottle volume
2935 0d9e a6 6d               LDA     #BOTTLE_VOLUME  *to bottle volume
2936 0da0 cd 19 fa            JSR     TRANSFER_3
2937                      *
2938 0da3 cc 09 34            JMP     GO_TO_NEXT_STEP *otherwise, return to option select screen
2939                      SPEC_11_ABORT
2940 0da6 cc 0c 25            JMP     SPECIAL_REPEAT  *return to bottle volume screen
2941                      *
2942                      *    when entering time paced sample time interval
2943                      *    or time switched flow paced continuous bottle interval
2944                      *    both hours and minutes cannot be zero
2945                      *
2946                      SPECIAL_12
2947 0da9 b6 be               LDA     TEMP_HOUR
2948 0dab ba bf               ORA     TEMP_MINUTE
2949 0dad 27 0a               BEQ     SPEC_12_ABORT   *branch if both hours and minutes zero
2950                      *
2951 0daf ae be               LDX     #TEMP_HOUR      *transfer temp hour and minute
```

```
2952 0db1 a6 69              LDA  #INTERVAL_HOURS   *to interval hours and minute
2953 0db3 cd 19 fc            JSR  TRANSFER_2
2954 0db6 cc 09 34            JMP  GO_TO_NEXT_STEP  *otherwise, go on to next screen
2955                     SPEC_12_ABORT
2956 0db9 cc 0c 25            JMP  SPECIAL_REPEAT   *enter bottle interval again
2957                     *
2958                     *    at manual sample in calibrate sample volume
2959                     *    add or subtract difference between nominal sample volume
2960                     *    delivered sample volume to nominal count
2961                     *
2962                     SPECIAL_13
2963 0dbc ae 9e               LDX  #VOLUME_DELIVER  *compare volume delivered
2964 0dbe a6 57               LDA  #NOMINAL_VOLUME  *to nominal sample volume
2965 0dc0 cd 19 d2            JSR  COMPARE_2
2966 0dc3 27 2c               BEQ  SPEC_13_EXIT     *branch if equal
2967 0dc5 22 15               BHI  SPEC_13_PASS     *branch if too high
2968 0dc7 ae 5f               LDX  #CALIBRATE_COUNT
2969 0dc9 a6 28               LDA  #MAXIMUM_COUNT
2970 0dcb cd 19 d2            JSR  COMPARE_2
2971 0dce 27 21               BEQ  SPEC_13_EXIT     *branch if at limit
2972 0dd0 a6 9e               LDA  #VOLUME_DELIVER
2973 0dd2 cd 1a 87            JSR  BCD_INCREMENT_2  *increment volume delivered
2974 0dd5 a6 5f               LDA  #CALIBRATE_COUNT
2975 0dd7 cd 1a 87            JSR  BCD_INCREMENT_2  *increment calibrate count
2976 0dda 20 e0               BRA  SPECIAL_13
2977                     SPEC_13_PASS
2978 0ddc ae 5f               LDX  #CALIBRATE_COUNT
2979 0dde a6 2a               LDA  #MINIMUM_COUNT
2980 0de0 cd 19 d2            JSR  COMPARE_2
2981 0de3 27 0c               BEQ  SPEC_13_EXIT     *branch if at limit
2982 0de5 a6 9e               LDA  #VOLUME_DELIVER
2983 0de7 cd 1a 9d            JSR  BCD_DECREMENT_2  *decrement volume delivered
2984 0dea a6 5f               LDA  #CALIBRATE_COUNT
2985 0dec cd 1a 9d            JSR  BCD_DECREMENT_2  *decrement calibrate count
2986 0def 20 cb               BRA  SPECIAL_13
2987                     SPEC_13_EXIT
2988 0df1 cd 0b 98            JSR  CALIBRATION      *otherwise, calculate nominal count
2989 0df4 cc 09 34            JMP  GO_TO_NEXT_STEP  *and go to calibrate sample screen
2990                     *
2991                     *    clear rtc_second in real time clock
2992                     *
2993                     SPECIAL_14
2994 0df7 ae bb               LDX  #TEMP_YEAR       *compare temporary date/time
2995 0df9 a6 91               LDA  #RTC_YEAR        *to current date/time
2996 0dfb cd 19 cc            JSR  COMPARE_5
2997 0dfe 27 21               BEQ  SPEC_14_EXIT     *branch if no changes
2998                     *
2999 0e00 ae bb               LDX  #TEMP_YEAR       *transfer temporary date/time
3000 0e02 a6 91               LDA  #RTC_YEAR        *to current date/time
3001 0e04 cd 19 f6            JSR  TRANSFER_5
3002                     *
3003 0e07 3f 96               CLR  RTC_SECOND       *clear seconds
3004 0e09 3f 97               CLR  RTC_MILLISECOND  *and milliseconds in ram
3005                     *
```

```
3006 0e0b cd 01 b1        JSR  RTC_STORE          *write date/time to rtc
3007                      *
3008 0e0e ae 64           LDX  #YEAR_OF_FIRST     *compare date/time of first/next sample
3009 0e10 a6 91           LDA  #RTC_YEAR          *to new current date/time
3010 0e12 cd 19 cc        JSR  COMPARE_5
3011 0e15 22 0a           BHI  SPEC_14_EXIT       *branch if still valid
3012 0e17 ae 91           LDX  #RTC_YEAR          *transfer new current date/time
3013 0e19 a6 64           LDA  #YEAR_OF_FIRST     *to date/time of first/next sample
3014 0e1b cd 19 f6        JSR  TRANSFER_5
3015 0e1e cd 1c 06        JSR  INC_MINUTE         *add one minute to first/next
3016                    SPEC_14_EXIT
3017 0e21 cc 09 34        JMP  GO_TO_NEXT_STEP    *go to select option screen
3018                      *
3019                      *  clears calibrate count if disable calibrate sampler
3020                      *
3021                    SPECIAL_15
3022 0e24 01 79 04        BRCLR  0,CALIBRATE,SPEC_15_EXIT
3023                      *                       *branch if not disable calibrate sampler
3024 0e27 3f 5f           CLR  CALIBRATE_COUNT    *otherwise, clear calibrate count
3025 0e29 3f 60           CLR  CALIBRATE_COUNT+1
3026                    SPEC_15_EXIT
3027 0e2b cc 09 34        JMP  GO_TO_NEXT_STEP    *go to select option screen
3028                      *
3029                      *  compares pass number entered against model number
3030                      *
3031                    SPECIAL_16
3032 0e2e ae 9c           LDX  #PASS_NUMBER       *compare entered pass number
3033 0e30 a6 20           LDA  #MODEL_NUMBER      *against model number
3034 0e32 cd 19 d2        JSR  COMPARE_2
3035 0e35 27 1a           BEQ  SPEC_16_EXIT       *branch if same
3036 0e37 cd 18 2c        JSR  ERROR_BEEP         *otherwise, error beep
3037 0e3a b6 db           LDA  PGM_SAVE
3038 0e3c b7 a1           STA  PGM_BRANCH         *restore pgm branch
3039 0e3e cd 09 6c        JSR  LOAD_DISPLAY       *restore display
3040 0e41 b6 a0           LDA  KEY_MASK
3041 0e43 a1 08           CMP  #MASK_PGM_SELECT
3042 0e45 27 3c           BEQ  SPEC_16_RETURN     *branch if select screen
3043 0e47 ae db           LDX  #PGM_SAVE
3044 0e49 a6 a1           LDA  #PGM_BRANCH        *restore pgm branch and choice
3045 0e4b cd 19 fa        JSR  TRANSFER_3
3046 0e4e cc 09 4b        JMP  NEXT_NUMERIC       *return to screen
3047                    SPEC_16_EXIT
3048 0e51 b6 db           LDA  PGM_SAVE
3049 0e53 b7 a1           STA  PGM_BRANCH         *restore pgm branch
3050 0e55 cd 09 6c        JSR  LOAD_DISPLAY       *restore display
3051 0e58 1a c1           BSET PGM_UNLOCK_BIT,PGM_UNLOCK_BYTE
3052                      *                       *set program unlocked bit
3053 0e5a b6 a0           LDA  KEY_MASK
3054 0e5c a1 0c           CMP  #MASK_PGM_ENTER
3055 0e5e 26 1f           BNE  SPEC_16_PASS       *branch if not numeric entry screen
3056 0e60 ae db           LDX  #PGM_SAVE          *restore buffer
3057 0e62 a6 a1           LDA  #PGM_BRANCH        *to program parameters
3058 0e64 cd 19 fa        JSR  TRANSFER_3
3059 0e67 cd 0a cf        JSR  LOAD_PARAMETERS    *load numeric entry parameters
```

```
3060 0e6a cd 0a dc            JSR  POSITION_CLEAR
3061 0e6d b6 a3               LDA  PGM_VALUE
3062 0e6f aa 30               ORA  #$30
3063 0e71 cd 02 90            JSR  LCD_DATA_WRITE    *display digit entered
3064 0e74 3c af               INC  PGM_DIGIT
3065 0e76 3f b1               CLR  FLASH
3066 0e78 a6 0f               LDA  #$0F              *display control
3067 0e7a cd 02 dc            JSR  LCD_CMD_WRITE     *display on, cursor on, blink on
3068 0e7d 20 04               BRA  SPEC_16_RETURN
3069                      SPEC_16_PASS
3070 0e7f b6 dc               LDA  PGM_SAVE+1
3071 0e81 b7 a2               STA  PGM_CHOICE        *restore new selection
3072                      SPEC_16_RETURN
3073 0e83 cc 09 67            JMP  BRANCH_CHECK
3074                          *
3075                          *   programming complete
3076                          *
3077                      SPECIAL_17
3078 0e86 01 79 03            BRCLR  0,CALIBRATE,SPEC_17_EXIT
3079                          *                      *branch if disable calibrate sampler
3080 0e89 cc 06 a1            JMP  KEY_ON
3081                      SPEC_17_EXIT
3082 0e8c 10 70               BSET 0,YES_NO_QUESTION *set response to no
3083 0e8e 81                  RTS                    *go to calibrate sample volume screen
3084                          *
3085                          *   changes take first sample at
3086                          *   to start flow count at
3087                          *   if flow paced and no sample at start time
3088                          *
3089                      SPECIAL_18
3090 0e8f ae 65               LDX  #MONTH_OF_FIRST   *transfer date/time of first
3091 0e91 a6 bc               LDA  #TEMP_MONTH       *to temporary date/time
3092 0e93 cd 19 f8             JSR  TRANSFER_4
3093 0e96 01 53 0a            BRCLR  0,SAMPLER_PACE,SPEC_18_EXIT
3094                          *                      *branch if not flow paced
3095 0e99 01 75 07            BRCLR  0,FLOW_SAMPLE,SPEC_18_EXIT
3096                          *                      *branch if flow sample at time of first
3097 0e9c a6 21               LDA  #33
3098 0e9e b7 a1               STA  PGM_BRANCH        *go to start flow count at screen
3099 0ea0 cc 09 64            JMP  NEXT_PROGRAM
3100                      SPEC_18_EXIT
3101 0ea3 81                  RTS
3102                          *
3103                          *   determines year of first sample
3104                          *   compares number of days per month to day of first
3105                          *
3106                      SPECIAL_19
3107 0ea4 ae bb               LDX  #TEMP_YEAR        *transfer temporary date/time
3108 0ea6 a6 64               LDA  #YEAR_OF_FIRST    *to date/time of first
3109 0ea8 cd 19 f6            JSR  TRANSFER_5
3110 0eab cc 0c 20            JMP  SPECIAL_NEXT_1    *go on to sample interval entry screens
3111                          *
3112                          *   goes to program options if selected
3113                          *
```

```
3114                    SPECIAL_20
3115 0eae 00 70 01         BRSET   0,YES_NO_QUESTION,SPEC_20_ABORT
3116                    *                           *branch if program options selected
3117 0eb1 81               RTS                      *otherwise, continue with pgm sampler
3118                    SPEC_20_ABORT
3119 0eb2 3f 52            CLR  PROGRAM_CHOICE      *clear option number
3120 0eb4 a6 13            LDA  #19
3121 0eb6 b7 a1            STA  PGM_BRANCH          *go to select option screen
3122 0eb8 cc 09 64         JMP  NEXT_PROGRAM
3123                    *
3124                    *   initializes reset pump counter to no
3125                    *
3126                    SPECIAL_21
3127 0ebb 10 70            BSET 0,YES_NO_QUESTION
3128 0ebd 81               RTS
3129                    *
3130                    *   branches to selected option
3131                    *
3132                    SPECIAL_22
3133 0ebe be 52            LDX  PROGRAM_CHOICE
3134 0ec0 d6 12 dd         LDA  OPTIONS_FLOW,X      *input selected option branch
3135 0ec3 b7 a1            STA  PGM_BRANCH
3136 0ec5 3c 52            INC  PROGRAM_CHOICE      *move to next option
3137 0ec7 b6 52            LDA  PROGRAM_CHOICE
3138 0ec9 b1 ad            CMP  PGM_SELECTIONS
3139 0ecb 25 02            BLO  SPEC_22_EXIT        *branch if next option exists
3140 0ecd 3f 52            CLR  PROGRAM_CHOICE      *otherwise, choose first option
3141                    SPEC_22_EXIT
3142 0ecf cc 09 64         JMP  NEXT_PROGRAM        *go to selected option
3143                    *
3144                    *   if entering both sample volume and number of samples
3145                    *   calculate and display limit on number of samples
3146                    *   if zero, return to sample volume entry screen
3147                    *   if current value greater than limit, set number of samples to limit
3148                    *   then calibrate pump counts
3149                    *
3150                    SPECIAL_23
3151 0ed2 ae 5a            LDX  #NUM_OF_SAMPLES     *transfer number of samples
3152 0ed4 a6 be            LDA  #TEMP_SAMPLES       *to temp samples
3153 0ed6 cd 19 fc         JSR  TRANSFER_2
3154 0ed9 a6 43            LDA  #3+LEADING_0_YES
3155 0edb b7 ae            STA  PGM_LENGTH
3156 0edd ae 0f            LDX  #15
3157 0edf a6 62            LDA  #LIMIT_SAMPLES
3158 0ee1 cd 03 5d         JSR  DISPLAY_NUMBER      *display calculated limit of samples
3159 0ee4 81               RTS
3160                    *
3161                    *   if entering sample volume or number of samples only
3162                    *   if number of samples or sample volume ok, calibrate pump counts
3163                    *   otherwise, return to sample volume or number of samples entry screen
3164                    *
3165                    SPECIAL_24
3166 0ee5 00 70 06         BRSET   0,YES_NO_QUESTION,SPEC_24_ABORT
3167                    *                           *branch if not ok
```

```
3168 0ee8 cd 0b 98          JSR  CALIBRATION          *otherwise, calibrate pump counts
3169 0eeb cc 09 34          JMP  GO_TO_NEXT_STEP      *and move on to time of first sample
3170                    SPEC_24_ABORT
3171 0eee 3a a1             DEC  PGM_BRANCH
3172 0ef0 3a a1             DEC  PGM_BRANCH           *return to sample volume entry screen
3173 0ef2 cc 09 64          JMP  NEXT_PROGRAM
3174                    *
3175                    *   goes to flow pulses entry screen if not time paced
3176                    *
3177                    SPECIAL_25
3178 0ef5 00 53 08          BRSET   0,SAMPLER_PACE,SPEC_25_ABORT
3179                    *                            *branch if not time paced
3180 0ef8 ae 69             LDX  #INTERVAL_HOURS      *transfer interval hours and minute
3181 0efa a6 be             LDA  #TEMP_HOUR           *to temporary hours and minute
3182 0efc cd 19 fc          JSR  TRANSFER_2
3183 0eff 81                RTS
3184                    SPEC_25_ABORT
3185 0f00 cc 0c 1e          JMP  SPECIAL_NEXT_2       *go to flow pulses entry screen
3186                    *
3187                    *   in calibrate sample volume
3188                    *   exits if answer no
3189                    *   returns if answer yes
3190                    *
3191                    SPECIAL_26
3192 0f03 00 70 08          BRSET   0,YES_NO_QUESTION,SPEC_26_ABORT
3193                    *                            *branch if no answer to question
3194 0f06 ae 57             LDX  #NOMINAL_VOLUME      *transfer nominal volume
3195 0f08 a6 9e             LDA  #VOLUME_DELIVER      *to volume delivered
3196 0f0a cd 19 fc          JSR  TRANSFER_2
3197 0f0d 81                RTS
3198                    SPEC_26_ABORT
3199 0f0e cc 06 a1          JMP  KEY_ON               *otherwise, exit programming
3200                    *
3201                    *   transfers bottle volume to temp bottle
3202                    *
3203                    SPECIAL_27
3204 0f11 ae 6d             LDX  #BOTTLE_VOLUME
3205 0f13 a6 bd             LDA  #TEMP_BOTTLE
3206 0f15 cd 19 fa          JSR  TRANSFER_3
3207 0f18 81                RTS
3208                    *
3209                    *   program table
3210                    *
3211                    PROGRAM_STEP
3212 0f19 0f 1b             FDB  BRANCHES
3213                    BRANCHES
3214                    *1
3215 0f1b 70                FCB  YES_NO_QUESTION
3216 0f1c 06                FCB  6
3217 0f1d c2                FCB  V_PROGRAM_
3218 0f1e df                FCB  END_OF_MESSAGE
3219 0f1f 41                FCB  LCD_LINE_2+1
3220 0f20 5b                FCC  '['
3221 0f21 df                FCB  END_OF_MESSAGE
```

```
3222  0f22 49              FCB  LCD_LINE_2+9
3223  0f23 2c              FCC  ','
3224  0f24 df              FCB  END_OF_MESSAGE
3225  0f25 52              FCB  LCD_LINE_2+18
3226  0f26 5d              FCC  ']'
3227  0f27 e0              FCB  END_OF_DISPLAY
3228
3229  0f28 42              FCB  LCD_LINE_2+2
3230  0f29 ca              FCB  V_SAMPLE
3231  0f2a 52              FCC  'R'
3232  0f2b df              FCB  END_OF_MESSAGE
3233  0f2c 4b              FCB  LCD_LINE_2+11
3234  0f2d be              FCB  V_OPTION
3235  0f2e 53              FCC  'S'
3236  0f2f e1              FCB  END_OF_BRANCH
3237                 *2
3238  0f30 f5              FCB  PGM_SPECIAL_20
3239  0f31 53              FCB  SAMPLER_PACE
3240  0f32 04              FCB  4
3241  0f33 5b              FCC  '['
3242  0f34 df              FCB  END_OF_MESSAGE
3243  0f35 09              FCB  9
3244  0f36 2c              FCC  ','
3245  0f37 df              FCB  END_OF_MESSAGE
3246  0f38 0f              FCB  15
3247  0f39 5d              FCC  ']'
3248  0f3a df              FCB  END_OF_MESSAGE
3249  0f3b 43              FCB  LCD_LINE_2+3
3250  0f3c bf              FCB  V_PACED
3251  0f3d 20              FCC  ' '
3252  0f3e cc              FCB  V_SAMPLING
3253  0f3f e0              FCB  END_OF_DISPLAY
3254
3255  0f40 05              FCB  5
3256  0f41 d3              FCB  V_TIME
3257  0f42 df              FCB  END_OF_MESSAGE
3258  0f43 0b              FCB  11
3259  0f44 af              FCB  V_FLOW
3260  0f45 e1              FCB  END_OF_BRANCH
3261                 *3
3262  0f46 54              FCB  SAMPLER_MODE
3263  0f47 00              FCB  0
3264  0f48 5b              FCC  '['
3265  0f49 df              FCB  END_OF_MESSAGE
3266  0f4a 0b              FCB  11
3267  0f4b 2c              FCC  ','
3268  0f4c df              FCB  END_OF_MESSAGE
3269  0f4d 12              FCB  18
3270  0f4e 5d              FCC  ']'
3271  0f4f df              FCB  END_OF_MESSAGE
3272  0f50 46              FCB  LCD_LINE_2+6
3273  0f51 cc              FCB  V_SAMPLING
3274  0f52 e0              FCB  END_OF_DISPLAY
3275
```

```
3276 0f53 01                      FCB  I
3277 0f54 a4                      FCB  V_CONTINUOUS
3278 0f55 df                      FCB  END_OF_MESSAGE
3279 0f56 0d                      FCB  13
3280 0f57 ce                      FCB  V_SPLIT
3281 0f58 e1                      FCB  END_OF_BRANCH
3282                         *4
3283 0f59 e7                      FCB  PGM_SPECIAL_6
3284 0f5a 55                      FCB  SWITCH_MODE
3285 0f5b 00                      FCB  0
3286 0f5c d0                      FCB  V_SWITCH
3287 0f5d 20                      FCC  ' '
3288 0f5e a2                      FCB  V_BOTTLE
3289 0f5f 53                      FCC  'S'
3290 0f60 a1                      FCB  V__BASED
3291 0f61 df                      FCB  END_OF_MESSAGE
3292 0f62 42                      FCB  LCD_LINE_2+2
3293 0f63 4f 4e 20 5b             FCC  'ON ['
3294 0f67 df                      FCB  END_OF_MESSAGE
3295 0f68 4a                      FCB  LCD_LINE_2+10
3296 0f69 2c                      FCC  ','
3297 0f6a df                      FCB  END_OF_MESSAGE
3298 0f6b 50                      FCB  LCD_LINE_2+16
3299 0f6c 5d                      FCC  ']'
3300 0f6d e0                      FCB  END_OF_DISPLAY
3301
3302 0f6e 46                      FCB  LCD_LINE_2+6
3303 0f6f d3                      FCB  V_TIME
3304 0f70 df                      FCB  END_OF_MESSAGE
3305 0f71 4c                      FCB  LCD_LINE_2+12
3306 0f72 af                      FCB  V_FLOW
3307 0f73 e1                      FCB  END_OF_BRANCH
3308                         *5
3309 0f74 e9                      FCB  PGM_SPECIAL_8
3310 0f75 0c                      FCB  MASK_PGM_ENTER
3311 0f76 01                      FCB  I
3312 0f77 ca                      FCB  V_SAMPLE
3313 0f78 20                      FCC  ' '
3314 0f79 d5                      FCB  V_VOLUME
3315 0f7a 53 20 4f 46             FCC  'S OF'
3316 0f7e df                      FCB  END_OF_MESSAGE
3317 0f7f 44                      FCB  LCD_LINE_2+4
3318 0f80 ba                      FCB  V_ml_
3319 0f81 a7                      FCB  V_EACH
3320 0f82 20 28 31 30 2d 39       FCC  ' (10-999)'
     39 39 29
3321 0f8b e0                      FCB  END_OF_DISPLAY
3322
3323 0f8c be                      FCB  TEMP_VOLUME
3324 0f8d 23                      FCB  3+VALID_0_NO+LEADING_0_NO+LIMIT_9_YES
3325 0f8e 40                      FCB  LCD_LINE_2
3326 0f8f e1                      FCB  END_OF_BRANCH
3327                         *6
3328 0f90 eb                      FCB  PGM_SPECIAL_10
```

```
3329 0f91 70              FCB  YES_NO_QUESTION
3330 0f92 04              FCB  4
3331 0f93 cb              FCB  V_SAMPLES
3332 0f94 20 20 20        FCC  '   '
3333 0f97 bd              FCB  V___OK_
3334 0f98 df              FCB  END_OF_MESSAGE
3335 0f99 45              FCB  LCD_LINE_2+5
3336 0f9a d9              FCB  V__YES__NO_
3337 0f9b e0              FCB  END_OF_DISPLAY
3338
3339 0f9c 46              FCB  LCD_LINE_2+6
3340 0f9d d8              FCB  V_YES
3341 0f9e df              FCB  END_OF_MESSAGE
3342 0f9f 4b              FCB  LCD_LINE_2+11
3343 0fa0 bb              FCB  V_NO
3344 0fa1 e1              FCB  END_OF_BRANCH
3345                 *7
3346 0fa2 f9              FCB  PGM_SPECIAL_24
3347 0fa3 e1              FCB  END_OF_BRANCH
3348                 *8
3349 0fa4 f8              FCB  PGM_SPECIAL_23
3350 0fa5 0c              FCB  MASK_PGM_ENTER
3351 0fa6 04              FCB  4
3352 0fa7 cb              FCB  V_SAMPLES
3353 0fa8 20 28 31 2d     FCC  ' (1-'
3354 0fac df              FCB  END_OF_MESSAGE
3355 0fad 12              FCB  18
3356 0fae 29              FCC  ')'
3357 0faf e0              FCB  END_OF_DISPLAY
3358
3359 0fb0 be              FCB  TEMP_SAMPLES
3360 0fb1 23              FCB  3+VALID_0_NO+LEADING_0_NO+LIMIT_9_YES
3361 0fb2 00              FCB  0
3362 0fb3 e1              FCB  END_OF_BRANCH
3363                 *9
3364 0fb4 ea              FCB  PGM_SPECIAL_9
3365 0fb5 70              FCB  YES_NO_QUESTION
3366 0fb6 04              FCB  4
3367 0fb7 ba              FCB  V_al_
3368 0fb8 cb              FCB  V_SAMPLES
3369 0fb9 bd              FCB  V___OK_
3370 0fba df              FCB  END_OF_MESSAGE
3371 0fbb 45              FCB  LCD_LINE_2+5
3372 0fbc d9              FCB  V__YES__NO_
3373 0fbd e0              FCB  END_OF_DISPLAY
3374
3375 0fbe 46              FCB  LCD_LINE_2+6
3376 0fbf d8              FCB  V_YES
3377 0fc0 df              FCB  END_OF_MESSAGE
3378 0fc1 4b              FCB  LCD_LINE_2+11
3379 0fc2 bb              FCB  V_NO
3380 0fc3 e1              FCB  END_OF_BRANCH
3381                 *10
3382 0fc4 f9              FCB  PGM_SPECIAL_24
```

```
3383 0fc5 e1              FCB  END_OF_BRANCH
3384                 #11
3385 0fc6 f3              FCB  PGM_SPECIAL_1B
3386 0fc7 0c              FCB  MASK_PGM_ENTER
3387 0fc8 00              FCB  0
3388 0fc9 d1              FCB  V_TAKE
3389 0fca 20              FCC  ' '
3390 0fcb ae              FCB  V_FIRST
3391 0fcc 20              FCC  ' '
3392 0fcd ca              FCB  V_SAMPLE
3393 0fce 20 41 54        FCC  ' AT'
3394 0fd1 df              FCB  END_OF_MESSAGE
3395 0fd2 46              FCB  LCD_LINE_2+6
3396 0fd3 3a              FCB  COLON
3397 0fd4 df              FCB  END_OF_MESSAGE
3398 0fd5 4d              FCB  LCD_LINE_2+13
3399 0fd6 2f              FCB  SLASH
3400 0fd7 e0              FCB  END_OF_DISPLAY
3401
3402 0fd8 be              FCB  TEMP_HOUR
3403 0fd9 82              FCB  2+VALID_0_YES+LEADING_0_NO+LIMIT_9_NO
3404 0fda 44              FCB  LCD_LINE_2+4
3405 0fdb 23              FCB  $23
3406
3407 0fdc bf              FCB  TEMP_MINUTE
3408 0fdd c2              FCB  2+VALID_0_YES+LEADING_0_YES+LIMIT_9_NO
3409 0fde 47              FCB  LCD_LINE_2+7
3410 0fdf 59              FCB  $59
3411
3412 0fe0 bc              FCB  TEMP_MONTH
3413 0fe1 02              FCB  2+VALID_0_NO+LEADING_0_NO+LIMIT_9_NO
3414 0fe2 4b              FCB  LCD_LINE_2+11
3415 0fe3 12              FCB  $12
3416
3417 0fe4 bd              FCB  TEMP_DAY
3418 0fe5 42              FCB  2+VALID_0_NO+LEADING_0_YES+LIMIT_9_NO
3419 0fe6 4e              FCB  LCD_LINE_2+14
3420 0fe7 31              FCB  $31
3421 0fe8 e1              FCB  END_OF_BRANCH
3422                 #12
3423 0fe9 f4              FCB  PGM_SPECIAL_19
3424 0fea e1              FCB  END_OF_BRANCH
3425                 #13
3426 0feb fa              FCB  PGM_SPECIAL_25
3427 0fec 0c              FCB  MASK_PGM_ENTER
3428 0fed 01              FCB  1
3429 0fee d2              FCB  V_THEN_
3430 0fef ca              FCB  V_SAMPLE
3431 0ff0 20              FCC  ' '
3432 0ff1 aa              FCB  V_EVERY
3433 0ff2 df              FCB  END_OF_MESSAGE
3434 0ff3 43              FCB  LCD_LINE_2+3
3435 0ff4 b2              FCB  V_HOURS
3436 0ff5 df              FCB  END_OF_MESSAGE
```

```
3437 0ff6 4d              FCB  LCD_LINE_2+13
3438 0ff7 b9              FCB  V_MINUTES
3439 0ff8 e0              FCB  END_OF_DISPLAY
3440
3441 0ff9 be              FCB  TEMP_HOUR
3442 0ffa a2              FCB  2+VALID_0_YES+LEADING_0_NO+LIMIT_9_YES
3443 0ffb 40              FCB  LCD_LINE_2
3444
3445 0ffc bf              FCB  TEMP_MINUTE
3446 0ffd 82              FCB  2+VALID_0_YES+LEADING_0_NO+LIMIT_9_NO
3447 0ffe 4a              FCB  LCD_LINE_2+10
3448 0fff 59              FCB  $59
3449 1000 e1              FCB  END_OF_BRANCH
3450                 *14
3451 1001 ed              FCB  PGM_SPECIAL_12
3452 1002 e1              FCB  END_OF_BRANCH
3453                 *15
3454 1003 0c              FCB  MASK_PGM_ENTER
3455 1004 01              FCB  1
3456 1005 d2              FCB  V_THEN_
3457 1006 ca              FCB  V_SAMPLE
3458 1007 20              FCC  ' '
3459 1008 aa              FCB  V_EVERY
3460 1009 df              FCB  END_OF_MESSAGE
3461 100a 45              FCB  LCD_LINE_2+5
3462 100b c3              FCB  V_PULSES
3463 100c 20 28 31 2d 39 39   FCC  ' (1-9999)'
     39 39 29
3464 1015 e0              FCB  END_OF_DISPLAY
3465
3466 1016 6b              FCB  INTERVAL_FLOW
3467 1017 24              FCB  4+VALID_0_NO+LEADING_0_NO+LIMIT_9_YES
3468 1018 40              FCB  LCD_LINE_2
3469 1019 e1              FCB  END_OF_BRANCH
3470                 *16
3471 101a e8              FCB  PGM_SPECIAL_7
3472 101b 0c              FCB  MASK_PGM_ENTER
3473 101c 00              FCB  0
3474 101d d0              FCB  V_SWITCH
3475 101e 20              FCC  ' '
3476 101f a2              FCB  V_BOTTLE
3477 1020 53 20           FCC  'S '
3478 1022 aa              FCB  V_EVERY
3479 1023 df              FCB  END_OF_MESSAGE
3480 1024 43              FCB  LCD_LINE_2+3
3481 1025 b2              FCB  V_HOURS
3482 1026 df              FCB  END_OF_MESSAGE
3483 1027 4d              FCB  LCD_LINE_2+13
3484 1028 b9              FCB  V_MINUTES
3485 1029 e0              FCB  END_OF_DISPLAY
3486
3487 102a be              FCB  TEMP_HOUR
3488 102b a2              FCB  2+VALID_0_YES+LEADING_0_NO+LIMIT_9_YES
3489 102c 40              FCB  LCD_LINE_2
```

```
3490
3491 102d bf              FCB  TEMP_MINUTE
3492 102e 82              FCB  2+VALID_0_YES+LEADING_0_NO+LIMIT_9_NO
3493 102f 4a              FCB  LCD_LINE_2+10
3494 1030 59              FCB  $59
3495 1031 e1              FCB  END_OF_BRANCH
3496                *17
3497 1032 ed              FCB  PGM_SPECIAL_12
3498 1033 e1              FCB  END_OF_BRANCH
3499                *18
3500 1034 f2              FCB  PGM_SPECIAL_17
3501 1035 70              FCB  YES_NO_QUESTION
3502 1036 02              FCB  2
3503 1037 a3              FCB  V_CALIBRATE_
3504 1038 ca              FCB  V_SAMPLE
3505 1039 df              FCB  END_OF_MESSAGE
3506 103a 41              FCB  LCD_LINE_2+1
3507 103b d5              FCB  V_VOLUME
3508 103c 3f 20           FCC  '? '
3509 103e d9              FCB  V__YES__NO_
3510 103f e0              FCB  END_OF_DISPLAY
3511
3512 1040 4a              FCB  LCD_LINE_2+10
3513 1041 d8              FCB  V_YES
3514 1042 df              FCB  END_OF_MESSAGE
3515 1043 4f              FCB  LCD_LINE_2+15
3516 1044 bb              FCB  V_NO
3517 1045 e1              FCB  END_OF_BRANCH
3518                *19
3519 1046 52              FCB  PROGRAM_CHOICE
3520 1047 01              FCB  1
3521 1048 53 45 4c 45 43 54   FCC  'SELECT '
     20
3522 104f be              FCB  V_OPTION
3523 1050 20 28           FCC  ' ('
3524 1052 7f              FCB  $7F
3525 1053 7e              FCB  $7E
3526 1054 29              FCC  ')'
3527 1055 e0              FCB  END_OF_DISPLAY
3528
3529 1056 40              FCB  LCD_LINE_2
3530 1057 20 20 20 20 20 53   FCC  '    SET CLOCK    '
     45 54 20 43 4c 4f
     43 4b 20 20 20 20
     20 20
3531 106b df              FCB  END_OF_MESSAGE
3532 106c 40              FCB  LCD_LINE_2
3533 106d 20 20 20 20     FCC  '    '
3534 1071 a2              FCB  V_BOTTLE
3535 1072 20 53 49 5a 45 20   FCC  ' SIZE    '
     20 20 20 20
3536 107c df              FCB  END_OF_MESSAGE
3537 107d 40              FCB  LCD_LINE_2
3538 107e d4              FCB  V_TUBING
```

```
3539 107f 20 4c 49 46 45 20    FCC   ' LIFE '
3540 1085 d6                    FCB   V_WARNING
3541 1086 20                    FCC   ' '
3542 1087 df                    FCB   END_OF_MESSAGE
3543 1088 40                    FCB   LCD_LINE_2
3544 1089 20                    FCC   ' '
3545 108a af                    FCB   V_FLOW
3546 108b 20 4d 4f 44 45 20    FCC   ' MODE '
3547 1091 cc                    FCB   V_SAMPLING
3548 1092 20                    FCC   ' '
3549 1093 df                    FCB   END_OF_MESSAGE
3550 1094 40                    FCB   LCD_LINE_2
3551 1095 20                    FCC   ' '
3552 1096 c0                    FCB   V_POWER_
3553 1097 ab                    FCB   V_FAIL_
3554 1098 ca                    FCB   V_SAMPLE
3555 1099 20 20                 FCC   ' '
3556 109b df                    FCB   END_OF_MESSAGE
3557 109c 40                    FCB   LCD_LINE_2
3558 109d 20                    FCC   ' '
3559 109e a8                    FCB   V_ENABLE
3560 109f 20 50 49 4e 20       FCC   ' PIN '
3561 10a4 be                    FCB   V_OPTION
3562 10a5 53 20                 FCC   'S '
3563 10a7 df                    FCB   END_OF_MESSAGE
3564 10a8 40                    FCB   LCD_LINE_2
3565 10a9 20                    FCC   ' '
3566 10aa a3                    FCB   V_CALIBRATE_
3567 10ab ca                    FCB   V_SAMPLE
3568 10ac 52 20 20              FCC   'R '
3569 10af df                    FCB   END_OF_MESSAGE
3570 10b0 40                    FCB   LCD_LINE_2
3571 10b1 20 20 20 20          FCC   '    '
3572 10b5 c2                    FCB   V_PROGRAM_
3573 10b6 b7                    FCB   V_LOCK_
3574 10b7 20 20 20              FCC   '   '
3575 10ba df                    FCB   END_OF_MESSAGE
3576 10bb 40                    FCB   LCD_LINE_2
3577 10bc 20                    FCC   ' '
3578 10bd c4                    FCB   V_PUMP_
3579 10be c9                    FCB   V_RUNNING_
3580 10bf b6                    FCB   V_LIGHT
3581 10c0 20                    FCC   ' '
3582 10c1 df                    FCB   END_OF_MESSAGE
3583 10c2 40                    FCB   LCD_LINE_2
3584 10c3 ca                    FCB   V_SAMPLE
3585 10c4 53 2f                 FCC   'S/'
3586 10c6 d5                    FCB   V_VOLUME
3587 10c7 20 45 4e 54 52 59   FCC   ' ENTRY'
3588 10cd df                    FCB   END_OF_MESSAGE
3589 10ce 40                    FCB   LCD_LINE_2
3590 10cf 20                    FCC   ' '
3591 10d0 cd                    FCB   V_SOFTWARE_
3592 10d1 cb                    FCB   V_REVISION
```

```
3593 10d2 20 20            FCC  '  '
3594 10d4 df               FCB  END_OF_MESSAGE
3595 10d5 40               FCB  LCD_LINE_2
3596 10d6 20 20 20 20 45 58  FCC  '    EXIT '
     49 54 20
3597 10df be               FCB  V_OPTION
3598 10e0 53 20 20 20 20   FCC  'S    '
3599 10e5 e1               FCB  END_OF_BRANCH
3600                    *20
3601 10e6 f7               FCB  PGM_SPECIAL_22
3602 10e7 e1               FCB  END_OF_BRANCH
3603                    *21
3604 10e8 e6               FCB  PGM_SPECIAL_5
3605 10e9 e1               FCB  END_OF_BRANCH
3606                    *22
3607 10ea 0c               FCB  MASK_PGM_ENTER
3608 10eb 02               FCB  2
3609 10ec 48 48            FCC  'HH'
3610 10ee 3a               FCB  COLON
3611 10ef 4d 4d 20 20 20 59  FCC  'MM   YY/MM/DD'
     59 2f 4d 4d 2f 44
     44
3612 10fc df               FCB  END_OF_MESSAGE
3613 10fd 44               FCB  LCD_LINE_2+4
3614 10fe 3a               FCB  COLON
3615 10ff df               FCB  END_OF_MESSAGE
3616 1100 4c               FCB  LCD_LINE_2+12
3617 1101 2f               FCB  SLASH
3618 1102 df               FCB  END_OF_MESSAGE
3619 1103 4f               FCB  LCD_LINE_2+15
3620 1104 2f               FCB  SLASH
3621 1105 e0               FCB  END_OF_DISPLAY
3622
3623 1106 be               FCB  TEMP_HOUR
3624 1107 82               FCB  2+VALID_0_YES+LEADING_0_NO+LIMIT_9_NO
3625 1108 42               FCB  LCD_LINE_2+2
3626 1109 23               FCB  $23
3627
3628 110a bf               FCB  TEMP_MINUTE
3629 110b c2               FCB  2+VALID_0_YES+LEADING_0_YES+LIMIT_9_NO
3630 110c 45               FCB  LCD_LINE_2+5
3631 110d 59               FCB  $59
3632
3633 110e bb               FCB  TEMP_YEAR
3634 110f e2               FCB  2+VALID_0_YES+LEADING_0_YES+LIMIT_9_YES
3635 1110 4a               FCB  LCD_LINE_2+10
3636
3637 1111 bc               FCB  TEMP_MONTH
3638 1112 42               FCB  2+VALID_0_NO+LEADING_0_YES+LIMIT_9_NO
3639 1113 4d               FCB  LCD_LINE_2+13
3640 1114 12               FCB  $12
3641
3642 1115 bd               FCB  TEMP_DAY
3643 1116 42               FCB  2+VALID_0_NO+LEADING_0_YES+LIMIT_9_NO
```

```
3644 1117 50              FCB   LCD_LINE_2+16
3645 1118 31              FCB   $31
3646 1119 e1              FCB   END_OF_BRANCH
3647                  #23
3648 111a ef              FCB   PGM_SPECIAL_14
3649 111b e1              FCB   END_OF_BRANCH
3650                  #24
3651 111c fc              FCB   PGM_SPECIAL_27
3652 111d 0c              FCB   MASK_PGM_ENTER
3653 111e 03              FCB   3
3654 111f d5              FCB   V_VOLUME
3655 1120 bc              FCB   V__OF_
3656 1121 a7              FCB   V_EACH
3657 1122 df              FCB   END_OF_MESSAGE
3658 1123 41              FCB   LCD_LINE_2+1
3659 1124 a2              FCB   V_BOTTLE
3660 1125 20 49 53        FCC   ' IS'
3661 1128 df              FCB   END_OF_MESSAGE
3662 1129 51              FCB   LCD_LINE_2+17
3663 112a ba              FCB   V_ml_
3664 112b e0              FCB   END_OF_DISPLAY
3665
3666 112c bd              FCB   TEMP_BOTTLE
3667 112d a5              FCB   5+VALID_0_YES+LEADING_0_NO+LIMIT_9_YES
3668 112e 4b              FCB   LCD_LINE_2+11
3669 112f e1              FCB   END_OF_BRANCH
3670                  #25
3671 1130 ec              FCB   PGM_SPECIAL_11
3672 1131 e1              FCB   END_OF_BRANCH
3673                  #26
3674 1132 e3              FCB   PGM_SPECIAL_2
3675 1133 1c              FCB   MASK_PGM_NONE
3676 1134 09              FCB   9
3677 1135 c4              FCB   V_PUMP_
3678 1136 a5              FCB   V_COUNT
3679 1137 53              FCC   'S'
3680 1138 df              FCB   END_OF_MESSAGE
3681 1139 42              FCB   LCD_LINE_2+2
3682 113a 53 49 4e 43 45 20  FCC  'SINCE LAST '
     4c 41 53 54 20
3683 1145 c6              FCB   V_RESET_
3684 1146 e1              FCB   END_OF_BRANCH
3685                  #27
3686 1147 f6              FCB   PGM_SPECIAL_21
3687 1148 70              FCB   YES_NO_QUESTION
3688 1149 00              FCB   0
3689 114a c6              FCB   V_RESET_
3690 114b c4              FCB   V_PUMP_
3691 114c a5              FCB   V_COUNT
3692 114d 45 52 3f        FCC   'ER?'
3693 1150 df              FCB   END_OF_MESSAGE
3694 1151 45              FCB   LCD_LINE_2+5
3695 1152 d9              FCB   V__YES_NO_
3696 1153 e0              FCB   END_OF_DISPLAY
```

```
3697
3698 1154 46                FCB  LCD_LINE_2+6
3699 1155 d8                FCB  V_YES
3700 1156 df                FCB  END_OF_MESSAGE
3701 1157 4b                FCB  LCD_LINE_2+11
3702 1158 bb                FCB  V_NO
3703 1159 e1                FCB  END_OF_BRANCH
3704                  *28
3705 115a e2                FCB  PGM_SPECIAL_1
3706 115b 0c                FCB  MASK_PGM_ENTER
3707 115c 09                FCB  9
3708 115d c4                FCB  V_PUMP_
3709 115e a5                FCB  V_COUNT
3710 115f 53                FCC  '5'
3711 1160 df                FCB  END_OF_MESSAGE
3712 1161 45                FCB  LCD_LINE_2+5
3713 1162 54 4f 20          FCC  'TO '
3714 1165 d6                FCB  V_WARNING
3715 1166 e0                FCB  END_OF_DISPLAY
3716
3717 1167 71                FCB  WARN_COUNT
3718 1168 28                FCB  8+VALID_0_NO+LEADING_0_NO+LIMIT_9_YES
3719 1169 00                FCB  0
3720 116a e1                FCB  END_OF_BRANCH
3721                  *29
3722 116b 76                FCB  INHIBIT_SAMPLE
3723 116c 00                FCB  0
3724 116d ca                FCB  V_SAMPLE
3725 116e d7                FCB  V__WHEN_
3726 116f a8                FCB  V_ENABLE
3727 1170 44 3f             FCC  'D?'
3728 1172 df                FCB  END_OF_MESSAGE
3729 1173 45                FCB  LCD_LINE_2+5
3730 1174 d9                FCB  V__YES__NO_
3731 1175 e0                FCB  END_OF_DISPLAY
3732
3733 1176 46                FCB  LCD_LINE_2+6
3734 1177 d8                FCB  V_YES
3735 1178 df                FCB  END_OF_MESSAGE
3736 1179 4b                FCB  LCD_LINE_2+11
3737 117a bb                FCB  V_NO
3738 117b e1                FCB  END_OF_BRANCH
3739                  *30
3740 117c 77                FCB  INHIBIT_LOAD_T
3741 117d 04                FCB  4
3742 117e c6                FCB  V_RESET_
3743 117f ca                FCB  V_SAMPLE
3744 1180 df                FCB  END_OF_MESSAGE
3745 1181 40                FCB  LCD_LINE_2
3746 1182 49 4e 54 45 52 56 FCC  'INTERVAL? '
     41 4c 3f 20
3747 118c d9                FCB  V__YES__NO_
3748 118d e0                FCB  END_OF_DISPLAY
3749
```

```
3750 118e 4b              FCB  LCD_LINE_2+11
3751 118f d8              FCB  V_YES
3752 1190 df              FCB  END_OF_MESSAGE
3753 1191 50              FCB  LCD_LINE_2+16
3754 1192 bb              FCB  V_NO
3755 1193 e1              FCB  END_OF_BRANCH
3756                 *31
3757 1194 e4              FCB  PGM_SPECIAL_3
3758 1195 78              FCB  INHIBIT_COUNT
3759 1196 01              FCB  1
3760 1197 b3              FCB  V_INHIBIT
3761 1198 20              FCC  ' '
3762 1199 a5              FCB  V_COUNT
3763 119a 44 4f 57 4e 3f  FCC  'DOWN?'
3764 119f df              FCB  END_OF_MESSAGE
3765 11a0 45              FCB  LCD_LINE_2+5
3766 11a1 d9              FCB  V_YES_NO_
3767 11a2 e0              FCB  END_OF_DISPLAY
3768
3769 11a3 46              FCB  LCD_LINE_2+6
3770 11a4 d8              FCB  V_YES
3771 11a5 df              FCB  END_OF_MESSAGE
3772 11a6 4b              FCB  LCD_LINE_2+11
3773 11a7 bb              FCB  V_NO
3774 11a8 e1              FCB  END_OF_BRANCH
3775                 *32
3776 11a9 75              FCB  FLOW_SAMPLE
3777 11aa 00              FCB  0
3778 11ab d1              FCB  V_TAKE
3779 11ac 20              FCC  ' '
3780 11ad ca              FCB  V_SAMPLE
3781 11ae 20 41 54 20     FCC  ' AT '
3782 11b2 cf              FCB  V_START
3783 11b3 df              FCB  END_OF_MESSAGE
3784 11b4 42              FCB  LCD_LINE_2+2
3785 11b5 d3              FCB  V_TIME
3786 11b6 3f 20           FCC  '? '
3787 11b8 d9              FCB  V__YES_NO_
3788 11b9 e0              FCB  END_OF_DISPLAY
3789
3790 11ba 49              FCB  LCD_LINE_2+9
3791 11bb d8              FCB  V_YES
3792 11bc df              FCB  END_OF_MESSAGE
3793 11bd 4e              FCB  LCD_LINE_2+14
3794 11be bb              FCB  V_NO
3795 11bf e1              FCB  END_OF_BRANCH
3796                 *33
3797 11c0 0c              FCB  MASK_PGM_ENTER
3798 11c1 00              FCB  0
3799 11c2 cf              FCB  V_START
3800 11c3 20              FCC  ' '
3801 11c4 af              FCB  V_FLOW
3802 11c5 20              FCC  ' '
3803 11c6 a5              FCB  V_COUNT
```

```
3804 11c7 20 41 54 20        FCC   ' AT '
3805 11cb df                 FCB   END_OF_MESSAGE
3806 11cc 46                 FCB   LCD_LINE_2+6
3807 11cd 3a                 FCB   COLON
3808 11ce df                 FCB   END_OF_MESSAGE
3809 11cf 4d                 FCB   LCD_LINE_2+13
3810 11d0 2f                 FCB   SLASH
3811 11d1 e0                 FCB   END_OF_DISPLAY
3812
3813 11d2 be                 FCB   TEMP_HOUR
3814 11d3 82                 FCB   2+VALID_0_YES+LEADING_0_NO+LIMIT_9_NO
3815 11d4 44                 FCB   LCD_LINE_2+4
3816 11d5 23                 FCB   $23
3817
3818 11d6 bf                 FCB   TEMP_MINUTE
3819 11d7 c2                 FCB   2+VALID_0_YES+LEADING_0_YES+LIMIT_9_NO
3820 11d8 47                 FCB   LCD_LINE_2+7
3821 11d9 59                 FCB   $59
3822
3823 11da bc                 FCB   TEMP_MONTH
3824 11db 02                 FCB   2+VALID_0_NO+LEADING_0_NO+LIMIT_9_NO
3825 11dc 4b                 FCB   LCD_LINE_2+11
3826 11dd 12                 FCB   $12
3827
3828 11de bd                 FCB   TEMP_DAY
3829 11df 42                 FCB   2+VALID_0_NO+LEADING_0_YES+LIMIT_9_NO
3830 11e0 4e                 FCB   LCD_LINE_2+14
3831 11e1 31                 FCB   $31
3832 11e2 e1                 FCB   END_OF_BRANCH
3833                    *34
3834 11e3 7a                 FCB   PROGRAM_LOCK
3835 11e4 01                 FCB   1
3836 11e5 5b                 FCC   '['
3837 11e6 df                 FCB   END_OF_MESSAGE
3838 11e7 08                 FCB   8
3839 11e8 2c                 FCC   ','
3840 11e9 df                 FCB   END_OF_MESSAGE
3841 11ea 11                 FCB   17
3842 11eb 5d                 FCC   ']'
3843 11ec df                 FCB   END_OF_MESSAGE
3844 11ed 44                 FCB   LCD_LINE_2+4
3845 11ee c2                 FCB   V_PROGRAM_
3846 11ef b7                 FCB   V_LOCK_
3847 11f0 e0                 FCB   END_OF_DISPLAY
3848
3849 11f1 02                 FCB   2
3850 11f2 a8                 FCB   V_ENABLE
3851 11f3 df                 FCB   END_OF_MESSAGE
3852 11f4 0a                 FCB   10
3853 11f5 a6                 FCB   V_DISABLE
3854 11f6 e1                 FCB   END_OF_BRANCH
3855                    *35
3856 11f7 7b                 FCB   PUMP_LIGHT_MODE
3857 11f8 01                 FCB   1
```

```
3858 11f9 c4          FCB   V_PUMP_
3859 11fa c9          FCB   V_RUNNING_
3860 11fb b6          FCB   V_LIGHT
3861 11fc df          FCB   END_OF_MESSAGE
3862 11fd 40          FCB   LCD_LINE_2
3863 11fe 5b          FCC   '['
3864 11ff df          FCB   END_OF_MESSAGE
3865 1200 48          FCB   LCD_LINE_2+8
3866 1201 2c          FCC   ','
3867 1202 df          FCB   END_OF_MESSAGE
3868 1203 4d          FCB   LCD_LINE_2+13
3869 1204 2c          FCC   ','
3870 1205 df          FCB   END_OF_MESSAGE
3871 1206 52          FCB   LCD_LINE_2+18
3872 1207 5d          FCC   ']'
3873 1208 e0          FCB   END_OF_DISPLAY
3874
3875 1209 41          FCB   LCD_LINE_2+1
3876 120a b0          FCB   V_FWD
3877 120b 26          FCC   '&'
3878 120c c7          FCB   V_REV
3879 120d df          FCB   END_OF_MESSAGE
3880 120e 4a          FCB   LCD_LINE_2+10
3881 120f b0          FCB   V_FWD
3882 1210 df          FCB   END_OF_MESSAGE
3883 1211 4f          FCB   LCD_LINE_2+15
3884 1212 c7          FCB   V_REV
3885 1213 e1          FCB   END_OF_BRANCH
3886                  *36
3887 1214 7c          FCB   ENTER_MODE
3888 1215 00          FCB   0
3889 1216 a9          FCB   V_ENTER_
3890 1217 5b          FCC   '['
3891 1218 df          FCB   END_OF_MESSAGE
3892 1219 13          FCB   19
3893 121a 2c          FCC   ','
3894 121b df          FCB   END_OF_MESSAGE
3895 121c 4d          FCB   LCD_LINE_2+13
3896 121d 2c          FCC   ','
3897 121e df          FCB   END_OF_MESSAGE
3898 121f 53          FCB   LCD_LINE_2+19
3899 1220 5d          FCC   ']'
3900 1221 e0          FCB   END_OF_DISPLAY
3901
3902 1222 07          FCB   7
3903 1223 23          FCC   '#'
3904 1224 bc          FCB   V__OF_
3905 1225 cb          FCB   V_SAMPLES
3906 1226 df          FCB   END_OF_MESSAGE
3907 1227 40          FCB   LCD_LINE_2
3908 1228 ca          FCB   V_SAMPLE
3909 1229 20          FCC   ' '
3910 122a d5          FCB   V_VOLUME
3911 122b df          FCB   END_OF_MESSAGE
```

```
3912 122c 4f              FCB  LCD_LINE_2+15
3913 122d 42 4f 54 48     FCC  'BOTH'
3914 1231 e1              FCB  END_OF_BRANCH
3915                 *37
3916 1232 0c              FCB  MASK_PGM_ENTER
3917 1233 02              FCB  2
3918 1234 a9              FCB  V_ENTER_
3919 1235 50 41 53 53 4e 55   FCC  'PASSNUMBER'
     4d 42 45 52
3920 123f e0              FCB  END_OF_DISPLAY
3921
3922 1240 9c              FCB  PASS_NUMBER
3923 1241 e4              FCB  4+VALID_0_YES+LEADING_0_YES+LIMIT_9_YES
3924 1242 48              FCB  LCD_LINE_2+8
3925 1243 e1              FCB  END_OF_BRANCH
3926                 *38
3927 1244 f1              FCB  PGM_SPECIAL_16
3928 1245 e1              FCB  END_OF_BRANCH
3929                 *39
3930 1246 fb              FCB  PGM_SPECIAL_26
3931 1247 14              FCB  MASK_PGM_MANUAL
3932 1248 00              FCB  0
3933 1249 c1              FCB  V_PRESS_
3934 124a b8              FCB  V_MANUAL_
3935 124b ca              FCB  V_SAMPLE_
3936 124c df              FCB  END_OF_MESSAGE
3937 124d 41              FCB  LCD_LINE_2+1
3938 124e b5              FCB  V_KEY
3939 124f d7              FCB  V__WHEN_
3940 1250 c5              FCB  V_READY_
3941 1251 e1              FCB  END_OF_BRANCH
3942                 *40
3943 1252 e0              FCB  END_OF_DISPLAY
3944
3945 1253 03              FCB  3
3946 1254 b8              FCB  V_MANUAL_
3947 1255 ca              FCB  V_SAMPLE_
3948 1256 df              FCB  END_OF_MESSAGE
3949 1257 44              FCB  LCD_LINE_2+4
3950 1258 b1              FCB  V_GRAB_
3951 1259 ca              FCB  V_SAMPLE_
3952 125a e1              FCB  END_OF_BRANCH
3953                 *41
3954 125b 0c              FCB  MASK_PGM_ENTER
3955 125c 08              FCB  8
3956 125d ba              FCB  V_al_
3957 125e d5              FCB  V_VOLUME
3958 125f df              FCB  END_OF_MESSAGE
3959 1260 45              FCB  LCD_LINE_2+5
3960 1261 44 45 4c 49 56 45   FCC  'DELIVERED'
     52 45 44
3961 126a e0              FCB  END_OF_DISPLAY
3962
3963 126b 9e              FCB  VOLUME_DELIVER
```

```
3964 126c 24              FCB  4+VALID_0_NO+LEADING_0_NO+LIMIT_9_YES
3965 126d 03              FCB  3
3966 126e e1              FCB  END_OF_BRANCH
3967              *42
3968 126f ee              FCB  PGM_SPECIAL_13
3969 1270 e1              FCB  END_OF_BRANCH
3970              *43
3971 1271 e5              FCB  PGM_SPECIAL_4
3972 1272 e1              FCB  END_OF_BRANCH
3973              *44
3974 1273 7d              FCB  RESTORE_SAMPLE
3975 1274 01              FCB  1
3976 1275 ca              FCB  V_SAMPLE
3977 1276 d7              FCB  V__WHEN_
3978 1277 c0              FCB  V_POWER_
3979 1278 df              FCB  END_OF_MESSAGE
3980 1279 40              FCB  LCD_LINE_2
3981 127a 52 45 53 54 4f 52   FCC  'RESTORED? '
     45 44 3f 20
3982 1284 d9              FCB  V__YES__NO_
3983 1285 e0              FCB  END_OF_DISPLAY
3984
3985 1286 4b              FCB  LCD_LINE_2+11
3986 1287 d8              FCB  V_YES
3987 1288 df              FCB  END_OF_MESSAGE
3988 1289 50              FCB  LCD_LINE_2+16
3989 128a bb              FCB  V_NO
3990 128b e1              FCB  END_OF_BRANCH
3991              *45
3992 128c 79              FCB  CALIBRATE
3993 128d 01              FCB  1
3994 128e 5b              FCC  '['
3995 128f df              FCB  END_OF_MESSAGE
3996 1290 08              FCB  8
3997 1291 2c              FCC  ','
3998 1292 df              FCB  END_OF_MESSAGE
3999 1293 11              FCB  17
4000 1294 5d              FCC  ']'
4001 1295 df              FCB  END_OF_MESSAGE
4002 1296 41              FCB  LCD_LINE_2+1
4003 1297 a3              FCB  V_CALIBRATE_
4004 1298 ca              FCB  V_SAMPLE
4005 1299 52              FCC  'R'
4006 129a e0              FCB  END_OF_DISPLAY
4007
4008 129b 02              FCB  2
4009 129c a8              FCB  V_ENABLE
4010 129d df              FCB  END_OF_MESSAGE
4011 129e 0a              FCB  10
4012 129f a6              FCB  V_DISABLE
4013 12a0 e1              FCB  END_OF_BRANCH
4014              *46
4015 12a1 f0              FCB  PGM_SPECIAL_15
4016 12a2 e1              FCB  END_OF_BRANCH
```

```
4017                    *47
4018 12a3 1c            FCB  MASK_PGM_NONE
4019 12a4 01            FCB  1
4020 12a5 cd            FCB  V_SOFTWARE_
4021 12a6 c8            FCB  V_REVISION
4022 12a7 df            FCB  END_OF_MESSAGE
4023 12a8 48            FCB  LCD_LINE_2+8
4024 12a9 23 30 2e 32   FCC  '#0.2'
4025 12ad e1            FCB  END_OF_BRANCH
4026                    *
4027                    PROGRAM_FLOW
4028 12ae 02            FCB  02
4029 12af 03            FCB  03
4030 12b0 04            FCB  04
4031 12b1 05            FCB  05
4032 12b2 06            FCB  06      *5
4033 12b3 07            FCB  07
4034 12b4 0b            FCB  11
4035 12b5 09            FCB  09
4036 12b6 0a            FCB  10
4037 12b7 0b            FCB  11      *10
4038 12b8 0c            FCB  12
4039 12b9 0d            FCB  13
4040 12ba 0e            FCB  14
4041 12bb 12            FCB  18
4042 12bc 10            FCB  16      *15
4043 12bd 11            FCB  17
4044 12be 12            FCB  18
4045 12bf 27            FCB  39
4046 12c0 14            FCB  20
4047 12c1 00            FCB  00      *20
4048 12c2 16            FCB  22
4049 12c3 17            FCB  23
4050 12c4 13            FCB  19
4051 12c5 19            FCB  25
4052 12c6 13            FCB  19      *25
4053 12c7 1b            FCB  27
4054 12c8 1c            FCB  28
4055 12c9 13            FCB  19
4056 12ca 1e            FCB  30
4057 12cb 1f            FCB  31      *30
4058 12cc 13            FCB  19
4059 12cd 13            FCB  19
4060 12ce 0c            FCB  12
4061 12cf 13            FCB  19
4062 12d0 13            FCB  19      *35
4063 12d1 13            FCB  19
4064 12d2 26            FCB  38
4065 12d3 00            FCB  00
4066 12d4 29            FCB  41
4067 12d5 00            FCB  00      *40
4068 12d6 2a            FCB  42
4069 12d7 12            FCB  18
4070 12d8 00            FCB  00
```

```
4071 12d9 13              FCB   19
4072 12da 2e              FCB   46        *45
4073 12db 13              FCB   19
4074 12dc 13              FCB   19
4075                   *
4076                   OPTIONS_FLOW
4077 12dd 15              FCB   21
4078 12de 18              FCB   24
4079 12df 1a              FCB   26
4080 12e0 20              FCB   32
4081 12e1 2c              FCB   44
4082 12e2 1d              FCB   29
4083 12e3 2d              FCB   45
4084 12e4 22              FCB   34
4085 12e5 23              FCB   35
4086 12e6 24              FCB   36
4087 12e7 2f              FCB   47
4088 12e8 2b              FCB   43
4089                   *
4090                   *  program run
4091                   *
4092                   *  if sample number 1, go to start program
4093                   *  if continuous sampling,
4094                   *  check that sample bottle is present
4095                   *  if so, set bottle number
4096                   *  if not, error beep and return
4097                   *  if split sampling,
4098                   *  check that both bottles are present
4099                   *  if so, set bottle number to left bottle
4100                   *  if not, error beep and return
4101                   *  set sampler state and keypad mask
4102                   *  and continue sampling
4103                   *
4104                   *****************
4105                   ** resume program *
4106                   *****************
4107                   KEY_RESUME_PGM
4108 12e9 a6 09           LDA   #9
4109 12eb b7 cb           STA   MATH_COUNTER
4110 12ed ae 53           LDX   #SAMPLER_PACE
4111 12ef a6 d2           LDA   #RUN_PARAMETERS    *compare sampling parameters at resume pgm
4112 12f1 cd 19 d6        JSR   COMPARE            *to compare buffer of start pgm
4113 12f4 26 3a           BNE   RESUME_NOT_OK      *branch if unable to resume
4114                   *
4115 12f6 a6 8e           LDA   #SAMPLES_TAKEN
4116 12f8 ae 5a           LDX   #NUM_OF_SAMPLES    *compare number of samples taken
4117 12fa cd 19 d2        JSR   COMPARE_2          *to programmed number of samples
4118 12fd 27 31           BEQ   RESUME_NOT_OK      *branch if already full
4119                   *
4120 12ff ae 8e           LDX   #SAMPLES_TAKEN
4121 1301 a6 81           LDA   #SAMPLE_NUMBER     *otherwise, transfer number of samples taken
4122 1303 cd 19 fc        JSR   TRANSFER_2         *to current sample number
4123 1306 cd 14 a4        JSR   NEXT_SAMPLE        *and increment sample number
4124                   *
```

```
4125 1309 ae 8a          LDX   #SAMPLES_TAKEN
4126 130b cd 19 bd       JSR   COMPARE_TO_0_2
4127 130e 27 24          BEQ   KEY_START_PGM      *branch if no samples taken
4128                  ***** what if flow paced and no sample at start time?
4129                  ***** then, resume goes to start when it should resume at sample 1
4130                     *
4131 1310 00 54 0a       BRSET  0,SAMPLER_MODE,RESUME_SPLIT
4132                     *                        *branch if split sampling
4133 1313 01 8d 02       BRCLR  0,SAMPLE_BOTTLE,RESUME_RIGHT
4134                     *                        *branch if not left sample bottle
4135 1316 20 08          BRA   RESUME_LEFT
4136                  RESUME_RIGHT
4137 1318 0b 03 15       BRCLR  BOTTLE_RIGHT,BOTTLE_RIGHT_P,RESUME_NOT_OK
4138                     *                        *branch if right bottle missing
4139 131b 20 06          BRA   RESUME_BOTTLE
4140                  RESUME_SPLIT
4141 131d 0b 03 10       BRCLR  BOTTLE_RIGHT,BOTTLE_RIGHT_P,RESUME_NOT_OK
4142                     *                        *branch if right bottle missing
4143                  RESUME_LEFT
4144 1320 0f 03 0d       BRCLR  BOTTLE_LEFT,BOTTLE_LEFT_P,RESUME_NOT_OK
4145                     *                        *branch if left bottle missing
4146                  RESUME_BOTTLE
4147 1323 a6 10          LDA   #MASK_RUN
4148 1325 b7 a0          STA   KEY_MASK           *set keypad mask
4149 1327 cd 15 c7       JSR   TAKE_0_SAMPLES     *clear samples to be taken
4150 132a 01 53 2b       BRCLR  0,SAMPLER_PACE,NO_TP_SAMPLE
4151                     *                        *branch if time paced
4152 132d cc 13 8a       JMP   NO_FP_SAMPLE       *otherwise, flow paced
4153                  RESUME_NOT_OK
4154 1330 cd 18 2c       JSR   ERROR_BEEP         *error beep
4155 1333 81             RTS
4156                     *
4157                  *###############
4158                  *# start program #
4159                  *###############
4160                  KEY_START_PGM
4161 1334 9c             RSP                      *reset stack pointer
4162 1335 a6 09          LDA   #9
4163 1337 b7 cb          STA   MATH_COUNTER
4164 1339 ae 53          LDX   #SAMPLER_PACE      *transfer sampling parameters at start pgm
4165 133b a6 d2          LDA   #RUN_PARAMETERS    *to resume pgm compare buffer
4166 133d cd 1a 00       JSR   TRANSFER
4167                     *
4168 1340 00 53 29       BRSET  0,SAMPLER_PACE,FP_SAMPLING
4169                     *                        *branch if not time paced sampling
4170                     *
4171                     * time paced sampling
4172                     *
4173                  TP_SAMPLING
4174 1343 cd 14 2e       JSR   C_OR_S_OK          *check that bottles are ready
4175                  NEW_TP
4176 1346 cd 14 5c       JSR   START_INITIAL      *initialize flags and display
4177                  RESTORE_TIME_1
4178 1349 cd 08 40       JSR   ENFORCE_BOTTLE     *position distributor
```

```
4179 134c cd 14 83         JSR   TIMED_SAMPLE      ;wait for time of first sample
4180 134f 00 c1 12         BRSET INHIBIT_BIT,INHIBIT_BYTE,TP_INHIBIT
4181                     *
4182                                                ;branch if inhibited at time of first
                         TP_SAMPLE
4183 1352 cd 16 67         JSR   C_OR_S_SAMPLE     ;set sample flags
4184 1355 cd 14 a4         JSR   NEXT_SAMPLE       ;increment sample number
4185                     NO_TP_SAMPLE
4186 1358 cd 14 aa         JSR   NXT_TIME_SAMPLE   ;display time of next sample
4187                     RESTORE_TIME_2
4188 135b cd 08 40         JSR   ENFORCE_BOTTLE    ;position distributor
4189 135e cd 14 83         JSR   TIMED_SAMPLE      ;wait for time of next sample
4190 1361 01 c1 ee         BRCLR INHIBIT_BIT,INHIBIT_BYTE,TP_SAMPLE
4191                     *
4192                                                ;branch if not inhibited
                         TP_INHIBIT
4193 1364 cd 15 74         JSR   INHIBIT_TIME      ;otherwise, wait for enable
4194 1367 01 76 e8         BRCLR 0,INHIBIT_SAMPLE,TP_SAMPLE
4195                     *
                                                   ;branch if sample when enabled
4196 136a 20 ec            BRA   NO_TP_SAMPLE
4197                     *
4198                     *
4199                     *   flow paced sampling
4200                     *
                         FP_SAMPLING
4201 136c cd 14 2e         JSR   C_OR_S_OK         ;check that bottles are ready
4202                     NEW_FP
4203 136f cd 14 5c         JSR   START_INITIAL     ;initialize flags and display
4204                     RESTORE_FLOW_1
4205 1372 cd 08 40         JSR   ENFORCE_BOTTLE    ;position distributor
4206 1375 cd 14 83         JSR   TIMED_SAMPLE      ;wait for time of first sample
4207 1378 cd 14 d0         JSR   ZERO_FLOW_PULSE   ;clear flow pulses counter
4208                     NEXT_FP
4209 137b cd 14 c8         JSR   LOAD_FLOW_COUNT   ;load flow pulse count
4210 137e 00 c1 18         BRSET INHIBIT_BIT,INHIBIT_BYTE,FP_INHIBIT
4211                     *
                                                   ;branch if inhibited at time of first
4212 1381 00 75 06         BRSET 0,FLOW_SAMPLE,NO_FP_SAMPLE
4213                     *
4214                                                ;branch if no sample at first time
                         FP_SAMPLE
4215 1384 cd 16 67         JSR   C_OR_S_SAMPLE     ;set sample flags
4216 1387 cd 14 a4         JSR   NEXT_SAMPLE       ;increment sample number
4217                     NO_FP_SAMPLE
4218 138a cd 15 cc         JSR   SAMPLE_DISPLAY    ;display sample number
4219 138d cd 14 d7         JSR   NXT_FLOW_SAMPLE   ;display flow to next sample
4220                     RESTORE_FLOW_2
4221 1390 cd 08 40         JSR   ENFORCE_BOTTLE    ;position distributor
4222 1393 cd 14 f2         JSR   FP_FLOW_CHECK     ;wait for flow pulses
4223 1396 01 c1 eb         BRCLR INHIBIT_BIT,INHIBIT_BYTE,FP_SAMPLE
4224                     *
4225                                                ;branch if not inhibited
                         FP_INHIBIT
4226 1399 cd 15 47         JSR   INHIBIT_FLOW      ;otherwise, wait for enable
4227 139c 01 76 e5         BRCLR 0,INHIBIT_SAMPLE,FP_SAMPLE
4228                     *
                                                   ;branch if sample when enabled
4229 139f 20 e9            BRA   NO_FP_SAMPLE
4230                     *
4231                     *  reinitializes sampler in run state after power restoration
4232                     *
```

```
4233                RUN_STATE
4234 13a1 00 54 08      BRSET   0,SAMPLER_MODE,RESTORE_SPLIT
4235                *                       *branch if split sampling
4236 13a4 02 8d 08      BRSET   1,SAMPLE_BOTTLE,RESTORE_RIGHT
4237                *                       *branch if right sample bottle
4238 13a7 0f 03 1b      BRCLR   BOTTLE_LEFT,BOTTLE_LEFT_P,RESTORE_NOT_OK
4239                *                       *branch if left bottle missing
4240 13aa 20 06         BRA     RESTORE_BOTTLE
4241                RESTORE_SPLIT
4242 13ac 0f 03 16      BRCLR   BOTTLE_LEFT,BOTTLE_LEFT_P,RESTORE_NOT_OK
4243                *                       *branch if left bottle missing
4244                RESTORE_RIGHT
4245 13af 0b 03 13      BRCLR   BOTTLE_RIGHT,BOTTLE_RIGHT_P,RESTORE_NOT_OK
4246                *                       *branch if right bottle missing
4247                RESTORE_BOTTLE
4248 13b2 cd 1d 2b      JSR     RESTORE_DISPLAY
4249 13b5 b6 51         LDA     SAMPLER_STATE
4250 13b7 a1 04         CMP     #STATE_RUN_FIRST
4251 13b9 26 05         BNE     RESTORE_AFTER_1
4252 13bb 00 53 b4      BRSET   0,SAMPLER_PACE,RESTORE_FLOW_1
4253                *                       *continue waiting for flow paced
4254 13be 20 89         BRA     RESTORE_TIME_1  *or time paced sample number 1
4255                RESTORE_AFTER_1
4256 13c0 00 53 cd      BRSET   0,SAMPLER_PACE,RESTORE_FLOW_2
4257                *                       *continue with flow paced
4258 13c3 20 96         BRA     RESTORE_TIME_2  *or time paced sampling
4259                RESTORE_NOT_OK
4260 13c5 cc 06 a1      JMP     KEY_ON
4261                *
4262
4263                *//////////////////////////////////////////////////////////////
4264                *
4265                *   in continuous sampling
4266                *   checks if other bottle is ready and present
4267                *   aborts and goes to full if not
4268                *   otherwise, switches to other bottle and returns
4269                *
                    OTHER_READY
4270 13c8 02 8d 07      BRSET   1,SAMPLE_BOTTLE,LEFT_NOW
4271                *                       *branch if going to left bottle
4272 13cb 03 c0 0a      BRCLR   READY_RIGHT,READY_RIGHT_B,FULL_CONTINUOUS
4273                *                       *branch if right bottle used
4274 13ce 0b 03 07      BRCLR   BOTTLE_RIGHT,BOTTLE_RIGHT_P,FULL_CONTINUOUS
4275                *                       *branch if right bottle missing
4276                READY_FOR_OTHER
4277 13d1 81           RTS
4278                LEFT_NOW
4279 13d2 01 c0 03      BRCLR   READY_LEFT,READY_LEFT_B,FULL_CONTINUOUS
4280                *                       *branch if left bottle used
4281 13d5 0e 03 f9      BRSET   BOTTLE_LEFT,BOTTLE_LEFT_P,READY_FOR_OTHER
4282                *                       *branch if left bottle present
4283                FULL_SPLIT
4284                FULL_CONTINUOUS
4285 13d8 9c          RSP
4286 13d9 a6 03        LDA     #STATE_FULL
```

```
4287 13db b7 51             STA  SAMPLER_STATE    ;set state to standby
4288 13dd a6 04             LDA  #MASK_FULL
4289 13df b7 a0             STA  KEY_MASK         ;set keypad mask
4290 13e1 19 c0             BCLR SAMPLING_BIT,SAMPLING_BYTE
4291                   FULL_STATE
4292 13e3 cd 16 49          JSR  NO_RUN_DISPLAY
4293 13e6 26 03             BNE  FULL_LOOP        ;branch if review pgm or display fault
4294 13e8 cd 13 f0          JSR  FULL_DISPLAY     ;display full message
4295                   FULL_LOOP
4296 13eb cd 05 65          JSR  PERIODIC_SCAN    ;continuously scan routines
4297 13ee 20 fb             BRA  FULL_LOOP
4298                        *
4299                        *////////////////////////////////////////////////////////////
4300                        *
4301                        *  displays full message and number of samples taken
4302                        *
4303                   FULL_DISPLAY
4304 13f0 cd 02 d6          JSR  CLEAR_LCD
4305 13f3 5f                CLRX
4306                   NEXT_MSG_FULL
4307 13f4 d6 17 f9          LDA  MSG_FULL,X
4308 13f7 cd 03 54          JSR  DISPLAY          ;display full message
4309 13fa 26 f8             BNE  NEXT_MSG_FULL
4310 13fc a6 8e             LDA  #SAMPLES_TAKEN
4311 13fe cd 15 f7          JSR  DISPLAY_SAMPLE   ;display number of samples
4312 1401 cd 02 ed          JSR  LCD_DATE_TIME    ;and current date/time
4313 1404 81                RTS
4314                        *
4315                        *////////////////////////////////////////////////////////////
4316                        *
4317                        *  in time switched flow paced continuous sampling
4318                        *  when time of first expires before all flow samples taken
4319                        *  if not sampling
4320                        *  turns on full light
4321                        *  if ready and present, switches to other bottle and continues
4322                        *  if sampling
4323                        *  switches to other bottle if ready
4324                        *
4325                   TSFP_TIMEOUT
4326 1405 9c                RSP
4327 1406 02 8d 0c          BRSET    1,SAMPLE_BOTTLE,TSFP_LEFT_NOW
4328                        *                      ;branch if on right bottle
4329 1409 11 c0             BCLR READY_LEFT,READY_LEFT_B
4330                        *                      ;clear left bottle ready flag
4331 140b 14 c0             BSET LEFT_FULL,LEFT_FULL_B
4332                        *                      ;set left bottle full flag
4333 140d 03 c0 c8          BRCLR    READY_RIGHT,READY_RIGHT_B,FULL_CONTINUOUS
4334                        *                      ;branch if right bottle used
4335 1410 0b 03 c5          BRCLR    BOTTLE_RIGHT,BOTTLE_RIGHT_P,FULL_CONTINUOUS
4336                        *                      ;branch if right bottle missing
4337 1413 20 0a             BRA  TSFP_READY
4338                   TSFP_LEFT_NOW
4339 1415 13 c0             BCLR READY_RIGHT,READY_RIGHT_B
4340                        *                      ;clear right bottle ready flag
```

```
4341 1417 16 c0              BSET  RIGHT_FULL,RIGHT_FULL_B
4342                      *                           *set right bottle full flag
4343 1419 01 c0 bc            BRCLR  READY_LEFT,READY_LEFT_B,FULL_CONTINUOUS
4344                      *                           *branch if left bottle used
4345 141c 0f 03 b9            BRCLR  BOTTLE_LEFT,BOTTLE_LEFT_P,FULL_CONTINUOUS
4346                      *                           *branch if left bottle missing
4347                      TSFP_READY
4348 141f cd 08 39            JSR   BOTTLE_CHANGE     *change bottle and move distributor
4349 1422 cd 15 c2            JSR   TAKEN_0_SAMPLES
4350 1425 cd 14 d0            JSR   ZERO_FLOW_PULSE
4351 1428 cd 15 bb            JSR   SAMPLE_NUMBER_1   *set sample number to one
4352 142b cc 13 7b            JMP   NEXT_FP           *and restart sampling
4353                      *
4354                      *////////////////////////////////////////////////////////////////
4355                      *
4356                      *   clears samples to be taken
4357                      *   if continuous sampling
4358                      *       if left bottle is present and ready, uses it
4359                      *       if right bottle is presnet and ready, uses it
4360                      *       if neither is ready, beeps and aborts start
4361                      *   if split sampling
4362                      *       checks that both bottles are ready
4363                      *       if not, beeps and aborts start
4364                      *
4365                      C_OR_S_OK
4366 142e cd 15 c7            JSR   TAKE_0_SAMPLES    *clear samples to be taken
4367 1431 00 54 1a            BRSET  0,SAMPLER_MODE,SPLIT_OK
4368                      *                           *branch if split sampling
4369 1434 a6 01              LDA   #LEFT_BOTTLE       *assume left bottle is present and ready
4370 1436 0f 03 03            BRCLR  BOTTLE_LEFT,BOTTLE_LEFT_P,TRY_RIGHT
4371                      *                           *branch if left bottle missing
4372 1439 00 c0 08            BRSET  READY_LEFT,READY_LEFT_B,C_OR_S_OK_EXIT
4373                      *                           *branch if left bottle ready
4374                      TRY_RIGHT
4375 143c a6 02              LDA   #RIGHT_BOTTLE      *assume right bottle is present and ready
4376                      CONT_OK_RIGHT
4377 143e 0b 03 15            BRCLR  BOTTLE_RIGHT,BOTTLE_RIGHT_P,C_OR_S_NOT_OK
4378                      *                           *branch if right bottle missing
4379 1441 03 c0 12            BRCLR  READY_RIGHT,READY_RIGHT_B,C_OR_S_NOT_OK
4380                      *                           *branch if right bottle not ready
4381                      C_OR_S_OK_EXIT
4382 1444 b7 8d              STA   SAMPLE_BOTTLE
4383 1446 a6 10              LDA   #MASK_RUN
4384 1448 b7 a0              STA   KEY_MASK           *set keypad mask
4385 144a cd 15 c2            JSR   TAKEN_0_SAMPLES   *clear number of samples taken
4386 144d 81              RTS
4387                      SPLIT_OK
4388 144e a6 01              LDA   #LEFT_BOTTLE
4389 1450 0f 03 03            BRCLR  BOTTLE_LEFT,BOTTLE_LEFT_P,C_OR_S_NOT_OK
4390                      *                           *branch if left bottle missing
4391 1453 00 c0 e8            BRSET  READY_LEFT,READY_LEFT_B,CONT_OK_RIGHT
4392                      *                           *branch if left bottle not used
4393                      C_OR_S_NOT_OK
4394 1456 cd 18 2c            JSR   ERROR_BEEP        *beep three times
```

```
4395 1459 cc 06 a1          JMP  KEY_ON           *return to standby state
4396                    *
4397                    *////////////////////////////////////////////////////////////////////
4398                    *
4399                    *   sets flags
4400                    *   displays time/date of first sample
4401                    *
4402                    START_INITIAL
4403 145c a6 04             LDA  #STATE_RUN_FIRST
4404 145e b7 51             STA  SAMPLER_STATE    *sampler in run state
4405 1460 a6 10             LDA  #MASK_RUN
4406 1462 b7 a0             STA  KEY_MASK         *set keypad mask
4407 1464 cd 15 bb           JSR  SAMPLE_NUMBER_1  *set sample number to one
4408 1467 cd 16 49           JSR  NO_RUN_DISPLAY
4409 146a 26 03             BNE  START_INITIAL_X  *branch if review pgm or display fault
4410 146c cd 14 70           JSR  DATE_TIME_FIRST  *display date/time of first sample
4411                    START_INITIAL_X
4412 146f 81              RTS
4413                    *
4414                    *////////////////////////////////////////////////////////////////////
4415                    *
4416                    *   display at and date/time of first sample
4417                    *
4418                    DATE_TIME_FIRST
4419 1470 cd 02 d6           JSR  CLEAR_LCD
4420 1473 5f              CLRX
4421                    NEXT_MSG_DELAY
4422 1474 d6 17 dc           LDA  MSG_DELAY,X
4423 1477 cd 03 54           JSR  DISPLAY          *display delay message
4424 147a 26 f8             BNE  NEXT_MSG_DELAY
4425                    ***** could make display character into vocabulary
4426                    ***** then load acc with v and jsr lcd data write
4427 147c cd 03 22           JSR  NEXT_DATE_TIME   *display date/time of first sample
4428 147f cd 02 ed           JSR  LCD_DATE_TIME
4429 1482 81              RTS
4430                    *
4431                    *////////////////////////////////////////////////////////////////////
4432                    *
4433                    *   waits for time of first/next sample
4434                    *
4435                    TIMED_SAMPLE
4436 1483 cd 05 65           JSR  PERIODIC_SCAN    *periodic diagnostic routine
4437 1486 b6 51             LDA  SAMPLER_STATE
4438 1488 a1 04             CMP  #STATE_RUN_FIRST
4439 148a 27 03             BEQ  NO_TIME_INHIBIT  *branch if no samples taken
4440 148c 00 c1 0c           BRSET    INHIBIT_BIT,INHIBIT_BYTE,TIMED_SAMPLE_X
4441                    *                           *branch if inhibited
4442                    NO_TIME_INHIBIT
4443 148f ae 7f             LDX  #TAKE_A_SAMPLE
4444 1491 cd 19 bd           JSR  COMPARE_TO_0_2
4445 1494 27 ed             BEQ  TIMED_SAMPLE     *branch if not time for sample
4446 1496 a6 7f             LDA  #TAKE_A_SAMPLE
4447 1498 cd 1a 9d           JSR  BCD_DECREMENT_2  *otherwise, decrement time for sample
4448                    TIMED_SAMPLE_X
```

```
4449 149b 81              RTS
4450                  *
4451                  *////////////////////////////////////////////////////////////
4452                  *
4453                  *   checks if sampler full
4454                  *
4455                  FULL_CHECK
4456 149c ae 81           LDX  #SAMPLE_NUMBER    *compare sample number
4457 149e a6 5a           LDA  #NUM_OF_SAMPLES   *with number of samples
4458 14a0 cd 19 d2        JSR  COMPARE_2
4459 14a3 81              RTS
4460                  *
4461                  *////////////////////////////////////////////////////////////
4462                  *
4463                  *   increments sampler number
4464                  *
4465                  NEXT_SAMPLE
4466 14a4 a6 81           LDA  #SAMPLE_NUMBER
4467 14a6 cd 1a 87        JSR  BCD_INCREMENT_2   *increment sample number
4468 14a9 81              RTS
4469                  *
4470                  *////////////////////////////////////////////////////////////
4471                  *
4472                  *   displays time of next sample
4473                  *
4474                  NXT_TIME_SAMPLE
4475 14aa a6 05           LDA  #STATE_RUN_TIME
4476 14ac b7 51           STA  SAMPLER_STATE     *sampler in next run state
4477 14ae cd 16 49        JSR  NO_RUN_DISPLAY
4478 14b1 26 14           BNE  NXT_TIME_X        *branch if review pgm or display fault
4479 14b3 cd 15 cc        JSR  SAMPLE_DISPLAY    *display sample number
4480 14b6 a6 40           LDA  #LCD_LINE_2
4481 14b8 cd 02 da        JSR  LCD_CURSOR        *position cursor
4482 14bb 5f              CLRX
4483                  NEXT_MSG_AT
4484 14bc d6 17 e9        LDA  MSG_AT,X
4485 14bf cd 03 54        JSR  DISPLAY           *display at message
4486 14c2 26 f8           BNE  NEXT_MSG_AT
4487 14c4 cd 03 3a        JSR  NEXT_TIME_HERE    *display time of next sample
4488                  NXT_TIME_X
4489 14c7 81              RTS
4490                  *
4491                  *////////////////////////////////////////////////////////////
4492                  *
4493                  *   in flow paced
4494                  *   loads flow interval into flow to next
4495                  *
4496                  LOAD_FLOW_COUNT
4497 14c8 ae 6b           LDX  #INTERVAL_FLOW    *load flow interval
4498 14ca a6 8a           LDA  #FLOW_TO_NEXT     *into flow to next sample
4499 14cc cd 19 fc        JSR  TRANSFER_2
4500 14cf 81              RTS
4501                  *
4502                  *////////////////////////////////////////////////////////////
```

```
4503                        *
4504                        *   clears flow pulses
4505                        *
4506                        ZERO_FLOW_PULSE
4507 14d0 3f 87                 CLR  FLOW_PULSES
4508 14d2 3f 88                 CLR  FLOW_PULSES+1      *clear flow pulses counter
4509 14d4 3f 89                 CLR  FLOW_PULSES+2
4510 14d6 81                    RTS
4511                        *
4512                        *////////////////////////////////////////////////////////////////
4513                        *
4514                        *   in flow paced
4515                        *   displays flow to next sample
4516                        *
4517                        NXT_FLOW_SAMPLE
4518 14d7 a6 06                 LDA  #STATE_RUN_FLOW
4519 14d9 b7 51                 STA  SAMPLER_STATE      *set state to run, flow
4520 14db cd 16 49              JSR  NO_RUN_DISPLAY
4521 14de 26 11                 BNE  NXT_FLOW_X         *branch if review pgm or display fault
4522 14e0 a6 40                 LDA  #LCD_LINE_2
4523 14e2 cd 02 da              JSR  LCD_CURSOR         *position cursor
4524 14e5 5f                    CLRX
4525                        NEXT_MSG_FLOW
4526 14e6 d6 17 ed              LDA  MSG_FLOW,X
4527 14e9 cd 03 54              JSR  DISPLAY            *display in flow pulses message
4528 14ec 26 18                 BNE  NEXT_MSG_FLOW
4529 14ee cd 16 01              JSR  FLOW_DISPLAY
4530                        NXT_FLOW_X
4531 14f1 81                    RTS
4532                        *
4533                        *////////////////////////////////////////////////////////////////
4534                        *
4535                        *   in flow paced sampling
4536                        *   waits for flow to next to go to zero
4537                        *   aborts if inhibited
4538                        *   if time switched flow paced continuous sampling
4539                        *   aborts at time for next bottle
4540                        *
4541                        FP_FLOW_CHECK
4542 14f2 cd 05 65              JSR  PERIODIC_SCAN
4543 14f5 00 c1 31              BRSET   INHIBIT_BIT,INHIBIT_BYTE,FP_FLOW_RTS
4544                        *                           *branch if inhibited
4545 14f8 ae 87                 LDX  #FLOW_PULSES
4546 14fa cd 19 bb              JSR  COMPARE_TO_0_3
4547 14fd 27 14                 BEQ  FP_TSFP_CHECK      *branch if no flow pulses
4548 14ff a6 87                 LDA  #FLOW_PULSES
4549 1501 cd 1a 9b              JSR  BCD_DECREMENT_3    *otherwise, decrement flow pulses
4550 1504 a6 8a                 LDA  #FLOW_TO_NEXT
4551 1506 cd 1a 9d              JSR  BCD_DECREMENT_2    *and flow to next
4552 1509 ae 8a                 LDX  #FLOW_TO_NEXT
4553 150b cd 19 bd              JSR  COMPARE_TO_0_2
4554 150e 27 16                 BEQ  FP_FLOW_EXIT       *branch if flow to next expired
4555 1510 cd 16 01              JSR  FLOW_DISPLAY       *otherwise, display flow to next
4556                        FP_TSFP_CHECK
```

```
4557 1513 00 54 dc          BRSET   0,SAMPLER_MODE,FP_FLOW_CHECK
4558                    *                           *branch if not continuous sampling
4559 1516 00 55 d9          BRSET   0,SWITCH_MODE,FP_FLOW_CHECK
4560                    *                           *branch if not time switched
4561 1519 ae 7f             LDX     #TAKE_A_SAMPLE
4562 151b cd 19 bd          JSR     COMPARE_TO_0_2
4563 151e 27 d2             BEQ     FP_FLOW_CHECK   *branch if not time for sample
4564 1520 cd 15 c7          JSR     TAKE_0_SAMPLES  *clear samples to be taken
4565 1523 cc 14 05          JMP     TSFP_TIMEOUT    *otherwise, switch bottles
4566                    FP_FLOW_EXIT
4567 1526 cd 14 c8          JSR     LOAD_FLOW_COUNT *load flow pulse count
4568                    FP_FLOW_RTS
4569 1529 81               RTS
4570                    *
4571                    *////////////////////////////////////////////////////////////////
4572                    *
4573                    *   monitors pin c flow pulses
4574                    *
4575                    FLOW_CHECK
4576 152a a6 f6             LDA     #FLOW_PULSE
4577 152c b7 00             STA     DATA_BUS_P      *select flow pulse input
4578 152e a6 ff             LDA     #DATA_BUS_OUT
4579 1530 b7 04             STA     DATA_BUS_PD     *set data bus as output
4580 1532 02 c1 0c          BRSET   FLOW_PIN,FLOW_BYTE,FLOW_CHECK_ON
4581                    *                           *branch if flow pin previously on
4582 1535 02 03 0e          BRSET   MUX,MUX_P,FLOW_CHECK_EXIT
4583                    *                           *branch if flow pin still off
4584 1538 12 c1             BSET    FLOW_PIN,FLOW_BYTE
4585                    *                           *set flow pin to previously on
4586 153a a6 87             LDA     #FLOW_PULSES
4587 153c cd 1a 85          JSR     BCD_INCREMENT_3 *increment flow pulses
4588 153f 20 05             BRA     FLOW_CHECK_EXIT
4589                    FLOW_CHECK_ON
4590 1541 03 03 02          BRCLR   MUX,MUX_P,FLOW_CHECK_EXIT
4591                    *                           *branch if flow pin still on
4592 1544 13 c1             BCLR    FLOW_PIN,FLOW_BYTE
4593                    *                           *set flow pin to previously off
4594                    FLOW_CHECK_EXIT
4595 1546 81               RTS
4596                    *
4597                    *////////////////////////////////////////////////////////////////
4598                    *
4599                    *   when inhibited in flow mode
4600                    *   displays sample number and inhibited
4601                    *   performs periodic scan
4602                    *   when enabled, may load flow interval into flow to next
4603                    *   and may take a sample
4604                    *   if time switched flow paced continuous sampling
4605                    *   aborts at time for next bottle
4606                    *
4607                    INHIBIT_FLOW
4608 1547 a6 05             LDA     #STATE_RUN_TIME
4609 1549 b7 51             STA     SAMPLER_STATE   *sampler in next run state
4610 154b cd 15 cc          JSR     SAMPLE_DISPLAY  *display sample number
```

```
4611 154e ad 57           BSR    LCD_INHIBIT      *and inhibited
4612                  INH_SCAN_FLOW
4613 1550 cd 05 65        JSR    PERIODIC_SCAN
4614 1553 01 c1 13        BRCLR  INHIBIT_BIT,INHIBIT_BYTE,INH_FLOW_DONE
4615                      *                       *branch if still inhibited
4616 1556 00 54 f7        BRSET  0,SAMPLER_MODE,INH_SCAN_FLOW
4617                      *                       *branch if not continuous sampling
4618 1559 00 55 f4        BRSET  0,SWITCH_MODE,INH_SCAN_FLOW
4619                      *                       *branch if not time switched
4620 155c ae 7f           LDX    #TAKE_A_SAMPLE
4621 155e cd 19 bd        JSR    COMPARE_TO_0_2
4622 1561 27 ed           BEQ    INH_SCAN_FLOW    *branch if not time for sample
4623 1563 cd 15 c7        JSR    TAKE_0_SAMPLES   *clear samples to be taken
4624 1566 cc 14 05        JMP    TSFP_TIMEOUT     *and switch bottles
4625                  INH_FLOW_DONE
4626 1569 a6 06           LDA    #STATE_RUN_FLOW
4627 156b b7 51           STA    SAMPLER_STATE    *sampler in next run state
4628 156d 00 77 03        BRSET  0,INHIBIT_LOAD_T,INH_SAMPLE_FLOW
4629                      *                       *branch if no to reset sample interval
4630 1570 cd 14 c8        JSR    LOAD_FLOW_COUNT  *otherwise, load flow sample interval
4631                  INH_SAMPLE_FLOW
4632 1573 81              RTS
4633                  *
4634                  *////////////////////////////////////////////////////////////////
4635                  *
4636                  *   when inhibited in time mode
4637                  *   displays sample number and inhibited
4638                  *   performs periodic scan
4639                  *   when enabled, may load current time into time of first
4640                  *   and add sample interval
4641                  *   and may take a sample
4642                  *
4643                  INHIBIT_TIME
4644 1574 a6 05           LDA    #STATE_RUN_TIME
4645 1576 b7 51           STA    SAMPLER_STATE    *sampler in next run state
4646 1578 cd 15 cc        JSR    SAMPLE_DISPLAY   *display sample number
4647 157b ad 2a           BSR    LCD_INHIBIT      *and inhibited
4648                  INH_COUNT_CHECK
4649 157d a6 3c           LDA    #60
4650 157f b7 c9           STA    MINUTE_PASSED
4651 1581 00 78 03        BRSET  0,INHIBIT_COUNT,INH_SCAN_TIME
4652                      *                       *branch if no to inhibit countdown
4653 1584 cd 1c 06        JSR    INC_MINUTE       *add one minute to first/next
4654                  INH_SCAN_TIME
4655 1587 cd 05 65        JSR    PERIODIC_SCAN
4656 158a 01 c1 06        BRCLR  INHIBIT_BIT,INHIBIT_BYTE,INH_TIME_DONE
4657                      *                       *branch if still inhibited
4658 158d b6 c9           LDA    MINUTE_PASSED
4659 158f 26 f6           BNE    INH_SCAN_TIME    *branch if another minute has not passed
4660 1591 20 ea           BRA    INH_COUNT_CHECK  *otherwise, may need to inhibit countdown
4661                  INH_TIME_DONE
4662 1593 cd 15 c7        JSR    TAKE_0_SAMPLES   *clear samples to be taken
4663 1596 00 77 0a        BRSET  0,INHIBIT_LOAD_T,INH_SAMPLE_TIME
4664                      *                       *branch if no to reset sample interval
```

```
4665 1599 ae 91              LDX  #RTC_YEAR          *transfer new current date/time
4666 159b a6 64              LDA  #YEAR_OF_FIRST     *to date/time of first/next sample
4667 159d cd 19 f6           JSR  TRANSFER_5
4668 15a0 cd 1b e4           JSR  TIME_OF_NEXT       *add sample interval to time of first
4669                    INH_SAMPLE_TIME
4670 15a3 cd 14 aa           JSR  NXT_TIME_SAMPLE    *display time of next sample
4671 15a6 81                 RTS
4672                    *
4673                    *////////////////////////////////////////////////////////////////
4674                    *
4675                    *    displays inhibited on lcd line 2
4676                    *
4677                    LCD_INHIBIT
4678 15a7 cd 16 49           JSR  NO_RUN_DISPLAY     ***** bsr
4679 15aa 26 0e              BNE  LCD_INHIBIT_RTS    *branch if review pgm or display fault
4680 15ac a6 40              LDA  #LCD_LINE_2
4681 15ae cd 02 da           JSR  LCD_CURSOR
4682 15b1 5f                 CLRX
4683                    NXT_MSG_INHIBIT
4684 15b2 d6 18 08           LDA  MSG_INHIBIT,X
4685 15b5 cd 03 54           JSR  DISPLAY            *display inhibit message
4686 15b8 26 f8              BNE  NXT_MSG_INHIBIT
4687                    LCD_INHIBIT_RTS
4688 15ba 81                 RTS
4689                    *
4690                    *////////////////////////////////////////////////////////////////
4691                    *
4692                    *    sets sample number to one
4693                    *
4694                    SAMPLE_NUMBER_1
4695 15bb 3f 81              CLR  SAMPLE_NUMBER
4696 15bd 3f 82              CLR  SAMPLE_NUMBER+1
4697 15bf 3c 82              INC  SAMPLE_NUMBER+1
4698 15c1 81                 RTS
4699                    *
4700                    *////////////////////////////////////////////////////////////////
4701                    *
4702                    *    clears number of samples taken
4703                    *
4704                    TAKEN_0_SAMPLES
4705 15c2 3f 8e              CLR  SAMPLES_TAKEN
4706 15c4 3f 8f              CLR  SAMPLES_TAKEN+1
4707 15c6 81                 RTS
4708                    *
4709                    *////////////////////////////////////////////////////////////////
4710                    *
4711                    *    clears samples to be taken
4712                    *
4713                    TAKE_0_SAMPLES
4714 15c7 3f 7f              CLR  TAKE_A_SAMPLE
4715 15c9 3f 80              CLR  TAKE_A_SAMPLE+1    *clear samples to be taken
4716 15cb 81                 RTS
4717                    *
4718                    *////////////////////////////////////////////////////////////////
```

```
4719                      *
4720                      *    displays sample number and number of samples on lcd
4721                      *
4722                      SAMPLE_DISPLAY
4723 15cc cd 16 49            JSR  NO_RUN_DISPLAY      ***** bsr
4724 15cf 26 25               BNE  SAMPLE_DISP_X       *branch if review pgm or display fault
4725 15d1 cd 02 d6            JSR  CLEAR_LCD
4726 15d4 5f                  CLRX
4727                      NEXT_MSG_SAMPLE
4728 15d5 d6 17 e3            LDA  MSG_SAMPLE,X
4729 15d8 cd 03 54            JSR  DISPLAY             *display sample message
4730 15db 26 f8               BNE  NEXT_MSG_SAMPLE
4731 15dd a6 81               LDA  #SAMPLE_NUMBER
4732 15df cd 15 f7            JSR  DISPLAY_SAMPLE      *display sample number
4733 15e2 5f                  CLRX
4734                      NEXT_MSG_OF
4735 15e3 d6 17 e7            LDA  MSG_OF,X
4736 15e6 cd 03 54            JSR  DISPLAY             *display of message
4737 15e9 26 f8               BNE  NEXT_MSG_OF
4738 15eb a6 04               LDA  #4+LEADING_0_NO     ***** three digits in number of samples
4739 15ed b7 ae               STA  PGM_LENGTH
4740 15ef a6 5a               LDA  #NUM_OF_SAMPLES
4741 15f1 b7 ac               STA  PGM_STORAGE
4742 15f3 cd 03 66            JSR  NUMBER_CURRENT      *display number of samples
4743                      SAMPLE_DISP_X
4744 15f6 81                  RTS
4745                      *
4746                      *///////////////////////////////////////////////////////////////
4747                      *
4748                      *    displays sample number
4749                      *    on lcd at location in accumulator
4750                      *
4751                      DISPLAY_SAMPLE
4752 15f7 ae 04               LDX  #4+LEADING_0_NO
4753 15f9 bf ae               STX  PGM_LENGTH
4754 15fb ae 08               LDX  #8
4755 15fd cd 03 5d            JSR  DISPLAY_NUMBER      *display sample number
4756 1600 81                  RTS
4757                      *
4758                      *///////////////////////////////////////////////////////////////
4759                      *
4760                      *    displays flow to next sample
4761                      *
4762                      FLOW_DISPLAY
4763 1601 cd 16 49            JSR  NO_RUN_DISPLAY      ***** bsr
4764 1604 26 0b               BNE  FLOW_DISPLAY_X      *branch if review pgm or display fault
4765 1606 a6 04               LDA  #4+LEADING_0_NO
4766 1608 b7 ae               STA  PGM_LENGTH
4767 160a ae 43               LDX  #LCD_LINE_2+3
4768 160c a6 8a               LDA  #FLOW_TO_NEXT
4769 160e cd 03 5d            JSR  DISPLAY_NUMBER      *display flow to next
4770                      FLOW_DISPLAY_X
4771 1611 81                  RTS
4772                      *
```

```
4773              */////////////////////////////////////////////////////////////////////
4774              *
4775              *    display sample number, number of samples, pumping
4776              *    and sample volume on lcd
4777              *
4778              PUMPING_DISPLAY
4779 1612 0a c0 09    BRSET   MANUAL_BIT,MANUAL_BYTE,NO_SAMPLE_DISP
4780              *                              *branch if grab or calibrate sample
4781 1615 ad 32       BSR  NO_RUN_DISPLAY
4782 1617 26 2f       BNE  PUMPING_DISP_X     *branch if review pgm or display fault
4783 1619 cd 15 cc    JSR  SAMPLE_DISPLAY     *display sample number
4784 161c 20 11       BRA  PUMPING_VOLUME
4785              NO_SAMPLE_DISP
4786 161e cd 02 d6    JSR  CLEAR_LCD
4787 1621 a6 03       LDA  #3
4788 1623 cd 02 da    JSR  LCD_CURSOR         *position cursor
4789 1626 5f          CLRX
4790              NEXT_MSG_MANUAL
4791 1627 d6 18 1a    LDA  MSG_MANUAL,X
4792 162a cd 03 54    JSR  DISPLAY            *display pumping ml message
4793 162d 26 f8       BNE  NEXT_MSG_MANUAL
4794              PUMPING_VOLUME
4795 162f a6 43       LDA  #LCD_LINE_2+3
4796 1631 cd 02 da    JSR  LCD_CURSOR         *position cursor
4797 1634 5f          CLRX
4798              NEXT_MSG_PUMPING
4799 1635 d6 18 0c    LDA  MSG_PUMPING,X
4800 1638 cd 03 54    JSR  DISPLAY            *display pumping ml message
4801 163b 26 f8       BNE  NEXT_MSG_PUMPING
4802 163d a6 03       LDA  #3+LEADING_0_NO
4803 163f b7 ae       STA  PGM_LENGTH
4804 1641 ae 4b       LDX  #LCD_LINE_2+11
4805 1643 a6 57       LDA  #NOMINAL_VOLUME
4806 1645 cd 03 5d    JSR  DISPLAY_NUMBER     *display nominal volume
4807              PUMPING_DISP_X
4808 1648 81          RTS
4809              *
4810              */////////////////////////////////////////////////////////////////////
4811              *
4812              *    checks if reviewing pgm or displaying faults or manual sampling
4813              *
4814              NO_RUN_DISPLAY
4815 1649 b6 c1       LDA  YES_NO_BYTE
4816 164b a4 18       AND  #YES_NO_B+READY_B
4817 164d ba c6       ORA  REVIEW_BRANCH
4818 164f 81          RTS
4819              *
4820              */////////////////////////////////////////////////////////////////////
4821              *
4822              *    clear pump run parameters
4823              *
4824              RUN_CLEAR
4825 1650 19 01       BCLR PUMP_FORWARD,PUMP_FORWARD_P
4826 1652 17 01       BCLR PUMP_REVERSE,PUMP_REVERSE_P
```

```
4827                    *                     *turn off pump in either direction
4828 1654 17 02             BCLR PUMP_LIGHT,PUMP_LIGHT_P
4829                    *                     *turn off pump running light/relay
4830 1656 1b 01             BCLR DIST_RIGHT,DIST_RIGHT_P  *turn off diverter right
4831 1658 1d 01             BCLR DIST_LEFT,DIST_LEFT_P    *turn off diverter left
4832 165a 3f c3             CLR  DIST_TIMER
4833 165c 3f 83             CLR  PUMP_CYCLE
4834 165e 1b c0             BCLR MANUAL_BIT,MANUAL_BYTE
4835 1660 19 c0             BCLR SAMPLING_BIT,SAMPLING_BYTE
4836 1662 3f c6             CLR  REVIEW_BRANCH
4837 1664 3f 86             CLR  SAMPLE_PAUSE
4838 1666 81                RTS
4839                    *
4840                    *///////////////////////////////////////////////////////////////
4841                    *
4842                    *   sets sample flags
4843                    *
4844                    C_OR_S_SAMPLE
4845 1667 18 c0             BSET SAMPLING_BIT,SAMPLING_BYTE
4846                    *                     *set sampling bit
4847                    CONT_SAMPLE
4848                    SPLIT_SAMPLE
4849 1669 ad a7             BSR  PUMPING_DISPLAY
4850                    SPLIT_SAMPLE_2
4851 166b cd 08 40          JSR  ENFORCE_BOTTLE    *position distributor
4852 166e cd 18 2c          JSR  ERROR_BEEP        *beep before pumping
4853 1671 cd 05 ec          JSR  EVENT_MARK_ON     *turn event mark output on
4854 1674 a6 01             LDA  #PRE_PURGE_HIGH
4855 1676 b7 84             STA  PUMP_COUNT        *store prepurge pump count
4856 1678 a6 00             LDA  #PRE_PURGE_LOW
4857 167a b7 85             STA  PUMP_COUNT+1
4858 167c 16 01             BSET PUMP_REVERSE,PUMP_REVERSE_P
4859                    *                     *turn on pump in reverse direction
4860 167e 00 7b 02          BRSET    0,PUMP_LIGHT_MODE,LIGHT_FWD_ONLY
4861                    *                     *branch if pump light on for fwd pmp cycles only
4862 1681 16 02             BSET PUMP_LIGHT,PUMP_LIGHT_P
4863                    *                     *turn on pump running light/relay
4864                    LIGHT_FWD_ONLY
4865 1683 a6 01             LDA  #1
4866 1685 cd 17 2a          JSR  PUMPING           *pump prepurge cycle
4867 1688 a6 08             LDA  #SAMPLE_PAUSE_1
4868 168a cd 17 9b          JSR  PUMPING_PAUSE
4869 168d 0a c0 11          BRSET    MANUAL_BIT,MANUAL_BYTE,PUMP_NOMINAL
4870                    *                     *branch if separate bottle manual sample
4871 1690 02 8d 04          BRSET    1,SAMPLE_BOTTLE,RIGHT_IN_USE
4872                    *                     *branch if using right bottle
4873 1693 11 c0             BCLR READY_LEFT,READY_LEFT_B      *clear left bottle ready
4874 1695 20 05             BRA  INC_SAMPLE
4875                    RIGHT_IN_USE
4876 1697 13 c0             BCLR READY_RIGHT,READY_RIGHT_B    *clear right bottle ready
4877 1699 00 54 05          BRSET    0,SAMPLER_MODE,PUMP_NOMINAL
4878                    *                     *branch if split sampling
4879                    INC_SAMPLE
4880 169c a6 8e             LDA  #SAMPLES_TAKEN
```

```
4881 169e cd 1a 87          JSR   BCD_INCREMENT_2    #increment samples taken
4882                  PUMP_NOMINAL
4883 16a1 a6 84             LDA   #PUMP_COUNT
4884 16a3 ae 5c             LDX   #NOMINAL_COUNT
4885 16a5 cd 19 fc          JSR   TRANSFER_2         #load nominal count into pump count
4886 16a8 18 01             BSET  PUMP_FORWARD,PUMP_FORWARD_P
4887                  *                                #turn on pump in forward direction
4888 16aa 02 7b 02          BRSET   1,PUMP_LIGHT_MODE,PUMP_FILL_CYCLE
4889                  *                                #branch if pump light not on for fwd pump cycles only
4890 16ad 16 02             BSET  PUMP_LIGHT,PUMP_LIGHT_P
4891                  *                                #turn on pump running light/relay
4892                  PUMP_FILL_CYCLE
4893 16af a6 02             LDA   #2
4894 16b1 cd 17 2a          JSR   PUMPING            #pump nominal volume
4895 16b4 a6 08             LDA   #SAMPLE_PAUSE_2
4896 16b6 cd 17 9b          JSR   PUMPING_PAUSE
4897 16b9 a6 03             LDA   #POST_PURGE_HIGH
4898 16bb b7 84             STA   PUMP_COUNT         #store postpurge pump count
4899 16bd a6 00             LDA   #POST_PURGE_LOW
4900 16bf b7 85             STA   PUMP_COUNT+1
4901 16c1 16 01             BSET  PUMP_REVERSE,PUMP_REVERSE_P
4902                  *                                #turn on pump in reverse direction
4903 16c3 03 7b 02          BRCLR   1,PUMP_LIGHT_MODE,PUMP_POSTPURGE
4904                  *                                #branch if pump light not on for rev pump cycles only
4905 16c6 16 02             BSET  PUMP_LIGHT,PUMP_LIGHT_P
4906                  *                                #turn on pump running light/relay
4907                  PUMP_POSTPURGE
4908 16c8 a6 03             LDA   #3
4909 16ca cd 17 2a          JSR   PUMPING            #pump postpurge cycle
4910 16cd a6 08             LDA   #SAMPLE_PAUSE_3
4911 16cf cd 17 9b          JSR   PUMPING_PAUSE
4912 16d2 17 02             BCLR  PUMP_LIGHT,PUMP_LIGHT_P
4913                  *                                #turn off pump running light/relay
4914 16d4 3f 83             CLR   PUMP_CYCLE
4915 16d6 0a c0 4d          BRSET   MANUAL_BIT,MANUAL_BYTE,BOTTLE_SWITCH_M
4916                  *                                #branch if separate bottle manual sample
4917 16d9 01 54 19          BRCLR   0,SAMPLER_MODE,NEXT_CONTINUOUS
4918                  *                                #branch if continuous sampling
4919 16dc 02 8d 0c          BRSET   1,SAMPLE_BOTTLE,SPLIT_RIGHT
4920                  *                                #branch if on right bottle
4921 16df cd 14 9c          JSR   FULL_CHECK
4922 16e2 26 02             BNE   LEFT_NOT_FULL      #branch if not full
4923 16e4 14 c0             BSET  LEFT_FULL,LEFT_FULL_B
4924                  *                                #set left bottle full flag
4925                  LEFT_NOT_FULL
4926 16e6 cd 08 39          JSR   BOTTLE_CHANGE
4927 16e9 20 80             BRA   SPLIT_SAMPLE_2
4928                  SPLIT_RIGHT
4929 16eb cd 14 9c          JSR   FULL_CHECK
4930 16ee 26 30             BNE   BOTTLE_SWITCH_W    #branch if not full
4931 16f0 16 c0             BSET  RIGHT_FULL,RIGHT_FULL_B
4932                  *                                #set right bottle full flag
4933 16f2 cc 13 d8          JMP   FULL_SPLIT
4934                  NEXT_CONTINUOUS
```

```
4935 16f5 cd 14 9c          JSR  FULL_CHECK
4936 16f8 26 29             BNE  SAMPLE_EXIT      *branch if not full
4937 16fa 02 8d 04          BRSET   1,SAMPLE_BOTTLE,CONT_RIGHT
4938                    *                          *branch if right bottle
4939 16fd 14 c0             BSET LEFT_FULL,LEFT_FULL_B
4940                    *                          *set left bottle full flag
4941 16ff 20 02             BRA  CONT_SWITCH
4942                    CONT_RIGHT
4943 1701 16 c0             BSET RIGHT_FULL,RIGHT_FULL_B
4944                    *                          *set right bottle full flag
4945                    CONT_SWITCH
4946 1703 cd 13 c8          JSR  OTHER_READY
4947 1706 cd 15 c2          JSR  TAKEN_0_SAMPLES  *clear number of samples taken
4948 1709 cd 15 bb          JSR  SAMPLE_NUMBER_1  *set sample number to one
4949 170c 19 c0             BCLR SAMPLING_BIT,SAMPLING_BYTE
4950 170e cd 08 39          JSR  BOTTLE_CHANGE    *change bottles
4951 1711 00 53 03          BRSET   0,SAMPLER_PACE,NEXT_FLOW
4952 1714 cc 13 46          JMP  NEW_TP
4953                    NEXT_FLOW
4954 1717 00 55 03          BRSET   0,SWITCH_MODE,NEXT_FP_SWITCH
4955                    *                          *branch if flow switched
4956 171a cc 13 6f          JMP  NEW_FP
4957                    NEXT_FP_SWITCH
4958 171d cc 13 7b          JMP  NEXT_FP
4959                    BOTTLE_SWITCH_W
4960 1720 cd 08 39          JSR  BOTTLE_CHANGE
4961                    SAMPLE_EXIT
4962 1723 19 c0             BCLR SAMPLING_BIT,SAMPLING_BYTE
4963                    BOTTLE_SWITCH_X
4964 1725 81                RTS
4965                    BOTTLE_SWITCH_M
4966 1726 1b c0             BCLR MANUAL_BIT,MANUAL_BYTE
4967                    *                          *clear clear bottle number flag
4968 1728 20 f9             BRA  SAMPLE_EXIT
4969                    *
4970                    *////////////////////////////////////////////////////////////
4971                    *
4972                    *   during pump cycles, monitors pump volume pin
4973                    *   and decrements pump counts
4974                    *
4975                    PUMPING
4976 172a b7 83             STA  PUMP_CYCLE
4977 172c a6 ff             LDA  #PUMP_JAM_MAX
4978 172e b7 c7             STA  PUMP_JAM         *initialize pump jam count
4979                    PUMP_PERIODIC
4980 1730 cd 05 62          JSR  SCAN_N_ENFORCE   *periodic scan, check distributor position
4981 1733 cd 17 48          JSR  NEXT_PUMP
4982 1736 ae 84             LDX  #PUMP_COUNT
4983 1738 cd 19 bd          JSR  COMPARE_TO_0_2
4984 173b 26 f3             BNE  PUMP_PERIODIC    *branch if pump count not zero
4985 173d 19 01             BCLR PUMP_FORWARD,PUMP_FORWARD_P
4986 173f 17 01             BCLR PUMP_REVERSE,PUMP_REVERSE_P
4987                    *                          *turn off pump in either direction
4988 1741 3d 7b             TST  PUMP_LIGHT_MODE  *branch if pump light on
```

```
4989 1743 27 02            BEQ   PUMP_RETURN      *for both fwd and rev pump cycles
4990 1745 17 02            BCLR  PUMP_LIGHT,PUMP_LIGHT_P
4991                   *                           *turn off pump running light/relay
4992                   PUMP_RETURN
4993 1747 81               RTS
4994                   *
4995                   NEXT_PUMP
4996 1748 a6 f7            LDA   #PUMP_VOLUME     ***** should this be E7?
4997 174a b7 00            STA   DATA_BUS_P       *select pump volume input
4998 174c a6 ff            LDA   #DATA_BUS_OUT
4999 174e b7 04            STA   DATA_BUS_PD      *set data bus as output
5000 1750 04 c1 17         BRSET VOLUME_PIN,VOLUME_BYTE,VOLUME_ON
5001                   *                           *branch if volume pin previously on
5002 1753 02 03 1f         BRSET MUX,MUX_P,VOLUME_JAM_EXIT
5003                   *                           *branch if volume pin still off
5004 1756 14 c1            BSET  VOLUME_PIN,VOLUME_BYTE
5005                   *                           *set volume pin to previously on
5006 1758 a6 ff            LDA   #PUMP_JAM_MAX
5007 175a b7 c7            STA   PUMP_JAM         *reinitialize pump jam count
5008 175c ad 26            BSR   TUBING_WEAR_CHK  *increment pump tubing wear accumulation
5009 175e 09 c0 08         BRCLR SAMPLING_BIT,SAMPLING_BYTE,PUMP_EXIT
5010                   *                           *branch if not sampling into bottle
5011 1761 cd 17 ab         JSR   RUN_BOTTLE_CHK   *check that bottle still present
5012 1764 a6 84            LDA   #PUMP_COUNT
5013 1766 cd 1a 9d         JSR   BCD_DECREMENT_2  *decrement pump count
5014                   PUMP_EXIT
5015 1769 81               RTS
5016                   VOLUME_ON
5017 176a 03 03 08         BRCLR MUX,MUX_P,VOLUME_JAM_EXIT
5018                   *                           *branch if volume pin still on
5019 176d 15 c1            BCLR  VOLUME_PIN,VOLUME_BYTE
5020                   *                           *set volume pin to previously off
5021 176f a6 ff            LDA   #PUMP_JAM_MAX
5022 1771 b7 c7            STA   PUMP_JAM         *reinitialize pump jam count
5023 1773 20 f4            BRA   PUMP_EXIT
5024                   VOLUME_JAM_EXIT
5025 1775 3d c7            TST   PUMP_JAM
5026 1777 26 f0            BNE   PUMP_EXIT        *branch if pump jam not expired
5027 1779 ae 02            LDX   #B_PUMP_JAM
5028 177b cd 06 1b         JSR   NEW_FAULT        *set pump jam fault
5029 177e cd 16 50         JSR   RUN_CLEAR        *clear run parameters
5030 1781 cc 06 a1         JMP   KEY_ON           *return to standby
5031                   *
5032                   *///////////////////////////////////////////////////////////////
5033                   *
5034                   *   increment pump tubing wear accumulation
5035                   *
5036                   TUBING_WEAR_CHK
5037 1784 08 90 13         BRSET B_TUBING,FAULT_BYTE,TUBING_WEAR_X
5038                   *                           *branch if tubing fault already set
5039 1787 a6 98            LDA   #TUBING_WEAR
5040 1789 cd 1a 83         JSR   BCD_INCREMENT_4  *increment pump tubing wear accumulation
5041 178c ae 98            LDX   #TUBING_WEAR
5042 178e a6 71            LDA   #WARN_COUNT
```

```
5043 1790 cd 19 ce          JSR    COMPARE_4           *compare to max
5044 1793 25 05             BLO    TUBING_WEAR_X       *branch if not equal
5045 1795 ae 04             LDX    #B_TUBING
5046 1797 cd 06 1b          JSR    NEW_FAULT           *set tubing worn fault
5047                    TUBING_WEAR_X
5048 179a 81                RTS
5049                    *
5050                    *///////////////////////////////////////////////////////////////
5051                    *
5052                    *   during pump cycles, waits for intercycle delays
5053                    *
5054                    PUMPING_PAUSE
5055 179b b7 86             STA    SAMPLE_PAUSE
5056                    NEXT_PAUSE
5057 179d 09 c0 03          BRCLR  SAMPLING_BIT,SAMPLING_BYTE,PAUSE_PERIODIC
5058                    *                               *branch if not sampling into bottle
5059 17a0 cd 17 ab          JSR    RUN_BOTTLE_CHK      *check that bottle still present
5060                    PAUSE_PERIODIC
5061 17a3 cd 05 62          JSR    SCAN_W_ENFORCE      *periodic scan, check distributor position
5062 17a6 3a 86             DEC    SAMPLE_PAUSE
5063 17a8 26 f3             BNE    NEXT_PAUSE
5064 17aa 81                RTS
5065                    *
5066                    *///////////////////////////////////////////////////////////////
5067                    *
5068                    *   checks that bottle still present during run cycles
5069                    *
5070                    RUN_BOTTLE_CHK
5071 17ab 0a c0 0c          BRSET  MANUAL_BIT,MANUAL_BYTE,RUN_BOTTLE_X
5072                    *                               *branch if separate bottle manual sample
5073 17ae 01 8d 06          BRCLR  0,SAMPLE_BOTTLE,RUN_CHECK_RIGHT
5074                    *                               *branch if right bottle in use
5075 17b1 0e 03 06          BRSET  BOTTLE_LEFT,BOTTLE_LEFT_P,RUN_BOTTLE_X
5076                    *                               *branch if left bottle not missing
5077                    BOTTLE_ABORT
5078 17b4 cc 06 a1          JMP    KEY_ON
5079                    RUN_CHECK_RIGHT
5080 17b7 0b 03 fa          BRCLR  BOTTLE_RIGHT,BOTTLE_RIGHT_P,BOTTLE_ABORT
5081                    *                               *branch if right bottle missing
5082                    RUN_BOTTLE_X
5083 17ba 81                RTS
5084                    *
5085                    *///////////////////////////////////////////////////////////////
5086                    *
5087                    *   monitors presence of bottles
5088                    *   sets ready flag if bottle removed
5089                    *   controls left and right bottle full lights
5090                    *
5091                    BOTTLE_MONITOR
5092 17bb 0e 03 04          BRSET  BOTTLE_LEFT,BOTTLE_LEFT_P,RIGHT_MONITOR
5093                    *                               *branch if left bottle not missing
5094 17be 10 c0             BSET   READY_LEFT,READY_LEFT_B
5095                    *                               *set left bottle ready flag
5096 17c0 15 c0             BCLR   LEFT_FULL,LEFT_FULL_B
```

```
5097                         *               *clear left bottle full flag
5098                 RIGHT_MONITOR
5099 17c2 0a 03 04       BRSET    BOTTLE_RIGHT,BOTTLE_RIGHT_P,FULL_LIGHTS
5100                     *               *branch if right bottle not missing
5101 17c5 12 c0          BSET READY_RIGHT,READY_RIGHT_B
5102                     *               *set right bottle ready flag
5103 17c7 17 c0          BCLR RIGHT_FULL,RIGHT_FULL_B
5104                     *               *clear right bottle full flag
5105                 FULL_LIGHTS
5106 17c9 05 c0 04       BRCLR    LEFT_FULL,LEFT_FULL_B,LEFT_LIGHT_OFF
5107                     *               *branch if left bottle not full
5108 17cc 10 02          BSET LEFT_LIGHT,LEFT_LIGHT_P      *turn on left full light
5109 17ce 20 02          BRA  RIGHT_LIGHTS
5110                 LEFT_LIGHT_OFF
5111 17d0 11 02          BCLR LEFT_LIGHT,LEFT_LIGHT_P      *turn off left full light
5112                 RIGHT_LIGHTS
5113 17d2 07 c0 04       BRCLR    RIGHT_FULL,RIGHT_FULL_B,RIGHT_LIGHT_OFF
5114                     *               *branch if right bottle not full
5115 17d5 1e 01          BSET RIGHT_LIGHT,RIGHT_LIGHT_P    *turn on right full light
5116 17d7 20 02          BRA  MONITOR_EXIT
5117                 RIGHT_LIGHT_OFF
5118 17d9 1f 01          BCLR RIGHT_LIGHT,RIGHT_LIGHT_P    *turn off right full light
5119                 MONITOR_EXIT
5120 17db 81             RTS
5121                     *
5122                 *///////////////////////////////////////////////////////////
5123                     *
5124                 MSG_DELAY
5125 17dc 44 45 4c 41 59 20   FCC  'DELAY '
5126 17e2 df              FCB  END_OF_MESSAGE
5127                     *
5128                 MSG_SAMPLE
5129 17e3 20              FCC  ' '
5130 17e4 ca              FCB  V_SAMPLE
5131 17e5 20              FCC  ' '
5132 17e6 df              FCB  END_OF_MESSAGE
5133                     *
5134                 MSG_OF
5135 17e7 bc              FCB  V_OF
5136 17e8 df              FCB  END_OF_MESSAGE
5137                     *
5138                 MSG_AT
5139 17e9 41 54 20        FCC  'AT '
5140 17ec df              FCB  END_OF_MESSAGE
5141                     *
5142                 MSG_FLOW
5143 17ed 49 4e 20 20 20 20   FCC  'IN     '
     20 20
5144 17f5 af              FCB  V_FLOW
5145 17f6 20              FCC  ' '
5146 17f7 c3              FCB  V_PULSES
5147 17f8 df              FCB  END_OF_MESSAGE
5148                     *
5149                 MSG_FULL
```

```
5150 17f9 20 20 20 46 55 4c       FCC   ' FULL    '
     4c 20 20 20 20 20
     20
5151 1806 cb                      FCB   V_SAMPLES
5152 1807 df                      FCB   END_OF_MESSAGE
5153                          *
5154                          MSG_INHIBIT
5155 1808 b3                      FCB   V_INHIBIT
5156 1809 45 44                   FCC   'ED'
5157 180b df                      FCB   END_OF_MESSAGE
5158                          *
5159                          MSG_PUMPING
5160 180c 50 55 4d 50 49 4e       FCC   'PUMPING  '
     47 20 20 20 20 20
5161 1818 ba                      FCB   V_ml_
5162 1819 df                      FCB   END_OF_MESSAGE
5163                          *
5164                          MSG_MANUAL
5165 181a b8                      FCB   V_MANUAL_
5166 181b ca                      FCB   V_SAMPLE
5167 181c df                      FCB   END_OF_MESSAGE
5168                          *
5169                          *   program sub
5170                          *
5171                          *   delays
5172                          ***** cannot neglect real time clock
5173                          ***** could use internal timer to perform delay decrement
5174                          ***** until real time clock interrupts functional
5175                          ***** or simply return
5176                          DELAY
5177 181d a6 02                   LDA   #DELAY_TIME
5178 181f b7 c5                   STA   DELAY_TIMER     *store delay time in timer
5179                          DELAY_AGAIN
5180                          ***** must save registers before entering scan no keypad
5181                          ***** must check that scan routines do not corrupt temp variables
5182 1821 cd 05 68                JSR   SCAN_NO_KEYPAD  *periodic scan without keypad
5183 1824 9a                      CLI
5184 1825 9d                      NOP                   *allow for interrupts
5185 1826 9b                      SEI
5186 1827 b6 c5                   LDA   DELAY_TIMER
5187 1829 26 f6                   BNE   DELAY_AGAIN     *branch if delay not finished
5188 182b 81                      RTS                   *otherwise, return
5189                          *
5190                          *   beeps five times
5191                          *
5192                          ERROR_BEEP
5193 182c ad 08                   BSR   BEEP
5194 182e ad 04                   BSR   DELAY_BEEP
5195 1830 ad 02                   BSR   DELAY_BEEP
5196 1832 ad 00                   BSR   DELAY_BEEP
5197                          DELAY_BEEP
5198 1834 ad e7                   BSR   DELAY
5199                          BEEP
5200 1836 14 02                   BSET  BUZZER,BUZZER_P
```

```
5201 1838 ad a3           BSR  DELAY
5202 183a 15 02           BCLR BUZZER,BUZZER_P
5203 183c 81              RTS
5204                  *
5205                  *   returns days per month in index register
5206                  *   given year in acc and month in index register
5207                  *
5208                  DAYS_PER_MONTH
5209 183d 5a              DECX
5210 183e de 1B 50        LDX  MONTH_DAYS,X
5211 1841 a3 28           CPX  #$28
5212 1843 26 0a           BNE  DAYS_PER_EXIT
5213 1845 cd 1a c6        JSR  CONVERT_TO_HEX    *convert year to hex, destroys x
5214 1848 ae 28           LDX  #$28              *restore x
5215 184a a4 03           AND  #$03
5216 184c 26 01           BNE  DAYS_PER_EXIT
5217 184e 5c              INCX
5218                  DAYS_PER_EXIT
5219 184f 81              RTS
5220                  *
5221                  MONTH_DAYS
5222 1850 31              FCB  $31
5223 1851 28              FCB  $28
5224 1852 31              FCB  $31
5225 1853 30              FCB  $30
5226 1854 31              FCB  $31
5227 1855 30              FCB  $30
5228 1856 31              FCB  $31
5229 1857 31              FCB  $31
5230 1858 30              FCB  $30
5231 1859 00              FCB  $00
5232 185a 00              FCB  $00
5233 185b 00              FCB  $00
5234 185c 00              FCB  $00
5235 185d 00              FCB  $00
5236 185e 00              FCB  $00
5237 185f 31              FCB  $31
5238 1860 30              FCB  $30
5239 1861 31              FCB  $31
5240                  *
5241                  *   scans matrix keypad input
5242                  *   ignores multiple key presses
5243                  *   must see key pressed a number of times
5244                  *   before it acknowledges it
5245                  *   returns key number in acc,
5246                  *   no key if none or key mask bit set
5247                  *
5248                  SCAN_AND_DECODE
5249 1862 9a              CLI                    ***** this should be in scan no keypad
5250 1863 9d              NOP                    *allow interrupts
5251 1864 9b              SEI
5252 1865 b6 b3           LDA  KEY_CODE
5253 1867 b7 b6           STA  TEMP              *save previous key code pressed
5254 1869 3f b7           CLR  TEMP2             *holds count of keys pressed
```

```
5255 186b ae 03              LDX   #$03
5256 186d a6 e0              LDA   #$E0
5257 186f b7 00              STA   DATA_BUS_P       *set all columns high except one
5258 1871 a6 ff              LDA   #DATA_BUS_OUT
5259 1873 b7 04              STA   DATA_BUS_PD      *set data bus as output
5260              NEXT_COLUMN
5261 1875 a6 05              LDA   #5               *row counter
5262              NEXT_ROW
5263 1877 02 03 10           BRSET MUX,MUX_P,NOT_PRESSED
5264                   *                             *branch if not pressed
5265 187a 3c b7              INC   TEMP2            *otherwise, increment count
5266 187c bf b3              STX   KEY_CODE         *combine acc and x to form key code
5267 187e 38 b3              LSL   KEY_CODE
5268 1880 38 b3              LSL   KEY_CODE
5269 1882 38 b3              LSL   KEY_CODE         *column in bits 3 and 4
5270 1884 ba b3              ORA   KEY_CODE         *append row in bits 0, 1, and 2
5271 1886 b7 b3              STA   KEY_CODE
5272 1888 a4 07              AND   #$07             *restore acc to column number
5273              NOT_PRESSED
5274 188a 3c 00              INC   DATA_BUS_P       *move to next row
5275 188c 4a                 DECA
5276 188d 2a e8              BPL   NEXT_ROW         *branch if more rows
5277 188f 3c 00              INC   DATA_BUS_P       *set high bit of low nibble
5278 1891 3c 00              INC   DATA_BUS_P
5279 1893 38 00              LSL   DATA_BUS_P
5280 1895 5a                 DECX                   *go on to next column
5281 1896 2a dd              BPL   NEXT_COLUMN
5282 1898 3a b7              DEC   TEMP2
5283 189a 26 70              BNE   ILLEGAL          *branch if not exactly one key pressed
5284                   *
5285 189c b6 b3              LDA   KEY_CODE
5286 189e b1 b6              CMP   TEMP
5287 18a0 26 64              BNE   NEW_KEY          *branch if new key
5288 18a2 b6 b4              LDA   KEY_COUNT
5289 18a4 a1 03              CMP   #KEY_COUNT_MAX
5290 18a6 27 68              BEQ   SCAN_EXIT        *branch if count already at max
5291 18a8 3c b4              INC   KEY_COUNT
5292 18aa b6 b4              LDA   KEY_COUNT
5293 18ac a1 03              CMP   #KEY_COUNT_MAX
5294 18ae 26 60              BNE   SCAN_EXIT        *branch if count not max now
5295                   *
5296 18b0 b6 b3              LDA   KEY_CODE
5297 18b2 09 c1 0c           BRCLR YES_NO_BIT,YES_NO_BYTE,CHECK_READY
5298                   *                             *branch if not flashing yes no
5299 18b5 a1 1d              CMP   #CODE_ENTER_PGM
5300 18b7 27 66              BEQ   YES_NO_ENTER     *branch if enter pgm
5301 18b9 a1 1a              CMP   #CODE_LEFT
5302 18bb 27 54              BEQ   YES_NO_ARROW     *branch if left arrow
5303 18bd a1 1c              CMP   #CODE_RIGHT
5304 18bf 27 50              BEQ   YES_NO_ARROW     *branch if right arrow
5305              CHECK_READY
5306 18c1 07 c1 07           BRCLR READY_BIT,READY_BYTE,CHECK_MASK
5307                   *                             *branch if not ready for manual sample
5308 18c4 a1 11              CMP   #CODE_MANUAL
```

```
5309 18c6 26 03         BNE   CHECK_MASK              *branch if not manual sample key
5310 18c8 cc 07 48      JMP   TAKE_GRAB               *otherwise, take grab sample
5311                *
5312                CHECK_MASK
5313 18cb b6 b3         LDA   KEY_CODE
5314 18cd 44            LSRA
5315 18ce 44            LSRA
5316 18cf 44            LSRA
5317 18d0 a4 03         AND   #$03                    *clear all but column bits
5318 18d2 ba a0         ORA   KEY_MASK                *append current key mask number
5319 18d4 97            TAX
5320 18d5 de 19 9b      LDX   KEYPAD_MASKS,X          *load current mask for this column
5321 18d8 b6 b3         LDA   KEY_CODE
5322 18da a4 07         AND   #$07                    *clear all but row bits
5323                MASK_CHECK
5324 18dc 54            LSRX                          *rotate to mask bit for this key
5325 18dd 4a            DECA
5326 18de 2a fc         BPL   MASK_CHECK              *branch if not bit for this key
5327 18e0 24 2e         BCC   SCAN_EXIT               *branch if mask bit not set
5328 18e2 cd 1B 36      JSR   BEEP                    *otherwise, beep
5329 18e5 3f b1         CLR   FLASH
5330 18e7 a6 0c         LDA   #$0C                    *display control
5331 18e9 cd 02 dc      JSR   LCD_CMD_WRITE           *display on, cursor off, blink off
5332 18ec 09 c1 05      BRCLR YES_NO_BIT,YES_NO_BYTE,NO_CLR_YES_NO
5333 18ef 19 c1         BCLR  YES_NO_BIT,YES_NO_BYTE
5334                *                                 *otherwise, clear yes no flashing flag
5335 18f1 cd 1d 2b      JSR   RESTORE_DISPLAY         *and restore display
5336                NO_CLR_YES_NO
5337 18f4 07 c1 05      BRCLR READY_BIT,READY_BYTE,NO_CLR_READY
5338 18f7 17 c1         BCLR  READY_BIT,READY_BYTE
5339 18f9 cd 1d 2b      JSR   RESTORE_DISPLAY
5340                NO_CLR_READY
5341 18fc b6 b3         LDA   KEY_CODE                *and return with code in acc
5342 18fe 48            ASLA
5343 18ff bb b3         ADD   KEY_CODE                *multiply key code by 3
5344 1901 97            TAX
5345 1902 4f            CLRA                          *clear acc for numeric key routine
5346 1903 dc 19 3b      JMP   KEY_ROUTINES,X          *branch to key routine ***** could be bra
5347                *
5348                NEW_KEY
5349 1906 a6 01         LDA   #1
5350 1908 b7 b4         STA   KEY_COUNT
5351 190a 20 04         BRA   SCAN_EXIT
5352                ILLEGAL
5353 190c 1e b3         BSET  7,KEY_CODE              *set key code to invalid key
5354 190e 3f b4         CLR   KEY_COUNT               *clear press count
5355                SCAN_EXIT
5356 1910 81            RTS
5357                *
5358                YES_NO_ARROW
5359 1911 cd 1B 36      JSR   BEEP
5360 1914 cd 09 f6      JSR   FLASH_ON                *display previous choice
5361 1917 b6 a2         LDA   PGM_CHOICE
5362 1919 a8 01         EOR   #$01                    *toggle yes no choice
```

```
5363 191b b7 a2              STA  PGM_CHOICE
5364 191d 20 f1              BRA  SCAN_EXIT
5365                    YES_NO_ENTER
5366 191f 3f b1              CLR  FLASH              *clear flash
5367 1921 cd 18 36            JSR  BEEP
5368 1924 19 c1              BCLR YES_NO_BIT,YES_NO_BYTE
5369                    *                            *clear clearing all faults flag
5370 1926 3d c6              TST  REVIEW_BRANCH
5371 1928 27 0e              BEQ  SAMPLE_CHOICE      *branch if not clear all faults
5372 192a 00 a2 06           BRSET  0,PGM_CHOICE,CLEAR_FAULTS_NO
5373                    *                            *branch if no flashing
5374 192d b6 90              LDA  FAULT_BYTE
5375 192f a4 f0              AND  #FAULTS_W_O_TUBE   *clear all faults except pump tubing worn
5376 1931 b7 90              STA  FAULT_BYTE
5377                    CLEAR_FAULTS_NO
5378 1933 cd 1d 2b            JSR  RESTORE_DISPLAY
5379 1936 20 d8              BRA  SCAN_EXIT
5380                    SAMPLE_CHOICE
5381 1938 cc 07 53            JMP  SAMPLE_CHOSEN
5382                    *
5383                    ***** could this be handled better as self modifying code?
5384                    ***** acc would still need to be cleared
5385                    KEY_ROUTINES
5386 193b cc 06 9d            JMP  KEY_ON_OFF
5387 193e cc 13 34            JMP  KEY_START_PGM
5388 1941 cc 08 ac            JMP  KEY_7
5389 1944 cc 08 ab            JMP  KEY_8
5390 1947 cc 08 aa            JMP  KEY_9
5391 194a cc 1c 43            JMP  KEY_STATUS
5392 194d cc 19 10            JMP  SCAN_EXIT
5393 1950 cc 19 10            JMP  SCAN_EXIT
5394 1953 cc 06 5b            JMP  KEY_PUMP_REV
5395 1956 cc 12 e9            JMP  KEY_RESUME_PGM
5396 1959 cc 08 af            JMP  KEY_4
5397 195c cc 08 ae            JMP  KEY_5
5398 195f cc 08 ad            JMP  KEY_6
5399 1962 cc 08 e0            JMP  KEY_EXIT_PGM
5400 1965 cc 19 10            JMP  SCAN_EXIT
5401 1968 cc 19 10            JMP  SCAN_EXIT
5402 196b cc 06 47            JMP  KEY_PUMP_FWD
5403 196e cc 06 de            JMP  KEY_MANUAL
5404 1971 cc 08 b2            JMP  KEY_1
5405 1974 cc 08 b1            JMP  KEY_2
5406 1977 cc 08 b0            JMP  KEY_3
5407 197a cc 08 da            JMP  KEY_CLEAR_ENTRY
5408 197d cc 19 10            JMP  SCAN_EXIT
5409 1980 cc 19 10            JMP  SCAN_EXIT
5410 1983 cc 06 79            JMP  KEY_STOP
5411 1986 cc 08 15            JMP  KEY_NEXT_BOTTLE
5412 1989 cc 08 fd            JMP  KEY_LEFT_ARROW
5413 198c cc 08 b3            JMP  KEY_0
5414 198f cc 08 e3            JMP  KEY_RIGHT_ARROW
5415 1992 cc 09 20            JMP  KEY_ENTER_PGM
5416 1995 cc 19 10            JMP  SCAN_EXIT          ***** remove these two
```

```
5417 1998 cc 19 10            JMP   SCAN_EXIT        ##### key code max equ 1d
5418                      *
5419                      *   keypad masks
5420                      *   1 = enabled
5421                      *
5422                      KEYPAD_MASKS
5423 199b 01                  FCB   %0000001         *off
5424 199c 00                  FCB   %0000000
5425 199d 00                  FCB   %0000000
5426 199e 00                  FCB   %0000000
5427                      *
5428 199f 23                  FCB   %0100011         *standby, full
5429 19a0 03                  FCB   %0000011
5430 19a1 03                  FCB   %0000011
5431 19a2 23                  FCB   %0100011
5432                      *
5433 19a3 01                  FCB   %0000001         *pgm select
5434 19a4 20                  FCB   %0100000
5435 19a5 00                  FCB   %0000000
5436 19a6 34                  FCB   %0110100
5437                      *
5438 19a7 1d                  FCB   %0011101         *pgm enter
5439 19a8 3c                  FCB   %0111100
5440 19a9 3c                  FCB   %0111100
5441 19aa 3c                  FCB   %0111100
5442                      *
5443 19ab 21                  FCB   %0100001         *run
5444 19ac 00                  FCB   %0000000
5445 19ad 02                  FCB   %0000010
5446 19ae 01                  FCB   %0000001
5447                      *
5448 19af 01                  FCB   %0000001         *pgm manual
5449 19b0 20                  FCB   %0100000
5450 19b1 02                  FCB   %0000010
5451 19b2 00                  FCB   %0000000
5452                      *
5453 19b3 01                  FCB   %0000001         *pgm stop
5454 19b4 20                  FCB   %0100000
5455 19b5 00                  FCB   %0000000
5456 19b6 01                  FCB   %0000001
5457                      *
5458 19b7 01                  FCB   %0000001         *pgm none
5459 19b8 20                  FCB   %0100000
5460 19b9 00                  FCB   %0000000
5461 19ba 20                  FCB   %0100000
5462                      *
5463                      *   program math
5464                      *
5465                      *   multibyte compare to zero of bytes in ram
5466                      *   acc holds number of bytes, x holds high byte address
5467                      *   sets z flag if equal to zero, otherwise z flag is cleared
5468                      *   returns once a nonzero is found
5469                      *   falls out bottom if number of bytes goes to zero
5470                      *
```

```
5471                    COMPARE_TO_0_3
5472  19bb 3c cb            INC  MATH_COUNTER
5473                    COMPARE_TO_0_2
5474  19bd 3c cb            INC  MATH_COUNTER
5475  19bf 3c cb            INC  MATH_COUNTER
5476                    COMPARE_TO_ZERO
5477  19c1 7d              TST  ,X
5478  19c2 26 05           BNE  EXIT_COMPARE_0
5479  19c4 5c              INCX
5480  19c5 3a cb           DEC  MATH_COUNTER
5481  19c7 26 f8           BNE  COMPARE_TO_ZERO
5482                    EXIT_COMPARE_0
5483  19c9 ad 22           BSR  MATH_COUNTER_0
5484  19cb 81              RTS
5485                    *
5486                    *   multibyte compare of bytes in ram
5487                    *   enters at number of bytes to compare
5488                    *   or with number of bytes to compare in math counter
5489                    *   acc and x hold upper addresses
5490                    *   compares bytes at x to bytes at acc
5491                    *   returns once a mismatch is found
5492                    *   falls out bottom if number of bytes goes to zero
5493                    *
5494                    COMPARE_5
5495  19cc 3c cb           INC  MATH_COUNTER
5496                    COMPARE_4
5497  19ce 3c cb           INC  MATH_COUNTER
5498                    COMPARE_3
5499  19d0 3c cb           INC  MATH_COUNTER
5500                    COMPARE_2
5501  19d2 3c cb           INC  MATH_COUNTER
5502  19d4 3c cb           INC  MATH_COUNTER
5503                    COMPARE
5504  19d6 b7 b6           STA  TEMP
5505  19d8 bf b7           STX  TEMP2
5506                    NEXT_COMPARE
5507  19da f6              LDA  ,X
5508  19db be b6           LDX  TEMP
5509  19dd f1              CMP  ,X
5510  19de 26 0a           BNE  EXIT_COMPARE
5511  19e0 3c b6           INC  TEMP
5512  19e2 3c b7           INC  TEMP2
5513  19e4 be b7           LDX  TEMP2
5514  19e6 3a cb           DEC  MATH_COUNTER
5515  19e8 26 f0           BNE  NEXT_COMPARE
5516                    EXIT_COMPARE
5517  19ea ad 01           BSR  MATH_COUNTER_0
5518  19ec 81              RTS
5519                    *
5520                    *   clears math counter at end of math rountines
5521                    *
5522                    MATH_COUNTER_0
5523  19ed 17 cb           BCLR 3,MATH_COUNTER
5524  19ef 15 cb           BCLR 2,MATH_COUNTER
```

```
5525 19f1 13 cb          BCLR 1,MATH_COUNTER
5526 19f3 11 cb          BCLR 0,MATH_COUNTER
5527 19f5 81             RTS
5528                  *
5529                  *  multibyte transfer
5530                  *  enters at number of bytes to transfer
5531                  *  or with number of bytes to transfer in math counter
5532                  *  x holds upper source address
5533                  *  acc holds upper destination address
5534                  *
5535                  TRANSFER_5
5536 19f6 3c cb          INC  MATH_COUNTER
5537                  TRANSFER_4
5538 19f8 3c cb          INC  MATH_COUNTER
5539                  TRANSFER_3
5540 19fa 3c cb          INC  MATH_COUNTER
5541                  TRANSFER_2
5542 19fc 3c cb          INC  MATH_COUNTER
5543 19fe 3c cb          INC  MATH_COUNTER
5544                  TRANSFER
5545 1a00 b7 b6          STA  TEMP
5546 1a02 bf b7          STX  TEMP2
5547                  NEXT_TRANSFER
5548 1a04 f6             LDA  ,X
5549 1a05 be b6          LDX  TEMP
5550 1a07 f7             STA  ,X
5551 1a08 3c b6          INC  TEMP
5552 1a0a 3c b7          INC  TEMP2
5553 1a0c be b7          LDX  TEMP2
5554 1a0e 3a cb          DEC  MATH_COUNTER
5555 1a10 26 f2          BNE  NEXT_TRANSFER
5556 1a12 81             RTS
5557                  *
5558                  *  multibyte (2 bytes fixed for now) bcd division
5559                  *  x holds address of denominator
5560                  *  acc holds address of result
5561                  *
5562                  DIVIDE
5563 1a13 b7 bb          STA  TEMP6          *store address of result
5564 1a15 a6 6d          LDA  #BOTTLE_VOLUME  *load bottle volume into numerator
5565 1a17 b7 b9          STA  TEMP4
5566 1a19 bf ba          STX  TEMP5          *store address of denominator
5567 1a1b a6 bc          LDA  #TEMP7         *transfer denominator to comparison sum
5568 1a1d cd 19 fa       JSR  TRANSFER_3
5569 1a20 be bb          LDX  TEMP6
5570 1a22 7f             CLR  ,X
5571 1a23 5c             INCX
5572 1a24 7f             CLR  ,X
5573 1a25 5c             INCX
5574 1a26 7f             CLR  ,X             *clear result
5575                  NEXT_DIVIDE
5576 1a27 ae bc          LDX  #TEMP7         *compare denominator sum
5577 1a29 b6 b9          LDA  TEMP4          *with numerator
5578 1a2b cd 19 d0       JSR  COMPARE_3      *branch if result greater than or
```

```
5579 1a2e 22 10              BHI  DIVIDE_COMPLETE   *equal to numerator
5580 1a30 b6 bb              LDA  TEMP6
5581 1a32 cd 1a 85           JSR  BCD_INCREMENT_3   *increment result
5582 1a35 9a                 CLI
5583 1a36 9d                 NOP                    *allow interrupts
5584 1a37 9b                 SEI
5585 1a38 be ba              LDX  TEMP5             *add denominator
5586 1a3a a6 bc              LDA  #TEMP7            *to comparison sum
5587 1a3c ad 08              BSR  ADD_3
5588 1a3e 20 e7              BRA  NEXT_DIVIDE
5589                     DIVIDE_COMPLETE
5590 1a40 be bb              LDX  TEMP6
5591 1a42 cd 19 bb           JSR  COMPARE_TO_0_3    *compare result to zero
5592 1a45 81                 RTS
5593                     *
5594                     *   multibyte bcd addition
5595                     *   x holds address of one addend
5596                     *   acc holds address of second addend which becomes sum
5597                     *
5598                     ADD_3
5599 1a46 3c cb              INC  MATH_COUNTER
5600                     ADD_2
5601 1a48 3c cb              INC  MATH_COUNTER
5602 1a4a bb cb              ADD  MATH_COUNTER
5603 1a4c b7 b6              STA  TEMP
5604 1a4e 9f                 TXA
5605 1a4f bb cb              ADD  MATH_COUNTER
5606 1a51 b7 b7              STA  TEMP2
5607 1a53 97                 TAX
5608 1a54 3c cb              INC  MATH_COUNTER
5609 1a56 98                 CLC
5610                     ADD_NEXT
5611 1a57 f6                 LDA  ,X
5612 1a58 be b6              LDX  TEMP
5613 1a5a f9                 ADC  ,X
5614 1a5b ad 0c              BSR  DAA_ADD
5615 1a5d f7                 STA  ,X
5616 1a5e 3a b6              DEC  TEMP
5617 1a60 3a b7              DEC  TEMP2
5618 1a62 be b7              LDX  TEMP2
5619 1a64 3a cb              DEC  MATH_COUNTER
5620 1a66 26 ef              BNE  ADD_NEXT
5621 1a68 81                 RTS
5622                     *
5623                     *   decimal adjust accumulator after increment or add
5624                     *
5625                     ***** could this replace daa decrement?
5626                     ***** if not, does daa decrement work?
5627                     DAA_ADD
5628 1a69 25 04              BCS  DAA_HIGH
5629 1a6b a1 99               CMP  #$99
5630 1a6d 23 08              BLS  DAA_LOW
5631                     DAA_HIGH
5632 1a6f 40                 NEGA
```

```
5633 1a70 a0 60            SUB   #$60
5634 1a72 40               NEGA
5635 1a73 ad 02            BSR   DAA_LOW
5636 1a75 99               SEC
5637 1a76 81               RTS
5638                  DAA_LOW
5639 1a77 28 03            BHCC  DAA_NO
5640 1a79 ab 06            ADD   #6
5641 1a7b 81               RTS
5642                  DAA_NO
5643 1a7c ab 06            ADD   #6
5644 1a7e 29 02            BHCS  DAA_RTS
5645 1a80 a0 06            SUB   #6
5646                  DAA_RTS
5647 1a82 81               RTS
5648                  *
5649                  *   multibyte bcd increment of bytes in ram
5650                  *   enters at number of bytes to increment
5651                  *   acc holds high byte address
5652                  *
5653                  BCD_INCREMENT_4
5654 1a83 3c cb            INC   MATH_COUNTER
5655                  BCD_INCREMENT_3
5656 1a85 3c cb            INC   MATH_COUNTER
5657                  BCD_INCREMENT_2
5658 1a87 3c cb            INC   MATH_COUNTER
5659                  BCD_INCREMENT_1
5660 1a89 bb cb            ADD   MATH_COUNTER
5661 1a8b 97               TAX
5662 1a8c 3c cb            INC   MATH_COUNTER
5663 1a8e 99               SEC
5664                  NEXT_BCD_INC
5665 1a8f f6               LDA   ,X
5666 1a90 a9 00            ADC   #0
5667 1a92 ad d5            BSR   DAA_ADD
5668 1a94 f7               STA   ,X
5669 1a95 5a               DECX
5670 1a96 3a cb            DEC   MATH_COUNTER
5671 1a98 26 f5            BNE   NEXT_BCD_INC
5672 1a9a 81               RTS
5673                  *
5674                  *   multibyte bcd decrement of bytes in ram
5675                  *   enters at number of bytes to increment
5676                  *   acc holds high byte address
5677                  *
5678                  BCD_DECREMENT_3
5679 1a9b 3c cb            INC   MATH_COUNTER
5680                  BCD_DECREMENT_2
5681 1a9d 3c cb            INC   MATH_COUNTER
5682                  BCD_DECREMENT_1
5683 1a9f bb cb            ADD   MATH_COUNTER
5684 1aa1 97               TAX
5685 1aa2 3c cb            INC   MATH_COUNTER
5686 1aa4 99               SEC
```

```
5687                    NEXT_BCD_DEC
5688 1aa5 f6                LDA  ,X
5689 1aa6 a2 00             SBC  #0
5690 1aa8 ad 07             BSR  DAA_DECREMENT
5691 1aaa f7                STA  ,X
5692 1aab 5a                DECX
5693 1aac 3a cb             DEC  MATH_COUNTER
5694 1aae 26 f5             BNE  NEXT_BCD_DEC
5695 1ab0 81                RTS
5696                    *
5697                    *   decimal adjust accumulator after decrement
5698                    *
5699                    DAA_DECREMENT
5700 1ab1 ab 01             ADD  #$01
5701 1ab3 29 04             BHCS DAA_DEC_HIGH
5702 1ab5 a0 01             SUB  #$01
5703 1ab7 20 0c             BRA  DAA_DEC_EXIT
5704                    DAA_DEC_HIGH
5705 1ab9 a0 07             SUB  #$07
5706 1abb ab 10             ADD  #$10
5707 1abd 25 04             BCS  DAA_DEC_BORROW
5708 1abf a0 10             SUB  #$10
5709 1ac1 20 02             BRA  DAA_DEC_EXIT
5710                    DAA_DEC_BORROW
5711 1ac3 a0 70             SUB  #$70
5712                    DAA_DEC_EXIT
5713 1ac5 81                RTS
5714                    *
5715                    *   converts decimal number in acc to hex
5716                    *   destroys x register
5717                    *
5718                    CONVERT_TO_HEX
5719 1ac6 4d                TSTA
5720 1ac7 27 0a             BEQ  EXIT_CONVERT
5721 1ac9 5f                CLRX
5722                    NEXT_CONVERT
5723 1aca 5c                INCX
5724 1acb a0 01             SUB  #1
5725 1acd ad e2             BSR  DAA_DECREMENT
5726 1acf 4d                TSTA
5727 1ad0 26 f8             BNE  NEXT_CONVERT
5728 1ad2 9f                TXA
5729                    EXIT_CONVERT
5730 1ad3 81                RTS
5731                    *
5732                    *   program rtc
5733                    *
5734                    *   writes data to real time clock chip
5735                    *   data in lower nibble of acc
5736                    *   address in upper nibble of acc
5737                    *   turns hold on, waits for busy to clear,
5738                    *   writes data, then turns hold off
5739                    *
5740                    RTC_WRITE
```

```
5741 1ad4 ad 38           BSR   RTC_BUSY
5742 1ad6 ad 03           BSR   WRITE_RTC
5743 1ad8 ad 51           BSR   RTC_HOLD_OFF
5744 1ada 81              RTS
5745                   WRITE_RTC
5746 1adb b7 00           STA   RTC_BUS_P
5747 1add a6 ff           LDA   #DATA_BUS_OUT
5748 1adf b7 04           STA   RTC_BUS_PD
5749 1ae1 1a 02           BSET  RTC_WR,RTC_WR_P
5750 1ae3 1c 02           BSET  RTC_RD,RTC_RD_P
5751 1ae5 1e 02           BSET  RTC_CS,RTC_CS_P
5752 1ae7 1f 02           BCLR  RTC_CS,RTC_CS_P
5753 1ae9 1b 02           BCLR  RTC_WR,RTC_WR_P
5754 1aeb 1a 02           BSET  RTC_WR,RTC_WR_P
5755 1aed 1e 02           BSET  RTC_CS,RTC_CS_P
5756 1aef 81              RTS
5757                   *
5758                   *   reads from real time clock chip
5759                   *   at address in upper nibble of acc
5760                   *   returns data in lower nibble of acc
5761                   *
5762                   RTC_READ
5763 1af0 ad 1c           BSR   RTC_BUSY
5764 1af2 ad 03           BSR   READ_RTC
5765 1af4 ad 35           BSR   RTC_HOLD_OFF
5766 1af6 81              RTS
5767                   READ_RTC
5768 1af7 b7 00           STA   RTC_BUS_P
5769 1af9 a6 f0           LDA   #DATA_BUS_IN_OUT
5770 1afb b7 04           STA   RTC_BUS_PD
5771 1afd 1a 02           BSET  RTC_WR,RTC_WR_P
5772 1aff 1c 02           BSET  RTC_RD,RTC_RD_P
5773 1b01 1e 02           BSET  RTC_CS,RTC_CS_P
5774 1b03 1f 02           BCLR  RTC_CS,RTC_CS_P
5775 1b05 1d 02           BCLR  RTC_RD,RTC_RD_P
5776 1b07 b6 00           LDA   RTC_BUS_P
5777 1b09 1c 02           BSET  RTC_RD,RTC_RD_P
5778 1b0b 1e 02           BSET  RTC_CS,RTC_CS_P
5779 1b0d 81              RTS
5780                   *
5781                   *   waits for real time clock to clear busy, then returns
5782                   *
5783                   RTC_BUSY
5784                   *   TAX
5785 1b0e b7 cd           STA   RTC_SAVE
5786                   BUSY_RTC
5787 1b10 ad 12           BSR   RTC_HOLD_ON
5788 1b12 a6 d0           LDA   #$D0
5789 1b14 ad e1           BSR   READ_RTC
5790 1b16 a4 02           AND   #$02
5791 1b18 27 07           BEQ   RTC_BUSY_EXIT
5792 1b1a ad 0f           BSR   RTC_HOLD_OFF
5793 1b1c cd 18 1d        JSR   DELAY
5794 1b1f 20 ef           BRA   BUSY_RTC
```

```
5795                    RTC_BUSY_EXIT
5796               *       TXA
5797 1b21 b6 cd            LDA   RTC_SAVE
5798 1b23 81              RTS
5799                   *
5800                   *   asserts hold on real time clock, allowing reads and writes
5801                   *
5802                    RTC_HOLD_ON
5803 1b24 97              TAX
5804 1b25 a6 d1           LDA   #$D1
5805 1b27 ad b2           BSR   WRITE_RTC
5806 1b29 9f              TXA
5807 1b2a 81              RTS
5808                   *
5809                   *   clears hold on real time clock, allowing clock to run
5810                   *
5811                    RTC_HOLD_OFF
5812 1b2b 97              TAX
5813 1b2c a6 d0           LDA   #$D0
5814 1b2e ad ab           BSR   WRITE_RTC
5815 1b30 9f              TXA
5816 1b31 81              RTS
5817                   *
5818                   *   real time clock routine
5819                   *   runs off internal timer overflow
5820                   *
5821                    TIMER_UPDATE
5822 1b32 b6 b5           LDA   IRQ_INTERRUPT
5823 1b34 26 01           BNE   UPDATE_TIMER         *branch if no timer interrupt
5824                    REAL_TIME_EXIT
5825 1b36 81              RTS
5826                    UPDATE_TIMER
5827 1b37 3a b5           DEC   IRQ_INTERRUPT
5828 1b39 3a c5           DEC   DELAY_TIMER
5829                   *
5830 1b3b 3a c7           DEC   PUMP_JAM
5831 1b3d cd 05 fc        JSR   EVENT_MARK_OFF       *check to turn event mark output off
5832                   *
5833 1b40 b6 97           LDA   RTC_MILLISECOND
5834 1b42 cd 1a c6        JSR   CONVERT_TO_HEX
5835 1b45 a4 0f           AND   #$0F
5836 1b47 26 03           BNE   NO_FLASH_CHOICE
5837 1b49 cd 09 ef        JSR   FLASH_CHOICE
5838                   *
5839                    NO_FLASH_CHOICE
5840 1b4c a6 97           LDA   #RTC_MILLISECOND     *increment millisecond counter
5841 1b4e cd 1a 89        JSR   BCD_INCREMENT_1
5842 1b51 a1 64           CMP   #$64
5843 1b53 25 e1           BLO   REAL_TIME_EXIT
5844 1b55 3f 97           CLR   RTC_MILLISECOND
5845                   *
5846 1b57 cd 06 07        JSR   DIST_TIMER_CHK
5847                   *
5848 1b5a 3a c9           DEC   MINUTE_PASSED
```

```
5849 1b5c 3d c4              TST    DISPLAY_TIMEOUT
5850 1b5e 27 02              BEQ    NO_DISPLAY_TIME          *branch if display timeout not set
5851 1b60 3a c4              DEC    DISPLAY_TIMEOUT          *otherwise, decrement
5852                  NO_DISPLAY_TIME
5853                  *
5854 1b62 a6 96              LDA    #RTC_SECOND
5855 1b64 cd 1a 89           JSR    BCD_INCREMENT_1          *increment seconds counter
5856 1b67 a1 59              CMP    #$59
5857 1b69 23 43              BLS    DATE_DISPLAY
5858 1b6b 3f 96              CLR    RTC_SECOND
5859                  *
5860 1b6d a6 95              LDA    #RTC_MINUTE
5861 1b6f cd 1a 89           JSR    BCD_INCREMENT_1          *increment minutes counter
5862 1b72 a1 59              CMP    #$59
5863 1b74 23 36              BLS    TIME_CHECK
5864 1b76 3f 95              CLR    RTC_MINUTE
5865                  *
5866
5867                  ***** bcd increment always points to next byte
5868                  ***** arrange minute of first and rtc time in this order
                      *
5869 1b78 a6 94              LDA    #RTC_HOUR
5870 1b7a cd 1a 89           JSR    BCD_INCREMENT_1          *increment hours counter
5871 1b7d a1 23              CMP    #$23
5872 1b7f 23 2b              BLS    TIME_CHECK
5873 1b81 3f 94              CLR    RTC_HOUR
5874                  *
5875 1b83 cd 05 af           JSR    EPROM_CHECKSUM           *check eprom checksum
5876                  *
5877 1b86 a6 93              LDA    #RTC_DAY
5878 1b88 cd 1a 89           JSR    BCD_INCREMENT_1          *increment days counter
5879 1b8b b6 91              LDA    RTC_YEAR                 *current year
5880 1b8d be 92              LDX    RTC_MONTH                *and month
5881 1b8f cd 1B 3d           JSR    DAYS_PER_MONTH           *calculate days per this month
5882 1b92 b3 93              CPX    RTC_DAY
5883 1b94 24 16              BHS    TIME_CHECK
5884 1b96 a6 01              LDA    #1
5885 1b98 b7 93              STA    RTC_DAY
5886                  *
5887 1b9a a6 92              LDA    #RTC_MONTH
5888 1b9c cd 1a 89           JSR    BCD_INCREMENT_1          *increment months counter
5889 1b9f a1 12              CMP    #$12
5890 1ba1 23 09              BLS    TIME_CHECK
5891 1ba3 a6 01              LDA    #1
5892 1ba5 b7 92              STA    RTC_MONTH
5893                  *
5894 1ba7 a6 91              LDA    #RTC_YEAR
5895 1ba9 cd 1a 89           JSR    BCD_INCREMENT_1          *increment year counter
5896                  *
5897                  TIME_CHECK
5898 1bac ad 25              BSR    NEXT_TIME_CHECK          *compare time to time of first/next
5899                  *
5900                  DATE_DISPLAY
5901 1bae 08 c0 1f           BRSET  SAMPLING_BIT,SAMPLING_BYTE,NO_DATE_TIME
5902                  *                                       *branch if sampling
```

```
5903 1bb1 cd 16 49          JSR   NO_RUN_DISPLAY      *no time display
5904 1bb4 26 1a             BNE   NO_DATE_TIME        *during pgm review or fault display
5905 1bb6 b6 51             LDA   SAMPLER_STATE
5906 1bb8 a1 01             CMP   #STATE_STANDBY
5907 1bba 27 11             BEQ   DISPLAY_DATE
5908 1bbc a1 04             CMP   #STATE_RUN_FIRST
5909 1bbe 27 0d             BEQ   DISPLAY_DATE
5910 1bc0 a1 03             CMP   #STATE_FULL
5911 1bc2 27 09             BEQ   DISPLAY_DATE
5912 1bc4 a1 05             CMP   #STATE_RUN_TIME
5913 1bc6 26 08             BNE   NO_DATE_TIME
5914 1bc8 cd 03 05          JSR   LCD_TIME            *display current time during next run state
5915 1bcb 20 03             BRA   NO_DATE_TIME
5916                     DISPLAY_DATE
5917 1bcd cd 02 ed          JSR   LCD_DATE_TIME       *display current date/time
5918                     *                            *during standby or first run or full state
5919                     NO_DATE_TIME
5920 1bd0 cc 1b 36          JMP   REAL_TIME_EXIT
5921                     *
5922                     *   compares current time/date
5923                     *   with time/date of first/next sample
5924                     *
5925                     NEXT_TIME_CHECK
5926 1bd3 a6 92             LDA   #RTC_MONTH          *compare current date/time
5927 1bd5 ae 65             LDX   #MONTH_OF_FIRST     *with date/time of next sample
5928 1bd7 cd 19 ce          JSR   COMPARE_4
5929 1bda 26 07             BNE   NEXT_TIME_EXIT      *branch if not time for next
5930 1bdc ad 06             BSR   TIME_OF_NEXT        *else, update time of next sample
5931 1bde a6 7f             LDA   #TAKE_A_SAMPLE
5932 1be0 cd 1a 87          JSR   BCD_INCREMENT_2     *increment samples to be taken
5933                     NEXT_TIME_EXIT
5934 1be3 81                RTS
5935                     *
5936                     *   adds time interval pointed to by index register
5937                     *   to time/date of first sample
5938                     *   to determine time of next sample
5939                     *
5940                     TIME_OF_NEXT
5941 1be4 ae 69             LDX   #INTERVAL_HOURS     *assume not time switched flow paced continuous
5942 1be6 a6 b8             LDA   #TEMP3              *and minutes to temp5
5943 1be8 cd 19 fc          JSR   TRANSFER_2
5944                     NEXT_HOUR
5945 1beb 3d b8             TST   TEMP3
5946 1bed 27 09             BEQ   NEXT_MINUTE         *branch if no more hour increments
5947 1bef ad 20             BSR   INC_HOUR            *otherwise, increment hour of next
5948 1bf1 a6 b8             LDA   #TEMP3
5949 1bf3 cd 1a 9f          JSR   BCD_DECREMENT_1     *decrement hour increment
5950 1bf6 20 f3             BRA   NEXT_HOUR
5951                     NEXT_MINUTE
5952 1bf8 3d b9             TST   TEMP4
5953 1bfa 27 09             BEQ   TIME_NEXT_EXIT      *bra if no more minute increments
5954 1bfc ad 08             BSR   INC_MINUTE          *otherwise, inc minute of next
5955 1bfe a6 b9             LDA   #TEMP4
5956 1c00 cd 1a 9f          JSR   BCD_DECREMENT_1     *decrement minute increment
```

```
5957 1c03 20 f3              BRA   NEXT_MINUTE
5958                  TIME_NEXT_EXIT
5959 1c05 81                 RTS
5960                  *
5961                  *   increments time of first sample by one minute or one hour
5962                  *
5963                  INC_MINUTE
5964 1c06 a6 68              LDA   #MINUTE_OF_FIRST
5965 1c08 cd 1a 89           JSR   BCD_INCREMENT_1      *increment minute of first sample
5966 1c0b a1 59              CMP   #$59
5967 1c0d 23 33              BLS   INC_MINUTE_EXIT      *branch if hour not finished
5968 1c0f 3f 68              CLR   MINUTE_OF_FIRST      *otherwise, clear minute
5969                  *
5970                  INC_HOUR
5971 1c11 a6 67              LDA   #HOUR_OF_FIRST
5972 1c13 cd 1a 89           JSR   BCD_INCREMENT_1      *increment hour of first sample
5973 1c16 a1 23              CMP   #$23
5974 1c18 23 28              BLS   INC_MINUTE_EXIT      *branch if day not finished
5975 1c1a 3f 67              CLR   HOUR_OF_FIRST        *otherwise, clear hour
5976                  *
5977 1c1c a6 66              LDA   #DAY_OF_FIRST
5978 1c1e cd 1a 89           JSR   BCD_INCREMENT_1      *increment day of first sample
5979 1c21 b6 64              LDA   YEAR_OF_FIRST
5980 1c23 be 65              LDX   MONTH_OF_FIRST
5981 1c25 cd 18 3d           JSR   DAYS_PER_MONTH       *calculate days per month
5982 1c28 b3 66              CPX   DAY_OF_FIRST
5983 1c2a 24 16              BHS   INC_MINUTE_EXIT      *branch if month not finished
5984 1c2c a6 01              LDA   #1
5985 1c2e b7 66              STA   DAY_OF_FIRST         *otherwise, set day to one
5986                  *
5987 1c30 a6 65              LDA   #MONTH_OF_FIRST
5988 1c32 cd 1a 89           JSR   BCD_INCREMENT_1      *increment month of first sample
5989 1c35 a1 12              CMP   #$12
5990 1c37 23 09              BLS   INC_MINUTE_EXIT      *branch if year not finished
5991 1c39 a6 01              LDA   #1
5992 1c3b b7 65              STA   MONTH_OF_FIRST       *otherwise, set month to one
5993                  *
5994 1c3d a6 64              LDA   #YEAR_OF_FIRST
5995 1c3f cd 1a 89           JSR   BCD_INCREMENT_1      *increment year of first sample
5996                  *
5997                  INC_MINUTE_EXIT
5998 1c42 81                 RTS
5999                  *
6000                  *   program review
6001                  *
6002                  *##################
6003                  ** display status *
6004                  *##################
6005                  KEY_STATUS
6006 1c43 be c6              LDX   REVIEW_BRANCH        *current review pgm branch
6007 1c45 d6 1e 62           LDA   REVIEW_TABLE,X       *obtain next branch from table
6008 1c48 b7 c6              STA   REVIEW_BRANCH        *and store
6009 1c4a 26 06              BNE   REVIEW_PGM           *branch if not finished
6010 1c4c cd 1d 2b           JSR   RESTORE_DISPLAY      *restore display
```

```
6011  1c4f cc 1d 15        JMP   PGM_REVIEW_EXIT
6012                *
6013                REVIEW_PGM
6014  1c52 cd 02 d6        JSR   CLEAR_LCD        *clear display
6015                CONTINUE_REVIEW
6016  1c55 b6 c6           LDA   REVIEW_BRANCH
6017  1c57 97              TAX
6018  1c58 58              ASLX
6019  1c59 dc 1c 5a        JMP   STATUS_TABLE-2,X
6020                *
6021                STATUS_TABLE
6022  1c5c 20 22           BRA   STATUS_1
6023  1c5e 20 20           BRA   STATUS_2
6024  1c60 20 1e           BRA   STATUS_3
6025  1c62 20 1c           BRA   STATUS_4
6026  1c64 20 25           BRA   STATUS_5
6027  1c66 20 76           BRA   STATUS_6
6028  1c68 20 74           BRA   STATUS_7
6029  1c6a 20 25           BRA   STATUS_8
6030  1c6c 20 2a           BRA   STATUS_9
6031  1c6e 20 6e           BRA   STATUS_10
6032  1c70 20 2c           BRA   STATUS_11
6033  1c72 20 34           BRA   STATUS_12
6034  1c74 20 3a           BRA   STATUS_13
6035  1c76 20 3c           BRA   STATUS_14
6036  1c78 20 3e           BRA   STATUS_15
6037  1c7a 20 40           BRA   STATUS_16
6038  1c7c 20 42           BRA   STATUS_17
6039  1c7e 20 4b           BRA   STATUS_18
6040                *
6041                STATUS_1
6042                STATUS_2
6043                STATUS_3
6044                STATUS_4
6045  1c80 01 53 02        BRCLR  0,SAMPLER_PACE,STATUS_1_2_3_4
6046                *                             *branch if time paced
6047  1c83 4c              INCA
6048  1c84 4c              INCA                   *otherwise, flow paced status
6049                STATUS_1_2_3_4
6050  1c85 01 54 54        BRCLR  0,SAMPLER_MODE,STATUS_NEW
6051                *                             *branch if continuous sampling
6052  1c88 4c              INCA                   *otherwise, split sampling status
6053  1c89 20 51           BRA   STATUS_NEW
6054                *
6055                STATUS_5
6056  1c8b 01 55 4e        BRCLR  0,SWITCH_MODE,STATUS_NEW
6057                *                             *branch if time switched
6058  1c8e 4c              INCA                   *otherwise, flow switched status
6059  1c8f 20 4b           BRA   STATUS_NEW
6060                *
6061                STATUS_8
6062  1c91 cd 03 1e        JSR   FIRST_NEXT_TIME  *display date/time of next sample
6063  1c94 b6 c6           LDA   REVIEW_BRANCH
6064  1c96 20 46           BRA   REVIEW_NUMBER
```

```
6065    *
6066    STATUS_9
6067 1c98 01 53 41       BRCLR   0,SAMPLER_PACE,STATUS_NEW
6068    *                                *branch if time paced
6069 1c9b 4c             INCA            *otherwise, flow paced status
6070 1c9c 20 3e          BRA     STATUS_NEW
6071    *
6072
6073 1c9e 3c c6          INC     REVIEW_BRANCH
6074 1ca0 00 54 b2       BRSET   0,SAMPLER_MODE,CONTINUE_REVIEW
6075    *                                *branch if split sampling
6076 1ca3 00 55 af       BRSET   0,SWITCH_MODE,CONTINUE_REVIEW
6077    *                                *branch if flow switched
6078 1ca6 20 34          BRA     STATUS_NEW
6079    *
6080    STATUS_12
6081 1ca8 3d 90          TST     FAULT_BYTE
6082 1caa 27 32          BEQ     REVIEW_NUMBER   *branch if no faults
6083 1cac 3c c6          INC     REVIEW_BRANCH   *otherwise, display faults
6084 1cae 20 a5          BRA     CONTINUE_REVIEW
6085    *
6086    STATUS_13
6087 1cb0 a6 01          LDA     #F_POWER_FAIL   *check if power fail fault
6088 1cb2 20 0e          BRA     REVIEW_FAULT
6089    *
6090    STATUS_14
6091 1cb4 a6 02          LDA     #F_EPROM_FAIL   *check if eprom checksum fault
6092 1cb6 20 0a          BRA     REVIEW_FAULT
6093    *
6094    STATUS_15
6095 1cb8 a6 04          LDA     #F_PUMP_JAM     *check if pump jammed fault
6096 1cba 20 06          BRA     REVIEW_FAULT
6097    *
6098    STATUS_16
6099 1cbc a6 08          LDA     #F_DIST_JAM     *check if distributor jammed fault
6100 1cbe 20 02          BRA     REVIEW_FAULT
6101    *
6102    STATUS_17
6103 1cc0 a6 10          LDA     #F_TUBING       *check if pump tubing warning fault
6104    *
6105    REVIEW_FAULT
6106 1cc2 be c6          LDX     REVIEW_BRANCH
6107 1cc4 b4 90          AND     FAULT_BYTE
6108 1cc6 26 17          BNE     REVIEW_NUMBERS  *branch if this fault bit set
6109    NEXT_STATUS
6110 1cc8 cc 1c 43       JMP     KEY_STATUS      *otherwise, check next fault
6111    *
6112    STATUS_18
6113 1ccb be 90          LDX     FAULT_BYTE
6114 1ccd a3 10          CPX     #F_TUBING       *do not ask clear all faults
6115 1ccf 27 f7          BEQ     NEXT_STATUS     *if pump tubing worn is only fault
6116 1cd1 ae 01          LDX     #1
6117 1cd3 a6 06          LDA     #6
6118 1cd5 cd 1d 16       JSR     FLASH_YES_NO    *set yes or no parameters
```

```
6119 1cd8 b6 c6          LDA  REVIEW_BRANCH
6120 1cda 20 02          BRA  REVIEW_NUMBER
6121                *
6122                STATUS_NEW
6123 1cdc b7 c6          STA  REVIEW_BRANCH      *store review branch number
6124                STATUS_6
6125                STATUS_7
6126                STATUS_10
6127                REVIEW_NUMBER
6128 1cde 97             TAX
6129                REVIEW_NUMBERS
6130 1cdf c6 1d 6e       LDA  REVIEW_STEP
6131 1ce2 b7 cf          STA  EXTENDED+1          *position pointer to branch table
6132 1ce4 c6 1d 6f       LDA  REVIEW_STEP+1
6133 1ce7 cd 0a a0       JSR  FIND_REV_BRANCH
6134 1cea bd 2c          JSR  LDA_EXTENDED        *load pgm node
6135 1cec 4d             TSTA
6136 1ced 27 12          BEQ  NO_VALUES
6137 1cef b7 b8          STA  TEMP3
6138                REVIEW_VALUES
6139 1cf1 bd 2c          JSR  LDA_EXTENDED        *load and store length and leading 0
6140 1cf3 b7 ae          STA  PGM_LENGTH
6141 1cf5 bd 2c          JSR  LDA_EXTENDED        *and lcd position
6142 1cf7 97             TAX
6143 1cf8 bd 2c          JSR  LDA_EXTENDED        *and pgm storage
6144 1cfa cd 03 5d       JSR  DISPLAY_NUMBER      *display value
6145 1cfd 3a b8          DEC  TEMP3
6146 1cff 26 f0          BNE  REVIEW_VALUES       *branch if more values to display
6147                *
6148                NO_VALUES
6149 1d01 bd 2c          JSR  LDA_EXTENDED        *load display end or lcd position
6150 1d03 cd 02 da       JSR  LCD_CURSOR          *otherwise, position cursor
6151                NXT_REVIEW_CHAR
6152 1d06 bd 2c          JSR  LDA_EXTENDED
6153 1d08 a1 df          CMP  #END_OF_MESSAGE
6154 1d0a 27 f5          BEQ  NO_VALUES           *branch if end of message
6155 1d0c a1 e1          CMP  #END_OF_BRANCH
6156 1d0e 27 05          BEQ  PGM_REVIEW_EXIT     *branch if end of displays
6157 1d10 cd 02 90       JSR  LCD_DATA_WRITE      *otherwise, display character
6158 1d13 20 f1          BRA  NXT_REVIEW_CHAR     *and go on to next byte
6159                PGM_REVIEW_EXIT
6160 1d15 81             RTS
6161                *
6162                *
6163                *   initializes flags for cursor selections outside of programming mode
6164                *   accumulator contains pgm branch with text to flash
6165                *   index register contains initial choice
6166                *
                    FLASH_YES_NO
6167 1d16 b7 a1          STA  PGM_BRANCH          *set pgm branch with text to flash
6168 1d18 bf a2          STX  PGM_CHOICE          *set initial choice
6169 1d1a a6 02          LDA  #2
6170 1d1c b7 b1          STA  FLASH               *set code to flash on
6171 1d1e 18 c1          BSET YES_NO_BIT,YES_NO_BYTE
6172                *                              *set yes no flashing flag
```

```
6173  1d20 a6 45            LDA   #LCD_LINE_2+5
6174  1d22 cd 02 da         JSR   LCD_CURSOR
6175  1d25 a6 d9            LDA   #V__YES__NO_
6176  1d27 cd 02 90         JSR   LCD_DATA_WRITE    *display yes no message
6177  1d2a 81               RTS
6178                      *
6179                      * restore display on exit from review pgm or display fault
6180                      *
6181                      RESTORE_DISPLAY
6182  1d2b 3f c6            CLR   REVIEW_BRANCH     ***** in case of timeout
6183  1d2d cd 02 d6         JSR   CLEAR_LCD
6184  1d30 08 c0 29         BRSET SAMPLING_BIT,SAMPLING_BYTE,RESTORE_PUMPING
6185                      *                         *branch if sampling
6186  1d33 b6 51            LDA   SAMPLER_STATE
6187  1d35 a1 04            CMP   #STATE_RUN_FIRST
6188  1d37 26 05            BNE   RESTORE_TIME
6189                      ***** could handle as branch table
6190  1d39 cd 14 70         JSR   DATE_TIME_FIRST   *display date/time of first sample
6191  1d3c 20 2f            BRA   RESTORE_EXIT
6192                      RESTORE_TIME
6193  1d3e a1 05            CMP   #STATE_RUN_TIME
6194  1d40 26 0e            BNE   RESTORE_FLOW
6195  1d42 cd 15 cc         JSR   SAMPLE_DISPLAY    *display sample number, number of samples,
6196  1d45 cd 14 aa         JSR   NXT_TIME_SAMPLE   *and time of next sample
6197  1d48 01 c1 22         BRCLR INHIBIT_BIT,INHIBIT_BYTE,RESTORE_EXIT
6198                      *                         *branch if not inhibited
6199  1d4b cd 15 a7         JSR   LCD_INHIBIT       *otherwise, display inhibited
6200  1d4e 20 1d            BRA   RESTORE_EXIT
6201                      RESTORE_FLOW
6202  1d50 a1 06            CMP   #STATE_RUN_FLOW
6203  1d52 26 0d            BNE   RESTORE_STANDBY
6204  1d54 cd 15 cc         JSR   SAMPLE_DISPLAY    *display sample number, number of samples,
6205  1d57 cd 14 d7         JSR   NXT_FLOW_SAMPLE   *and flow to next sample
6206  1d5a 20 11            BRA   RESTORE_EXIT
6207                      RESTORE_PUMPING
6208  1d5c cd 16 12         JSR   PUMPING_DISPLAY   *display sample number, number of samples,
6209  1d5f 20 0c            BRA   RESTORE_EXIT      *and volume pumping
6210                      RESTORE_STANDBY
6211  1d61 a1 01            CMP   #STATE_STANDBY
6212  1d63 26 05            BNE   RESTORE_FULL
6213  1d65 cd 06 ba         JSR   STANDBY_DISPLAY   *display standby and number of samples
6214  1d68 20 03            BRA   RESTORE_EXIT
6215                      RESTORE_FULL
6216  1d6a cd 13 f0         JSR   FULL_DISPLAY      *display full and number of samples
6217                      RESTORE_EXIT
6218  1d6d 81               RTS
6219                      *
6220                      REVIEW_STEP
6221  1d6e 1d 70            FDB   REVIEW_01
6222                      *1
6223                      REVIEW_01
6224  1d70 00               FCB   0
6225  1d71 05               FCB   5
6226  1d72 d3               FCB   V_TIME
```

```
6227 1d73 20           FCC  ' '
6228 1d74 bf           FCB  V_PACED
6229 1d75 df           FCB  END_OF_MESSAGE
6230 1d76 40           FCB  LCD_LINE_2
6231 1d77 a4           FCB  V_CONTINUOUS
6232 1d78 20           FCC  ' '
6233 1d79 cc           FCB  V_SAMPLING
6234 1d7a e1           FCB  END_OF_BRANCH
6235              *2
6236 1d7b 00           FCB  0
6237 1d7c 05           FCB  5
6238 1d7d d3           FCB  V_TIME
6239 1d7e 20           FCC  ' '
6240 1d7f bf           FCB  V_PACED
6241 1d80 df           FCB  END_OF_MESSAGE
6242 1d81 43           FCB  LCD_LINE_2+3
6243 1d82 ce           FCB  V_SPLIT
6244 1d83 20           FCC  ' '
6245 1d84 cc           FCB  V_SAMPLING
6246 1d85 e1           FCB  END_OF_BRANCH
6247              *3
6248 1d86 00           FCB  0
6249 1d87 05           FCB  5
6250 1d88 af           FCB  V_FLOW
6251 1d89 20           FCC  ' '
6252 1d8a bf           FCB  V_PACED
6253 1d8b df           FCB  END_OF_MESSAGE
6254 1d8c 40           FCB  LCD_LINE_2
6255 1d8d a4           FCB  V_CONTINUOUS
6256 1d8e 20           FCC  ' '
6257 1d8f cc           FCB  V_SAMPLING
6258 1d90 e1           FCB  END_OF_BRANCH
6259              *4
6260 1d91 00           FCB  0
6261 1d92 05           FCB  5
6262 1d93 af           FCB  V_FLOW
6263 1d94 20           FCC  ' '
6264 1d95 bf           FCB  V_PACED
6265 1d96 df           FCB  END_OF_MESSAGE
6266 1d97 43           FCB  LCD_LINE_2+3
6267 1d98 ce           FCB  V_SPLIT
6268 1d99 20           FCC  ' '
6269 1d9a cc           FCB  V_SAMPLING
6270 1d9b e1           FCB  END_OF_BRANCH
6271              *5
6272 1d9c 00           FCB  0
6273 1d9d 00           FCB  0
6274 1d9e d0           FCB  V_SWITCH
6275 1d9f 20           FCC  ' '
6276 1da0 a2           FCB  V_BOTTLE
6277 1da1 53           FCC  'S'
6278 1da2 a1           FCB  V__BASED
6279 1da3 df           FCB  END_OF_MESSAGE
6280 1da4 46           FCB  LCD_LINE_2+6
```

```
6281  1da5 4f 4e 20            FCC   'ON '
6282  1da8 d3                  FCB   V_TIME
6283  1da9 e1                  FCB   END_OF_BRANCH
6284                     *6
6285  1daa 00                  FCB   0
6286  1dab 00                  FCB   0
6287  1dac d0                  FCB   V_SWITCH
6288  1dad 20                  FCC   ' '
6289  1dae a2                  FCB   V_BOTTLE
6290  1daf 53                  FCC   'S'
6291  1db0 a1                  FCB   V_BASED
6292  1db1 df                  FCB   END_OF_MESSAGE
6293  1db2 46                  FCB   LCD_LINE_2+6
6294  1db3 4f 4e 20            FCC   'ON '
6295  1db6 af                  FCB   V_FLOW
6296  1db7 e1                  FCB   END_OF_BRANCH
6297                     *7
6298  1db8 02                  FCB   2
6299  1db9 03                  FCB   3+LEADING_0_NO
6300  1dba 04                  FCB   4
6301  1dbb 5a                  FCB   NUM_OF_SAMPLES
6302  1dbc 03                  FCB   3+LEADING_0_NO
6303  1dbd 46                  FCB   LCD_LINE_2+6
6304  1dbe 57                  FCB   NOMINAL_VOLUME
6305  1dbf 08                  FCB   8
6306  1dc0 cb                  FCB   V_SAMPLES
6307  1dc1 df                  FCB   END_OF_MESSAGE
6308  1dc2 43                  FCB   LCD_LINE_2+3
6309  1dc3 4f 46               FCC   'OF'
6310  1dc5 df                  FCB   END_OF_MESSAGE
6311  1dc6 4a                  FCB   LCD_LINE_2+10
6312  1dc7 ba                  FCB   V_al_
6313  1dc8 a7                  FCB   V_EACH
6314  1dc9 e1                  FCB   END_OF_BRANCH
6315                     *8
6316                     ***** if flow paced and after first sample, should show flow to next
6317  1dca 00                  FCB   0
6318  1dcb 00                  FCB   0
6319  1dcc ae                  FCB   V_FIRST
6320  1dcd 2f 4e 45 58 54 20   FCC   '/NEXT '
6321  1dd3 ca                  FCB   V_SAMPLE
6322  1dd4 20 41 54            FCC   ' AT'
6323  1dd7 e1                  FCB   END_OF_BRANCH
6324                     *9
6325  1dd8 02                  FCB   2
6326  1dd9 02                  FCB   2+LEADING_0_NO
6327  1dda 40                  FCB   LCD_LINE_2
6328  1ddb 69                  FCB   INTERVAL_HOURS
6329  1ddc 02                  FCB   2+LEADING_0_NO
6330  1ddd 4a                  FCB   LCD_LINE_2+10
6331  1dde 6a                  FCB   INTERVAL_MINUTE
6332  1ddf 04                  FCB   4
6333  1de0 ca                  FCB   V_SAMPLE
6334  1de1 20                  FCC   ' '
```

```
6335 1de2 aa         FCB  V_EVERY
6336 1de3 df         FCB  END_OF_MESSAGE
6337 1de4 43         FCB  LCD_LINE_2+3
6338 1de5 b2         FCB  V_HOURS
6339 1de6 df         FCB  END_OF_MESSAGE
6340 1de7 4d         FCB  LCD_LINE_2+13
6341 1de8 b9         FCB  V_MINUTES
6342 1de9 e1         FCB  END_OF_BRANCH
6343              *10
6344 1dea 01         FCB  1
6345 1deb 04         FCB  4+LEADING_0_NO
6346 1dec 44         FCB  LCD_LINE_2+4
6347 1ded 6b         FCB  INTERVAL_FLOW
6348 1dee 04         FCB  4
6349 1def ca         FCB  V_SAMPLE
6350 1df0 20         FCC  ' '
6351 1df1 aa         FCB  V_EVERY
6352 1df2 df         FCB  END_OF_MESSAGE
6353 1df3 49         FCB  LCD_LINE_2+9
6354 1df4 c3         FCB  V_PULSES
6355 1df5 e1         FCB  END_OF_BRANCH
6356              *11
6357 1df6 02         FCB  2
6358 1df7 02         FCB  2+LEADING_0_NO
6359 1df8 40         FCB  LCD_LINE_2
6360 1df9 69         FCB  INTERVAL_HOURS
6361 1dfa 02         FCB  2+LEADING_0_NO
6362 1dfb 4a         FCB  LCD_LINE_2+10
6363 1dfc 6a         FCB  INTERVAL_MINUTE
6364 1dfd 00         FCB  0
6365 1dfe d0         FCB  V_SWITCH
6366 1dff 20         FCC  ' '
6367 1e00 a2         FCB  V_BOTTLE
6368 1e01 53 20      FCC  'S '
6369 1e03 aa         FCB  V_EVERY
6370 1e04 df         FCB  END_OF_MESSAGE
6371 1e05 43         FCB  LCD_LINE_2+3
6372 1e06 b2         FCB  V_HOURS
6373 1e07 df         FCB  END_OF_MESSAGE
6374 1e08 4d         FCB  LCD_LINE_2+13
6375 1e09 b9         FCB  V_MINUTES
6376 1e0a e1         FCB  END_OF_BRANCH
6377              *12
6378 1e0b 00         FCB  0
6379 1e0c 05         FCB  5
6380 1e0d bb         FCB  V_NO
6381 1e0e ad         FCB  V__FAULTS
6382 1e0f e1         FCB  END_OF_BRANCH
6383              *13
6384 1e10 00         FCB  0
6385 1e11 04         FCB  4
6386 1e12 ac         FCB  V____FAULT___
6387 1e13 df         FCB  END_OF_MESSAGE
6388 1e14 45         FCB  LCD_LINE_2+5
```

```
6389 1e15 c0                      FCB  V_POWER_
6390 1e16 ab                      FCB  V_FAIL_
6391 1e17 e1                      FCB  END_OF_BRANCH
6392                         *14
6393 1e18 00                      FCB  0
6394 1e19 04                      FCB  4
6395 1e1a ac                      FCB  V___FAULT___
6396 1e1b df                      FCB  END_OF_MESSAGE
6397 1e1c 43                      FCB  LCD_LINE_2+3
6398 1e1d 45 50 52 4f 4d 20       FCC  'EPROM CHECKSUM'
     43 48 45 43 4b 53
     55 4d
6399 1e2b e1                      FCB  END_OF_BRANCH
6400                         *15
6401 1e2c 00                      FCB  0
6402 1e2d 04                      FCB  4
6403 1e2e ac                      FCB  V___FAULT___
6404 1e2f df                      FCB  END_OF_MESSAGE
6405 1e30 44                      FCB  LCD_LINE_2+4
6406 1e31 c4                      FCB  V_PUMP_
6407 1e32 b4                      FCB  V_JAMMED
6408 1e33 e1                      FCB  END_OF_BRANCH
6409                         *16
6410 1e34 00                      FCB  0
6411 1e35 04                      FCB  4
6412 1e36 ac                      FCB  V___FAULT___
6413 1e37 df                      FCB  END_OF_MESSAGE
6414 1e38 41                      FCB  LCD_LINE_2+1
6415 1e39 44 49 53 54 52 49       FCC  'DISTRIBUTOR '
     42 55 54 4f 52 20
6416 1e45 b4                      FCB  V_JAMMED
6417 1e46 e1                      FCB  END_OF_BRANCH
6418                         *17
6419 1e47 00                      FCB  0
6420 1e48 04                      FCB  4
6421 1e49 ac                      FCB  V___FAULT___
6422 1e4a df                      FCB  END_OF_MESSAGE
6423 1e4b 42                      FCB  LCD_LINE_2+2
6424 1e4c c4                      FCB  V_PUMP_
6425 1e4d d4                      FCB  V_TUBING
6426 1e4e 20 57 4f 52 4e          FCC  ' WORN'
6427 1e53 e1                      FCB  END_OF_BRANCH
6428                         *18
6429 1e54 00                      FCB  0
6430 1e55 01                      FCB  1
6431 1e56 43 4c 45 41 52 20       FCC  'CLEAR ALL'
     41 4c 4c
6432 1e5f ad                      FCB  V__FAULTS
6433 1e60 3f                      FCC  '?'
6434 1e61 e1                      FCB  END_OF_BRANCH
6435                         *
6436                         REVIEW_TABLE
6437 1e62 01                      FCB  01
6438 1e63 07                      FCB  07
```

```
6439 1e64 07        FCB  07
6440 1e65 05        FCB  05
6441 1e66 07        FCB  07
6442 1e67 07        FCB  07      *5
6443 1e68 07        FCB  07
6444 1e69 08        FCB  08
6445 1e6a 09        FCB  09
6446 1e6b 0c        FCB  12
6447 1e6c 0b        FCB  11      *10
6448 1e6d 0c        FCB  12
6449 1e6e 00        FCB  00
6450 1e6f 0e        FCB  14
6451 1e70 0f        FCB  15
6452 1e71 10        FCB  16      *15
6453 1e72 11        FCB  17
6454 1e73 12        FCB  18
6455 1e74 00        FCB  00
```

What is claimed is:

1. An intake nozzle for a wastewater sampler comprising:

a tapered tube having a bottom tip with an intake port;

said tapered tube having an upper opening near a top portion thereof;

hose means;

means for connecting the hose means to the upper opening of said tapered tube;

the intake port of said tapered tube being at an angle of between 5 and 40 degrees from a central longitudinal axis of an inlet port of a flow-through channel to which the tapered tube is adapted to be mounted, wherein a plane defining the plane of the intake port is at an angle with a longitudinal axis of the flow-through channel of between 5 and 40 degrees;

means for mounting the intake nozzle at an angle to a flow of wastewater at a location within a flow stream near the inlet port of the flow-through channel where it receives substantial flow of wastewater;

the means for mounting the intake nozzle includes means for mounting the intake nozzle in a range from the inlet port of the flow-through channel of between one-quarter inch away from the surface of the inlet port to four inches away from the surface of the inlet port.

2. An intake nozzle in accordance with claim 1 in which the means for mounting the intake nozzle includes means for mounting the intake nozzle such that the intake port is at a depth below a center of the inlet port, wherein the intake port is within downwardly flowing wastewater from the inlet port.

3. An intake nozzle in accordance with claim 2 in which the means for mounting the intake nozzle includes means for aligning the nozzle angularly.

4. An intake nozzle in accordance with claim 2 in which the means for mounting the intake nozzle includes means for adjusting the depth of the intake port.

* * * * *